(12) United States Patent
Peng et al.

(10) Patent No.: US 10,647,712 B2
(45) Date of Patent: May 12, 2020

(54) DIHYDROISOQUINOLINE COMPOUND

(71) Applicant: SUZHOU ARK BIOPHARMACEUTICAL CO., LTD., Suzhou (CN)

(72) Inventors: Cheng Peng, Suzhou (CN); Qing Xu, Suzhou (CN); Teng Feng, Suzhou (CN); Xiashi Lv, Suzhou (CN); Xiaogang Lai, Suzhou (CN); Rui Cui, Suzhou (CN); Shaoyun Zhang, Suzhou (CN); Jian Han, Suzhou (CN); Chaojun Gong, Suzhou (CN); Zhaoxiong Cai, Suzhou (CN); Yang Zhou, Suzhou (CN); Gang Zou, Suzhou (CN); Danbin Li, Suzhou (CN); Haiqing Yuan, Suzhou (CN); Zhen Jim Wu, Suzhou (CN)

(73) Assignee: SUZHOU ARK BIOPHARMACEUTICAL CO., LTD., Suzhou (CN)

( * ) Notice: Subject to any disclaimer, the term of this patent is extended or adjusted under 35 U.S.C. 154(b) by 0 days.

(21) Appl. No.: 16/477,533

(22) PCT Filed: Jan. 10, 2018

(86) PCT No.: PCT/CN2018/072057
§ 371 (c)(1),
(2) Date: Jul. 12, 2019

(87) PCT Pub. No.: WO2018/130152
PCT Pub. Date: Jul. 19, 2018

(65) Prior Publication Data
US 2019/0389855 A1  Dec. 26, 2019

(30) Foreign Application Priority Data

Jan. 13, 2017  (CN) .......................... 2017 1 0027443

(51) Int. Cl.
*C07D 455/06* (2006.01)
(52) U.S. Cl.
CPC .................................. *C07D 455/06* (2013.01)
(58) Field of Classification Search
CPC ..................................................... C07D 455/06
See application file for complete search history.

(56) References Cited

FOREIGN PATENT DOCUMENTS

CN      106810548 A    6/2017
WO      2015/173164 A1   11/2015

*Primary Examiner* — Timothy R Rozof
(74) *Attorney, Agent, or Firm* — SZDC Law PC

(57) ABSTRACT

A compound of general formula I:

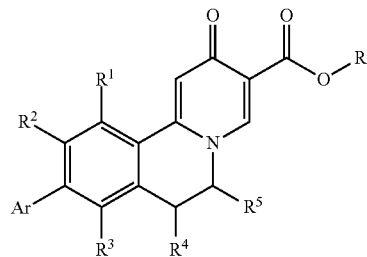

is disclosed. The compound be used to prevent or treat hepatitis B virus infection.

26 Claims, No Drawings

DIHYDROISOQUINOLINE COMPOUND

This application is the National Stage Application of PCT/CN2018/072057, filed on Jan. 10, 2018, which claims priority to Chinese Patent Application No.: 201710027443.3, filed on Jan. 13, 2017, which is incorporated by reference for all purposes as if fully set forth herein.

The invention belongs to the field of compounds, in particular to a dihydroisoquinoline compound, in particular to a dihydroisoquinoline compound and a mixture or composition containing dihydroisoquinoline compound, especially as a dihydroisoquinoline compound and mixtures or compositions of dihydroisoquinoline compounds used for preventing and treating hepatitis B virus infection.

FIELD OF THE INVENTION

According to WHO report, one third of the world's current population had evidences of HBV infection in the past and among them 350 to 500 million people are chronic carriers of HBV. HBV infection causes either acute hepatitis, or chronic hepatitis which will end up with cirrhosis and hepatocellular carcinoma (HCC) at a high probability. HBV can infect human via many different routes, leading to transmission of liver disease. It is estimated that 0.8 million people died because of acute or chronic HBV infection annually. As a result, HBV infection has become one of the major public health problems. Despite that the development of safe and effective HBV vaccines and extensive vaccination of new born infants have significantly reduced the incidence of HBV infection and even incidence of HCC, the global HBV health burden remains high as vaccination coverage is still low in certain low-income regions and many HBV patients are denied access of diagnosis and treatment in time due to economic reasons. Even though with more fundamental research into HBV infection inhibition and applications of new diagnostic and treatment methods, progress has been made in treatment and prevention of HBV recently, curing HBV is still not feasible, and it remains a huge unmet medical need.

The hepatitis B virus (HBV) is an enveloped virus with a partially single-stranded circular DNA genome of 3.2 kb, belonging to hepadnavirdae. HBV displays 8% nucleotide variation over whole genome and eight genotypes were defined based on the 4.2% nucleotide differences in S gene. These genotypes show different geographic distribution and ethnic distribution. Genotype B and C are mainly found in Asia; genotype A and D are dominant in Africa, Europe and India; genotype E is most common in West Africa; genotype F is observed in Central and South America while genotype G is mostly reported in France, German and North America. HBV genome consists of four overlapping open reading frames (ORF), encoding for core, polymerase (Pol), envelope and X-proteins respectively. HBV infectious particle relies on Sodium/bile acid cotransporter (NTCP) on hepatocyte surface for infection, and after infection, the partially double-stranded viral DNA is transported into nucleus and converted into covalently closed circular DNA (cccDNA), and this cccDNA serves as transcription template for viral pre-genomic RNA (pgRNA) and sub-genomic RNAs. The synthesized core protein then package pgRNA and polymerase together for replication (Lamontagne R J, et al. Hepatoma Res 2016; 2: 163-86.).

On the viral particle surface, there is a 7 nm layer of phospholipid membrane protein, called hepatitis B surface antigen (HBsAg). The HBsAg consists of proteins of large, middle and small size. They are encoded by the same S gene translated from three different start codons. All three proteins share the same S-domain at their C-termini. After synthesis, these proteins are inserted into ER membrane under the guidance of N-terminal signal peptide. In one aspect HBsAg is assembled into mature HBV particle as major structure protein, yet at the same time, it is able to form spherical or filamentous subviral particles (SVPs). The SVPs usually outnumber mature viral particles by at least 1000 fold. In serological test, being HBsAg positive for more than six months is marker of chronic HBV infection. Though SVP is not infectious, it can seriously affect host immune response. HBsAg can dampen the activation of monocytes in the innate immune system (Vanlandschoot P et al, J Gen Virol. 2002 June; 83(Pt 6): 1281-9), jeopardize the function of dendritic cells (Marjoleine L et al, Immunology. 2009 February; 126(2): 280-289.), and disrupt the activity of natural killer cells (Yang Y et al, Int Immunopharmacol. 2016 September; 38: 291-7). Prolonged exposure to HBsAg and other viral antigens results dysfunction of HBV-specific T cells and leads to immune tolerance of HBV (Carolina B et al, J Virol. 2007 April; 81(8): 4215-4225). Therefore, serum HBsAg level is regarded as one of the key biomarkers for prognosis and treatment response in chronic HBV patient. Serological clearance of HBsAg is considered as functional cure of CHB.

Until today, FDA has approved two kinds of therapies for HBV interferon (interferon α or pegylated interferon α) and nucleotide/nucleoside analogs. The nucleoside analogs include lamivudine (heptodin), adefovir (hepsera), entecavir (baraclude), telbivudine (Sebivo), and tenofovir (Viread). By regulating host innate immune system, interferon α is able to activate immune cells and induce production of multiple anti-viral cytokines to control HBV replication. Besides the anti-viral activity, interferon therapy can enhance host immunity with a long-lasting effect, and reduce risks of cirrhosis and HCC. However, this therapy is associated with some disadvantages such as unsatisfactory anti-viral potency, and a plethora of adverse side-effects including flu-like symptoms, muscle pain, thrombocytopenia, hair loss and depression. Long-term interferon therapy had only achieved 2.25% HBsAg clearance rate in western populations and a merely 0.43% clearance rate in Asian populations (C M Chun et al, Antivir Ther. 2010; 15(2): 133-43). Compared to interferon, nucleoside analogs control viral replication by directly inhibiting HBV viral DNA synthesis. Lamivudine, a once HIV drug, shows fast absorption after oral administration and can significantly reduce viral load by inhibiting HBV replication. It demonstrates both strong antiviral potency and good safety profile with less AE, but resistance mutations emerge after prolonged administration of this drug. Adefovir is more potent than lamivudine, and it shows potent anti-viral effect even for lamivudine-resistant patients, but long-term usage of this drug is associated with kidney toxicity. In general, nucleoside analogs, even with prolonged therapy, have demonstrated a disappointing HBsAg clearance rate of 0.5-1% in CHB patients annually (E Loggi et al, Dig Liver Dis. 2015 October; 47(10): 836-41).

To summarize it, current anti-HBV therapies are unable to eradicate HBV from chronic HBV patient, due to factors such as persistent presence and replication of HBV in hepatocytes and continues emergence of drug resistant mutations during treatment. To keep viral replication at low level, patients have to undergo long-term treatment and this prolonged treatment imposes enormous social and economic burden on the society and medical system. Therefore, curing HBV with a finite treatment represents a huge unmet medical need. Clearance of HBsAg possess the potential to break host immune tolerance of HBV, restore host immune response to achieve a cure of HBV, and thus points a new direction for HBV treatment. Therefore, developing HBsAg inhibitor will offer great opportunity for HBV treatment and produce enormous social and economic benefit in the future.

SUMMARY OF THE INVENTION

The present invention relates to novel compounds of general formula I:

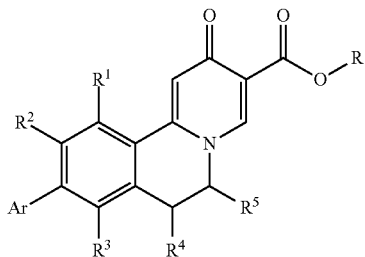

wherein:
R is any one of hydrogen and $C_{1-6}$ alkyl;
$R^1$ is any one of hydrogen, deuterium, halogen, $C_{1-6}$ alkyl, $C_{1-6}$ alkylamino, and $C_{1-6}$ alkoxy;
$R^2$ is any one of hydrogen, deuterium, halogen, $C_{1-6}$ alkyl, $C_{1-6}$ alkyl substituted with at least one fluorine, $C_{3-7}$ cycloalkyl, $C_{1-6}$ alkylamino, $C_{1-6}$ alkoxy, and heterocycloalkyl;
Ar is any one of phenyl, thienyl, pyridinyl, pyrimidinyl, pyrazinyl, pyridazinyl, pyridin-2(1H)-keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, oxadiazolyl, naphthyl, benzothiophenyl, indolyl, benzimidazolyl, benzothiazolyl, benzofuryl, quinolyl, isoquinolyl, and quinazolinyl;
$R^3$ is any one of hydrogen, deuterium, halogen, cyano, $C_{1-6}$ alkyl, $C_{3-7}$ cycloalkyl, $C_{1-6}$ alkylamino, $C_{1-6}$ alkoxy, and heterocycloalkyl;
$R^4$ is any one of hydrogen, deuterium, and $C_{1-6}$ alkyl;
$R^5$ is any one of hydrogen, deuterium, $C_{1-6}$ alkyl, $C_{1-6}$ alkyl substituted with at least one fluorine, and $C_{3-7}$ cycloalkyl.
Preferably, Ar is substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkoxy$C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, —N($R^7$)—C(=O)—$R^8$, —$C_{1-6}$ alkylamino-C(=O)—$C_{1-6}$ alkyl, and —$C_{1-6}$ alkylamino-C(=O)-amino $C_{1-6}$ alkyl, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein,
$R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;
$R^7$ is any one of hydrogen, deuterium, $C_{1-6}$ alkyl, and $C_{3-7}$ cycloalkyl;
$R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl.
Preferably, R is any one of hydrogen, methyl, ethyl, propyl, isopropyl, and tert-butyl;
$R^1$ is any one of hydrogen, deuterium, fluorine, chlorine, bromine, methyl, ethyl, isopropyl, tert-butyl, methylamino, ethylamino, methoxy, ethoxy, and isopropoxy;
$R^2$ is any one of hydrogen, deuterium, fluorine, chlorine, bromine, methyl, ethyl, isopropyl, tert-butyl, trifluoromethyl, trifluoromethylmethyl, cyclopropyl, cyclopentyl, methylamino, ethylamino, methoxy, ethoxy, isopropoxy, pyrrolidinyl, and morpholinyl;
Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, methyl, ethyl, and cyano;

$R^4$ is any one of hydrogen, deuterium, methyl, and ethyl;

$R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

Preferably, R is any one of hydrogen and $C_{1-6}$ alkyl;

$R^1$ is any one of hydrogen, deuterium, halogen, and $C_{1-6}$ alkyl;

$R^2$ is any one of hydrogen, deuterium, halogen, $C_{1-6}$ alkyl, $C_{1-6}$ alkyl substituted with at least one fluorine, $C_{3-7}$ cycloalkyl, and $C_{1-6}$ alkoxy;

Ar is any one of phenyl, thienyl, pyridinyl, pyrimidinyl, pyrazinyl, pyridazinyl, pyridin-2(1H)-keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, and oxadiazolyl;

$R^3$ is any one of hydrogen, deuterium, halogen, cyano, $C_{1-6}$ alkyl, and $C_{3-7}$ cycloalkyl;

$R^4$ is any one of hydrogen, deuterium, and $C_{1-6}$ alkyl;

$R^5$ is any one of hydrogen, deuterium, $C_{1-6}$ alkyl, $C_{1-6}$ alkyl substituted with at least one fluorine, and $C_{3-7}$ cycloalkyl.

Preferably, Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, and —N($R^7$)—C(=O)—$R^8$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

$R^7$ is any one of hydrogen, deuterium, and $C_{1-6}$ alkyl;

$R^8$ is any one of hydrogen, deuterium, $C_{1-6}$ alkyl, $C_{3-7}$ cycloalkyl, and $C_{3-7}$ heterocycloalkyl.

Preferably, R is any one of hydrogen, methyl, ethyl, and isopropyl;

$R^1$ is any one of hydrogen, deuterium, fluorine, chlorine, bromine, methyl, ethyl, isopropyl, and tert-butyl;

$R^2$ is any one of hydrogen, deuterium, fluorine, chlorine, bromine, methyl, ethyl, isopropyl, tert-butyl, trifluoromethyl, trifluoromethyl methyl, cyclopropyl, cyclopentyl, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, cyano, methyl, ethyl, and cyclopropyl;

$R^4$ is any one of hydrogen, deuterium, methyl, and ethyl;

R⁵ is any one of hydrogen, deuterium, methyl, ethyl, isopropyl, butyl, sec-butyl, isobutyl, tert-butyl, and cyclopropyl.

Preferably, R is any one of hydrogen and $C_{1-6}$ alkyl;

R¹ is any one of hydrogen, deuterium, halogen, and $C_{1-6}$ alkoxy;

R² is any one of hydrogen, deuterium, halogen, $C_{1-6}$ alkylamino, and $C_{1-6}$ alkoxy;

Ar is any one of phenyl, pyrazolyl, pyridinyl, thiazolyl, 1, 2, 4-triazolyl, pyrimidinyl, and pyridin-2(1H)-keto;

R³ is any one of hydrogen, deuterium, and halogen;

R⁴ is hydrogen or deuterium;

R⁵ is any one of hydrogen, deuterium, $C_{1-6}$ alkyl, $C_{1-6}$ alkyl substituted with at least one fluorine, and $C_{3-7}$ cycloalkyl.

Preferably, Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-R⁶, —C(=O)—R⁶, —$C_{1-6}$ alkyl-C(=O)—R⁶, —S(=O)₂—R⁶, —$C_{1-6}$ alkyl-S(=O)₂—R⁶, and —N(R⁷)—C(=O)—R⁸, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein, R⁶ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;

R⁷ is any one of hydrogen, deuterium, and $C_{1-6}$ alkyl;

R⁸ is any one of hydrogen, deuterium, $C_{1-6}$ alkyl, $C_{3-7}$ cycloalkyl, and $C_{3-7}$ heterocycloalkyl.

Preferably, R is any one of hydrogen, methyl, ethyl, and isopropyl;

R¹ is any one of hydrogen, deuterium, fluorine, chlorine, bromine, methoxy, ethoxy, and isopropoxy;

R² is any one of hydrogen, deuterium, fluorine, chlorine, bromine, methylamino, ethylamino, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

R³ is any one of hydrogen, deuterium, fluorine, chlorine, and bromine;

R⁴ is hydrogen or deuterium;

R⁵ is any one of hydrogen, deuterium, methyl, ethyl, isopropyl, butyl, sec-butyl, isobutyl, tert-butyl, trifluoromethyl, trifluoromethylmethyl, and cyclopropyl.

Preferably, R is any one of hydrogen, methyl, and ethyl.

Preferably, R¹ is hydrogen or deuterium.

Preferably, R² is any one of hydrogen, deuterium, fluorine, chlorine, bromine, methylamino, ethylamino, methoxy, ethoxy, and isopropoxy.

Preferably, Ar is phenyl substituted with any one or more of deuterium, halogen, hydroxy, cyano, $C_{1-6}$ alkyl, a substituted $C_{1-6}$ alkyl, $C_{1-6}$ alkoxy, and $C_{1-6}$ alkylamino, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl.

Preferably, Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino.

Preferably, Ar is pyrazolyl substituted with any one or more of deuterium, halogen, hydroxy, cyano, $C_{1-6}$ alkyl, a substituted $C_{1-6}$ alkyl, $C_{1-6}$ alkoxy, $C_{1-6}$ alkylamino, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

Preferably, Ar is pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl.

Preferably, Ar is pyridinyl substituted with any one or more of deuterium, halogen, hydroxy, amino, cyano, $C_{1-6}$ alkyl, a substituted $C_{1-6}$ alkyl, and $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —$C_{1-6}$ alkyl-C(=O)—$R^6$, and —N($R^7$)—C(=O)—$R^8$, wherein the substituted $C_{1-6}$ alkyl is substituted with any one or more of fluorine, $C_{1-6}$ alkoxy, $C_{1-6}$ alkylamino, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

$R^7$ is any one of hydrogen, deuterium, $C_{1-6}$ alkyl, and $C_{3-7}$ cycloalkyl;

$R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl.

Preferably, Ar is pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino.

Preferably, Ar is 1, 2, 4-triazolyl substituted with any one or more of deuterium, halogen, hydroxy, amino, $C_{1-6}$ alkyl, and $C_{1-6}$ alkyl substituted with any one or more of fluorine, hydroxy, amino, $C_{1-6}$ alkoxy, $C_{1-6}$ alkylamino, $C_{3-7}$ cycloalkyl, carboxyl, and $C_{3-7}$ heterocycloalkyl.

Preferably, Ar is 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl.

Preferably, Ar is thiazolyl substituted with any one or more of deuterium, halogen, hydroxy, amino, $C_{1-6}$ alkyl, a substituted $C_{1-6}$ alkyl, $C_{3-7}$ heterocycloalkyl, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

Preferably, Ar is thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl.

Preferably, Ar is pyrimidyl substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkylamino, di-$C_{1-6}$ alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

Preferably, Ar is pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino.

Preferably, Ar is pyridin-2(1H)-keto substituted with any one or more of deuterium, $C_{1-6}$ alkyl, a substituted $C_{1-6}$ alkyl, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

Preferably, Ar is pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl.

Preferably, $R^3$ is hydrogen or deuterium.

Preferably, $R^4$ is hydrogen or deuterium.

Preferably, $R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

Preferably, particular compounds of formula I according to the invention are the following:

6-isopropyl-10-methoxy-2-oxo-9-(1H-pyrazol-4-yl)-6,7-dihydro-2H-pyrido[2,1-a]isoquinoline-3-carboxylic acid;

6-isopropyl-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid;

6-isopropyl-10-methoxy-9-(1-(2-methoxyethyl)-1H-pyrazol-4-yl)-2-oxo-6,7-dihydro-2H-pyrido[2,1-a]isoquinoline-3-carboxylic acid;

9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylic acid;

9-(1-isobutyl-1H-pyrazol-4-yl)-6-isopropyl-10-methoxy-2-oxo-6,7-dihydro-2H-pyrido[2,1-a]isoquinoline-3-carboxylic acid;

6-isopropyl-10-methoxy-2-oxo-9-(1-propyl-1H-pyrazol-4-yl)-6,7-dihydro-2H-pyrido[2,1-a]isoquinoline-3-carboxylic acid;

6-isopropyl-10-methoxy-9-(6-methylpyridin-3-yl)-2-oxo-6,7-dihydro-2H-pyrido[2,1-a]isoquinoline-3-carboxylic acid;

6-(tert-butyl)-10-methoxy-2-oxo-9-(1H-pyrazol-4-yl)-6,7-dihydro-2H-pyrido[2,1-a]isoquinoline-3-carboxylic acid;

6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylic acid;

6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid;

6-(tert-butyl)-10-methoxy-9-(1-(oxetan-3-yl)-1H-pyrazol-4-yl)-2-oxo-6,7-dihydro-2H-pyrido[2,1-a]isoquinoline-3-carboxylic acid;

6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylic acid;

6-(tert-butyl)-10-methoxy-9-(1-methyl-1H-pyrazol-5-yl)-2-oxo-6,7-dihydro-2H-pyrido[2,1-a]isoquinoline-3-carboxylic acid;

6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylic acid;

6-(tert-butyl)-9-(1,3-dimethyl-1H-pyrazol-5-yl)-10-methoxy-2-oxo-6,7-dihydro-2H-pyrido[2,1-a]isoquinoline-3-carboxylic acid;

6-(tert-butyl)-10-methoxy-9-(1-(2-morpholinoethyl)-1H-pyrazol-4-yl)-2-oxo-6,7-dihydro-2H-pyrido[2,1-a]isoquinoline-3-carboxylic acid;

6-(tert-butyl)-10-methoxy-2-oxo-9-(1-(piperidin-4-yl)-1H-pyrazol-4-yl)-6,7-dihydro-2H-pyrido[2,1-a]isoquinoline-3-carboxylic acid hydrochloride;

6-(tert-butyl)-9-(1-isopropyl-1H-pyrazol-5-yl)-10-methoxy-2-oxo-6,7-dihydro-2H-pyrido[2,1-a]isoquinoline-3-carboxylic acid;

6-(tert-butyl)-9-(1,4-dimethyl-1H-pyrazol-5-yl)-10-methoxy-2-oxo-6,7-dihydro-2H-pyrido[2,1-a]isoquinoline-3-carboxylic acid;

6-(tert-butyl)-9-(1-(carboxymethyl)-1H-pyrazol-4-yl)-10-methoxy-2-oxo-6,7-dihydro-2H-pyrido[2,1-a]isoquinoline-3-carboxylic acid;

ethyl 6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylate;

6-(tert-butyl)-9-(1-(2-carboxyethyl)-1H-pyrazol-4-yl)-10-methoxy-2-oxo-6,7-dihydro-2H-pyrido[2,1-a]isoquinoline-3-carboxylic acid;

6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylic acid;

6-(tert-butyl)-9-(1-(3-carboxypropyl)-1H-pyrazol-4-yl)-10-methoxy-2-oxo-6,7-dihydro-2H-pyrido[2,1-a]isoquinoline-3-carboxylic acid;

6-(tert-butyl)-10-methoxy-9-(3-methyl-1H-pyrazol-4-yl)-2-oxo-6,7-dihydro-2H-pyrido[2,1-a]isoquinoline-3-carboxylic acid;

6-(tert-butyl)-9-(1-(1-carboxyethyl)-1H-pyrazol-4-yl)-10-methoxy-2-oxo-6,7-dihydro-2H-pyrido[2,1-a]isoquinoline-3-carboxylic acid;

6-(tert-butyl)-9-(1-(2-carboxypropan-2-yl)-1H-pyrazol-4-yl)-10-methoxy-2-oxo-6,7-dihydro-2H-pyrido[2,1-a]isoquinoline-3-carboxylic acid;

6-(tert-butyl)-10-methoxy-9-(2-methylthiazol-5-yl)-2-oxo-6,7-dihydro-2H-pyrido[2,1-a]isoquinoline-3-carboxylic acid;

6-(tert-butyl)-10-methoxy-2-oxo-9-(1H-1,2,4-triazol-3-yl)-6,7-dihydro-2H-pyrido[2,1-a]isoquinoline-3-carboxylic acid;

6-(tert-butyl)-9-(1-(carboxymethyl)-1H-1,2,4-triazol-3-yl)-10-methoxy-2-oxo-6,7-dihydro-2H-pyrido[2,1-a]isoquinoline-3-carboxylic acid;

6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylic acid;

6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylic acid;

6-(tert-butyl)-10-methoxy-2-oxo-9-phenyl-6,7-dihydro-2H-pyrido[2,1-a]isoquinoline-3-carboxylic acid;

6-(tert-butyl)-9-(4-ethylphenyl)-10-methoxy-2-oxo-6,7-dihydro-2H-pyrido[2,1-a]isoquinoline-3-carboxylic acid;

6-(tert-butyl)-10-methoxy-9-(4-methoxyphenyl)-2-oxo-6,7-dihydro-2H-pyrido[2,1-a]isoquinoline-3-carboxylic acid;

6-(tert-butyl)-10-methoxy-9-(3-methoxyphenyl)-2-oxo-6,7-dihydro-2H-pyrido[2,1-a]isoquinoline-3-carboxylic acid;

6-(tert-butyl)-10-methoxy-9-(6-methylpyridin-3-yl)-2-oxo-6,7-dihydro-2H-pyrido[2,1-a]isoquinoline-3-carboxylic acid;

6-(tert-butyl)-10-methoxy-9-(2-methylpyridin-4-yl)-2-oxo-6,7-dihydro-2H-pyrido[2,1-a]isoquinoline-3-carboxylic acid;

6-(tert-butyl)-10-methoxy-9-(2-methylpyridin-3-yl)-2-oxo-6,7-dihydro-2H-pyrido[2,1-a]isoquinoline-3-carboxylic acid;

6-(tert-butyl)-10-methoxy-9-(6-morpholinopyridin-3-yl)-2-oxo-6,7-dihydro-2H-pyrido[2,1-a]isoquinoline-3-carboxylic acid;

6-(tert-butyl)-10-methoxy-2-oxo-9-(6-(trifluoromethyl)pyridin-3-yl)-6,7-dihydro-2H-pyrido[2,1-a]isoquinoline-3-carboxylic acid;

6-(tert-butyl)-10-methoxy-9-(6-(2-methoxyethoxy)pyridin-3-yl)-2-oxo-6,7-dihydro-2H-pyrido[2,1-a]isoquinoline-3-carboxylic acid;

6-(tert-butyl)-9-(6-(dimethylamino)pyridin-3-yl)-10-methoxy-2-oxo-6,7-dihydro-2H-pyrido[2,1-a]isoquinoline-3-carboxylic acid;

6-(tert-butyl)-10-methoxy-2-oxo-9-(6-(pyrrolidin-1-yl)pyridin-3-yl)-6,7-dihydro-2H-pyrido[2,1-a]isoquinoline-3-carboxylic acid;

6-(tert-butyl)-10-methoxy-2-oxo-9-(6-(piperazin-1-yl)pyridin-3-yl)-6,7-dihydro-2H-pyrido[2,1-a]isoquinoline-3-carboxylic acid;

9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylic acid;

6-(tert-butyl)-9-(6-fluoro-4-methylpyridin-3-yl)-10-methoxy-2-oxo-6,7-dihydro-2H-pyrido[2,1-a]isoquinoline-3-carboxylic acid;

6-(tert-butyl)-9-(6-fluoropyridin-3-yl)-10-methoxy-2-oxo-6,7-dihydro-2H-pyrido[2,1-a]isoquinoline-3-carboxylic acid;

9-(6-(azetidin-1-yl)pyridin-3-yl)-6-(tert-butyl)-10-methoxy-2-oxo-6,7-dihydro-2H-pyrido[2,1-a]isoquinoline-3-carboxylic acid;

6-(tert-butyl)-9-(6-(4-hydroxypiperidin-1-yl)pyridin-3-yl)-10-methoxy-2-oxo-6,7-dihydro-2H-pyrido[2,1-a]isoquinoline-3-carboxylic acid;

6-(tert-butyl)-9-(6-((cyclopropylmethyl)amino)pyridin-3-yl)-10-methoxy-2-oxo-6,7-dihydro-2H-pyrido[2,1-a]isoquinoline-3-carboxylic acid;

9-(6-(azetidin-1-yl)-4-methylpyridin-3-yl)-6-(tert-butyl)-10-methoxy-2-oxo-6,7-dihydro-2H-pyrido[2,1-a]isoquinoline-3-carboxylic acid;

9-(6-aminopyridin-3-yl)-6-(tert-butyl)-10-methoxy-2-oxo-6,7-dihydro-2H-pyrido[2,1-a]isoquinoline-3-carboxylic acid;

ethyl 6-(tert-butyl)-10-methoxy-9-(6-methylpyridin-3-yl)-2-oxo-6,7-dihydro-2H-pyrido[2,1-a]isoquinoline-3-carboxylate;

6-(tert-butyl)-9-(6-(cyclobutylamino)pyridin-3-yl)-10-methoxy-2-oxo-6,7-dihydro-2H-pyrido[2,1-a]isoquinoline-3-carboxylic acid;

9-(6-acetamidopyridin-3-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(2-methylpyrimidin-5-yl)-2-oxo-6,7-dihydro-2H-pyrido[2,1-a]isoquinoline-3-carboxylic acid;

6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylic acid;

6-(tert-butyl)-10-methoxy-9-(2-(methylamino)pyrimidin-5-yl)-2-oxo-6,7-dihydro-2H-pyrido[2,1-a]isoquinoline-3-carboxylic acid;

6-(tert-butyl)-9-(2-(dimethylamino)pyrimidin-5-yl)-10-methoxy-2-oxo-6,7-dihydro-2H-pyrido[2,1-a]isoquinoline-3-carboxylic acid;

6-(tert-butyl)-10-methoxy-9-(2-morpholinopyrimidin-5-yl)-2-oxo-6,7-dihydro-2H-pyrido[2,1-a]isoquinoline-3-carboxylic acid;

6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylic acid;

6-(tert-butyl)-9-(2-(cyclopropylamino)pyrimidin-5-yl)-10-methoxy-2-oxo-6,7-dihydro-2H-pyrido[2,1-a]isoquinoline-3-carboxylic acid;

9-(2-aminopyrimidin-5-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(2-methoxypyrimidin-5-yl)-2-oxo-6,7-dihydro-2H-pyrido[2,1-a]isoquinoline-3-carboxylic acid;

6-(tert-butyl)-9-(2-((cyclopropylmethyl)amino)pyrimidin-5-yl)-10-methoxy-2-oxo-6,7-dihydro-2H-pyrido[2,1-a]isoquinoline-3-carboxylic acid;

6-(tert-butyl)-9-(2-chloropyrimidin-5-yl)-10-methoxy-2-oxo-6,7-dihydro-2H-pyrido[2,1-a]isoquinoline-3-carboxylic acid;

9-(2-(azetidin-1-yl)pyrimidin-5-yl)-6-(tert-butyl)-10-methoxy-2-oxo-6,7-dihydro-2H-pyrido[2,1-a]isoquinoline-3-carboxylic acid;

ethyl 6-(tert-butyl)-9-(1-(1-ethoxy-2-methyl-1-oxopropan-2-yl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(2-ethoxy-2-oxoethyl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(3-ethoxy-3-oxopropyl)-6-oxo-1,6-dihydropyridin-3-yl)-10-methoxy-2-oxo-6,7-dihydro-2H-pyrido[2,1-a]isoquinoline-3-carboxylate;

6-(tert-butyl)-9-(2-(4-carboxypiperidin-1-yl)pyrimidin-5-yl)-10-methoxy-2-oxo-6,7-dihydro-2H-pyrido[2,1-a]isoquinoline-3-carboxylic acid;

ethyl 6-(tert-butyl)-9-(1-(1-ethoxy-1-oxopropan-2-yl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(4-ethoxy-4-oxobutyl)-6-oxo-1,6-dihydropyridin-3-yl)-10-methoxy-2-oxo-6,7-dihydro-2H-pyrido[2,1-a]isoquinoline-3-carboxylate;

6-(tert-butyl)-9-(2-(cyclobutylamino)pyrimidin-5-yl)-10-methoxy-2-oxo-6,7-dihydro-2H-pyrido[2,1-a]isoquinoline-3-carboxylic acid;

6-(tert-butyl)-9-(2-(3-carboxypyrrolidin-1-yl)pyrimidin-5-yl)-10-methoxy-2-oxo-6,7-dihydro-2H-pyrido[2,1-a]isoquinoline-3-carboxylic acid;

6-(tert-butyl)-9-(2-((carboxymethyl)amino)pyrimidin-5-yl)-10-methoxy-2-oxo-6,7-di hydro-2H-pyrido[2,1-a]isoquinoline-3-carboxylic acid.

Preferably, the compounds described herein are made into corresponding enantiomers, diastereoisomers, solvates, hydrates, prodrugs, stable isotope derivatives and pharmaceutically acceptable salts.

Preferably, the compounds described herein are made into corresponding pharmaceutically acceptable derivatives, wherein the derivative is any one of a prodrug, a salt, an ester, an amide, a salt of the ester, a salt of the amide, and a metabolite.

Preferably, the compounds described herein are made into corresponding salts, wherein acid used to form the salt is selected from:

hydrochloric acid, hydrobromic acid, hydroiodic acid, perchloric acid, sulfuric acid or phosphoric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid, and malic acid.

Base used to form the salt is selected from:

lithium hydroxide, sodium hydroxide, potassium hydroxide, sodium carbonate, sodium bicarbonate, potassium carbonate, potassium bicarbonate, magnesium carbonate, calcium carbonate, ammonia liquor, triethylamine, and tetrabutylammonium hydroxide.

Preferably, the compounds described herein are made into any composition, wherein the composition also comprises:
a pharmaceutically acceptable carrier;
an auxiliary agent; and/or
an excipient.

Preferably, the compounds described herein are made into dosage form, wherein the dosage form is any one of a tablet, a capsule, an injection, a granule, a pulvis, a suppository, a pill, a cream, a paste, a gel, a powder, an oral solution, an inhalation, a suspension, a dry suspension, a patch, and a lotion.

Preferably, the compounds described herein are made into composition comprising at least one of the following substances:
an HBV polymerase inhibitor, interferon α-2a, interferon α-2b, a pegylated interferon α-2a, ribavirin, an HBV preventive vaccine, an HBV therapeutic vaccine, an HBV capsid inhibitor, an RNA replication inhibitor of HBV, an siRNA, an inhibitor of HBsAg generation or secretion, an HBV antibody, and a TLR7 agonist.

Preferably, the compounds described herein are used for medical use.

Preferably, the compounds described herein are used to prevent or treat hepatitis B virus infection.

Compounds described in the invention can be used to prevent or treat hepatitis B virus infection.

DETAILED DESCRIPTION OF THE INVENTION

For a clearer description of the contents of the present invention, all terms involved in this application are defined as follows:

As used herein, the term "$C_{1-6}$ alkyl" alone or in combination signifies a saturated, linear or branched chain alkyl group containing 1 to 6 carbon atoms, particularly 1 to 4 carbon atoms, including methyl, ethyl, propyl, isopropyl, n-butyl, iso-butyl, sec-butyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, or 3,3-dimethyl-2-butyl and the like. Particular, "$C_{1-6}$ alkyl" is any one of methyl, ethyl, isopropyl, tert-butyl.

As used herein, the term "$C_{3-7}$ cycloalkyl" alone or in combination signifies a saturated carbon ring containing from 3 to 7 carbon atoms, particularly from 3 to 6 carbon atoms, including cyclopropyl, cyclobutyl, cyclopentyl, cyclohexyl, cycloheptyl and the like. Particular, "$C_{3-7}$ cycloalkyl" groups are cyclopropyl, cyclopentyl and cyclohexyl.

As used herein, the term "amino" alone or in combination, refers to primary (—NH$_2$), secondary (—NH—) or tertiary amino

As used herein, the term "$C_{1-6}$ alkylamino" alone or in combination, refers to amino group as defined above wherein at least one of the hydrogen atoms of the amino group is replaced by a $C_{1-6}$ alkyl group, wherein the "$C_{1-6}$ alkyl" is as defined above. "$C_{1-6}$ alkylamino" groups include methylamino, ethylamino, propylamino, isopropylamino, n-butylamino, iso-butylamino, sec-butylamino, tert-butylamino, n-pentylamino, 2-pentylamino, 3-pentylamino, 2-methyl-2-butylamino, 3-methyl-2-butylamino, 3-methyl-1-butylamino, 2-methyl-1-butylamino, n-hexylamino, 2-hexylamino, 3-hexylamino, 2-methyl-2-pentylamino, 3-methyl-2-pentylamino, 4-methyl-2-pentylamino, 3-methyl-3-pentylamino, 2-methyl-3-pentylamino, 2,3-dimethyl-2-butylamino, or 3,3-dimethyl-2-butylamino and the like. Particular, "$C_{1-6}$ alkylamino" groups are methylamino, ethylamino, isopropylamino, tert-butylamino and the like.

As used herein, the term "$C_{1-6}$ alkoxyl" alone or in combination, refers to a group of $C_{1-6}$ alkyl-O—, wherein the "$C_{1-6}$ alkyl" is as defined above.

As used herein, the term "halogen" alone or in combination, refers to fluorine, chlorine, bromine, or iodine. Halogen is particularly fluorine, chlorine or bromine.

As used herein, the term "heterocycloalkyl" refers to a saturated or partly unsaturated monocyclic or bicyclic non-aromatic ring (containing 1 to 2 double bonds) which can comprise atoms selected from nitrogen, oxygen and/or sulfur. In this invention, the number of carbon atoms in "heterocycloalkyl" group is 2 to 11, and the number of hetero atoms is preferably 1, 2, 3 or 4, and the nitrogen, carbon or sulfur atom in the "heterocycloalkyl" group can be optionally oxidated. The hydrogen atom on the "heterocycloalkyl" group is independently optionally substituted by any one or more of substituents described herein. "Heterocycloalkyl" can be attached to the parent molecule through any ring atom on the ring.

As used herein, the term "$C_{3-7}$ heterocycloalkyl" refers to a monocyclic heterocycloalkyl including from 3 to 7 carbon atoms and hetero atoms. For example, aziridinyl, azetidinyl, oxetanyl, pyrrolidinyl, tetrahydrofuranyl, tetrahydrothienyl, piperidinyl, morpholinyl, piperazinyl, thiomorpholyl, tetrahydropyranyl, 1,1-dioxathiomorpholinyl.

As used herein, the term "$C_{3-7}$ cycloalkylamino" alone or in combination, refers to amino group as defined above wherein at least one of the hydrogen atoms of the amino group is replaced by a $C_{3-7}$ cycloalkyl group, wherein the "$C_{3-7}$ cycloalkyl" is as defined above.

As used herein, the term "$C_{3-7}$ heterocycloalkylamino" alone or in combination, refers to amino group as defined above wherein at least one of the hydrogen atoms of the amino group is replaced by a $C_{3-7}$ heterocycloalkyl group, wherein the "$C_{3-7}$ heterocycloalkyl" is as defined above.

As used herein, the term "Aryl" refers to any stable 6-10 membered monocyclic or bicyclic aromatic group including phenyl, naphthyl, tetrahydronaphthyl, indanyl or biphenyl. The hydrogen atom on the "aryl" is, independently, optionally substituted by any one of substituents described herein.

As used herein, the term "heteroaryl" refers to an aromatic ring formed by the replacement of a carbon atom on the ring with at least one heteroatom selected from sulfur, oxygen or nitrogen, which can be a 5-7 membered monocyclic ring or 7-12 bicyclic group. In this invention, the number of hetero atoms in the heteroaryl group is preferably 1, 2, 3 or 4, for example thienyl, pyridyl, pyrimidinyl, pyrazinyl, pyridazinyl, pyridine-2(1H)-one, pyridin-4(1H)-keto, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, oxadiazolyl, naphthyl, benzothienyl, indolyl, benzimidazolyl, benzothiazolyl, benzofuranyl, quinolyl, isoquinolyl, quinazolinyl and the like. The hydrogen atom on the "heteroaryl" is, independently, optionally substituted by any one of substituents described herein.

As used herein, the term "Aryl $C_{1-6}$ alkyl" refers to a group of $C_{1-6}$ alkyl as defined above, wherein at least one of the hydrogen atoms on the $C_{1-6}$ alkyl group is replaced by at least one aryl group, wherein the "aryl" is as defined above.

As used herein, the term "Heteroaryl $C_{1-6}$ alkyl" refers to a group of $C_{1-6}$ alkyl as defined above, wherein at least one of the hydrogen atoms on the $C_{1-6}$ alkyl group is replaced by at least one heteroaryl group, wherein the "heteroaryl" is as defined above.

As used herein, the term "cyano" alone or in combination, refers to —CN.

As used herein, the term "carboxyl" alone or in combination, refers to —COOH.

As used herein, the term "hydroxyl" alone or in combination, refers to —OH.

As used herein, the term "isomer" encompasses all isomeric forms including enantiomers, diastereomers, and geometric isomers including cis and trans isomers. Thus, a single stereochemical isomer of a compound designed in this invention, or an enantiomer, diastereomer, or mixture of geometric isomers (or cis and trans isomers thereof) thereof, is belonging to the scope of this invention As used herein, the term "pharmaceutically acceptable salts" refers to that the compounds of the invention exist in the form of their pharmaceutically acceptable salts, including both acid and base addition salts. Pharmaceutically acceptable salts are described by S. M. Berge in J. Pharmaceutical Sciences (Vol. 66: Page 1-19, 1977). In this invention, a pharmaceutically acceptable non-toxic acid addition salt means a salt of a compound in this invention with an organic or inorganic acid including, but not limited to, hydrochloric acid, sulfuric acid, hydrobromic acid, and hydroiodic acid, phosphoric acid, nitric acid, perchloric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid, malic acid and the like. A pharmaceutically acceptable non-toxic base addition salt means a salt of a compound of the invention with an organic or inorganic base, including but not limited to an alkali metal salts such as a lithium, sodium or potassium salts; an alkaline earth metal salts such as calcium or a magnesium salts; an organic base salts, for example, an ammonium salt or an N+$(C_{1-6}$ alkyl$)_4$ salt formed by an organic base containing an N group.

As used herein, the term "solvate" refers to an association compound of one or more solvent molecules with a compound in this invention. Solvents include, but are not limited to, water, methanol, ethanol, isopropanol, ethyl acetate, tetrahydrofuran, N,N-dimethylformamide, dimethyl sulfoxide, and the like. "Pharmaceutically acceptable salts" can be synthesized by general chemical methods.

As used herein, the term "hydrate" refers to an association compound of water with a compound in this invention.

As used herein, the term "prodrug" refers to a chemical derivative of a compound in the invention, which can be converted into a compound represented by the formula I by chemical reaction in vivo.

As used herein, the term "isotopic derivative" refers to an isotope derivative obtained by substituting a hydrogen atom of the formula I with 1-6 deuterium atoms, and an isotope derivative obtained by substituting a carbon atom of the formula I with 1 to 3 carbon-14 atoms.

The terms involved in this invention has been defined above, and those skilled in the art can also understand the above terms in combination with current technology. The following description based on the content of this invention and the definition of the terms are further described.

A compound of general formula I:

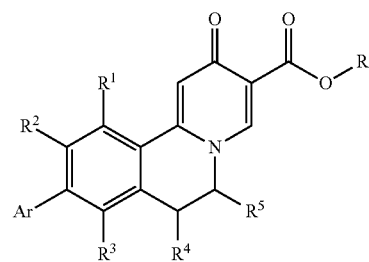

wherein:

R is any one of hydrogen and $C_{1-6}$ alkyl; Preferably, R is any one of hydrogen, methyl and ethyl.

$R^1$ is any one of hydrogen, deuterium, halogen, $C_{1-6}$ alkyl, $C_{1-6}$ alkylamino, and $C_{1-6}$ alkoxyl; Preferably, R is hydrogen or deuterium.

$R^2$ is any one of hydrogen, deuterium, halogen, $C_{1-6}$ alkyl, $C_{1-6}$ alkyl substituted with at least one fluorine, $C_{3-7}$ cycloalkyl, $C_{1-6}$ alkylamino, $C_{1-6}$ alkoxy, and heterocycloalkyl; Preferably, $R^2$ is any one of hydrogen, deuterium, halogen, $C_{1-6}$ alkoxyl; More preferably, $R^2$ is $C_{1-6}$ alkoxyl.

Ar is any one of phenyl, thienyl, pyridinyl, pyrimidinyl, pyrazinyl, pyridazinyl, pyridin-2(1H)-keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, oxadiazolyl, naphthyl, benzothiophenyl, indolyl, benzimidazolyl, benzothiazolyl, benzofuryl, quinolyl, isoquinolyl, and quinazolinyl; As an variant, Ar is substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, —N($R^7$)—C(=O)—$R^8$, —$C_{1-6}$ alkylamino-C(=O)—$C_{1-6}$ alkyl, and —$C_{1-6}$ alkylamino-C(=O)-amino $C_{1-6}$ alkyl, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein, $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl; $R^7$ is any one of hydrogen, deuterium, $C_{1-6}$ alkyl, and $C_{3-7}$ cycloalkyl; $R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl. Preferably, Ar is any one of phenyl, thienyl, pyridyl, pyrimidinyl, pyrazinyl, pyridazinyl, pyridine-2(1H)-keto, pyridin-4(1H)-keto, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, and oxadiazolyl.

$R^3$ is any one of hydrogen, deuterium, halogen, cyano, $C_{1-6}$ alkyl, $C_{3-7}$ cycloalkyl, $C_{1-6}$ alkylamino, $C_{1-6}$ alkoxy, and heterocycloalkyl; Preferably, $R^3$ is hydrogen or deuterium.

$R^4$ is any one of hydrogen, deuterium, and $C_{1-6}$ alkyl; Preferably, $R^4$ is hydrogen or deuterium.

$R^5$ is any one of hydrogen, deuterium, $C_{1-6}$ alkyl, $C_{1-6}$ alkyl substituted with at least one fluorine, and $C_{3-7}$ cycloalkyl. Preferably, $R^5$ is any one of hydrogen, deuterium, methyl, ethyl, isopropyl, butyl, sec-butyl, isobutyl, tert-butyl, trifluoromethyl, trifluoromethylmethyl, and cyclopropyl. More preferably, $R^5$ is any one of isopropyl, tert-butyl and cyclopropyl.

A compound as the first embodiment of formula I, wherein:

R is any one of hydrogen, methyl, ethyl, propyl, isopropyl, and tert-butyl;

$R^1$ is any one of hydrogen, deuterium, fluorine, chlorine, bromine, methyl, ethyl, isopropyl, tert-butyl, methylamino, ethylamino, methoxy, ethoxy, and isopropoxy.

$R^2$ is any one of hydrogen, deuterium, fluorine, chlorine, bromine, methyl, ethyl, isopropyl, tert-butyl, trifluoromethyl, trifluoromethylmethyl, cyclopropyl, cyclopentyl, methylamino, ethylamino, methoxy, ethoxy, isopropoxy, pyrrolidinyl, and morpholinyl.

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, methyl, ethyl, and cyano;

$R^4$ is any one of hydrogen, deuterium, methyl, and ethyl;

$R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

A compound as the second embodiment of formula I, wherein:

R is any one of hydrogen and $C_{1-6}$ alkyl;

$R^1$ is any one of hydrogen, deuterium, halogen, and $C_{1-6}$ alkyl;

$R^2$ is any one of hydrogen, deuterium, halogen, $C_{1-6}$ alkyl, $C_{1-6}$ alkyl substituted with at least one fluorine, $C_{3-7}$ cycloalkyl, and $C_{1-6}$ alkoxy;

Ar is any one of phenyl, thienyl, pyridinyl, pyrimidinyl, pyrazinyl, pyridazinyl, pyridin-2(1H)keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, and oxadiazolyl. Preferably, Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, and —N($R^7$)—C(=O)—$R^8$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

$R^7$ is any one of hydrogen, deuterium, and $C_{1-6}$ alkyl;

$R^8$ is any one of hydrogen, deuterium, $C_{1-6}$ alkyl, $C_{3-7}$ cycloalkyl, and $C_{3-7}$ heterocycloalkyl.

$R^3$ is any one of hydrogen, deuterium, halogen, cyano, $C_{1-6}$ alkyl, and $C_{3-7}$ cycloalkyl;

$R^4$ is any one of hydrogen, deuterium, and $C_{1-6}$ alkyl;

$R^5$ is any one of hydrogen, deuterium, $C_{1-6}$ alkyl, $C_{1-6}$ alkyl substituted with at least one fluorine, and $C_{3-7}$ cycloalkyl.

A compound as the third embodiment of formula I, wherein:

R is any one of hydrogen, methyl, ethyl, and isopropyl;

$R^1$ is any one of hydrogen, deuterium, fluorine, chlorine, bromine, methyl, ethyl, isopropyl, and tert-butyl;

$R^2$ is any one of hydrogen, deuterium, fluorine, chlorine, bromine, methyl, ethyl, isopropyl, tert-butyl, trifluoromethyl, trifluoromethylmethyl, cyclopropyl, cyclopentyl, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, cyano, methyl, ethyl, and cyclopropyl;

$R^4$ is any one of hydrogen, deuterium, methyl, and ethyl;

$R^5$ is any one of hydrogen, deuterium, methyl, ethyl, isopropyl, butyl, sec-butyl, isobutyl, tert-butyl, and cyclopropyl.

A compound as the fourth embodiment of formula I, wherein:

R is any one of hydrogen and $C_{1-6}$ alkyl;

$R^1$ is any one of hydrogen, deuterium, halogen, and $C_{1-6}$ alkoxy;

$R^2$ is any one of hydrogen, deuterium, halogen, $C_{1-6}$ alkylamino, and $C_{1-6}$ alkoxy;

Ar is any one of phenyl, pyrazolyl, pyridinyl, thiazolyl, 1, 2, 4-triazolyl, pyrimidinyl, pyridin-2(1H)keto. Preferably, Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, and —N($R^7$)—C(=O)—$R^8$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;

$R^7$ is any one of hydrogen, deuterium, and $C_{1-6}$ alkyl;

$R^8$ is any one of hydrogen, deuterium, $C_{1-6}$ alkyl, $C_{3-7}$ cycloalkyl, and $C_{3-7}$ heterocycloalkyl.

$R^3$ is any one of hydrogen, deuterium, and halogen;

$R^4$ is hydrogen or deuterium;

$R^5$ is any one of hydrogen, deuterium, $C_{1-6}$ alkyl, $C_{1-6}$ alkyl substituted with at least one fluorine, and $C_{3-7}$ cycloalkyl.

A compound as the fifth embodiment of formula I, wherein:

R is any one of hydrogen, methyl, ethyl, and isopropyl;

$R^1$ is any one of hydrogen, deuterium, fluorine, chlorine, bromine, methoxy, ethoxy, and isopropoxy;

$R^2$ is any one of hydrogen, deuterium, fluorine, chlorine, bromine, methylamino, ethylamino, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, and bromine;

$R^4$ is hydrogen or deuterium;

$R^5$ is any one of hydrogen, deuterium, methyl, ethyl, isopropyl, butyl, sec-butyl, isobutyl, tert-butyl, trifluoromethyl, trifluoromethyl methyl, and cyclopropyl.

A compound as the sixth embodiment of formula I, wherein:

Ar is phenyl substituted with any one or more of deuterium, halogen, hydroxy, cyano, $C_{1-6}$ alkyl, a substituted $C_{1-6}$ alkyl, $C_{1-6}$ alkoxy, and $C_{1-6}$ alkylamino, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl.

A compound as the seventh embodiment of formula I, wherein:

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino.

A compound as the eighth embodiment of formula I, wherein:

Ar is pyrazolyl substituted with any one or more of deuterium, halogen, hydroxy, cyano, $C_{1-6}$ alkyl, a substituted $C_{1-6}$ alkyl, $C_{1-6}$ alkoxy, $C_{1-6}$ alkylamino, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

A compound as the ninth embodiment of formula I, wherein:

Ar is pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl.

A compound as the tenth embodiment of formula I, wherein:

Ar is pyridinyl substituted with any one or more of deuterium, halogen, hydroxy, amino, cyano, $C_{1-6}$ alkyl, a substituted $C_{1-6}$ alkyl, and $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —$C_{1-6}$ alkyl-C(=O)—$R^6$, and —N($R^7$)—C(=O)—$R^8$, wherein the substituted $C_{1-6}$ alkyl is substituted with any one or more of fluorine, $C_{1-6}$ alkoxy, $C_{1-6}$ alkylamino, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;

$R^7$ is any one of hydrogen, deuterium, $C_{1-6}$ alkyl, and $C_{3-7}$ cycloalkyl;

$R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl.

A compound as the eleventh embodiment of formula I, wherein:

Ar is pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino.

A compound as the twelfth embodiment of formula I, wherein:

Ar is 1, 2, 4-triazolyl substituted with any one or more of deuterium, halogen, hydroxy, amino, $C_{1-6}$ alkyl, and $C_{1-6}$ alkyl substituted with any one or more of fluorine, hydroxy, amino, $C_{1-6}$ alkoxy, $C_{1-6}$ alkylamino, $C_{3-7}$ cycloalkyl, carboxyl, and $C_{3-7}$ heterocycloalkyl.

A compound as the thirteenth embodiment of formula I, wherein:

Ar is 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl.

A compound as the fourteenth embodiment of formula I, wherein:

Ar is thiazolyl substituted with any one or more of deuterium, halogen, hydroxy, amino, $C_{1-6}$ alkyl, a substituted $C_{1-6}$ alkyl, $C_{3-7}$ heterocycloalkyl, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

A compound as the fifteenth embodiment of formula I, wherein:

Ar is thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl.

A compound as the sixteenth embodiment of formula I, wherein:

Ar is pyrimidyl substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkylamino, di-$C_{1-6}$ alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

A compound as the seventeenth embodiment of formula I, wherein:

Ar is pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino.

A compound as the eighteenth embodiment of formula I, wherein:

Ar is pyridin-2(1H)-keto substituted with any one or more of deuterium, $C_{1-6}$ alkyl, a substituted $C_{1-6}$ alkyl, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

A compound as the nineteenth embodiment of formula I, wherein:

Ar is pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl.

A typical approach to synthesize the compound of formula I is described below to further describe the technical solution of this invention, specific examples of which is shown below:

Compound 1 is condensed with TsNHNH$_2$ to give product 2;

Product 2 is treated with aldehyde 3 in the presence of EtONa to give product 4;

Product 4 is treated with ammonium acetate to give product 5 by reductive amination;

Product 5 is acylated with formic acid to give amide 6;

Amide 6 is treated with oxalyl chloride in the presence of FeCl$_3$ to give crude product, which is further treated with concentrated sulfuric acid in methanol to give product 7;

Compound 7 is treated with ethyl 2-acetyl-3-ethoxyacrylate 8 to give product 9 by ring-closing reaction;

Product 9 is oxidated to product 10 by chloranil;

Product 10 was treated with aryl or heteroaryl boronic acid to give product 11 by Suzuki coupling;

Product 11 is hydrolyzed by sodium hydroxide or lithium hydroxide to give product 12.

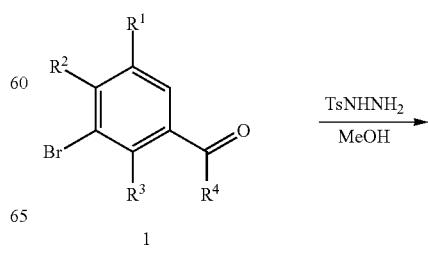

1

27

-continued

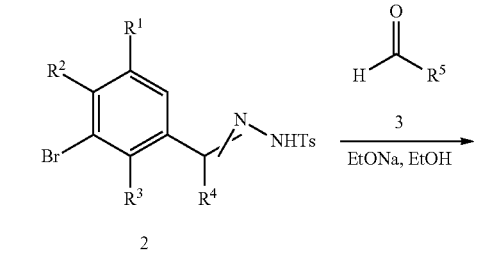
2

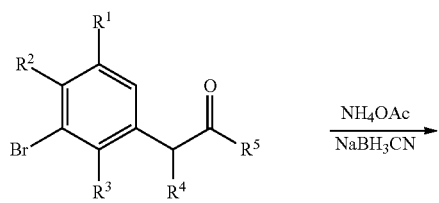
4

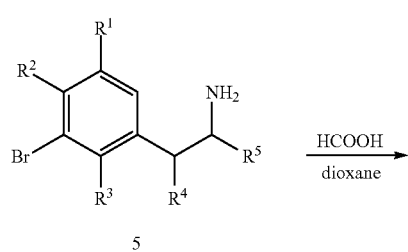
5

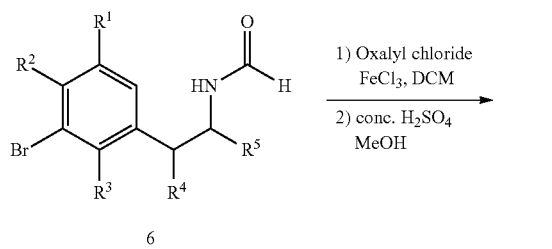
6

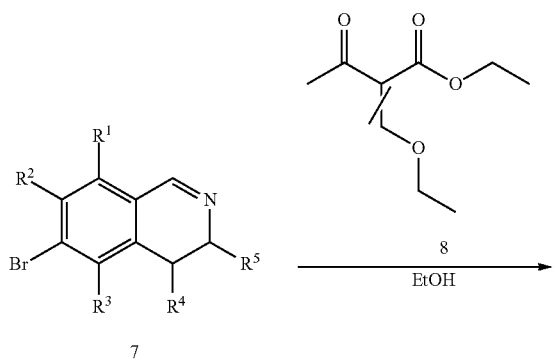
7

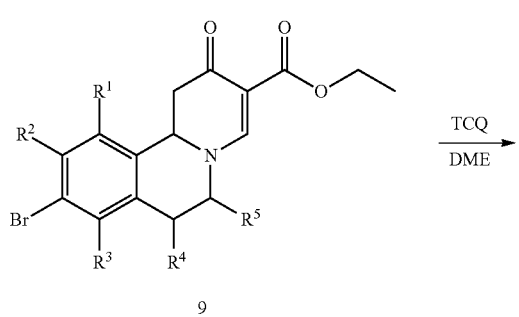
9

28

-continued

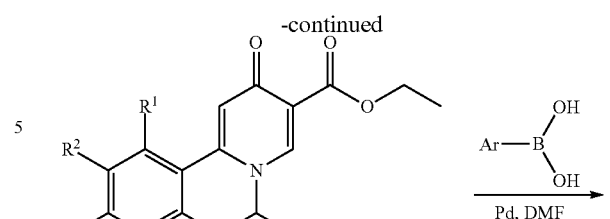
10

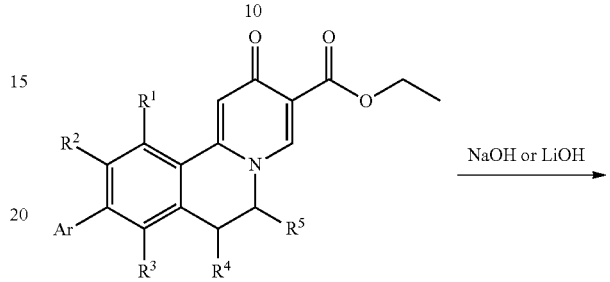
11

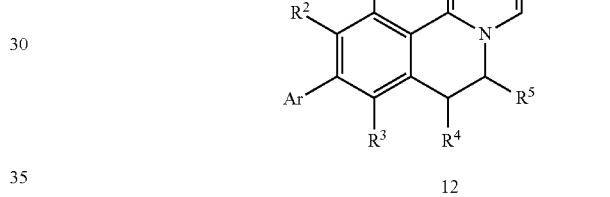
12

As a variation of the above typical approach, another reaction route is shown below. Wherein the reaction route of compound 1 to product 11 is unchanged, and only the partial reaction route which changes after the product 11 is shown below. Wherein Y refers to heteroaryl, Z refers to $C_{1-6}$ alkyl, or $C_{1-6}$ alkyl which is substituted with any one of fluorine, hydroxyl, cyano, aryl, heteroaryl, amino, $C_{1-6}$ alkoxy, $C_{1-6}$ alkylamino, $C_{3-7}$ cycloalkyl, carboxyl and heterocycloalkyl; X refers to halogen.

Further, when Y is heteroaryl, a substituent can be added by a modified approach into Y group. Product 11 is first treated with halide Z—X under basic conditions to give the product 13 by substitution reaction. Thereafter, product 13 is hydrolyzed by sodium hydroxide or lithium hydroxide to give product 14.

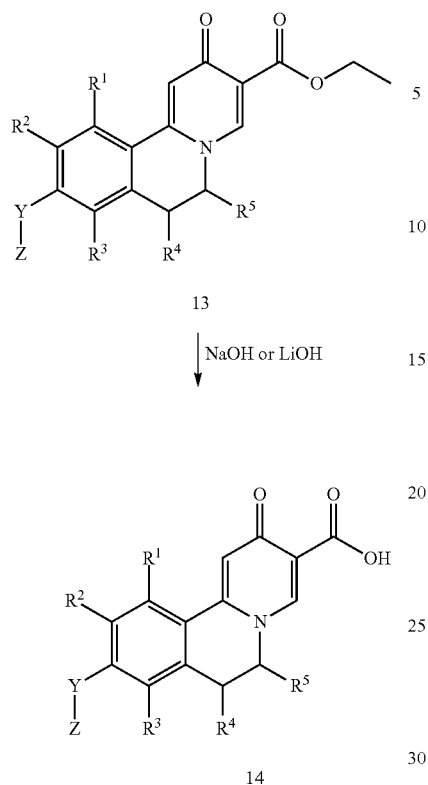

13

↓ NaOH or LiOH

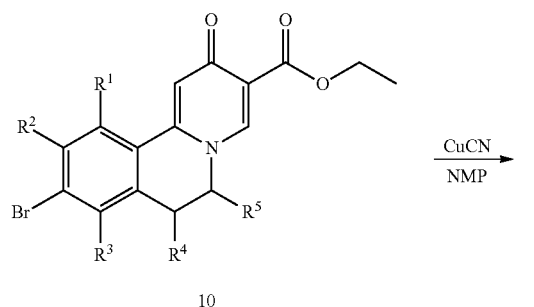

14

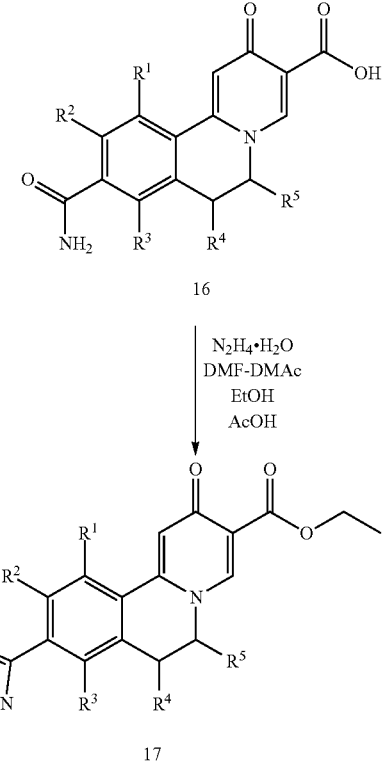

16

↓ N₂H₄·H₂O
DMF-DMAc
EtOH
AcOH

17

Further, when Ar is 1H-1,2,4-triazol-3-yl, it can also be obtained by a modified approach. Product 10 is first substituted with cuprous cyanide to give the product 15. Thereafter, product 15 is hydrolyzed by concentrated sulfuric acid to give product 16, which is then treated with hydrazine hydrate and DMF-DMAc to give product 17.

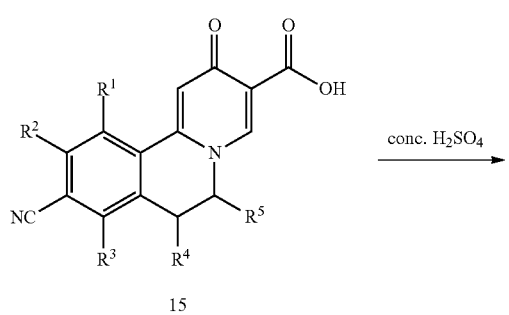

10

↓ CuCN / NMP

15

↓ conc. H₂SO₄

EXAMPLES

The invention will be more fully understood by reference to the following examples. They should not, however, be construed as limiting the scope of the invention.

Abbreviations used herein are as follows:
AcOH: acetic acid
CDCl3: deuterated chloroform
Dioxane: 1,4-dioxane
$CC_{50}$: 50% cytotoxic concentration
$CO_2$: carbon dioxide
Con. $H_2SO_4$: concentrated sulfuric acid
CuCN: Copper(I) cyanide
DCM: dichloromethane
DMAc: N,N-dimethylacetamide
DME: dimethoxyethane
DMF: N,N-dimethylformamide
DMSO: dimethylsufoxide
DMSO-$d_6$: dimethylsulfoxide-$d_6$
EtOH: ethanol
EtONa: sodium ethoxide
$FeCl_3$: iron (III) chloride
g: gram
HCOOH: formic acid
Hz: Hertz
h: hour
$IC_{50}$: half maximal inhibition concentration
LiOH: lithium hydroxide
MeOH: methanol
mg: milligram
mL: milliliter
mmol: millimolar
MHz: mega Hertz
$NaBH_3CN$: sodium cyanoborohydride NaOH: sodium hydroxide N₂H₄.H₂O: hydrazine hydrate NH₄OAc: ammonium acetate NMP: N-methyl-2-pyrolidone NMR: nuclear magnetic resonance M: molar/liter PBS: phosphate buffered saline Pd: Palladium PdCl2(dppf): [1,1'-bis(diphenylphosphino)ferrocene]dichloropalladium(II)

TCQ: tetrachloro-p-benzoquinone

TLC: thin layer chromatography

TsNHNH₂: p-toluenesulfonhydrazide

µM: micromolar/liter g: microgram

µL: microliter

δ: chemical shift

General Experimental Conditions

Generally, the reactions described in the examples were performed under nitrogen atmosphere.

The intermediates and final compounds were purified by column chromatography, preparative TLC and ICSO flash chromatography instrument.

LC-MS spectrometer is equipped with QDa detector and ESI ionization source from Waters ACQUITY Arc, and the molecular ion [M⁺] peak is normally reported as [M+H]⁺.

Injection volume is defined by sample concentrate, flow rate is 1.2 mL/min, and the peaks in chromatogram are recorded in the UV wavelength at 220 and 254 nm. Mobile phase A is 0.01% aqueous formic acid solution, and mobile phase B is 0.01% formic acid in CH₃CN. The gradient eluent conditions are shown as in Table 1 and Table 2.

TABLE 1 gradient eluent 1

| time (min) | A(H₂O, 0.01% HCOOH) | B(CH₃CN, 0.01% HCOOH) |
| --- | --- | --- |
| 0.0-0.3 | 95-85 | 5-15 |
| 0.3-3.2 | 85-20 | 15-80 |
| 3.2-3.8 | 20-5 | 80-95 |
| 3.8-3.81 | 5-95 | 95-5 |
| 3.81-4.0 | 95 | 5 |

TABLE 2 gradient eluent 2

| time (min) | A(H₂O, 0.01% HCOOH) | B(CH₃CN, 0.01% HCOOH) |
| --- | --- | --- |
| 0.00-5.90 | 95-5 | 5-95 |
| 5.90-5.91 | 5-95 | 95-5 |
| 5.91-6.00 | 95 | 5 |

NMR spectrums are recorded by Varian 400 MHz NMR spectrometer, CDCl₃ and DMSO-d₆ are often used as solvents, chemical shift is reported as ppm, and the peaks in the spectrum are described as follows: s (single peak), d (double peak), t (triple peak), q (quadruple peak), m (multiple peak), dd (double-double peak), and coupling constants are indicated as Hz.

Preparative Examples

Example 1

6-isopropyl-10-methoxy-2-oxo-9-(1H-pyrazol-4-yl)-6,7-dihydro-2H-pyrido[2,1-a]isoquinoline-3-carboxylic Acid

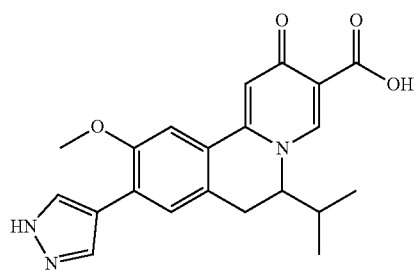 [SMILES: COc1cc2c(cc1-c1cn[nH]c1)CC(C(C)C)n1cc(C(=O)O)c(=O)cc1-2]

Step 1a: Preparation of N'-(3-bromo-4-methoxybenzylidene)-4-methylbenzenesulfonohydrazide

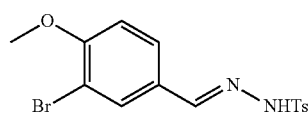

To a solution of 3-bromo-4-methoxybenzaldehyde (20 g, 93 mmol) in methanol (300 mL) was added p-toluenesulfonyl hydrazide (20.8 g, 111.6 mmol), and the reaction mixture was allowed to stir at RT (20° C.) for 16 h. A white solid was precipitated, then evaporation of half a volume of MeOH (150 mL), and collected by filtration. The resulted white solid was dried in vacuum as N'-(3-bromo-4-methoxybenzylidene)-4-methylbenzenesulfono hydrazide (34.5 g), which was used for next stage without further purification.

Step 1b: Preparation of 1-(3-bromo-4-methoxyphenyl)-3-methylbutan-2-one

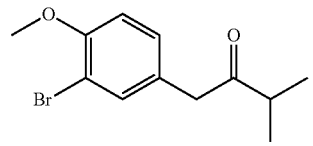

To a solution of N'-(3-bromo-4-methoxybenzylidene)-4-methylbenzenesulfonohydrazide (7.251 g, 45 mmol) in ethanol (400 mL) was added NaOEt (3.06 g, 45 mmol), and the reaction mixture was allowed to stir at RT for 15 min, followed by adding isobutyraldehyde (2.16 g, 30 mmol). Then, the mixture was heated at 60° C. for 1 day. Ethanol was evaporated under reduced pressure, and the resulted residue was partitioned between ethyl acetate (200 mL) and water (100 mL), allowed to stir for 10 min. The organic phase was collected, and the water phase was extracted with EtOAc four times (50 mL×4), the combined organic phase was washed with brine (100 mL×3), dried over anhydrous sodium sulfate. The drying agent was filtered off, and the filtrate was concentrated under reduced pressure to provide the crude product. The crude product was purified by flash column chromatography to provide 1-(3-bromo-4-methoxyphenyl)-3-methylbutan-2-one as colorless oil (4.1 g).

Step 1c: Preparation of 1-(3-bromo-4-methoxyphenyl)-3-methylbutan-2-amine

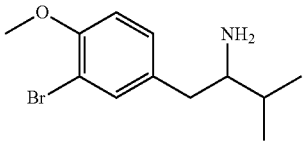

To a solution of 1-(3-bromo-4-methoxyphenyl)-3-methylbutan-2-one (4.1 g, 15.1 mmol) in MeOH (60 mL) was added ammonium acetate (17.46 g, 226.5 mmol) and NaBH$_3$CN (1.9 g, 30.2 mmol), and the reaction mixture was allowed to stir at RT for 2 days. TLC showed that the starting material was completely consumed. The reaction was quenched with water, followed by adding 2.0 M aqueous NaOH (20 mL), then, the mixture was allowed to stir for 1 h. The reaction mixture was extracted with EtOAc, and the organic phase was washed with water (50 mL×3) and brine, dried over anhydrous sodium sulfate, filtered, and concentrated to provide 1-(3-bromo-4-methoxyphenyl)-3-methylbutan-2-amine as colorless oil, which was used for next stage without further purification.

Step 1d: Preparation of N-(1-(3-bromo-4-methoxyphenyl)-3-methylbutan-2-yl)formamide

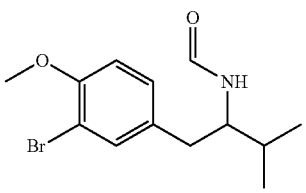 [SMILES: COc1ccc(CC(NC=O)C(C)C)cc1Br]

To a solution of 1-(3-bromo-4-methoxyphenyl)-3-methyl-2-butylamine (6.2 g, 22.8 mmol) in dioxane (60 mL) was added formic acid (3.1 g, 68.4 mmol), and the reaction mixture was heated at reflux for 16 h. TLC showed that the starting material was completely consumed. The volatiles were evaporated under reduced pressure, and the resulted residue was stirred in EtOAc (50 mL) and 1 M NaOH aqueous solution (20 mL) for 20 minutes. The organic phase was collected, and the water phase was extracted with EtOAc (30 mL×2). The combined organic phase was washed with brine (50 mL×3), dried over anhydrous sodium sulfate, filtered, and concentrated. The resulted crude product was purified by flash column chromatography to provide N-(1-(3-bromo-4-methoxyphenyl)-3-methylbutan-2-yl)formamide as colorless oil (4.1 g).

Step 1e: Preparation of 6-bromo-3-isopropyl-7-methoxy-3,4-dihydroisoquinoline

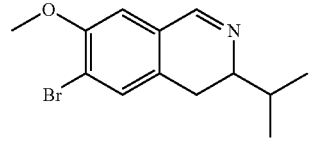 [SMILES: COc1cc2c(cc1Br)CC(C(C)C)N=C2]

To a solution of N-(1-(3-bromo-4-methoxyphenyl)-3-methylbutan-2-yl) formamide (150 mg, 0.5 mmol) in DCM (10 mL) was added oxalyl chloride (53 μL, 0.63 mmol) under nitrogen, and the reaction mixture was allowed to stir at RT for 1 h, then cooled to −10° C., followed by adding FeCl$_3$ (121.7 mg, 0.75 mmol). The reaction mixture was allowed to slowly rise to RT, and continue stirring for 20 h. Then, 2 M HCl (10 mL) was added to quench the reaction and the mixture was stirred for additional 1 h. The organic phase was washed with water and brine, dried over anhydrous sodium sulfate, filtered and concentrated. The resulted oily residue was dissolved in MeOH (10 mL) and con. Sulfuric acid (0.5 mL), and allowed to heat at reflux for 4 h. The reaction mixture was cooled to RT and the volatiles were evaporated under reduced pressure, and the residue was dissolved in EtOAc (20 mL), basified till pH=11 with saturated aqueous sodium carbonate solution, and the water phase was extracted with EtOAc (15 mL×3). The combined organic phase was dried over anhydrous sodium sulfate, filtered and concentrated, providing 6-bromo-3-isopropyl-7-methoxy-3,4-dihydroisoquinoline as a yellow oil (130 mg, 92.1% yield), which was used for next stage without further purification.

Step 1f: Preparation of ethyl 9-bromo-6-isopropyl-10-methoxy-2-oxo-1,6,7,11b-tetrahydro-2H-pyrido[2,1-a]isoquinoline-3-carboxylate

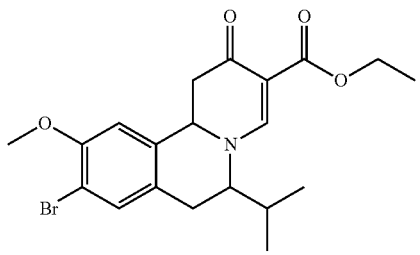 [SMILES: CCOC(=O)C1=CN2C(CC1=O)c1cc(OC)c(Br)cc1CC2C(C)C]

To a solution of 6-bromo-3-isopropyl-7-methoxy-3,4-dihydroisoquinoline (130 mg, 0.46 mmol) in EtOH (10 mL) was added ethyl 2-(ethoxymethylene)-3-oxo-butyrate (514 mg, 2.76 mmol) under nitrogen atmosphere, and the reaction mixture was heated at reflux for 20 h, then concentrated under reduced pressure to provide crude product ethyl 9-bromo-6-isopropyl-10-methoxy-2-oxo-1,6,7,11b-tetrahydro-2H-pyrido[2,1-a]isoquinoline-3-carboxylate as a brown oil (200 mg), which was used for next stage without further purification.

Step 1g: Preparation of ethyl 9-bromo-6-isopropyl-10-methoxy-2-oxo-6,7-dihydro-2H-pyrido[2,1-a]isoquinoline-3-carboxylate

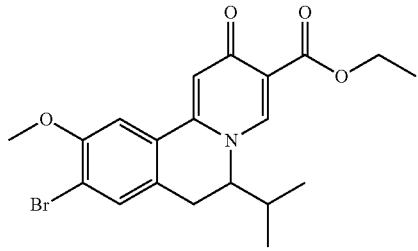 [SMILES: CCOC(=O)c1cn2c(cc1=O)-c1cc(OC)c(Br)cc1CC2C(C)C]

To a solution of ethyl 9-bromo-6-isopropyl-10-methoxy-2-oxo-1,6,7,11b-tetrahydro-2H-pyrido[2,1-a]isoquinoline-3-carboxylate (200 mg) in DME (5 mL) was added TCQ (113.1 mg, 0.46 mmol), and the reaction mixture was heated at reflux for 2 h. Then, the volatiles were evaporated and the resulted residue was partitioned between EtOAc (20 mL) and water (30 mL), the organic phase was collected and washed with brine (20 mL), dried over anhydrous sodium sulfate, filtered, and concentrated to provide a crude product, then purified by preparative TLC to give ethyl 9-bromo-6-isopropyl-10-methoxy-2-oxo-6,7-dihydro-2H-pyrido [2,1-a]isoquinoline-3-carboxylate as brown solid (78 mg).

Step 1h: Preparation of ethyl 6-isopropyl-10-methoxy-2-oxo-9-(1H-pyrazol-4-yl)-6,7-dihydro-2H-pyrido[2,1-a]isoquinoline-3-carboxylate

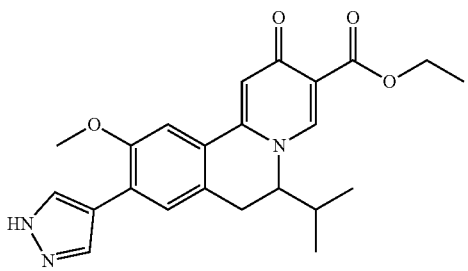 [SMILES: CCOC(=O)c1cn2c(cc1=O)-c1cc(OC)c(-c3cn[nH]c3)cc1CC2C(C)C]

To a solution of ethyl 9-bromo-6-isopropyl-10-methoxy-2-oxo-6,7-dihydro-2H-pyrido[2,1-a]isoquinoline-3-carboxylate (78 mg, 0.186 mmol) in dioxane (2 mL) and water (0.5 mL) was added (1H-pyrazol-4-yl)boronic acid (31.2 mg, 0.279 mmol), potassium carbonate (77.1 mg, 0.558 mmol) and PdCl$_2$(dppf) (14 mg, 0.019 mmol) under nitrogen, and the reaction mixture was allowed to heat at 85° C. and stirred for 20 h. The reaction mixture was partitioned between EtOAc (20 mL) and water (30 mL), and the organic phase was washed with brine, dried over anhydrous sodium sulfate, filtered and concentrated, and the resulted residue was purified by preparative TLC to provide ethyl 6-isopropyl-10-methoxy-2-oxo-9-(1H-pyrazol-4-yl)-6,7-dihydro-2H-pyrido[2,1-a]isoquino-line-3-carboxylate as a white solid (20 mg).

Step 1i: Preparation of 6-isopropyl-10-methoxy-2-oxo-9-(1H-pyrazol-4-yl)-6,7-dihydro-2H-pyrido[2,1-a]isoquinoline-3-carboxylic Acid

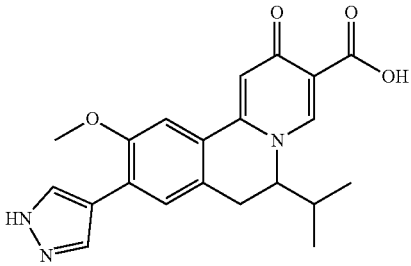 [SMILES: COc1cc2c(cc1-c1cn[nH]c1)CC(C(C)C)n1cc(C(=O)O)c(=O)cc1-2]

To a solution of ethyl 6-isopropyl-10-methoxy-2-oxo-9-(1H-pyrazol-4-yl)-6,7-dihydro-2H-pyrido[2,1-a]isoquinoline-3-carboxylate (20 mg, 0.049 mmol) in EtOH (2 mL) was added 10% NaOH solution (0.4 mL), and the reaction mixture was allowed to stir at RT for 4 h. Then, the volatiles were evaporated in vacuum, and the residue was partitioned between water (20 mL) and EtOAc (20 mL), the water phase was extracted with EtOAc (20 mL×4), and water phase was acidified till pH=2. Then, the water phase was extracted with EtOAc (10 mL×5), and the combined organic phase was washed with water (20 mL×5), then concentrated to afford 6-isopropyl-10-methoxy-2-oxo-9-(1H-pyrazol-4-yl)-6,7-dihydro-2H-pyrido[2,1-a]isoquinoline-3-carboxylic acid (13 mg) as white solid. $^1$H NMR (400 MHz, DMSO-d$_6$): δ 13.06 (s, 1H), 8.82 (s, 1H), 8.26 (s, 1H), 8.07 (s, 1H), 7.75 (s, 1H), 7.61 (s, 1H), 7.59 (s, 1H), 4.50-4.46 (m, 1H), 4.01 (s, 3H), 3.32-3.29 (m., 1H), 3.19-3.15 (m, 1H), 1.65-1.61 (m, 1H), 0.89 (d, J=6.4 Hz, 3H), 0.71 (d, J=6.8 Hz, 3H). MS observed (ESI$^+$) [(M+H)$^+$]: 380.

Example 2

6-isopropyl-10-methoxy-2-oxo-9-(1-(2,2,2-trifluoroethyl)-1H-pyrazol-4-yl)-6,7-dihydro-2H-pyrido[2,1-a]isoquinoline-3-carboxylic Acid

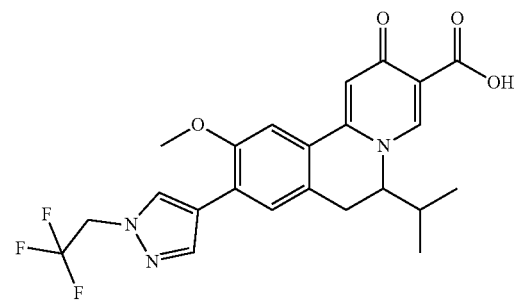 [SMILES: COc1cc2c(cc1-c1cnn(CC(F)(F)F)c1)CC(C(C)C)n1cc(C(=O)O)c(=O)cc1-2]

Step 2a: Preparation of ethyl 6-isopropyl-10-methoxy-2-oxo-9-(1-(2,2,2-trifluoroethyl)-1H-pyrazol-4-yl)-6,7-dihydro-2H-pyrido[2,1-a]isoquinoline-3-carboxylate

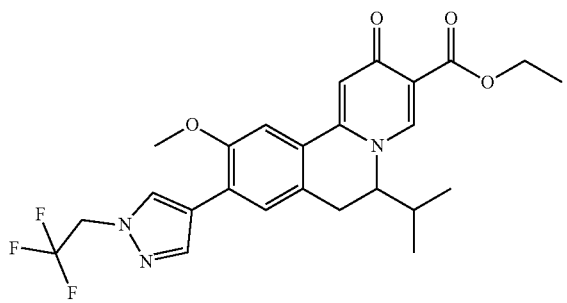 [SMILES: CCOC(=O)c1cn2c(cc1=O)-c1cc(OC)c(-c3cnn(CC(F)(F)F)c3)cc1CC2C(C)C]

To a solution of ethyl 6-isopropyl-10-methoxy-2-oxo-9-(1H-pyrazol-4-yl)-6,7-dihydro-2H-pyrido[2,1-a]isoquinoline-3-carboxylate (50 mg, 0.123 mmol) in DMF (1 mL) was added 1,1,1-trifluoro-2-iodoethane (103 mg, 0.491 mmol) and potassium carbonate (67.8 mg, 0.491 mmol), and the reaction mixture was heated at 75° C. and stirred for 4 h. TLC showed that the starting material was completely consumed, and the reaction mixture was partitioned between DCM and water, the water phase was extracted with DCM (10 mL×3), the combined organic phase was washed with brine (10 mL×3), dried over anhydrous sodium sulfate, filtered and concentrated. The resulted residue was purified by preparative TLC to provide ethyl 6-isopropyl-10-methoxy-2-oxo-9-(1-(2,2,2-trifluoroethyl)-1H-pyrazol-4-yl]-6,7-dihydro-2H-pyrido[2,1-a]isoquinoline-3-carboxylate as a light yellow solid (21 mg).

Step 2b: Preparation of 6-isopropyl-10-methoxy-2-oxo-9-[1-(2,2,2-trifluoroethyl)-1H-pyrazol-4-yl]-6,7-dihydro-2H-pyrido[2,1-a]isoquinoline-3-carboxylic Acid

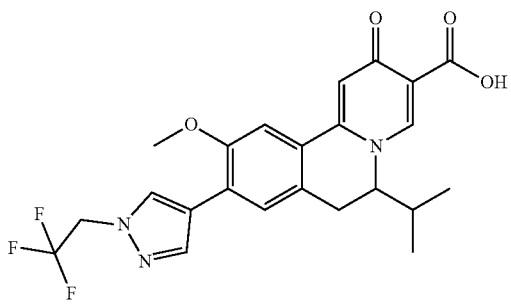 [SMILES: COc1cc2c(cc1-c1cnn(CC(F)(F)F)c1)CC(C(C)C)n1cc(C(=O)O)c(=O)cc1-2]

To a solution of ethyl 6-isopropyl-10-methoxy-2-oxo-9-(1-(2,2,2-trifluoro ethyl)-1H-pyrazol-4-yl)-6,7-dihydro-2H-pyrido[2,1-a]isoquinoline-3-carboxylate (21 mg, 0.043 mmol) in EtOH (1 mL) was added 10% NaOH solution (0.5 mL), and the reaction mixture was allowed to stir at RT for 2 h. TLC showed that the starting material was completely consumed, and the volatiles were evaporated in vacuum. The resulted residue was dissolved in water (20 mL), extracted with DCM (5 mL×2), and the water phase was acidified till pH=2, then extracted with DCM (10 mL×2), and the combined organic phase was washed with water (20 mL×5), concentrated to provide 6-isopropyl-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid (12 mg) as light brown solid. $^1$H NMR (400 MHz, DMSO-d$_6$): δ 8.23 (s, 1H), 8.40 (s, 1H), 8.18 (s, 1H), 7.79 (s, 1H), 7.64 (s, 1H), 7.61 (s, 1H), 5.21 (q, J=9.2 Hz, 2H), 4.53-4.45 (m, 1H), 4.03 (s, 3H), 3.30-3.14 (m, 2H), 1.68-1.55 (m, 1H), 0.88 (d, J=6.4 Hz, 3H), 0.71 (d, J=6.4 Hz, 3H). MS observed (ESI$^+$) [(M+H)$^+$]: 462.

Example 3

6-isopropyl-10-methoxy-9-(1-(2-methoxyethyl)-1H-pyrazol-4-yl)-2-oxo-6,7-dihydro-2H-pyrido[2,1-a]isoquinoline-3-carboxylic Acid

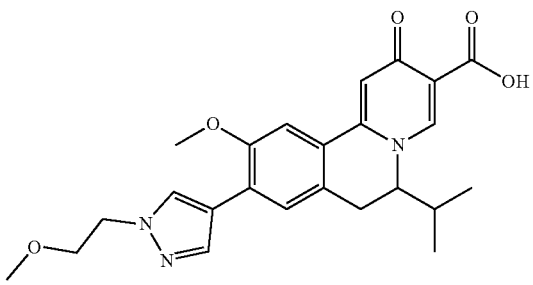 [SMILES: COCCn1cc(-c2cc3c(cc2OC)-c2cc(=O)c(C(=O)O)cn2C(C(C)C)C3)cn1]

Step 3a: Preparation of ethyl 6-isopropyl-10-methoxy-9-(1-(2-methoxyethyl)-1H-pyrazol-4-yl)-2-oxo-6,7-dihydro-2H-pyrido[2,1-a]isoquinoline-3-carboxylate

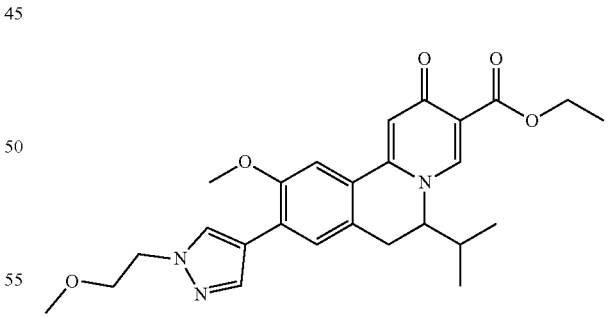

Ethyl 6-isopropyl-10-methoxy-9-(1-(2-methoxyethyl)-1H-pyrazol-4-yl)-2-oxo-6,7-dihydro-2H-pyrido[2,1-a]isoquinoline-3-carboxylate (36 mg) was prepared as yellowish oil by using ethyl 6-isopropyl-10-methoxy-2-oxo-9-(1H-pyrazol-4-yl)-6,7-dihydro-2H-pyrido[2,1-a]isoquinoline-3-carboxylate (50 mg, 0.123 mmol) and 1-bromo-2-methoxyethane (69.2 mg, 0.491 mmol) according to method in example 2, step 2a.

Step 3b: Preparation of 6-isopropyl-10-methoxy-9-(1-(2-methoxyethyl)-1H-pyrazol-4-yl)-2-oxo-6,7-dihydro-2H-pyrido[2,1-a]isoquinoline-3-carboxylic Acid

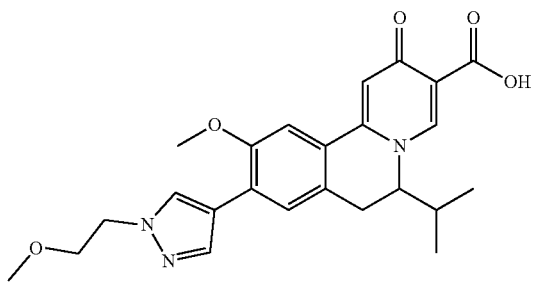 [SMILES: COCCn1cc(-c2cc3c(cc2OC)-c2cc(=O)c(C(=O)O)cn2C(C(C)C)C3)cn1]

6-isopropyl-10-methoxy-9-(1-(2-methoxyethyl)-1H-pyrazol-4-yl)-2-oxo-6,7-dihydro-2H-pyrido[2,1-a]isoquinoline-3-carboxylic acid (9 mg) was prepared as yellow solid by using ethyl 6-isopropyl-10-methoxy-9-(1-(2-methoxyethyl)-1H-pyrazol-4-yl)-2-oxo-6,7-dihydro-2H-pyrido[2,1-a]isoquinoline-3-carboxylate (36 mg, 0.08 mmol) according to method in example 2, step 2b. $^1$H NMR (400 MHz, DMSO-d$_6$): δ 8.82 (s, 1H), 8.25 (s, 1H), 8.03 (s, 1H), 7.73 (s, 1H), 7.61 (s, 1H), 7.59 (s, 1H), 4.52-4.40 (m, 1H), 4.31 (t, J=5.2 Hz, 2H), 4.01 (s, 3H), 3.71 (t, J=5.2 Hz, 2H), 3.32-3.29 (m, 1H), 3.24 (s, 3H), 3.22-3.10 (m, 1H), 1.68-1.54 (m, 1H), 0.88 (d, J=6.4 Hz, 3H), 0.71 (d, J=6.4 Hz, 3H). MS observed (ESI$^+$) [(M+H)$^+$]: 438.

Example 4

9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylic Acid

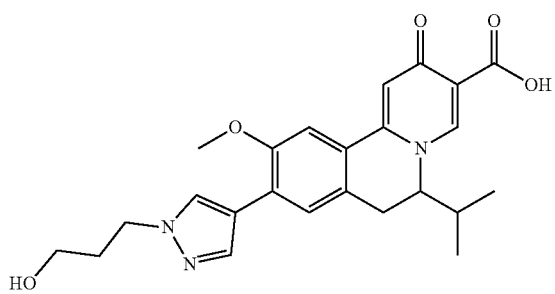

Step 4a: Preparation of ethyl 9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylate

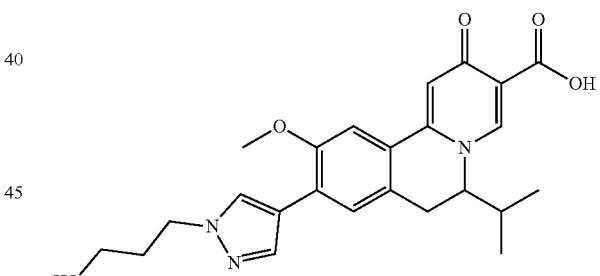

Ethyl 9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylate (40 mg) was prepared as yellow oil by using ethyl 6-isopropyl-10-methoxy-2-oxo-9-(1H-pyrazol-4-yl)-6,7-dihydro-2H-pyrido[2,1-a]isoquinoline-3-carboxylate (50 mg, 0.123 mmol) and 3-bromo-1-propanol (68 mg, 0.491 mmol) according to method in example 2, step 2a.

Steps 4b: Preparation of 9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylic Acid 9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylic acid (11.1 mg) was prepared as white solid by using ethyl 9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylate according to method in example 2, step 2b. $^1$H NMR (400 MHz, DMSO-d$_6$): δ 8.82 (s, 1H), 8.25 (s, 1H), 8.02 (s, 1H), 7.73 (s, 1H), 7.61 (s, 1H), 7.58 (s, 1H), 4.50-4.45 (m, 1H), 4.20 (t, J=6.4 Hz, 2H), 4.01 (s, 3H), 3.40 (t, J=6.4 Hz, 2H), 3.22-3.19 (m, 1H), 3.18-3.14 (m, 1H), 1.99-1.89 (m, 2H), 1.69-1.55 (m, 1H), 0.88 (d, J=6.4 Hz, 3H), 0.71 (d, J=6.4 Hz, 3H). MS observed (ESI$^+$) [(M+H)$^+$]: 438.

Example 5

9-(1-isobutyl-1H-pyrazol-4-yl)-6-isopropyl-10-methoxy-2-oxo-6,7-dihydro-2H-pyrido[2,1-a]isoquinoline-3-carboxylic Acid

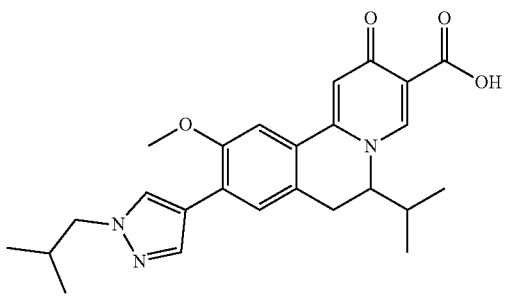 [SMILES: COc1cc2c(cc1-c1cnn(CC(C)C)c1)CC(C(C)C)n1cc(C(=O)O)c(=O)cc1-2]

Step 5a: Preparation of ethyl 9-(1-isobutyl-1H-pyrazolo-4-yl)-6-isopropyl-10-methoxy-2-oxo-6,7-dihydro-2H-pyrido[2,1-a]isoquinoline-3-carboxylate

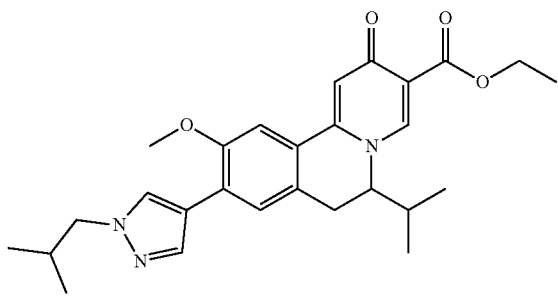 [SMILES: CCOC(=O)c1cn2c(cc1=O)-c1cc(OC)c(-c3cnn(CC(C)C)c3)cc1CC2C(C)C]

Ethyl 9-(1-isobutyl-1H-pyrazolo-4-yl)-6-isopropyl-10-methoxy-2-oxo-6,7-dihydro-2H-pyrido[2,1-a]isoquinoline-3-carboxylate (12 mg) as white solid was prepared by using ethyl 6-isopropyl-10-methoxy-2-oxo-9-(1H-pyrazol-4-yl)-6,7-dihydro-2H-pyrido[2,1-a]isoquinoline-3-carboxylate (50 mg, 0.123 mmol) and 1-bromo-2-methylpropane (168 mg, 1.23 mmol) according to method in example 2, step 2a.

Step 5b: Preparation of 9-(1-isobutyl-1H-pyrazol-4-yl)-6-isopropyl-10-methoxy-2-oxo-6,7-dihydro-2H-pyrido[2,1-a]isoquinoline-3-carboxylic Acid

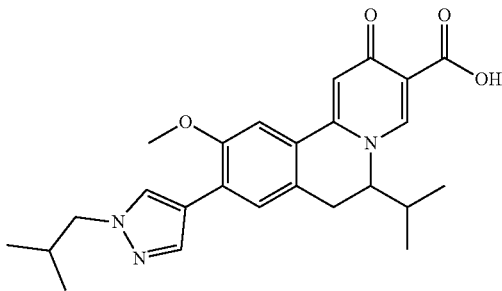 [SMILES: COc1cc2c(cc1-c1cnn(CC(C)C)c1)CC(C(C)C)n1cc(C(=O)O)c(=O)cc1-2]

9-(1-isobutyl-1H-pyrazol-4-yl)-6-isopropyl-10-methoxy-2-oxo-6,7-dihydro-2H-pyrido[2,1-a]isoquinoline-3-carboxylic acid as light yellow solid (9 mg) was prepared by using ethyl 9-(1-isobutyl-1H-pyrazol-4-yl)-6-isopropyl-10-methoxy-2-oxo-6,7-dihydro-2H-pyrido[2,1-a]isoquinoline-3-carboxylate (12 mg, 0.03 mmol) according to method in example 2, step 2b. $^1$H NMR (400 MHz, DMSO-$d_6$): δ 16.67 (s, 1H), 8.82 (s, 1H), 8.25 (s, 1H), 8.03 (s, 1H), 7.73 (s, 1H), 7.61 (s, 1H), 7.59 (s, 1H), 4.51-4.45 (m, 1H), 4.01 (s, 3H), 3.96 (d, J=7.2 Hz, 2H), 3.33-3.30 (m, 1H), 3.19-3.15 (m, 1H), 2.16-2.13 (m, 1H), 1.68-1.63 (m, 1H), 0.89-0.85 (m, 9H), 0.71 (d, J=6.8 Hz, 3H). MS observed (ESI$^+$) [(M+H)$^+$]: 436.

Example 6

6-isopropyl-10-methoxy-2-oxo-9-(1-propyl-1H-pyrazol-4-yl)-6,7-dihydro-2H-pyrido[2,1-a]isoquinoline-3-carboxylic Acid

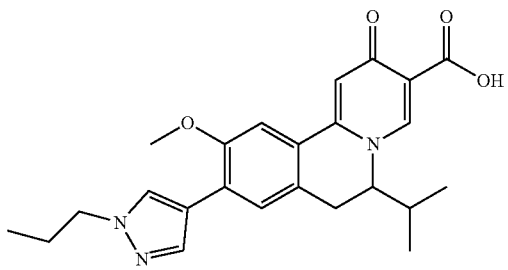 [SMILES: CCCn1cc(-c2cc3c(cc2OC)-c2cc(=O)c(C(=O)O)cn2C(C(C)C)C3)cn1]

Step 6a: Preparation of ethyl 6-isopropyl-10-methoxyl-2-oxo-9-(1-propyl-1H-pyrazol-4-yl)-6,7-dihydro-2H-pyrido[2,1-a]isoquinoline-3-carboxylate

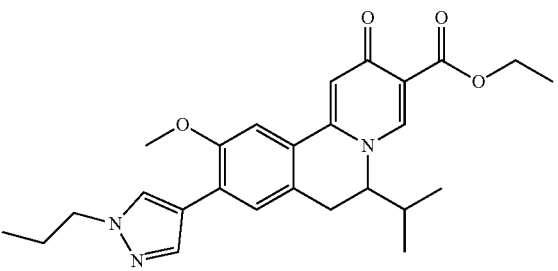 [SMILES: CCCn1cc(-c2cc3c(cc2OC)-c2cc(=O)c(C(=O)OCC)cn2C(C(C)C)C3)cn1]

Ethyl 6-isopropyl-10-methoxyl-2-oxo-9-(1-propyl-1H-pyrazol-4-yl)-6,7-dihydro-2H-pyrido[2,1-a]isoquinoline-3-carboxylate (32 mg) as white solid was prepared by using ethyl 6-isopropyl-10-methoxy-2-oxo-9-(1H-pyrazol-4-yl)-6,7-dihydro-2H-pyrido[2,1-a]isoquinoline-3-carboxylate (50 mg, 0.123 mmol) and 1-bromopropane (151 mg, 1.23 mmol) according to method in example 2, step 2a.

Step 6b: Preparation of 6-isopropyl-10-methoxy-2-oxo-9-(1-propyl-1H-pyrazol-4-yl)-6,7-dihydro-2H-pyrido[2,1-a]isoquinoline-3-carboxylic Acid

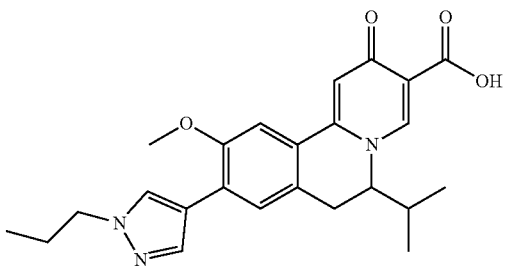 [SMILES: CCCn1cc(-c2cc3c(cc2OC)-c2cc(=O)c(C(=O)O)cn2C(C(C)C)C3)cn1]

6-isopropyl-10-methoxy-2-oxo-9-(1-propyl-1H-pyrazol-4-yl)-6,7-dihydro-2H-pyrido[2,1-a]isoquinoline-3-carboxylic acid (20 mg) as yellow solid was prepared by using ethyl 6-isopropyl-10-methoxy-2-oxo-9-(1-propyl-1H-pyrazol-4-yl)-6,7-dihydro-2H-pyrido[2,1-a]isoquinoline-3-carboxylate according to method in example 2, step 2b. $^1$H NMR (400 MHz, DMSO-d$_6$): δ 8.69 (s, 1H), 8.25 (s, 1H), 8.01 (s, 1H), 7.71 (s, 1H), 7.56 (s, 1H), 7.43 (s, 1H), 4.42-4.35 (m, 1H), 4.10 (t, J=6.8 Hz, 2H), 4.00 (s, 3H), 3.19-3.10 (m, 2H), 1.86-1.79 (m, 2H), 1.68-1.62 (m, 1H), 0.89-0.83 (m, 6H), 0.71 (d, J=6.4 Hz, 3H). MS observed (ESI$^+$) [(M+H)$^+$]: 422.

Example 7

6-isopropyl-10-methoxy-9-(6-methylpyridin-3-yl)-2-oxo-6,7-dihydro-2H-pyrido[2,1-a]isoquinoline-3-carboxylic Acid

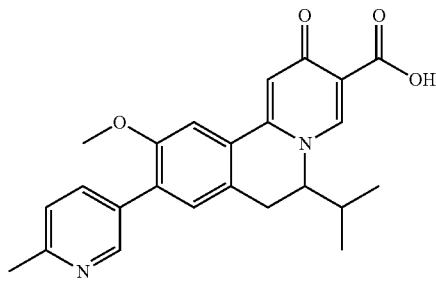 [SMILES: COc1cc2c(cc1-c1ccc(C)nc1)CC(C(C)C)n1cc(C(=O)O)c(=O)cc1-2]

Step 7a: Preparation of ethyl 6-isopropyl-10-methoxy-9-(6-methylpyridin-3-yl)-2-oxo-6,7-dihydro-2H-pyrido[2,1-a]isoquinoline-3-carboxylate

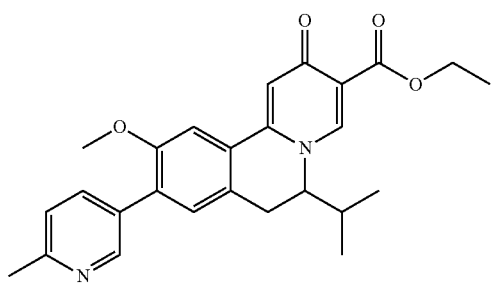 [SMILES: CCOC(=O)c1cn2c(cc1=O)-c1cc(OC)c(-c3ccc(C)nc3)cc1CC2C(C)C]

Ethyl 6-isopropyl-10-methoxy-9-(6-methylpyridin-3-yl)-2-oxo-6,7-dihydro-2H-pyrido[2,1-a]isoquinoline-3-carboxylate (61 mg) as yellow solid was prepared by using ethyl 9-bromo-6-isopropyl-10-methoxy-2-oxo-6,7-dihydro-2H-pyrido[2,1-a]isoquinoline-3-carboxylate (100 mg, 0.238 mmol) and (6-methylpyridin-3-yl)boronic acid (42.3 mg, 0.309 mmol) according to method in example 1, step 1h.

Step 7b: Preparation of 6-isopropyl-10-methoxy-9-(6-methylpyridin-3-yl)-2-oxo-6,7-dihydro-2H-pyrido[2,1-a]isoquinoline-3-carboxylic Acid

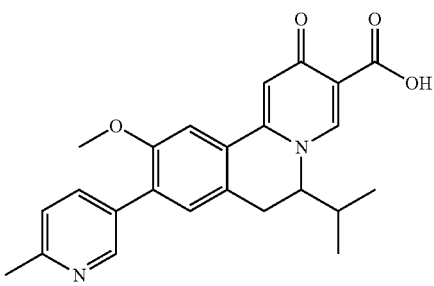 [SMILES: COc1cc2c(cc1-c1ccc(C)nc1)CC(C(C)C)n1cc(C(=O)O)c(=O)cc1-2]

6-isopropyl-10-methoxy-9-(6-methylpyridin-3-yl)-2-oxo-6,7-dihydro-2H-pyrido[2,1-a]isoquinoline-3-carboxylic acid (21 mg) as light yellow solid was prepared by using ethyl 6-isopropyl-10-methoxy-9-(6-methylpyridin-3-yl)-2-oxo-6,7-dihydro-2H-pyrido-[2,1-a]isoquinoline-3-carboxylate (61 mg, 0.14 mmol) according to method in example 1, step 1i. $^1$H NMR (400 MHz, DMSO-d$_6$): δ 8.87 (s, 1H), 8.83 (s, 1H), 7.75-7.71 (m, 4H), 7.59 (m, 1H), 4.54-4.51 (m, 1H), 3.95 (s, 3H), 3.26-3.22 (m, 2H), 2.68 (s, 3H), 1.26-1.23 (m, 1H), 0.89 (d, J=4.0 Hz, 3H), 0.73 (d, J=4.0 Hz, 3H). MS observed (ESI$^+$) [(M+H)$^+$]: 405

Example 8

6-(tert-butyl)-10-methoxy-2-oxo-9-(1H-pyrazol-4-yl)-6,7-dihydro-2H-pyrido[2,1-a]isoquinoline-3-carboxylic Acid

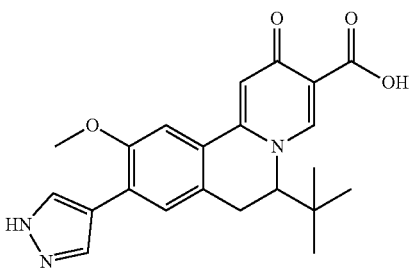 [SMILES: COc1cc2c(cc1-c1cn[nH]c1)CC(C(C)(C)C)n1cc(C(=O)O)c(=O)cc1-2]

Step 8a: Preparation of 1-(3-bromo-4-methoxyphenyl)-3,3-dimethylbutan-2-one

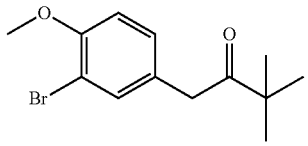 [SMILES: COc1ccc(CC(=O)C(C)(C)C)cc1Br]

1-(3-bromo-4-methoxyphenyl)-3,3-dimethylbutan-2-one (1.82 g) as colorless oil was prepared by using N'-(3-bromo-4-methoxybenzylidene)-4-methylbenzene sulfonylhydrazide (8.62 g, 22.5 mmol) and pivaldehyde (1.29 g, 15 mmol) according to method in example 1, step 1b.

Step 8b: Preparation of 1-(3-bromo-4-methoxyphenyl)-3,3-dimethylbutan-2-amine

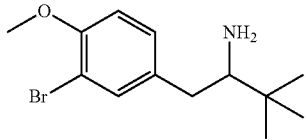 [SMILES: COc1ccc(CC(N)C(C)(C)C)cc1Br]

1-(3-bromo-4-methoxyphenyl)-3,3-dimethylbutan-2-amine as colorless oil (2.1 g) was prepared by using 1-(3-bromo-4-methoxyphenyl)-3,3-dimethylbutan-2-one (1.82 g, 6.38 mmol) and ammonium acetate (7.38 g, 95.7 mmol) according to method in example 1, step 1c.

Step 8c: Preparation of N-(1-(3-bromo-4-methoxyphenyl)-3,3-dimethylbutan-2-yl)formamide

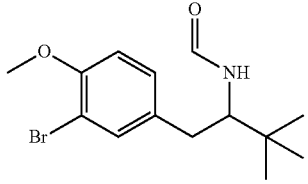 [SMILES: COc1ccc(CC(NC=O)C(C)(C)C)cc1Br]

N-(1-(3-bromo-4-methoxyphenyl)-3,3-dimethylbutan-2-yl)formamide as off-white solid (1.82 g) was prepared by using 1-(3-bromo-4-methoxyphenyl)-3,3-dimethylbutan-2-amine (2.1 g) and formic acid (2 mL) according to method in example 1, step 1d.

Step 8d: Preparation of 6-bromo-3-(tert-butyl)-7-methoxy-3,4-dihydroisoquinoline

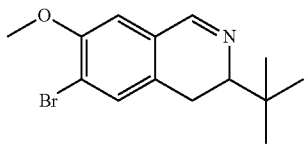 [SMILES: COc1cc2c(cc1Br)CC(C(C)(C)C)N=C2]

6-bromo-3-(tert-butyl)-7-methoxy-3,4-dihydroisoquinoline (1.62 g) as yellow oil was prepared by using N-(1-(3-bromo-4-methoxyphenyl)-3,3-dimethylbutan-2-yl) formamide (1.82 g, 5.8 mmol) according to method in example 1, step 1e.

Step 8e: Preparation of ethyl 9-bromo-6-(tert-butyl)-10-methoxy-2-oxo-1,6,7,11b-tetrahydro-2H-pyrido[2,1-a]isoquinoline-3-carboxylate

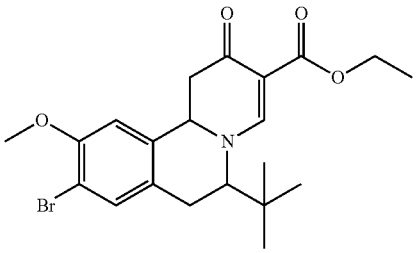 [SMILES: CCOC(=O)C1=CN2C(CC1=O)c1cc(OC)c(Br)cc1CC2C(C)(C)C]

Ethyl 9-bromo-6-(tert-butyl)-10-methoxy-2-oxo-1,6,7,11b-tetrahydro-2H-pyrido[2,1-a]isoquinoline-3-carboxylate as brown oil (3.2 g) was prepared by using 6-bromo-3-(tert-butyl)-7-methoxy-3,4-dihydroisoquinoline (1.62 g, 5.5 mmol) and ethyl 2-(ethoxymethylene)-3-oxo-butyrate (4.1 g, 22 mmol) according to method in example 1, step 1f.

Step 8f: Preparation of ethyl 9-bromo-6-(tert-butyl)-10-methoxy-2-oxo-6,7-dihydro-2H-pyrido[2,1-a]isoquinoline-3-carboxylate

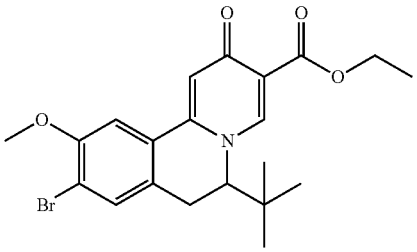 [SMILES: CCOC(=O)c1cn2c(cc1=O)-c1cc(OC)c(Br)cc1CC2C(C)(C)C]

Ethyl 9-bromo-6-(tert-butyl)-10-methoxy-2-oxo-6,7-dihydro-2H-pyrido[2,1-a]isoquinoline-3-carboxylate as brown solid (920 mg) was prepared by using ethyl 9-bromo-6-(tert-butyl)-10-methoxy-2-oxo-1,6,7,11b-tetrahydro-2H-pyrido[2,1-a]isoquinoline-3-carboxylate (3.2 g) and TCQ (1.35 g, 5.5 mmol) according to method in example 1, step 1g.

Step 8g: Preparation of ethyl 6-(tert-butyl)-10-methoxy-2-oxo-9-(1H-pyrazol-4-yl)-6,7-dihydro-2H-pyrido[2,1-a]isoquinoline-3-carboxylate

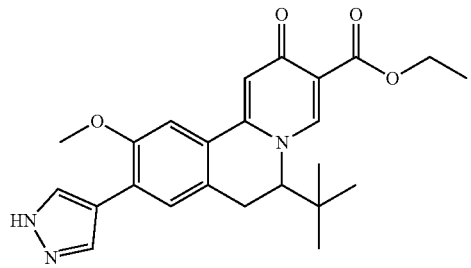 [SMILES: CCOC(=O)c1cn2c(cc1=O)-c1cc(OC)c(-c3cn[nH]c3)cc1CC2C(C)(C)C]

Ethyl 6-(tert-butyl)-10-methoxy-2-oxo-9-(1H-pyrazol-4-yl)-6,7-dihydro-2H-pyrido[2,1-a]isoquinoline-3-carboxylate as brown solid (150 mg) was prepared by using ethyl 9-bromo-6-(tert-butyl)-10-methoxy-2-oxo-6,7-dihydro-2H-pyrido[2,1-a]isoquinoline-3-carboxylate (600 mg, 1.38 mmol) and (1H-pyrazol-4-yl)boronic acid (463 mg, 4.14 mmol) according to method in example 1, step 1h.

Step 8h: Preparation of 6-(tert-butyl)-10-methoxy-2-oxo-9-(1H-pyrazol-4-yl)-6,7-dihydro-2H-pyrido[2,1-a]isoquinoline-3-carboxylic Acid

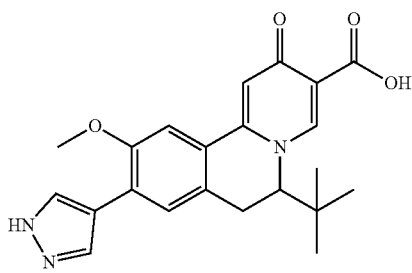 [SMILES: COc1cc2c(cc1-c1cn[nH]c1)CC(C(C)(C)C)n1cc(C(=O)O)c(=O)cc1-2]

6-(tert-butyl)-10-methoxy-2-oxo-9-(1H-pyrazol-4-yl)-6,7-dihydro-2H-pyrido[2,1-a]isoquinoline-3-carboxylic acid (3 mg) as light yellowish solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.119) according to method in example 1, step 1i. $^1$H NMR (400 MHz, DMSO-$d_6$): δ 8.76 (s, 1H), 8.16 (s, 2H), 7.74 (s, 1H), 7.58 (s, 1H), 7.57 (s, 1H), 4.63-4.58 (m, 1H), 4.00 (s, 3H), 3.45-3.38 (m, 1H), 3.28-3.24 (m, 1H), 0.74 (s, 9H). MS observed (ESI$^+$) [(M+H)$^+$]: 394.

Example 9

6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylic Acid

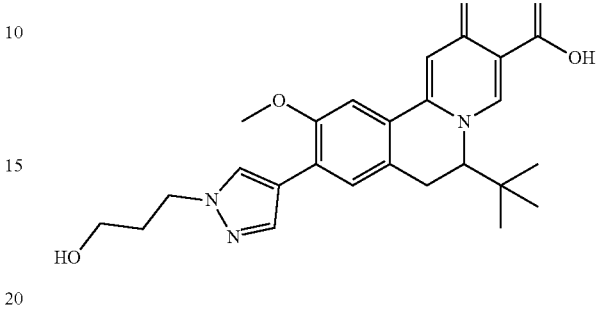

Step 9a: Preparation of ethyl 6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylate

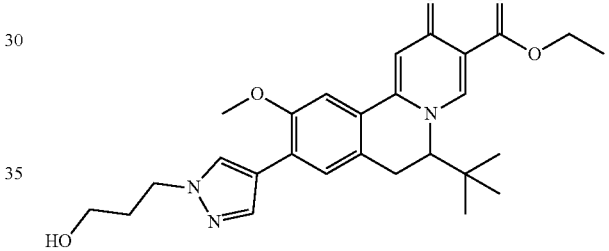

Ethyl 6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylate (40 mg) as yellow solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (80 mg, 0.19 mmol) and 3-bromopropanol (264 mg, 1.9 mmol) according to method in example 2, step 2a.

Step 9b: Preparation of 6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylic Acid

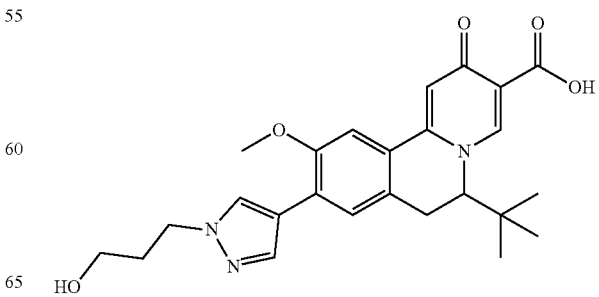

6-(tert-butyl)-9-(1-(3-hydroxypropyl)-1H-pyrazol-4-yl]-10-methoxy-2-oxo-6,7-dihydro-2H-pyrido[2,1-a]isoquinoline-3-carboxylic acid (20.7 mg) as white solid was prepared by using ethyl 6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylate (40 mg, 0.09 mmol) according to method in example 2, step 2b. $^1$H NMR (400 MHz, DMSO-d$_6$): δ 16.61 (s, 1H), 8.75 (s, 1H), 8.25 (s, 1H), 8.01 (s, 1H), 7.72 (s, 1H), 7.58 (s, 1H), 7.57 (s, 1H), 4.61-4.59 (m, 2H), 4.20 (t, J=6.8 Hz, 2H), 4.00 (s, 3H), 3.43-3.38 (m, 4H), 1.95 (dd, J=12.8, 6.4 Hz, 2H), 0.74 (s, 9H). MS observed (ESI$^+$) [(M+H)$^+$]: 452.

Example 10

6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylic Acid

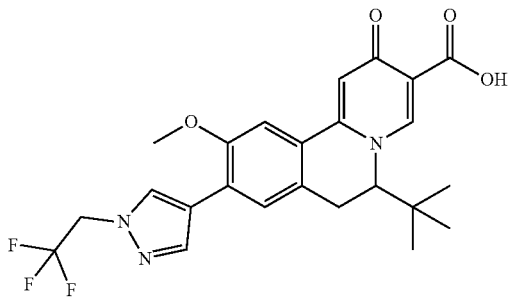 [SMILES: COc1cc2c(cc1-c1cnn(CC(F)(F)F)c1)CC(C(C)(C)C)n1cc(C(=O)O)c(=O)cc1-2]

Step 10a: Preparation of ethyl 6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylate

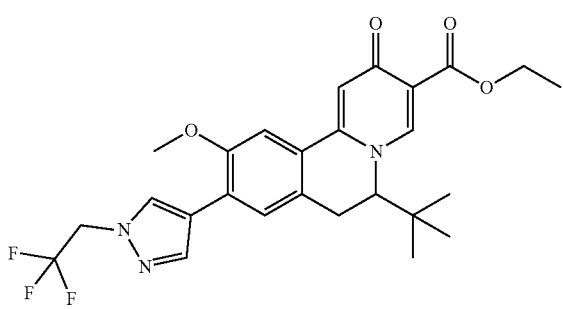 [SMILES: CCOC(=O)c1cn2c(cc1=O)-c1cc(OC)c(-c3cnn(CC(F)(F)F)c3)cc1CC2C(C)(C)C]

Ethyl 6-(tert-butyl)-10-methoxy-2-oxo-9-(1-(2,2,2-trifluoroethyl)-1H-pyrazol-4-yl]-6,7-dihydro-2H-pyrido[2,1-a]isoquinoline-3-carboxylate (10 mg) as yellow solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and 2-bromo-1,1,1-trifluoroethane (193 mg, 1.2 mmol) according to method in example 2, step 2a.

Step 10b: Preparation of 6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylic Acid

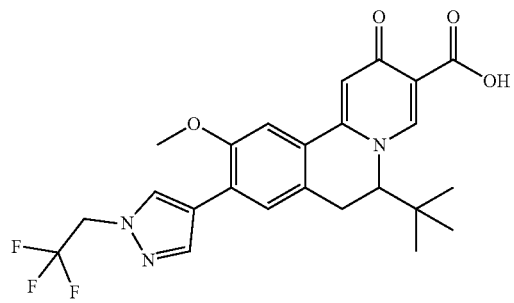 [SMILES: COc1cc2c(cc1-c1cnn(CC(F)(F)F)c1)CC(C(C)(C)C)n1cc(C(=O)O)c(=O)cc1-2]

6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid (5.8 mg) as grey solid was prepared by using ethyl 6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylate (10 mg, 0.02 mmol) according to method in example 2, step 2b. $^1$H NMR (400 MHz, DMSO-d$_6$): δ 8.76 (s, 1H), 8.40 (s, 1H), 8.17 (s, 1H), 7.77 (s, 1H), 7.61 (s, 1H), 7.60 (s, 1H), 5.20 (q, J=9.2 Hz, 2H), 4.61 (d, J=6.0 Hz, 1H), 4.01 (s, 3H), 3.45-3.38 (m, 2H), 0.74 (s, 9H). MS observed (ESI$^+$) [(M+H)$^+$]: 476.

Example 11

6-(tert-butyl)-10-methoxy-9-(1-(oxetan-3-yl)-1H-pyrazol-4-yl)-2-oxo-6,7-dihydro-2H-pyrido[2,1-a]isoquinoline-2-carboxylic Acid

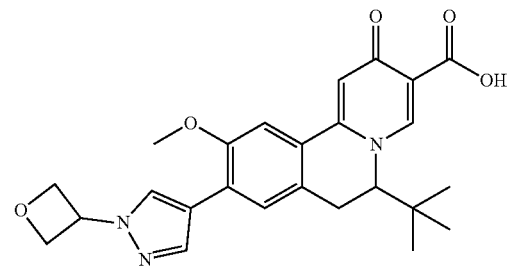 [SMILES: COc1cc2c(cc1-c1cnn(C3COC3)c1)CC(C(C)(C)C)n1cc(C(=O)O)c(=O)cc1-2]

Step 11a: Preparation of ethyl 6-(tert-butyl)-10-methoxy-9-(1-(oxetan-3-yl)-1H-pyrazol-4-yl)-2-oxo-6,7-dihydro-2H-pyrido[2,1-a]isoquinoline-3-carboxylate

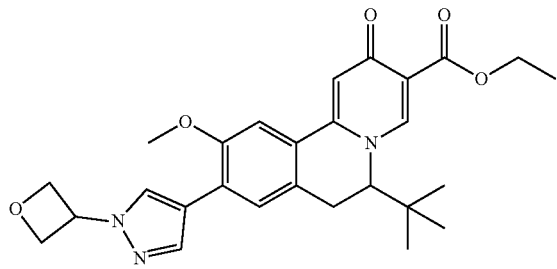 [SMILES: CCOC(=O)c1cn2c(cc1=O)-c1cc(OC)c(-c3cnn(C4COC4)c3)cc1CC2C(C)(C)C]

Ethyl 6-(tert-butyl)-10-methoxy-9-(1-(oxetan-3-yl)-1H-pyrazol-4-yl]-2-oxo-6,7-dihydro-2H-pyrido[2,1-a]isoquinoline-3-carboxylate (10 mg) as yellow solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and 3-bromooxetane (179 mg, 1.2 mmol) according to method in example 2, step 2a.

Step 11b: Preparation of 6-(tert-butyl)-10-methoxy-9-(1-(oxetan-3-yl)-1H-pyrazol-4-yl)-2-oxo-6,7-dihydro-2H-pyrido[2,1-a]isoquinoline-3-carboxylic Acid

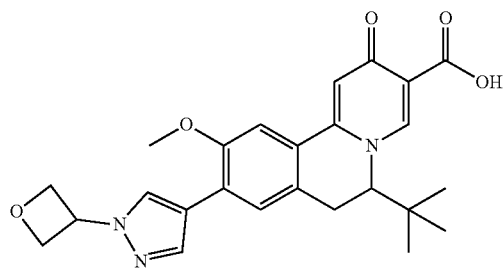 [SMILES: COc1cc2c(cc1-c1cnn(C3COC3)c1)CC(C(C)(C)C)n1cc(C(=O)O)c(=O)cc1-2]

6-(tert-butyl)-10-methoxy-9-(1-(oxetan-3-yl)-1H-pyrazol-4-yl]-2-oxo-6,7-dihydro-2H-pyrido[2,1-a]isoquinoline-3-carboxylic acid (6.7 mg) as yellow solid was prepared by using ethyl 6-(tert-butyl)-10-methoxy-9-(1-(oxetan-3-yl)-1H-pyrazol-4-yl)-2-oxo-6,7-dihydro-2H-pyrido[2,1-a]isoquinoline-3-carboxylate (10 mg, 0.03 mmol) according to method in example 2, step 2b. $^1$H NMR (400 MHz, DMSO-$d_6$): δ 8.76 (s, 1H), 8.40 (s, 1H), 8.17 (s, 1H), 7.76 (s, 1H), 7.59 (s, 1H), 7.58 (s, 1H), 4.95-4.93 (m, 4H), 4.61 (d, J=6.4 Hz, 1H), 4.04 (s, 4H), 3.45-3.38 (m, 2H), 0.74 (s, 9H). MS observed (ESI$^+$) [(M+H)$^+$]: 450.

Example 12

6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylic Acid

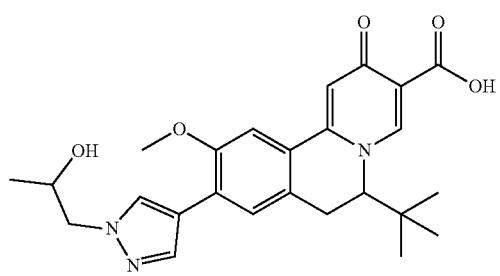

Step 12a: Preparation of ethyl 6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylate

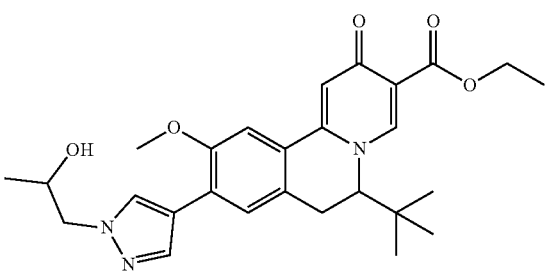 [SMILES: CCOC(=O)c1cn2c(cc1=O)-c1cc(OC)c(-c3cnn(CC(C)O)c3)cc1CC2C(C)(C)C]

Ethyl 6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylate (29 mg) as white solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and 1-bromo-2-propanol (165 mg, 1.2 mmol) according to method in example 2, step 2a.

Step 12b: Preparation of 6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylic Acid

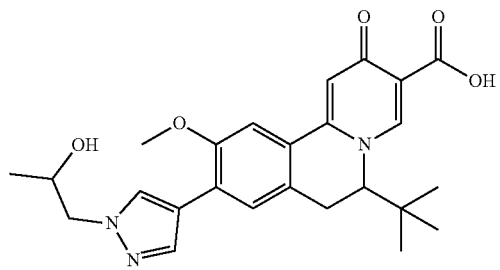 [SMILES: COc1cc2c(cc1-c1cnn(CC(C)O)c1)CC(C(C)(C)C)n1cc(C(=O)O)c(=O)cc1-2]

6-(tert-butyl)-9-(1-(2-hydroxypropyl)-1H-pyrazol-4-yl]-10-methoxy-2-oxo-6,7-dihydro-2H-pyrido[2,1-a]isoquinoline-3-carboxylic acid (13.4 mg) as white solid was prepared by using ethyl 6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylate (29 mg, 0.06 mmol) according to method in example 2, step 2b. $^1$H NMR (400 MHz, DMSO-d$_6$): δ 8.75 (s, 1H), 8.22 (s, 1H), 8.02 (s, 1H), 7.73 (s, 1H), 7.58 (s, 1H), 7.57 (s, 1H), 4.93 (t, J=4.4 Hz, 1H), 4.61 (d, J=5.6 Hz, 1H), 4.04 (s, 2H), 4.00 (s, 3H), 3.42-3.39 (m, 2H), 1.09-1.02 (m, 3H), 0.74 (s, 9H). MS observed (ESI$^+$) [(M+H)$^+$]: 452.

Example 13

6-(tert-butyl)-10-methoxy-9-(1-methyl-1H-pyrazol-5-yl)-2-oxo-6,7-dihydro-2H-pyrido[2,1-a]isoquinoline-3-carboxylic Acid

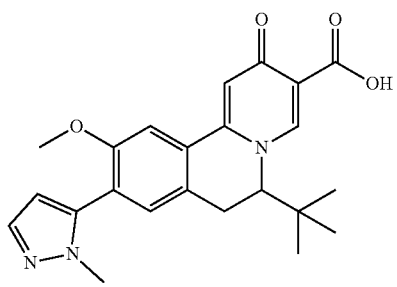 [SMILES: COc1cc2c(cc1-c1ccnn1C)CC(C(C)(C)C)n1cc(C(=O)O)c(=O)cc1-2]

Step 13a: Preparation of ethyl 6-(tert-butyl)-10-methoxy-9-(1-methyl-1H-pyrazol-5-yl)-2-oxo-6,7-dihydro-2H-pyrido[2,1-a]isoquinoline-3-carboxylate

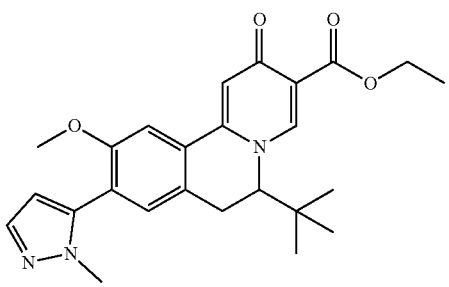 [SMILES: CCOC(=O)c1cn2c(cc1=O)-c1cc(OC)c(-c3ccnn3C)cc1CC2C(C)(C)C]

Ethyl 6-(tert-butyl)-10-methoxy-9-(1-methyl-1H-pyrazol-5-yl)-2-oxo-6,7-dihydro-2H-pyrido[2,1-a]isoquinoline-3-carboxylate (64 mg) as yellow solid was prepared by using ethyl 9-bromo-6-(tert-butyl)-10-methoxy-2-oxo-6,7-dihydro-2H-pyrido-[2,1-a]isoquinoline-3-carboxylate (100 mg, 0.23 mmol) and 1-methyl-5-(4,4,5,5-tetramethyl-1,3,2-dioxaborolan-2-yl)-1H-pyrazole (53 mg, 0.253 mmol) according to method in example 1, step 1h.

Step 13b: Preparation of 6-(tert-butyl)-10-methoxy-9-(1-methyl-1H-pyrazol-5-yl)-2-oxo-6,7-dihydro-2H-pyrido[2,1-a]isoquinoline-3-carboxylic Acid

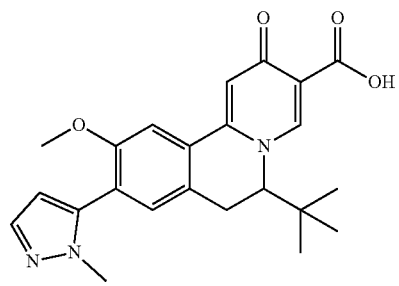 [SMILES: COc1cc2c(cc1-c1ccnn1C)CC(C(C)(C)C)n1cc(C(=O)O)c(=O)cc1-2]

6-(tert-butyl)-10-methoxy-9-(1-methyl-1H-pyrazol-5-yl)-2-oxo-6,7-dihydro-2H-pyrido[2,1-a]isoquinoline-3-carboxylic acid (33 mg) as light yellow solid was prepared by using ethyl 6-(tert-butyl)-10-methoxy-9-(1-methyl-1H-pyrazol-5-yl)-2-oxo-6,7-dihydro-2H-pyrido-[2,1-a]isoquinoline-3-carboxylate (64 mg, 0.15 mmol) according to method in example 1i, step 1i. $^1$H NMR (400 MHz, DMSO-d$_6$): δ 16.48 (s, 1H), 8.79 (s, 1H), 7.70 (s, 1H), 7.69 (s, 1H), 7.48-7.47 (m, 1H), 7.39 (s, 1H), 6.34-6.33 (m, 1H), 4.65-4.64 (m, 1H), 3.93 (s, 3H), 3.65 (s, 3H), 3.44-3.36 (m, 2H), 0.75 (s, 9H). MS observed (ESI$^+$) [(M+H)$^+$]: 408.

Example 14

6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylic Acid

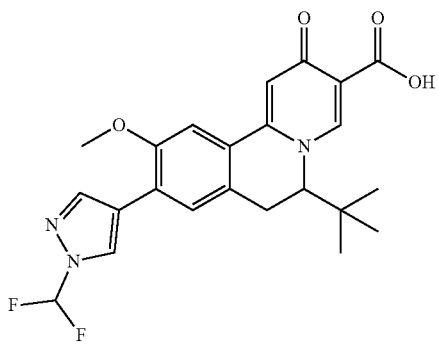 [SMILES: COc1cc2c(cc1-c1cnn(C(F)F)c1)CC(C(C)(C)C)n1cc(C(=O)O)c(=O)cc1-2]

Step 14a: Preparation of ethyl 6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylate

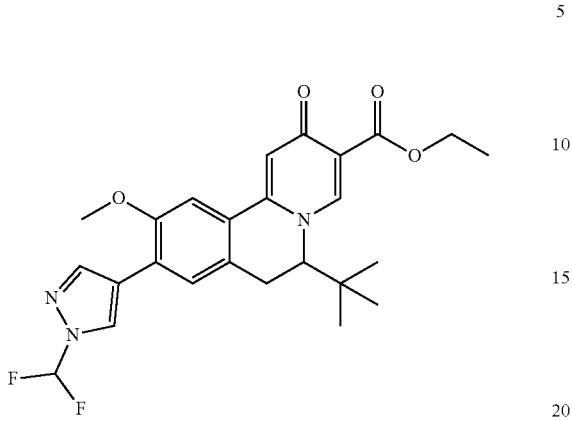

Ethyl 6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylate (56 mg) as yellow solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and 1-(difluoromethyl)-4-(4,4,5,5-tetramethyl-1,3,2-dioxaborolan-2-yl)-1H-pyrazole (62 mg, 0.253 mmol) according to method in example 1, step 1h.

Step 14b: Preparation of 6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylic Acid

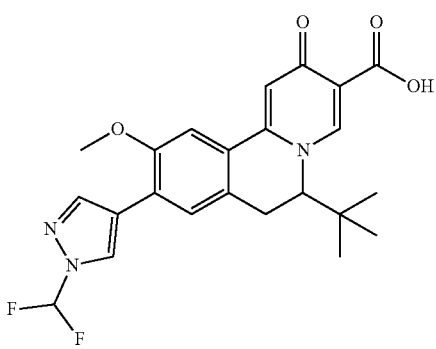 [SMILES: COc1cc2c(cc1-c1cnn(C(F)F)c1)CC(C(C)(C)C)n1cc(C(=O)O)c(=O)cc1-2]

6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylic acid (18.4 mg) as light yellow solid was prepared by using ethyl 6-(tert-butyl)-9-(1-difluoromethyl-1H-pyrazol-4-yl)-10-methoxy-2-oxo-6,7-dihydro-2H-pyrido[2,1-a]isoquinoline-3-carboxylate (56 mg, 0.12 mmol) according to method in example 1, step 1i. $^1$H NMR (400 MHz, DMSO-$d_6$): δ 16.55 (s, 1H), 8.78 (s, 1H), 8.71 (s, 1H), 8.38 (s, 1H), 8.02-7.73 (m, 2H), 7.64 (s, 2H), 4.64-4.62 (m, 1H), 4.03 (s, 3H), 3.46-3.40 (m, 2H), 0.74 (s, 9H). MS observed (ESI$^+$) [(M+H)$^+$]: 444.

Example 15

6-(tert-butyl)-9-(1,3-dimethyl-1H-pyrazol-5-yl)-10-methoxy-2-oxo-6,7-dihydro-2H-pyrido[2,1-a]isoquinoline-3-carboxylic Acid

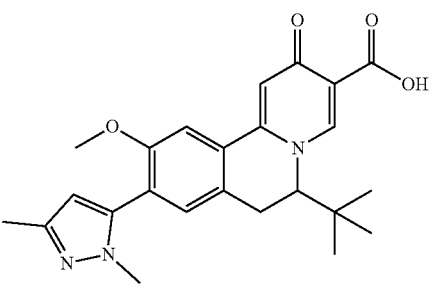 [SMILES: COc1cc2c(cc1-c1cc(C)nn1C)CC(C(C)(C)C)n1cc(C(=O)O)c(=O)cc1-2]

Step 15a: Preparation of ethyl 6-(tert-butyl)-9-(1,3-dimethyl-1H-pyrazol-5-yl)-10-methoxy-2-oxo-6,7-dihydro-2H-pyrido[2,1-a]isoquinoline-3-carboxylate

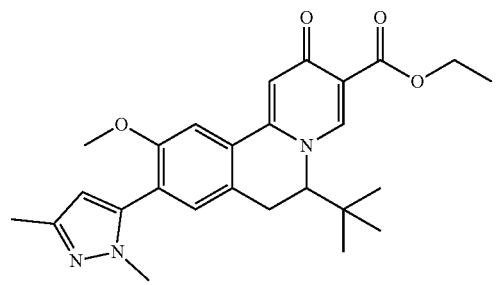 [SMILES: CCOC(=O)c1cn2c(cc1=O)-c1cc(OC)c(-c3cc(C)nn3C)cc1CC2C(C)(C)C]

Ethyl 6-(tert-butyl)-9-(1,3-dimethyl-1H-pyrazol-5-yl)-10-methoxy-2-oxo-6,7-dihydro-2H-pyrido[2,1-a]isoquinoline-3-carboxylate (68 mg) as yellow solid was prepared by using ethyl 9-bromo-6-(tert-butyl)-10-methoxy-2-oxo-6,7-dihydro-2H-pyrido-[2,1-a]isoquinoline-3-carboxylate (100 mg, 0.23 mmol) and 1,3-dimethyl-5-(4,4,5,5-tetramethyl-1,3,2-dioxaborolan-2-yl)-1H-pyrazole (56 mg, 0.253 mmol) according to method in example 1, step 1h.

Step 15b: Preparation of 6-(tert-butyl)-9-(1,3-dimethyl-1H-pyrazol-5-yl)-10-methoxy-2-oxo-6,7-dihydro-2H-pyrido[2,1-a]isoquinoline-3-carboxylic Acid

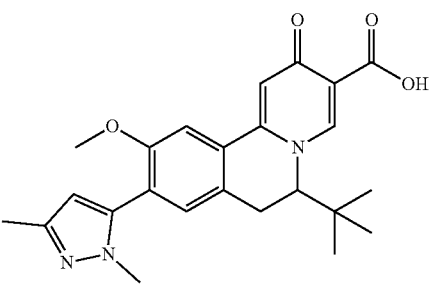 [SMILES: COc1cc2c(cc1-c1cc(C)nn1C)CC(C(C)(C)C)n1cc(C(=O)O)c(=O)cc1-2]

6-(tert-butyl)-9-(1,3-dimethyl-1H-pyrazol-5-yl)-10-methoxy-2-oxo-6,7-dihydro-2H-pyrido[2,1-a]isoquinoline-3-carboxylic acid (7.7 mg) as light yellow solid was prepared by using ethyl 6-(tert-butyl)-9-(1,3-dimethyl-1H-pyrazol-5-yl)-10-methoxy-2-oxo-6,7-dihydro-2H-pyrido[2,1-a]isoquinoline-3-carboxylate (68 mg, 0.15 mmol) according to method in example 1, step 1i. $^1$H NMR (400 MHz, DMSO-d$_6$): δ 16.60 (s, 1H), 8.76 (s, 1H), 8.74 (s, 1H), 7.84 (s, 1H), 7.60 (s, 1H), 7.56 (s, 1H), 7.34 (s, 1H), 4.61-4.60 (m, 1H), 3.91 (s, 3H), 3.80 (s, 3H), 3.42-3.33 (m, 2H), 2.20 (s, 3H), 0.74 (s, 9H). MS observed ESI$^+$) [(M+H)$^+$]: 422.

Example 16

6-(tert-butyl)-10-methoxy-9-(1-(2-morpholinylethyl)-1H-pyrazol-4-yl)-2-oxo-6,7-dihydro-2H-pyrido[2,1-a]isoquinoline-3-carboxylic Acid

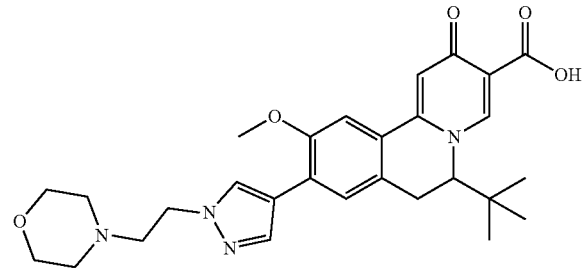 [SMILES: COc1cc2c(cc1-c1cnn(CCN3CCOCC3)c1)CC(C(C)(C)C)n1cc(C(=O)O)c(=O)cc1-2]

Step 16a: Preparation of ethyl 6-(tert-butyl)-10-methoxy-9-(1-(2-morpholinylethyl)-1H-pyrazol-4-yl)-2-oxo-6,7-dihydro-2H-pyrido[2,1-a]isoquinoline-3-carboxylate

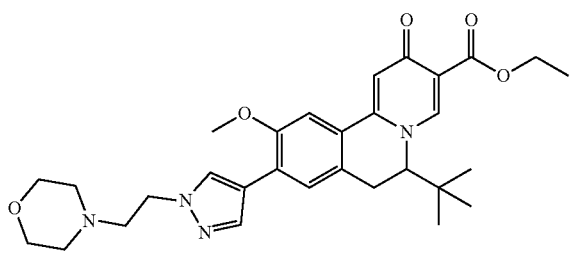 [SMILES: CCOC(=O)c1cn2c(cc1=O)-c1cc(OC)c(-c3cnn(CCN4CCOCC4)c3)cc1CC2C(C)(C)C]

To a solution of ethyl 9-bromo-6-(tert-butyl)-10-methoxy-2-oxo-6,7-dihydro-2H-pyrido[2,1-a]isoquinoline-3-carboxylate (50 mg, 0.115 mmol) in DMF (1 mL) was added 4-(2-(4-(4,4,5,5-tetramethyl-1,3,2-dioxaborolan-2-yl)-1H-pyrazol-1-yl)ethyl)morpholine (53 mg, 0.173 mmol), K$_2$CO$_3$ (48 mg, 0.345 mmol) and PdCl$_2$(dppf) (17 mg, 0.023) under nitrogen, and the reaction mixture was heated at 95° C. and stirred for 16 h. The reaction mixture was filtered through a celite pad, and the filtrate was diluted with EtOAc, the organic phase was washed with water (10 mL) and brine (10 mL), dried over anhydrous sodium sulfate, filtered and concentrated under reduced pressure. The crude product was purified by flash column chromatography to provide ethyl 6-(tert-butyl)-10-methoxy-9-(1-(2-morpholinylethyl)-1H-pyrazol-4-yl)-2-oxo-6,7-dihydro-2H-pyrido[2,1-a]isoquinoline-3-carboxylate (50 mg) as grey-white solid.

Step 16b: Preparation of 6-(tert-butyl)-10-methoxy-9-(1-(2-morpholinylethyl)-1H-pyrazol-4-yl)-2-oxo-6,7-dihydro-2H-pyrido[2,1-a]isoquinoline-3-carboxylic Acid

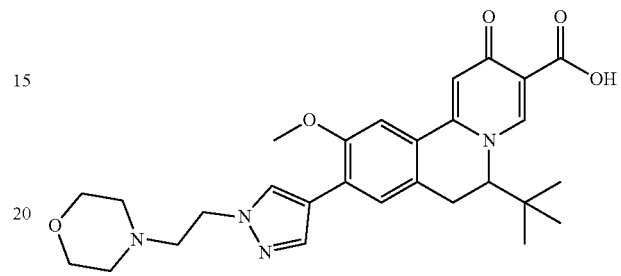

To a solution of ethyl 6-(tert-butyl)-10-methoxy-9-(1-(2-morpholinylethyl)-1H-pyrazol-4-yl)-2-oxo-6,7-dihydro-2H-pyrido[2,1-a]isoquinoline-3-carboxylate (50 mg, 0.094 mmol) in MeOH (1 mL) was added 10% NaOH solution (0.2 mL), and the reaction mixture was allowed to stir at RT for 2 h. The volatile was evaporated and the resulted residue was dissolved in water (5 mL), washed with DCM (10 mL×3). Then the water phase was acidified till pH=2 with 1M HCl, extracted with DCM (10 mL×5), and the combined organic phase was washed with water (10 mL×2), dried over anhydrous sodium sulfate, filtered and concentrated, the crude product was purified by preparative TLC to provide title compound (21 mg) as yellow solid. $^1$H NMR (400 MHz, DMSO-d$_6$): δ 16.62 (s, 1H), 8.76 (s, 1H), 8.30 (s, 1H), 8.01 (s, 1H), 7.72 (s, 1H), 7.58 (s, 1H), 7.57 (s, 1H), 4.60 (d, J=6.0 Hz, 1H), 4.28 (t, J=6.2 Hz, 2H), 4.00 (s, 3H), 3.56 (t, J=4.4 Hz, 2H), 3.44-3.37 (m, 1H), 3.31-3.24 (m, 2H), 2.74 (t, J=6.4 Hz, 2H), 2.43 (br, 3H), 0.74 (s, 9H). MS observed (ESI$^+$) [(M+H)$^+$]: 507.

Example 17

6-(tert-butyl)-10-methoxy-2-oxo-9-(1-(piperidin-4-yl)-1H-pyrazol-4-yl)-6,7-dihydro-2H-pyrido[2,1-a]isoquinoline-3-carboxylic Acid Hydrochloride

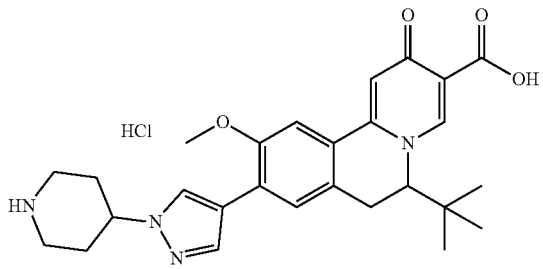 [SMILES: COc1cc2c(cc1-c1cnn(C3CCNCC3)c1)CC(C(C)(C)C)n1cc(C(=O)O)c(=O)cc1-2 ; Cl]

Step 17a: Preparation of ethyl 9-(1-(1-tert-butoxy-carbonylpiperidin-4-yl)-1H-pyrazol-4-yl)-6-(tert-butyl)-10-methoxy-2-oxo-6,7-dihydro-2H-pyrido[2,1-a]isoquinoline-3-carboxylate

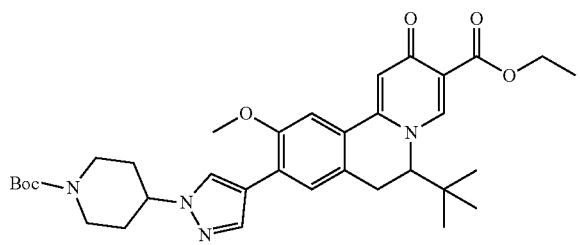 [SMILES: CCOC(=O)c1cn2c(cc1=O)-c1cc(OC)c(-c3cnn(C4CCN(C(=O)OC(C)(C)C)CC4)c3)cc1CC2C(C)(C)C]

Ethyl 9-(1-(1-tert-butoxycarbonylpiperidin-4-yl)-1H-pyrazol-4-yl]-6-(tert-butyl)-10-methoxy-2-oxo-6,7-dihydro-2H-pyrido[2,1-a]isoquinoline-3-carboxylate (100 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (1-(1-tert-(butoxycarbonyl) piperidin-4-yl)-1H-pyrazol-4-yl) boronic acid (136 mg, 0.46 mmol) according to method in example 1, step 1h.

Step 17b: Preparation of 9-(1-(1-(tert-butoxycarbonyl)piperidin-4-yl)-1H-pyrazol-4-yl)-6-(tert-butyl)-10-methoxy-2-oxo-6,7-dihydro-2H-pyrido[2,1-a]isoquinoline-3-carboxylic Acid

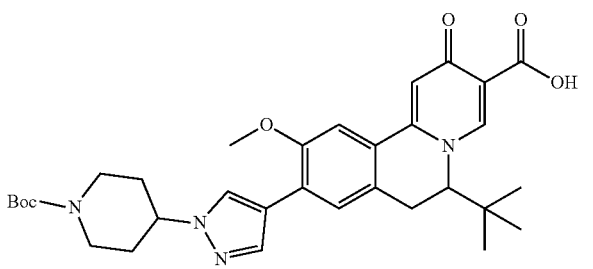 [SMILES: COc1cc2c(cc1-c1cnn(C3CCN(C(=O)OC(C)(C)C)CC3)c1)CC(C(C)(C)C)n1cc(C(=O)O)c(=O)cc1-2]

9-(1-(1-tert-(butoxycarbonyl)piperidin-4-yl)-1H-pyrazol-4-yl]-6-(tert-butyl)-10-meth oxy-2-oxo-6,7-dihydro-2H-pyrido[2,1-a]isoquinoline-3-carboxylic acid (60 mg) as yellow solid was prepared by using ethyl 9-(1-(1-(tert-butoxycarbonyl)-piperidin-4-yl)-1H-pyrazol-4-yl)-6-(tert-butyl)-10-methoxy-2-oxo-6,7-dihydro-2H-pyrido[2,1-a]isoquinoline-3-carboxylate (100 mg, 0.17 mmol) according to method in example 1, step 1i.

Step 17c: Preparation of 6-(tert-butyl)-10-methoxy-2-oxo-9-(1-(piperidin-4-yl)-1H-pyrazol-4-yl)-6,7-dihydro-2H-pyrido[2,1-a]isoquinoline-3-carboxylic Acid Hydrochloride

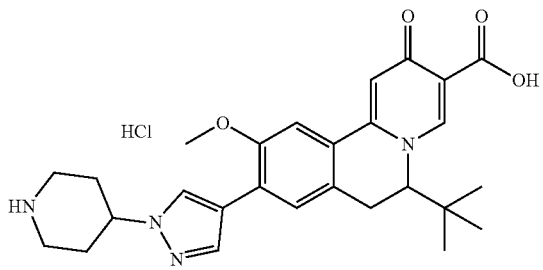 [SMILES: COc1cc2c(cc1-c1cnn(C3CCNCC3)c1)CC(C(C)(C)C)n1cc(C(=O)O)c(=O)cc1-2 ; Cl]

To a solution of 9-(1-(1-(tert-butoxycarbonyl)piperidin-4-yl)-1H-pyrazol-4-yl)-6-(tert-butyl)-10-methoxy-2-oxo-6,7-dihydro-2H-pyrido[2,1-a]isoquinoline-3-carboxylic acid (60 mg, 0.1 mmol) in dioxane was added 1 M HCl solution (5 mL), and the reaction mixture was stirred at RT for 1 h, concentrated to provide 6-(tert-butyl)-10-methoxy-2-oxo-9-(1-(piperidin-4-yl)-1H-pyrazol-4-yl)-6,7-dihydro-2H-pyrido[2,1-a]isoquinoline-3-carboxylic acid hydrochloride (47.8 mg) as yellow solid. $^1$H NMR (400 MHz, DMSO-$d_6$): δ 8.76 (s, 1H), 8.29 (s, 1H), 8.08 (s, 1H), 7.75 (s, 1H), 7.59 (s, 1H), 7.58 (s, 1H), 4.62-4.54 (m, 2H), 4.00 (s, 3H), 3.39-3.33 (m, 2H), 3.30-3.26 (m, 2H), 3.07 (s, 2H), 2.20 (s, 4H), 0.73 (s, 9H). MS observed (ESI$^+$) [(M+H)$^+$]: 477.

Example 18

6-(tert-butyl)-9-(1-isopropyl-1H-pyrazol-5-yl)-10-methoxy-2-oxo-6,7-dihydro-2H-pyrido[2,1-a]isoquinoline-3-carboxylic Acid

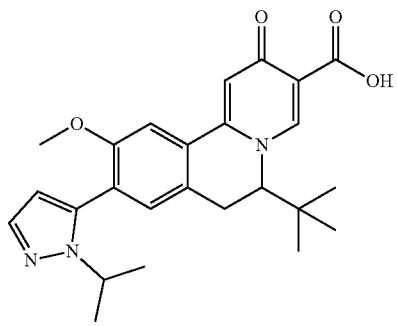 [SMILES: COc1cc2c(cc1-c1ccnn1C(C)C)CC(C(C)(C)C)n1cc(C(=O)O)c(=O)cc1-2]

Step 18a: Preparation of ethyl 6-(tert-butyl)-9-(1-isopropyl-1H-pyrazol-5-yl)-10-methoxy-2-oxo-6,7-dihydro-2H-pyrido[2,1-a]isoquinoline-3-carboxylate

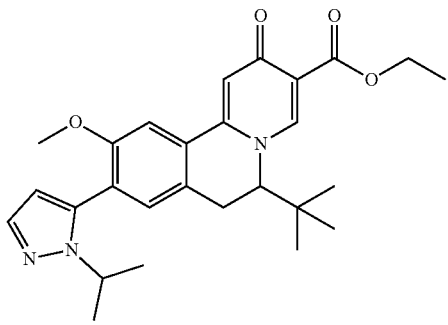 [SMILES: CCOC(=O)c1cn2c(cc1=O)-c1cc(OC)c(-c3ccnn3C(C)C)cc1CC2C(C)(C)C]

Ethyl 6-(tert-butyl)-9-(1-isopropyl-1H-pyrazol-5-yl)-10-methoxy-2-oxo-6,7-dihydro-2H-pyrido[2,1-a]isoquinoline-3-carboxylate (80 mg) as off-white solid was prepared by using ethyl 9-bromo-6-(tert-butyl)-1-methoxy-2-oxo-6,7-dihydro-2H-pyrido[2,1-a]-isoquinoline-3-carboxylate (100 mg, 0.23 mmol) and 1-isopropyl-5-(4,4,5,5-tetramethyl-1,3,2-dioxaborolan-2-yl)-1H-pyrazole (60 mg, 0.253 mmol) according to method in example 16, step 16a.

Step 18b: Preparation of 6-(tert-butyl)-9-(1-isopropyl-1H-pyrazol-5-yl)-10-methoxy-2-oxo-6,7-dihydro-2H-pyrido[2,1-a]isoquinoline-3-carboxylic Acid

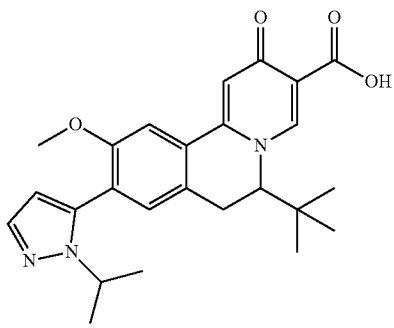 [SMILES: COc1cc2c(cc1-c1ccnn1C(C)C)CC(C(C)(C)C)n1cc(C(=O)O)c(=O)cc1-2]

6-(tert-butyl)-9-(1-isopropyl-1H-pyrazol-5-yl)-10-methoxy-2-oxo-6,7-dihydro-2H-pyrido[2,1-a]isoquinoline-3-carboxylic acid (35.7 mg) as white solid was prepared by using ethyl 6-(tert-butyl)-9-(1-isopropyl-1H-pyrazol-5-yl)-10-methoxy-2-oxo-6,7-dihydro-2H-pyrido[2,1-a]isoquinoline-3-carboxylate (80 mg, 0.17 mmol) according to method in example 16, step 16b. $^1$H NMR (400 MHz, DMSO-$d_6$): δ 16.47 (s, 1H), 8.79 (s, 1H), 7.69 (s, 1H), 7.68 (s, 1H), 7.52 (s, 1H), 7.35 (s, 1H), 6.24-6.23 (m, 1H), 4.64-4.63 (m, 1H), 4.17-4.10 (m, 1H), 3.90 (s, 3H), 3.43-3.37 (m, 2H), 1.33-1.29 (m, 6H), 0.74 (s, 9H). MS observed (ESI$^+$) [(M+H)$^+$]: 436.

Example 19

6-(tert-butyl)-9-(1,4-dimethyl-1H-pyrazol-5-yl)-10-methoxy-2-oxo-6,7-dihydro-2H-pyrido[2,1-a]isoquinoline-3-carboxylic Acid

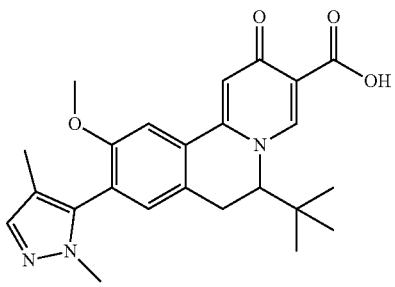 [SMILES: COc1cc2c(cc1-c1c(C)cnn1C)CC(C(C)(C)C)n1cc(C(=O)O)c(=O)cc1-2]

Step 19a: Preparation of ethyl 6-(tert-butyl)-9-(1,4-dimethyl-1H-pyrazol-5-yl)-10-methoxy-2-oxo-6,7-dihydro-2H-pyrido[2,1-a]isoquinoline-3-carboxylate

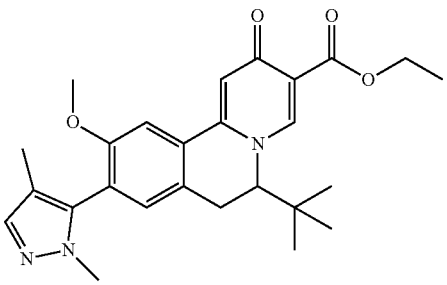 [SMILES: CCOC(=O)c1cn2c(cc1=O)-c1cc(OC)c(-c3c(C)cnn3C)cc1CC2C(C)(C)C]

Ethyl 6-(tert-butyl)-9-(1,4-dimethyl-1H-pyrazol-5-yl)-10-methoxy-2-oxo-6,7-dihydro-2H-pyrido[2,1-a]isoquinoline-3-carboxylate (40 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and 1,4-dimethyl-5-(4,4,5,5-tetramethyl-1,3,2-dioxaborolan-2-yl)-1H-pyrazole (56 mg, 0.253 mmol) according to method in example 16, step 16a.

Step 19b: Preparation of 6-(tert-butyl)-9-(1,4-dimethyl-1H-pyrazol-5-yl)-10-methoxy-2-oxo-6,7-dihydro-2H-pyrido[2,1-a]isoquinoline-3-carboxylic Acid

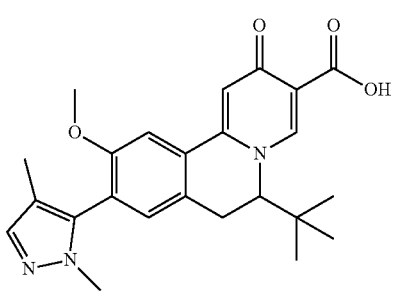 [SMILES: COc1cc2c(cc1-c1c(C)cnn1C)CC(C(C)(C)C)n1cc(C(=O)O)c(=O)cc1-2]

6-(tert-butyl)-9-(1,4-dimethyl-1H-pyrazol-5-yl)-10-methoxy-2-oxo-6,7-dihydro-2H-pyrido[2,1-a]isoquinoline-3-carboxylic acid (7.7 mg) as light yellow solid was prepared by using ethyl 6-(tert-butyl)-9-(1,4-dimethyl-1H-pyrazol-5-yl)-10-methoxy-2-oxo-6,7-dihydro-2H-pyrido[2,1-a]isoquinoline-3-carboxylate (40 mg, 0.089 mmol) according to method in example 16, step 16b. $^1$H NMR (400 MHz, DMSO-$d_6$): δ 8.79 (s, 1H), 7.69 (s, 1H), 7.68 (s, 1H), 7.33-7.32 (m, 2H), 4.65-4.64 (m, 1H), 3.91 (s, 3H), 3.57 (s, 3H), 3.44-3.37 (m, 2H), 1.87 (s, 3H), 0.74 (s, 9H). MS observed (ESI$^+$) [(M+H)$^+$]: 422.

Example 20

6-(tert-butyl)-9-(1-carboxymethyl-1H-pyrazol-4-yl)-10-methoxy-2-oxo-6,7-dihydro-2H-pyrido[2,1-a]isoquinoline-3-carboxylic Acid Step 20a: Preparation of ethyl 6-(tert-butyl)-9-(1-(2-ethoxy-2-oxoethyl)-1H-pyrazol-4-yl)-10-methoxy-2-oxo-6,7-dihydro-2H-pyrido[2,1-a]isoquinoline-3-carboxylate

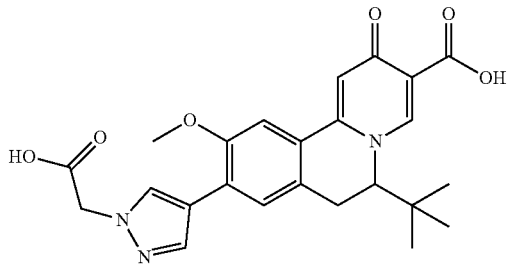 [SMILES: COc1cc2c(cc1-c1cnn(CC(=O)O)c1)CC(C(C)(C)C)n1cc(C(=O)O)c(=O)cc1-2]

Ethyl 6-(tert-butyl)-9-(1-(2-ethoxy-2-oxoethyl)-1H-pyrazol-4-yl]-10-methoxy-2-oxo-6,7-dihydro-2H-pyrido[2,1-a]isoquinoline-3-carboxylate (30 mg) as white solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and ethyl 2-bromoacetate (198 mg, 1.2 mmol) according to method in example 2, step 2a.

Step 20b: Preparation of 6-(tert-butyl)-9-(1-carboxymethyl-1H-pyrazol-4-yl)-10-methoxy-2-oxo-6,7-dihydro-2H-pyrido[2,1-a]isoquinoline-3-carboxylic Acid

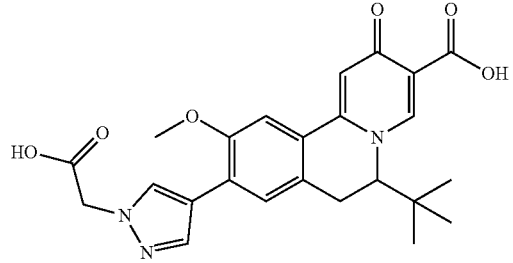 [SMILES: COc1cc2c(cc1-c1cnn(CC(=O)O)c1)CC(C(C)(C)C)n1cc(C(=O)O)c(=O)cc1-2]

6-(tert-butyl)-9-(1-carboxymethyl-1H-pyrazol-4-yl)-10-methoxy-2-oxo-6,7-dihydro-2H-pyrido[2,1-a]isoquinoline-3-carboxylic acid (11.3 mg) as white solid was prepared by using ethyl 6-(tert-butyl)-9-(1-(2-ethoxy-2-oxoethyl)-1H-pyrazol-4-yl)-10-methoxy-2-oxo-6,7-dihydro-2H-pyrido[2,1-a]isoquinoline-3-carboxylate (30 mg, 0.06 mmol) according to method in example 2, step 2b. $^1$H NMR (400 MHz, DMSO-$d_6$): δ 8.76 (s, 1H), 8.26 (s, 1H), 8.02 (s, 1H), 7.74 (s, 1H), 7.58 (s, 1H), 7.57 (s, 1H), 4.89 (s, 2H), 4.61 (d, J=6.0 Hz, 1H), 4.00 (s, 3H), 3.45-3.43 (m, 2H), 0.74 (s, 9H). MS observed (ESI$^+$) [(M+H)$^+$]: 452.

Example 21

Ethyl 6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylate

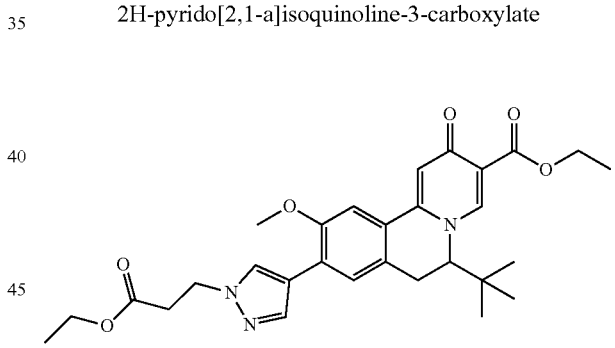

Step 21: Preparation of ethyl 6-(tert-butyl)-9-(1-(3-ethoxy-3-oxopropyl)-1H-pyrazolo-4-yl)-10-methoxy-2-oxo-6,7-dihydro-2H-pyrido[2,1-a]isoquinoline-3-carboxylate

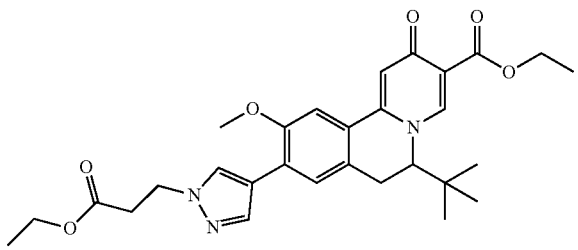 [SMILES: CCOC(=O)CCn1cc(-c2cc3c(cc2OC)-c2cc(=O)c(C(=O)OCC)cn2C(C(C)(C)C)C3)cn1]

Ethyl 6-(tert-butyl)-9-(1-(3-ethoxy-3-oxopropyl)-1H-pyrazolo-4-yl)-10-methoxy-2-oxo-6,7-dihydro-2H-pyrido[2,1-a]isoquinoline-3-carboxylate (312 mg) as white solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (400 mg, 0.95 mmol) and ethyl 3-bromopropionate (1.7 g, 95 mmol) according to method in example 2, step 2a. $^1$H NMR (DMSO-$d_6$, 400 MHz): δ 8.35 (s, 1H), 8.23 (s, 1H), 8.00 (s, 1H), 7.65 (s, 1H), 7.43 (s, 1H), 7.03 (s, 1H), 4.41-4.35 (m, 2H), 4.22 (q, J=7.2 Hz, 2H), 4.08 (q, J=7.2 Hz, 2H), 3.97 (s, 3H), 3.29-3.17 (m, 2H), 2.89 (t, J=6.8 Hz, 2H), 1.27 (t, J=7.2 Hz, 3H), 1.16 (t, J=7.2 Hz, 3H), 0.73 (s, 9H). MS observed (ESI$^+$) [(M+H)$^+$]: 522.

Example 22

6-(tert-butyl)-9-(1-(2-carboxyethyl)-1H-pyrazol-4-yl)-10-methoxy-2-oxo-6,7-dihydro-2H-pyrido[2,1-a]isoquinoline-3-carboxylic Acid

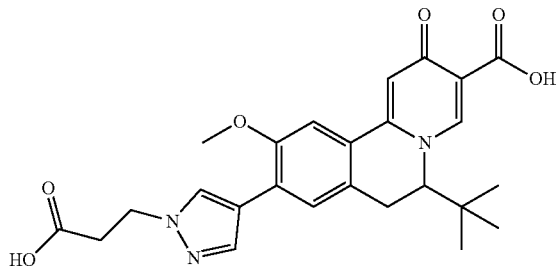 [SMILES: COc1cc2c(cc1-c1cnn(CCC(=O)O)c1)CC(C(C)(C)C)n1cc(C(=O)O)c(=O)cc1-2]

Step 22: Preparation of 6-(tert-butyl)-9-(1-(2-carboxyethyl)-1H-pyrazol-4-yl)-10-methoxy-2-oxo-6,7-dihydro-2H-pyrido[2,1-a]isoquinoline-3-carboxylic Acid

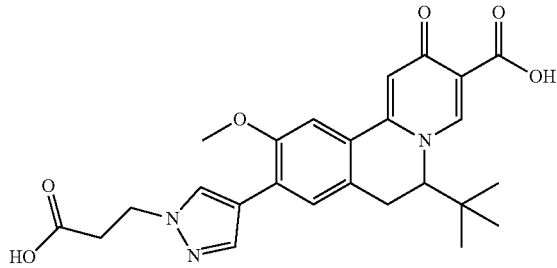 [SMILES: COc1cc2c(cc1-c1cnn(CCC(=O)O)c1)CC(C(C)(C)C)n1cc(C(=O)O)c(=O)cc1-2]

6-(tert-butyl)-9-(1-(2-carboxyethyl)-1H-pyrazol-4-yl)-10-methoxy-2-oxo-6,7-dihydro-2H-pyrido[2,1-a]isoquinoline-3-carboxylic acid (231.1 mg) as white solid was prepared by using ethyl 6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylate (312 mg, 0.6 mmol) according to method in example 2, step 2b.

$^1$H NMR (400 MHz, DMSO-$d_6$): δ 16.63 (s, 1H), 12.41 (s, 1H), 8.76 (s, 1H), 8.26 (s, 1H), 8.02 (s, 1H), 7.72 (s, 1H), 7.59 (s, 1H), 7.57 (s, 1H), 4.61 (d, J=6.0 Hz, 1H), 4.36 (t, J=6.4 Hz, 2H), 4.00 (s, 3H), 3.44-3.37 (m, 1H), 3.30-3.25 (m, 1H), 2.83 (t, J=6.8 Hz, 2H), 0.73 (s, 9H). MS observed (ESI$^+$) [(M+H)$^+$]: 466.

Example 23

6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylic Acid

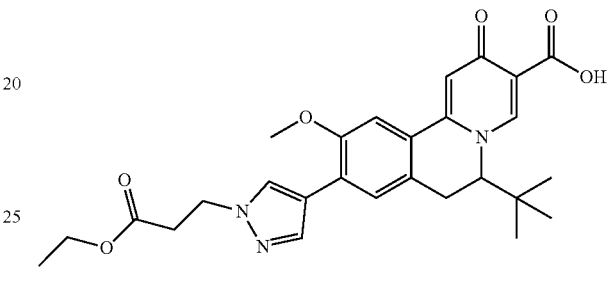

Step 23: Preparation of 6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylic Acid

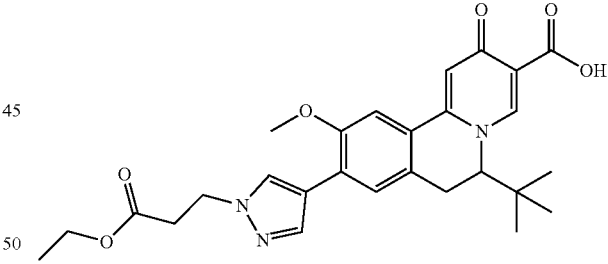

6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylic acid (7.1 mg) as white solid was prepared by using 6-(tert-butyl)-10-methoxy-2-oxo-9-(1H-pyrazol-4-yl)-6,7-dihydro-2H-pyrido[2,1-a]isoquinoline-3-carboxylic acid (60 mg, 0.15 mmol) and ethyl 3-bromopropionate (276 mg, 1.5 mmol) according to method in example 2, step 2a. $^1$H NMR (400 MHz, DMSO-$d_6$): δ 16.62 (s, 1H), 8.76 (s, 1H), 8.26 (s, 1H), 8.02 (s, 1H), 7.72 (s, 1H), 7.59 (s, 1H), 7.57 (s, 1H), 4.61 (d, J=6.0 Hz, 1H), 4.40 (t, J=6.8 Hz, 2H), 4.06 (q, J=7.2 Hz, 2H), 4.00 (s, 3H), 3.29-3.23 (m, 2H), 2.90 (t, J=6.4 Hz, 2H), 1.16 (t, J=7.2 Hz, 3H), 0.73 (s, 9H). MS observed (ESI$^+$) [(M+H)$^+$]: 494.

Example 24

6-(tert-butyl)-9-(1-(3-carboxypropyl)-1H-pyrazol-4-yl)-10-methoxy-2-oxo-6,7-dihydro-2H-pyrido[2,1-a]isoquinoline-3-carboxylic Acid

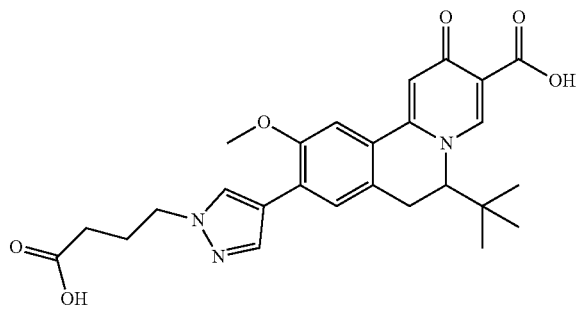 [SMILES: COc1cc2c(cc1-c1cnn(CCCC(=O)O)c1)CC(C(C)(C)C)n1cc(C(=O)O)c(=O)cc1-2]

Step 24a: Preparation of ethyl 6-(tert-butyl)-9-(1-(4-ethoxy-4-oxobutyl)-1H-pyrazol-4-yl)-10-methoxy-2-oxo-6,7-dihydro-2H-pyrido[2,1-a]isoquinoline-3-carboxylate

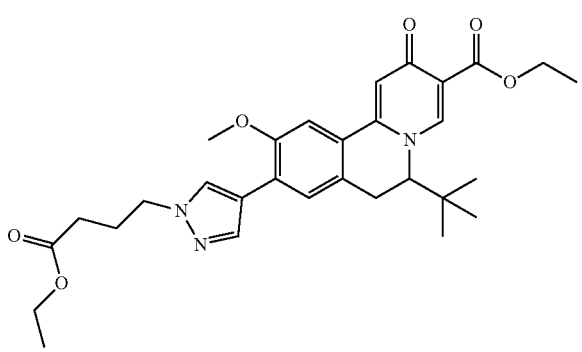 [SMILES: CCOC(=O)CCCn1cc(-c2cc3c(cc2OC)-c2cc(=O)c(C(=O)OCC)cn2C(C(C)(C)C)C3)cn1]

Ethyl 6-(tert-butyl)-9-(1-(4-ethoxy-4-oxobutyl)-1H-pyrazol-4-yl)-10-methoxy-2-oxo-6,7-dihydro-2H-pyrido[2,1-a]isoquinoline-3-carboxylate (30 mg) as yellow solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and ethyl 4-bromobutyrate (232 mg, 1.2 mmol) according to method in example 2, step 2a.

Step 24b: Preparation of 6-(tert-butyl)-9-(1-(3-carboxypropyl)-1H-pyrazol-4-yl)-10-methoxy-2-oxo-6,7-dihydro-2H-pyrido[2,1-a]isoquinoline-3-carboxylic Acid

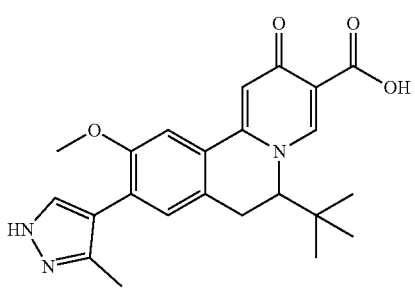 [SMILES: COc1cc2c(cc1-c1c[nH]nc1C)CC(C(C)(C)C)n1cc(C(=O)O)c(=O)cc1-2]

6-(tert-butyl)-9-(1-(3-carboxypropyl)-1H-pyrazol-4-yl)-10-methoxy-2-oxo-6,7-dihydro-2H-pyrido[2,1-a]isoquinoline-3-carboxylic acid (15.2 mg) as yellow solid was prepared by using ethyl 6-(tert-butyl)-9-(1-(4-ethoxy-4-oxobutyl)-1H-pyrazol-4-yl)-10-methoxy-2-oxo-6,7-dihydro-2H-pyrido[2,1-a]isoquinoline-3-carboxylate (30 mg, 0.06 mmol) according to method in example 2, step 2b. $^1$H NMR (400 MHz, DMSO-$d_6$): δ 8.76 (s, 1H), 8.26 (s, 1H), 8.03 (s, 1H), 7.73 (s, 1H), 7.58 (s, 1H), 7.57 (s, 1H), 4.61 (d, J=6.0 Hz, 1H), 4.17 (t, J=6.8 Hz, 2H), 4.00 (s, 3H). 3.43-3.42 (m, 2H), 2.24-2.18 (m, 2H), 2.05-2.00 (m, 2H), 0.73 (s, 9H). MS observed (ESI$^+$) [(M+H)$^+$]: 480.

Example 25

6-(tert-butyl)-10-methoxy-9-(3-methyl-1H-pyrazol-4-yl)-2-oxo-6,7-dihydro-2H-pyrido[2,1-a]isoquinoline-3-carboxylic Acid

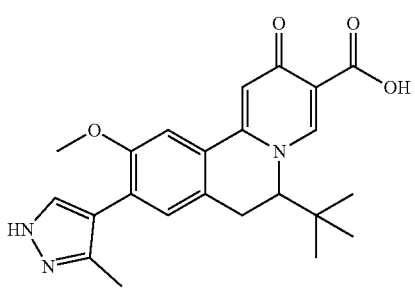 [SMILES: COc1cc2c(cc1-c1c[nH]nc1C)CC(C(C)(C)C)n1cc(C(=O)O)c(=O)cc1-2]

Step 25a: Preparation of 3-methyl-4-(4,4,5,5-tetramethyl-1,3,2-dioxaborolan-2-yl)-1H-pyrazole

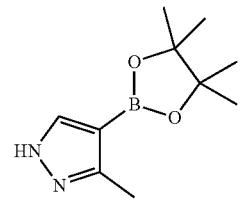

To a solution of 3-methyl-4-(4,4,5,5-tetramethyl-1,3,2-dioxaborolan-2-yl)-1H-pyrazole (1.0 gm 4.81 mmol) in CH$_3$CN (20 mL) was added di-tert-butyl dicarbonate (1.26 g, 5.77 mmol) and trimethylamine (730 mg, 7.21 mmol) under nitrogen, and the reaction mixture was stirred at RT for 16 h. TLC showed that the starting material was completely consumed. Then, the mixture was concentrated under reduced pressure and purified by flash column chromatography to provide 3-methyl-4-(4,4,5,5-tetramethyl-1,3,2-dioxaborolan-2-yl)-1H-pyrazole (1.2 g) as light yellow solid.

Step 25b: Preparation of ethyl 9-(1-tert-butoxycarbonyl-3-methyl-1H-pyrazol-4-yl)-6-(tert-butyl)-10-methoxy-2-oxo-6,7-dihydro-2H-pyrido[2,1-a]isoquinoline-3-carboxylate

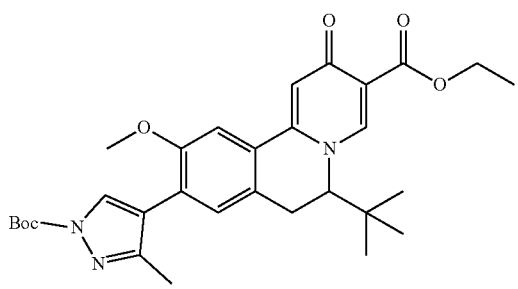 [SMILES: CCOC(=O)c1cn2c(cc1=O)-c1cc(OC)c(-c3cn(C(=O)OC(C)(C)C)nc3C)cc1CC2C(C)(C)C]

Ethyl 9-(1-tert-butoxycarbonyl-3-methyl-1H-pyrazol-4-yl)-6-(tert-butyl)-10-methoxy-2-oxo-6,7-dihydro-2H-pyrido[2,1-a]isoquinoline-3-carboxylate (140 mg) as orange solid was prepared by using ethyl 9-bromo-6-(tert-butyl)-10-methoxy-2-oxo-6,7-dihydro-2H-pyrido[2,1-a]isoquinoline-3-carboxylate (150 mg, 0.345 mmol) and 3-methyl-4-(4,4,5,5-tetramethyl-1,3,2-dioxaborolan-2-yl)-1H-pyrazole (128 mg, 0.414 mmol) according to method in example 16, step 16a.

Step 25c: Preparation of 6-(tert-butyl)-10-methoxy-9-(3-methyl-1H-pyrazol-4-yl)-2-oxo-6,7-dihydro-2H-pyrido[2,1-a]isoquinoline-3-carboxylic Acid

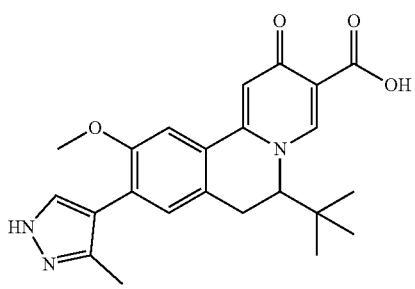 [SMILES: COc1cc2c(cc1-c1c[nH]nc1C)CC(C(C)(C)C)n1cc(C(=O)O)c(=O)cc1-2]

6-(tert-butyl)-10-methoxy-9-(3-methyl-1H-pyrazol-4-yl)-2-oxo-6,7-dihydro-2H-pyrido[2,1-a]isoquinoline-3-carboxylic acid (10 mg) as white solid was prepared by using ethyl 9-(1-tert-butoxycarbonyl-3-methyl-1H-pyrazol-4-yl)-6-(tert-butyl)-10-methoxy-2-oxo-6,7-dihydro-2H-pyrido[2,1-a]isoquinoline-3-carboxylate (140 mg, 0.261 mmol) according to method in example 16, step 16b. $^1$H NMR (400 MHz, DMSO-d$_6$): δ 16.62 (s, 1H), 8.76 (s, 1H), 7.60 (s, 1H), 7.56 (s, 1H), 7.33 (s, 1H), 4.61 (d, J=5.6 Hz, 1H), 3.90 (s, 3H), 3.43-3.35 (m, 2H), 2.56 (s, 3H), 0.74 (s, 9H). MS observed (ESI$^+$) [(M+H)$^+$]: 408.

Example 26

6-(tert-butyl)-9-(1-(1-carboxyethyl)-1H-pyrazol-4-yl)-10-methoxy-2-oxo-6,7-dihydro-2H-pyrido[2,1-a]isoquinoline-3-carboxylic Acid

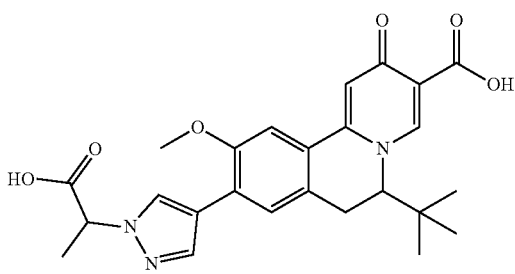 [SMILES: COc1cc2c(cc1-c1cnn(C(C)C(=O)O)c1)CC(C(C)(C)C)n1cc(C(=O)O)c(=O)cc1-2]

Step 26a: Preparation of ethyl 6-(tert-butyl)-9-(1-(1-ethoxy-1-oxoprop-2-yl)-1H-pyrazol-4-yl)-10-methoxy-2-oxo-6,7-dihydro-2H-pyrido[2,1-a]isoquinoline-3-carboxylate

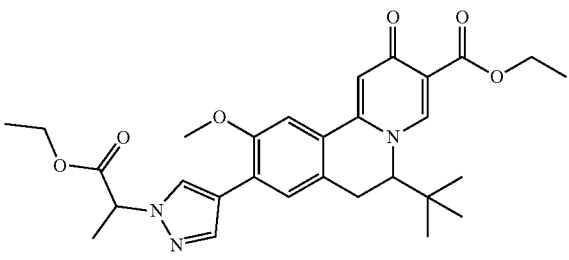 [SMILES: CCOC(=O)c1cn2c(cc1=O)-c1cc(OC)c(-c3cnn(C(C)C(=O)OCC)c3)cc1CC2C(C)(C)C]

Ethyl 6-(tert-butyl)-9-(1-(1-ethoxy-1-oxoprop-2-yl)-1H-pyrazol-4-yl]-10-methoxy-2-oxo-6,7-dihydro-2H-pyrido[2,1-a]isoquinoline-3-carboxylate (20 mg) as white solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and ethyl 2-bromopropionate (215 mg, 1.2 mmol) according to method in example 2, step 2a.

Step 26b: Preparation of 6-(tert-butyl)-9-(1-(1-carboxyethyl)-1H-pyrazol-4-yl)-10-methoxy-2-oxo-6,7-dihydro-2H-pyrido[2,1-a]isoquinoline-3-carboxylic Acid

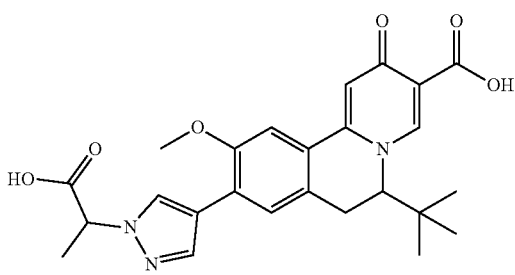 [SMILES: COc1cc2c(cc1-c1cnn(C(C)C(=O)O)c1)CC(C(C)(C)C)n1cc(C(=O)O)c(=O)cc1-2]

6-(tert-butyl)-9-(1-(1-carboxyethyl)-1H-pyrazol-4-yl]-10-methoxy-2-oxo-6,7-dihydro-2H-pyrido[2,1-a]isoquinoline-3-carboxylic acid (7.6 mg) as white solid was prepared by using ethyl 6-(tert-butyl)-9-(1-(1-ethoxy-1-oxopropyl-2-yl)-1H-pyrazol-4-yl)-10-methoxy-2-oxo-6,7-dihydro-2H-pyrido[2,1-a]isoquinoline-3-carboxylate (20 mg. 0.04 mmol) according to method in example 2, step 2b. $^1$H NMR (400 MHz, DMSO-d$_6$): δ 8.75 (s, 1H), 8.32 (s, 1H), 8.02 (s, 1H), 7.74 (s, 1H), 7.59 (s, 1H), 7.57 (s, 1H), 5.11 (d, J=7.2 Hz, 1H), 4.61 (d, J=6.0 Hz, 1H), 4.00 (s, 3H), 3.43-3.39 (m, 2H), 1.67 (d, J=7.6 Hz, 3H), 0.74 (s, 9H). MS observed (ESI$^+$) [(M+H)$^+$]: 466.

Example 27

6-(tert-butyl)-9-(1-(2-carboxyprop-2-yl)-1H-pyrazol-4-yl)-10-methoxy-2-oxo-6,7-dihydro-2H-pyrido[2,1-a]isoquinoline-3-carboxylic Acid

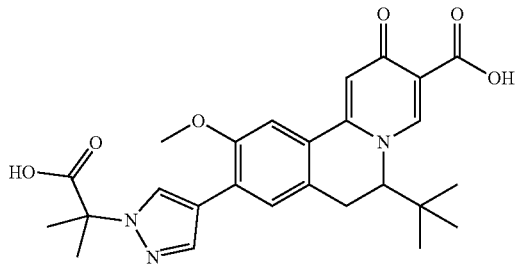 [SMILES: COc1cc2c(cc1-c1cnn(C(C)(C)C(=O)O)c1)CC(C(C)(C)C)n1cc(C(=O)O)c(=O)cc1-2]

Step 27a: Preparation of ethyl 6-(tert-butyl)-9-(1-(1-ethoxy-2-methyl-1-oxoprop-2-yl)-1H-pyrazol-4-yl)-10-methoxy-2-oxo-6,7-dihydro-2H-pyrido[2,1-a]isoquinoline-3-carboxylate

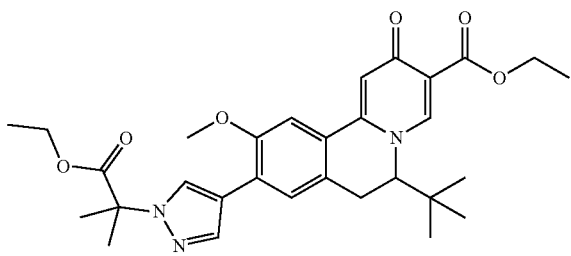 [SMILES: CCOC(=O)c1cn2c(cc1=O)-c1cc(OC)c(-c3cnn(C(C)(C)C(=O)OCC)c3)cc1CC2C(C)(C)C]

Ethyl 6-(tert-butyl)-9-(1-(1-ethoxy-2-methyl-1-oxoprop-2-yl)-1H-pyrazol-4-yl)-10-methoxy-2-oxo-6,7-dihydro-2H-pyrido[2,1-a]isoquinoline-3-carboxylate (20 mg) as yellow solid was prepared by using ethyl 6-(tert-butyl)-10-methoxy-2-oxo-9-(1H-pyrazol-4-yl)-6,7-dihydro-2H-pyrido[2,1-a]isoquinoline-3-carboxylate (50 mg, 0.12 mmol) and ethyl 2-bromo-2-methylpropionate (232 mg, 1.2 mmol) according to method in example 2, step 2a.

Step 27b: Preparation of 6-(tert-butyl)-9-(1-(2-carboxyprop-2-yl)-1H-pyrazol-4-yl)-10-methoxy-2-oxo-6,7-dihydro-2H-pyrido[2,1-a]isoquinoline-3-carboxylic Acid

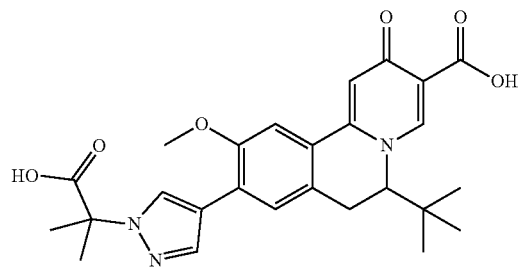 [SMILES: COc1cc2c(cc1-c1cnn(C(C)(C)C(=O)O)c1)CC(C(C)(C)C)n1cc(C(=O)O)c(=O)cc1-2]

6-(tert-butyl)-9-(1-(2-carboxyprop-2-yl)-1H-pyrazol-4-yl)-10-methoxy-2-oxo-6,7-dihydro-2H-pyrido[2,1-a]isoquinoline-3-carboxylic acid (11.8 mg) as yellow solid was prepared by using ethyl 6-(tert-butyl)-9-(1-(1-ethoxy-2-methyl-1-oxoprop-2-yl)-1H-pyrazol-4-yl)-10-methoxy-2-oxo-6,7-dihydro-2H-pyrido[2,1-a]isoquinoline-3-carboxylate (20 mg, 0.04 mmol) according to method in example 2, step 2b. $^1$H NMR (400 MHz, DMSO-d$_6$): δ 8.76 (s, 1H), 8.35 (s, 1H), 8.04 (s, 1H), 7.76 (s, 1H), 7.59 (s, 1H), 7.58 (s, 1H), 4.61 (d, J=6.0 Hz, 1H), 4.00 (s, 3H), 3.44-3.40 (m, 2H), 1.78 (s, 6H), 0.74 (s, 9H). MS observed (ESI$^+$) [(M+H)$^+$]: 480.

Example 28

6-(tert-butyl)-10-methoxy-9-(2-methylthiazol-5-yl)-2-oxo-6,7-dihydro-2H-pyrido[2,1-a]isoquinoline-3-carboxylic Acid

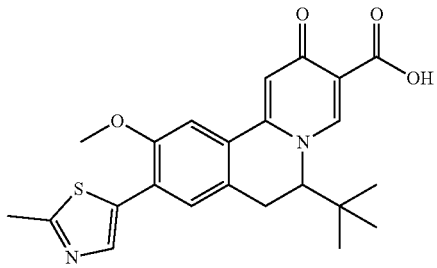

Step 28a: Preparation of ethyl 6-(tert-butyl)-10-methoxy-9-(2-methylthiazol-5-yl)-2-oxo-6,7-dihydro-2H-pyrido[2,1-a]isoquinoline-3-carboxylate

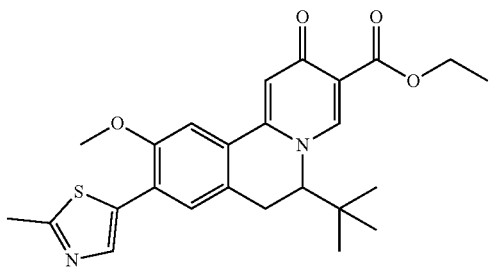 [SMILES: CCOC(=O)c1cn2c(cc1=O)-c1cc(OC)c(-c3cnc(C)s3)cc1CC2C(C)(C)C]

To a solution of ethyl 9-bromo-6-(tert-butyl)-10-methoxy-2-oxo-6,7-dihydro-2H-pyrido[2,1-a]isoquinoline-3-carboxylate (100 mg, 0.23 mmol) in toluene (50 mL) and water (5 mL) was added (2-methylthiazol-5-yl)boronic acid (49 mg, 0.35 mmol), sodium carbonate (49 mg, 0.46 mmol) and Pd(PPh₃)₄ (13 mg, 0.01 mmol) under nitrogen atmosphere, and the reaction mixture was allowed to heat at reflux for 16 h. Then, the reaction mixture was partitioned between DCM (20 mL) and water (30 mL), and the organic phase was washed with brine, dried over anhydrous sodium sulfate, filtered, and concentrated under reduced pressure, the resulted residue was purified by preparative TLC to provide ethyl 6-(tert-butyl)-10-methoxy-9-(2-methylthiazol-5-yl)-2-oxo-6,7-dihydro-2H-pyrido [2,1-a]isoquinoline-3-carboxylate (10 mg) as white solid.

Step 28b: Preparation of 6-(tert-butyl)-10-methoxy-9-(2-methylthiazol-5-yl)-2-oxo-6,7-dihydro-2H-pyrido[2,1-a]isoquinoline-3-carboxylic Acid

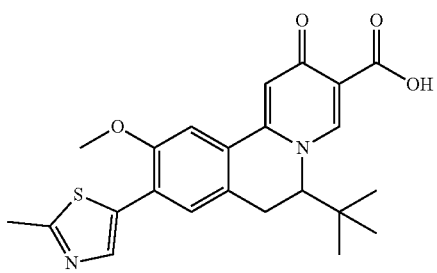 [SMILES: COc1cc2c(cc1-c1cnc(C)s1)CC(C(C)(C)C)n1cc(C(=O)O)c(=O)cc1-2]

6-(tert-butyl)-10-methoxy-9-(2-methylthiazol-5-yl)-2-oxo-6,7-dihydro-2H-pyrido[2,1-a]isoquinoline-3-carboxylic acid (7.6 mg) as yellow solid was prepared by using ethyl 6-(tert-butyl)-10-methoxy-9-(2-methylthiazol-5-yl)-2-oxo-6,7-dihydro-2H-pyrido-[2,1-a]isoquinoline-3-carboxylate (10 mg, 0.03 mmol) according to method in example 1, step 1i. ¹H NMR (400 MHz, DMSO-d₆): δ 16.52 (s, 1H), 8.78 (s, 1H), 8.26 (s, 1H), 7.89 (s, 1H), 7.69 (s, 1H), 7.67 (s, 1H), 4.64 (d, J=5.2 Hz, 1H), 4.03 (s, 3H), 3.41-3.36 (m, 2H), 2.68 (s, 3H), 0.74 (s, 9H). MS observed (ESI⁺) [(M+H)⁺]: 425.

Example 29

6-(tert-butyl)-10-methoxy-2-oxo-9-(1H-1,2,4-triazol-3-yl)-6,7-dihydro-2H-pyrido[2,1-a]isoquinoline-3-carboxylic Acid

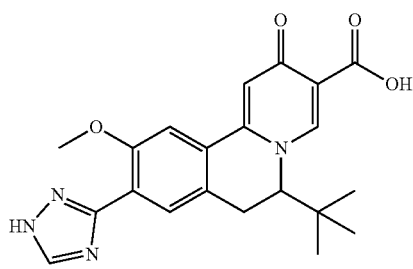 [SMILES: COc1cc2c(cc1-c1nc[nH]n1)CC(C(C)(C)C)n1cc(C(=O)O)c(=O)cc1-2]

Step 29a: Preparation of 6-(tert-butyl)-9-cyano-10-methoxy-2-oxo-6,7-dihydro-2H-pyrido[2,1-a]isoquinoline-3-carboxylic Acid

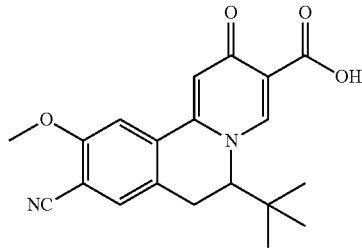 [SMILES: COc1cc2c(cc1C#N)CC(C(C)(C)C)n1cc(C(=O)O)c(=O)cc1-2]

To a solution of ethyl 9-bromo-6-(tert-butyl)-10-methoxy-2-oxo-6,7-dihydro-2H-pyrido[2,1-a]isoquinoline-3-carboxylate (1.6 g, 3.68 mmol) in NMP (20 mL) was added CuCN (660 mg, 7.37 mmol), and the reaction mixture was heated at 150° C. for 16 h. Then, the mixture was concentrated under reduced pressure, and the resulted residue was purified by column chromatography to provide 6-(tert-butyl)-9-cyano-10-methoxy-2-oxo-6,7-dihydro-2H-pyrido[2,1-a]isoquinoline-3-carboxylic acid (1.2 g).

Step 29b: Preparation of 6-(tert-butyl)-9-carbamoyl-10-methoxy-2-oxo-6,7-dihydro-2H-pyrido[2,1-a]isoquinoline-3-carboxylic Acid To a solution of 6-(tert-butyl)-9-cyano-10-methoxy-2-oxo-6,7-dihydro-2H-pyrido[2,1-a]isoquinoline-3-carboxylic acid (1.3 g, 3.42 mmol) was added dropwise con. Sulfuric acid (20 mL), and the reaction mixture was allowed to heat at reflux for 1 h. Then, the mixture was slowly added to ice-water (100 mL), extracted with DCM (200 mL), and the organic phase was washed with brine (100 mL), dried over anhydrous sodium sulfate, filtered and concentrate under reduce pressure, the resulted residue was purified by column chromatography to provide 6-(tert-butyl)-9-carbamoyl-10-methoxy-2-oxo-6,7-dihydro-2H-pyrido[2,1-a]isoquinoline-3-carboxylic acid (800 mg) as white solid.

Step 29c: Preparation of methyl 6-(tert-butyl)-10-methoxy-2-oxo-9-(1H-1,2,4-triazol-3-yl)-6,7-dihydro-2H-pyrido[2,1-a]isoquinoline-3-carboxylate

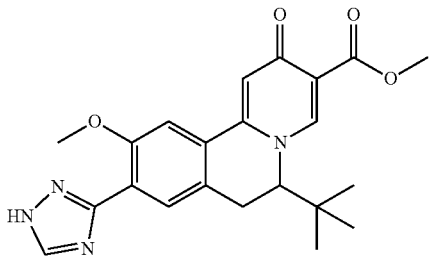 [SMILES: COC(=O)c1cn2c(cc1=O)-c1cc(OC)c(-c3nc[nH]n3)cc1CC2C(C)(C)C]

A solution of 6-(tert-butyl)-9-carbamoyl-10-methoxy-2-oxo-6,7-dihydro-2H-pyrido[2,1-a]isoquinoline-3-carboxylic acid (800 mg, 2.16 mmol) in DMF-DMAc (5 mL) was allowed to heat at reflux for 1 h. Then, the volatiles were evaporated and the resulted residue was dissolved into EtOH (5 mL) ready for next stage. Hydrazine hydrate (0.6 mL) was added slowly to a mixture of EtOH (25 mL) and acetic acid (6 mL) at ice-bath, then, to this solution was added the EtOH solution (5 mL) prepared from previous stage, and the reaction mixture was allowed to stir at RT for 16 h. The mixture was partitioned between DCM (100 mL) and water (100 mL), and the organic phase was washed with brine, dried over anhydrous sodium sulfate, filtered and concentrated under reduced pressure, the resulted residue was purified by column chromatography to provide methyl 6-(tert-butyl)-10-methoxy-2-oxo-9-(1H-1,2,4-triazol-3-yl)-6,7-dihydro-2H-pyrido[2,1-a]isoquinoline-3-carboxylate (370 mg) as white solid.

Step 29d: Preparation of 6-(tert-butyl)-10-methoxy-2-oxo-9-(1H-1,2,4-triazol-3-yl)-6,7-dihydro-2H-pyrido[2,1-a]isoquinoline-3-carboxylic Acid

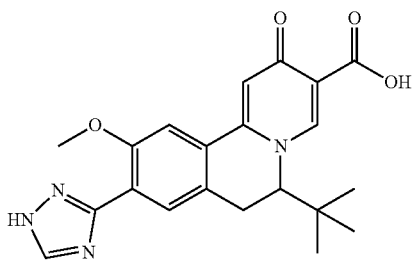 [SMILES: COc1cc2c(cc1-c1nc[nH]n1)CC(C(C)(C)C)n1cc(C(=O)O)c(=O)cc1-2]

6-(tert-butyl)-10-methoxy-2-oxo-9-(1H-1,2,4-triazol-3-yl)-6,7-dihydro-2H-pyrido[2,1-a]isoquinoline-3-carboxylic acid (5.3 mg) as white solid was prepared by using methyl 6-(tert-butyl)-10-methoxy-2-oxo-9-(1H-1,2,4-triazol-3-yl)-6,7-dihydro-2H-pyrido-[2,1-a]isoquinoline-3-carboxylate (20 mg, 0.05 mmol) according to method in example 2, step 2b. $^1$H NMR (400 MHz, DMSO-$d_6$): δ 16.46 (s, 1H), 13.93 (s, 1H), 8.80 (s, 1H), 8.16 (s, 1H), 8.09 (s, 1H), 7.74 (s, 1H), 7.72 (s, 1H), 4.66 (s, 1H), 4.09 (s, 3H), 3.44 (s, 2H), 0.73 (s, 9H). MS observed (ESI$^+$) [(M+H)$^+$]: 395.

Example 30

6-(tert-butyl)-9-(1-(carboxymethyl)-1H-1,2,4-triazol-3-yl)-10-methoxy-2-oxo-6,7-dihydro-2H-pyrido[2,1-a]isoquinoline-3-carboxylic Acid

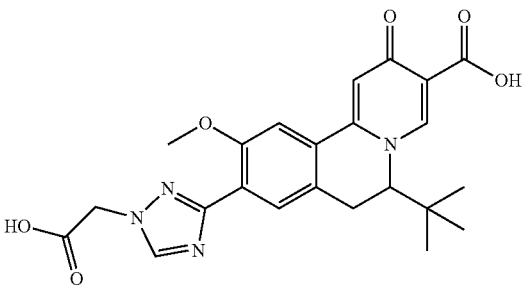 [SMILES: COc1cc2c(cc1-c1ncn(CC(=O)O)n1)CC(C(C)(C)C)n1cc(C(=O)O)c(=O)cc1-2]

Step 30a: Preparation of methyl 6-(tert-butyl)-9-(1-(2-ethoxy-2-oxoethyl)-1H-1,2,4-triazol-3-yl)-10-methoxy-2-oxo-6,7-dihydro-2H-pyrido[2,1-a]isoquinoline-3-carboxylate

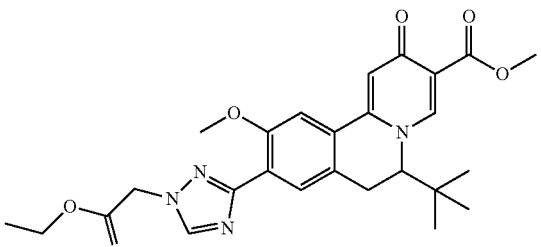

To a solution of methyl 6-(tert-butyl)-10-methoxy-2-oxo-9-(1H-1,2,4-triazol-3-yl)-6,7-dihydro-2H-pyrido[2,1-a]isoquinoline-3-carboxylate (40 mg, 0.1 mmol) in DMF (1 mL) was added ethyl 2-bromoacetate (163 mg, 1 mmol) and K$_2$CO$_3$ (136 mg, 1 mmol), and the reaction mixture was allowed to stir at RT for 16 h. Then, the mixture was partitioned between DCM (10 mL) and water (5 mL), the water phase was extracted with DCM (10 mL×2), and the combined organic phase was washed with brine (10 mL×3), dried over anhydrous sodium sulfate, filtered and concentrated, and the resulted residue was purified by preparative TLC to give methyl 6-(tert-butyl)-9-(1-(2-ethoxy-2-oxoethyl)-1H-1,2,4-triazol-3-yl)-10-methoxy-2-oxo-6,7-dihydro-2H-pyrido[2,1-a]isoquinoline-3-carboxylate (30 mg) as white solid.

Step 30b: Preparation of 6-(tert-butyl)-9-(1-(carboxymethyl)-1H-1,2,4-triazol-3-yl)-10-methoxy-2-oxo-6,7-dihydro-2H-pyrido[2,1-a]isoquinoline-3-carboxylic Acid

Example 32

6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylic Acid

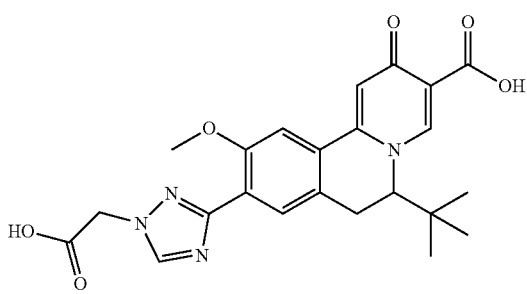 [SMILES: COc1cc2c(cc1-c1ncn(CC(=O)O)n1)CC(C(C)(C)C)n1cc(C(=O)O)c(=O)cc1-2]

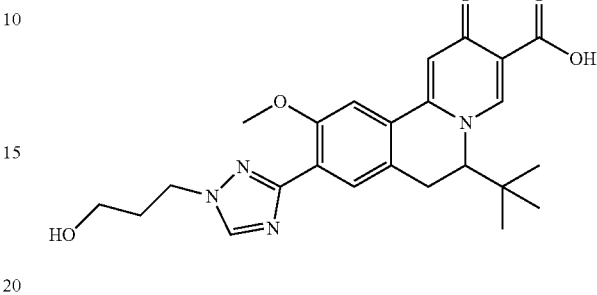

Step 31: Preparation of methyl 6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylate and methyl 6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylate 6-(tert-butyl)-9-(1-(carboxymethyl)-1H-1,2,4-triazol-3-yl)-10-methoxy-2-oxo-6,7-dihydro-2H-pyrido[2,1-a]isoquinoline-3-carboxylic acid (2.5 mg) as white solid was prepared by using methyl 6-(tert-butyl)-9-(1-(2-ethoxy-2-oxoethyl)-1H-1,2,4-triazol-3-yl)-10-methoxy-2-oxo-6,7-dihydro-2H-pyrido[2,1-a]isoquinoline-3-carboxylate (30 mg, 0.06 mmol) according to method in example 2, step 2b. $^1$H NMR (400 MHz, DMSO-$d_6$): δ 16.53 (s, 1H), 8.79 (s, 1H), 8.57 (s, 1H), 7.86 (s, 1H), 7.67 (s, 1H), 7.66 (s, 1H), 5.09 (s, 2H), 4.64 (s, 1H), 3.93 (s, 3H), 3.42-3.39 (m, 2H), 0.73 (s, 9H). MS observed (ESI$^+$) [(M+H)$^+$]: 453.

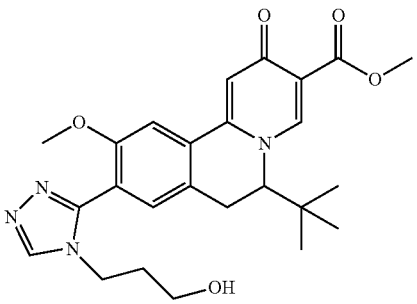

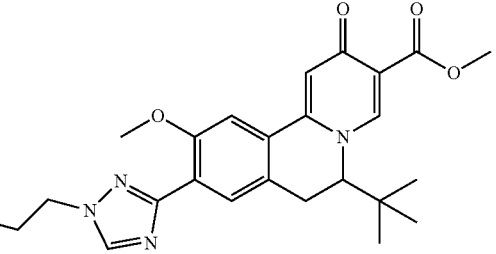

Example 31

6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylic Acid

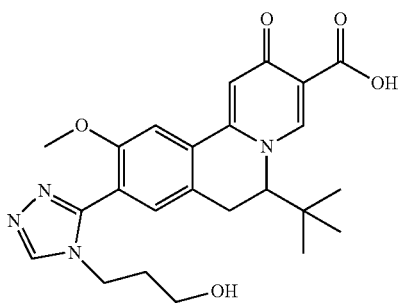 [SMILES: COc1cc2c(cc1-c1nncn1CCCO)CC(C(C)(C)C)n1cc(C(=O)O)c(=O)cc1-2]

To a solution of methyl 6-(tert-butyl)-10-methoxy-2-oxo-9-(1H-1,2,4-triazol-3-yl)-6,7-dihydro-2H-pyrido[2,1-a]isoquinoline-3-carboxylate (100 mg, 0.25 mmol) in CH$_3$CN (3 mL) was added 3-bromo-1-propanol (300 mg, 2.45 mmol) and K$_2$CO$_3$ (348 mg, 2.5 mmol), and the reaction mixture was allowed to stir at RT for 16 h. Water (5 mL) was added to the mixture, and extract with DCM (10 mL×3), the combined organic phase was washed with brine (10 mL×3), dried over anhydrous sodium sulfate, filtered and concentrated, the resulted residue was purified by preparative TLC to provide methyl 6-(tert-butyl)-9-(4-(3-hydroxypropyl)-4H-1,2,4-triazol-3-yl)-10-methoxy-2-oxo-6,7-dihydro-2H-pyrido[2,1-a]-isoquinoline-3-carboxylate (20 mg) and methyl 6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylate (50 mg) as white solid.

Step 32a: Preparation of 6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylic Acid

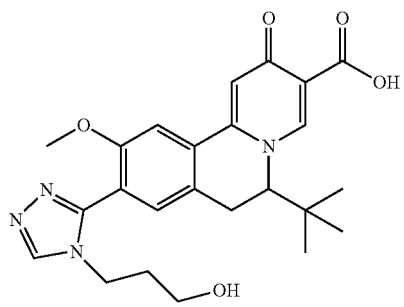 [SMILES: COc1cc2c(cc1-c1nncn1CCCO)CC(C(C)(C)C)n1cc(C(=O)O)c(=O)cc1-2]

6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylic acid (9.7 mg) as white solid was prepared by using methyl 6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylate (20 mg, 0.04 mmol) according to method in example 2, step 2b. $^1$H NMR (400 MHz, DMSO-$d_6$): δ 16.43 (s, 1H), 8.80 (s, 1H), 8.06 (s, 1H), 7.74 (s, 2H), 7.49 (s, 1H), 4.66 (d, J=3.6 Hz, 1H), 4.47 (s, 1H), 3.99 (t, J=7.2 Hz, 2H), 3.93 (s, 3H), 3.41-3.38 (m, 4H), 1.89-1.82 (m, 2H), 0.74 (s, 9H). MS observed (ESI$^+$) [(M+H)$^+$]: 453.

Step 32b: Preparation of 6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylic Acid

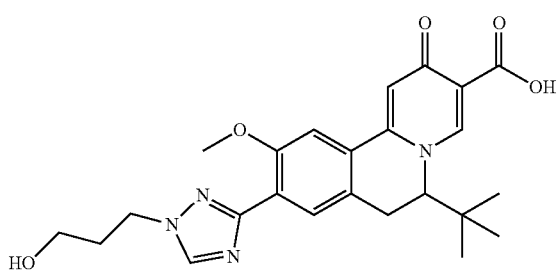 [SMILES: COc1cc2c(cc1-c1ncn(CCCO)n1)CC(C(C)(C)C)n1cc(C(=O)O)c(=O)cc1-2]

6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylic acid (39.5 mg) as white solid was prepared by using methyl 6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylate (50 mg, 0.11 mmol) according to method in example 2, step 2b. $^1$H NMR (400 MHz, DMSO-$d_6$): δ 8.79 (s, 1H), 8.59 (s, 1H), 7.83 (s, 1H), 7.67 (s, 1H), 7.66 (s, 1H), 4.65 (s, 1H), 4.29 (t, J=6.8 Hz, 2H), 3.93 (s, 3H), 3.47-3.41 (m, 4H), 1.97 (q, J=6.4 Hz, 2H), 0.74 (s, 9H). MS observed (ESI$^+$) [(M+H)$^+$]: 453.

Example 33

6-(tert-butyl)-10-methoxy-2-oxo-9-phenyl-6,7-dihydro-2H-pyrido[2,1-a]isoquinoline-3-carboxylic Acid

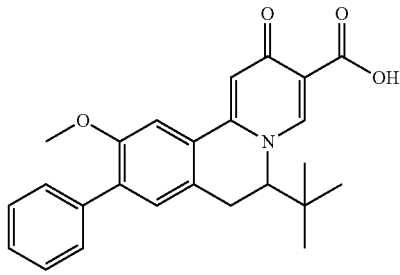 [SMILES: COc1cc2c(cc1-c1ccccc1)CC(C(C)(C)C)n1cc(C(=O)O)c(=O)cc1-2]

Step 33a: Preparation of ethyl 6-(tert-butyl)-10-methoxy-2-oxo-9-phenyl-6,7-dihydro-2H-pyrido[2,1-a]isoquinoline-3-carboxylate

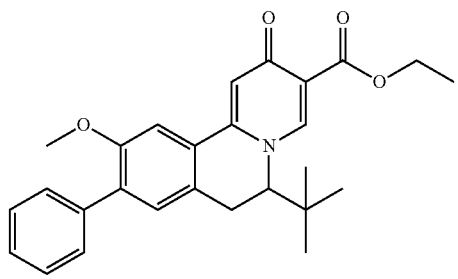 [SMILES: CCOC(=O)c1cn2c(cc1=O)-c1cc(OC)c(-c3ccccc3)cc1CC2C(C)(C)C]

Ethyl 6-(tert-butyl)-10-methoxy-2-oxo-9-phenyl-6,7-dihydro-2H-pyrido[2,1-a]isoquinoline-3-carboxylate (36 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and phenylboronic acid (84 mg, 0.69 mmol) according to method in example 1, step 1h.

Step 33b: Preparation of 6-(tert-butyl)-10-methoxy-2-oxo-9-phenyl-6,7-dihydro-2H-pyrido[2,1-a]isoquinoline-3-carboxylic Acid

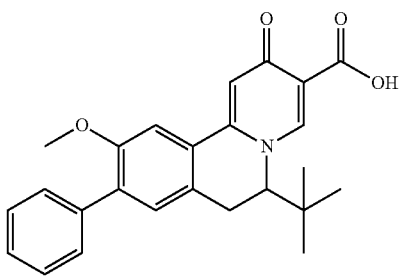 [SMILES: COc1cc2c(cc1-c1ccccc1)CC(C(C)(C)C)n1cc(C(=O)O)c(=O)cc1-2]

6-(tert-butyl)-10-methoxy-2-oxo-9-phenyl-6,7-dihydro-2H-pyrido[2,1-a]isoquinoline-3-carboxylic acid (16 mg) as brown solid was prepared by using ethyl 6-(tert-butyl)-10- methoxy-2-oxo-9-phenyl-6,7-dihydro-2H-pyrido[2,1-a]iso-quinoline-3-carboxylate (36 mg, 0.083 mmol) according to method in example 1, step 1i. ¹H NMR (400 MHz, DMSO-d₆): δ 8.49 (s, 1H), 7.56-7.51 (m, 3H), 7.45-7.41 (m, 3H), 7.38-7.34 (m, 2H), 4.45-4.41 (m, 1H), 3.88 (s, 3H), 3.24-3.18 (m, 2H), 0.75 (s, 9H). MS observed (ESI⁺) [(M+H)⁺]: 404.

Example 34

6-(tert-butyl)-9-(4-ethylphenyl)-10-methoxy-2-oxo-6,7-dihydro-2H-pyrido[2,1-a]isoquinoline-3-carboxylic Acid Step 34b: Preparation of 6-(tert-butyl)-9-(4-ethylphenyl)-10-methoxy-2-oxo-6,7-dihydro-2H-pyrido[2,1-a]isoquinoline-3-carboxylic Acid

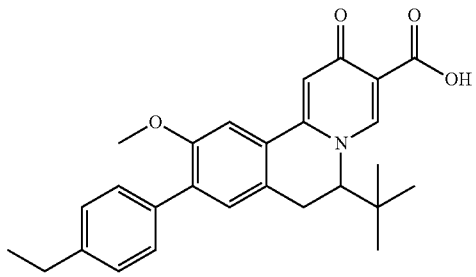 [SMILES: CCc1ccc(-c2cc3c(cc2OC)-c2cc(=O)c(C(=O)O)cn2C(C(C)(C)C)C3)cc1]

6-(tert-butyl)-9-(4-ethylphenyl)-10-methoxy-2-oxo-6,7-dihydro-2H-pyrido[2,1-a]isoquinoline-3-carboxylic acid (20 mg) as brown solid was prepared by using ethyl 6-(tert-butyl)-9-(4-ethylphenyl)-10-methoxy-2-oxo-6,7-dihydro-2H-pyrido[2, 1-a]isoquinoline-3-carboxylate (36 mg, 0.078 mmol) according to method in example 1, step 1i. ¹H NMR (400 MHz, DMSO-d₆): δ 8.78 (s, 1H), 7.65 (s, 1H), 7.62 (s, 1H), 7.47 (d, J=8.0 Hz, 2H), 7.40 (s, 1H), 7.28 (d, J=8.0 Hz, 2H), 4.65-4.62 (m, 1H), 3.89 (s, 3H), 3.44-3.33 (m, 2H), 2.65 (q, J=7.6 Hz, 2H), 1.21 (t, J=7.6 Hz, 3H), 0.75 (s, 9H). MS observed (ESI⁺) [(M+H)⁺]: 432.

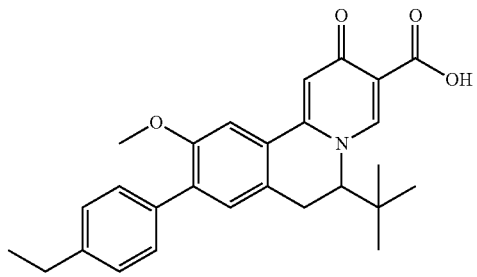 [SMILES: CCc1ccc(-c2cc3c(cc2OC)-c2cc(=O)c(C(=O)O)cn2C(C(C)(C)C)C3)cc1]

Example 35

6-(tert-butyl)-10-methoxy-9-(4-methoxyphenyl)-2-oxo-6,7-dihydro-2H-pyrido[2,1-a]isoquinoline-3-carboxylic Acid

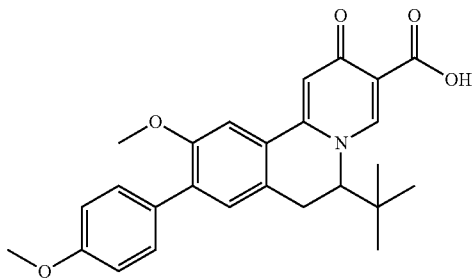 [SMILES: COc1ccc(-c2cc3c(cc2OC)-c2cc(=O)c(C(=O)O)cn2C(C(C)(C)C)C3)cc1]

Step 34a: Preparation of ethyl 6-(tert-butyl)-9-(4-ethylphenyl)-10-methoxy-2-oxo-6,7-dihydro-2H-pyrido[2,1-a]isoquinoline-3-carboxylate Step 35a: Preparation of ethyl 6-(tert-butyl)-10-methoxy-9-(4-methoxyphenyl)-2-oxo-6,7-dihydro-2H-pyrido[2,1-a]isoquinoline-3-carboxylate

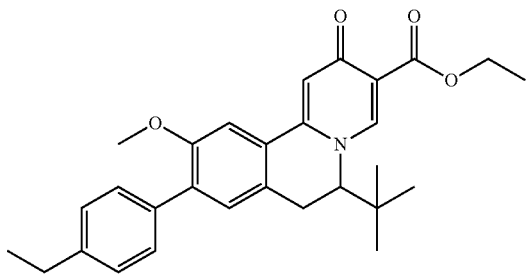

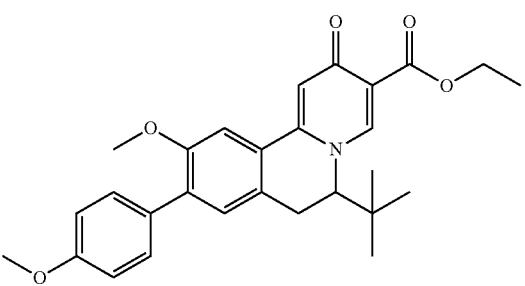 [SMILES: CCOC(=O)c1cn2c(cc1=O)-c1cc(OC)c(-c3ccc(OC)cc3)cc1CC2C(C)(C)C]

Ethyl 6-(tert-butyl)-9-(4-ethylphenyl)-10-methoxy-2-oxo-6,7-dihydro-2H-pyrido[2,1-a]-isoquinoline-3-carboxylate (36 mg) as brown solid was prepared by using ethyl 9-bromo-6-(tert-butyl)-10-methoxy-2-oxo-6,7-dihydro-2H-pyrido[2,1-a]isoquinoline-3-carboxylate (70 mg, 0.16 mmol) and 4-ethylphenylboronic acid (72 mg, 0.48 mmol) according to method in example 1, step 1h.

Ethyl 6-(tert-butyl)-10-methoxy-9-(4-methoxyphenyl)-2-oxo-6,7-dihydro-2H-pyrido[2,1-a]isoquinoline-3-carboxylate (15 mg) as brown solid was prepared by using ethyl 9-bromo-6-(tert-butyl)-10-methoxy-2-oxo-6,7-dihydro-2H-pyrido[2,1-a]isoquino-line-3-carboxylate (70 mg, 0.16 mmol) and 4-methoxyphenylboronic acid (73 mg, 0.48 mmol) according to method in example 1, step 1h.

Step 35b: Preparation of 6-(tert-butyl)-10-methoxy-9-(4-methoxyphenyl)-2-oxo-6,7-dihydro-2H-pyrido[2,1-a]isoquinoline-3-carboxylic Acid

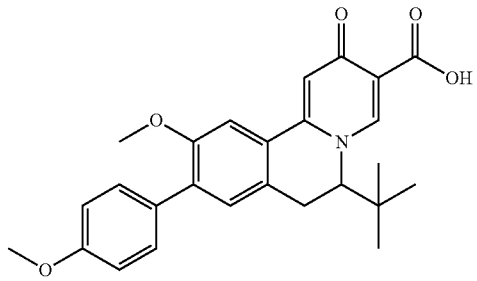 [SMILES: COc1ccc(-c2cc3c(cc2OC)-c2cc(=O)c(C(=O)O)cn2C(C(C)(C)C)C3)cc1]

6-(tert-butyl)-10-methoxy-9-(4-methoxyphenyl)-2-oxo-6,7-dihydro-2H-pyrido[2,1-a]isoquinoline-3-carboxylic acid (1.5 mg) as light yellow solid was prepared by using ethyl 6-(tert-butyl)-10-methoxy-9-(4-methoxyphenyl)-2-oxo-6,7-dihydro-2H-pyrido-[2,1-a]isoquinoline-3-carboxylate (15 mg, 0.033 mmol) according to method in example 1, step 1i. $^1$H NMR (400 MHz, DMSO-$d_6$): δ 8.76 (s, 1H), 7.62 (s, 1H), 7.58 (s, 1H), 7.49 (d, J=8.8 Hz, 2H), 7.37 (s, 1H), 6.98 (d, J=8.8 Hz, 2H), 4.63-4.59 (m., 1H), 3.87 (s, 3H), 3.78 (s, 3H), 3.74-3.70 (m, 1H), 3.68-3.62 (m, 1H), 0.73 (s, 9H). MS observed (ESI$^+$) [(M+H)$^+$]: 434.

Example 36

6-(tert-butyl)-10-methoxy-9-(3-methoxyphenyl)-2-oxo-6,7-dihydro-2H-pyrido[2,1-a]isoquinoline-3-carboxylic Acid

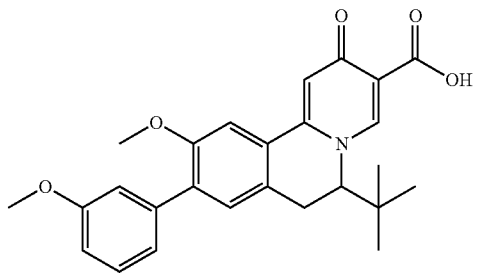 [SMILES: COc1cccc(-c2cc3c(cc2OC)-c2cc(=O)c(C(=O)O)cn2C(C(C)(C)C)C3)c1]

Step 36a: Preparation of ethyl 6-(tert-butyl)-10-methoxy-9-(3-methoxyphenyl)-2-oxo-6,7-dihydro-2H-pyrido[2,1-a]isoquinoline-3-carboxylate

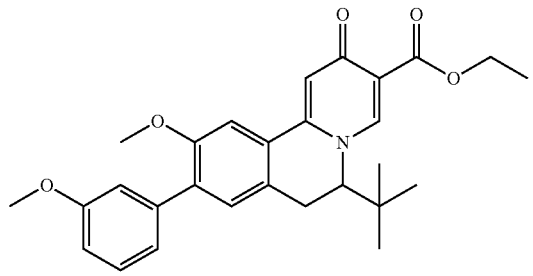 [SMILES: CCOC(=O)c1cn2c(cc1=O)-c1cc(OC)c(-c3cccc(OC)c3)cc1CC2C(C)(C)C]

ethyl 6-(tert-butyl)-10-methoxy-9-(3-methoxyphenyl)-2-oxo-6,7-dihydro-2H-pyrido[2,1-a]isoquinoline-3-carboxylate (20 mg) as brown solid was prepared by using ethyl 9-bromo-6-(tert-butyl)-10-methoxy-2-oxo-6,7-dihydro-2H-pyrido[2,1-a]isoquinoline-3-carboxylate (70 mg, 0.16 mmol) and 3-methoxyphenylboronic acid (73 mg, 0.48 mmol) according to method in example 1, step 1h.

Step 36b: Preparation of 6-(tert-butyl)-10-methoxy-9-(3-methoxyphenyl)-2-oxo-6,7-dihydro-2H-pyrido[2,1-a]isoquinoline-3-carboxylic Acid

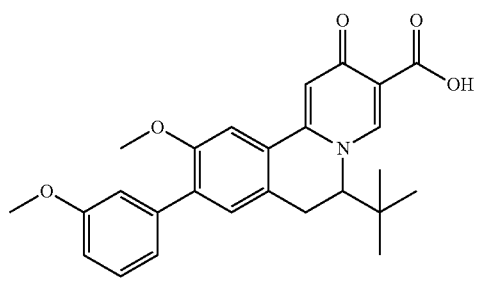 [SMILES: COc1cccc(-c2cc3c(cc2OC)-c2cc(=O)c(C(=O)O)cn2C(C(C)(C)C)C3)c1]

6-(tert-butyl)-10-methoxy-9-(3-methoxyphenyl)-2-oxo-6,7-dihydro-2H-pyrido[2,1-a]isoquinoline-3-carboxylic acid (3.3 mg) as light yellow solid was prepared by using ethyl 6-(tert-butyl)-9-(3-methoxyphenyl)-10-methoxy-2-oxo-6,7-dihydro-2H-pyrido-[2,1-a]isoquinoline-3-carboxylate (20 mg, 0.043 mmol) according to method in example 1, step 1i. $^1$H NMR (400 MHz, DMSO-$d_6$): δ 8.77 (s, 1H), 7.64 (s, 1H), 7.61 (s, 1H), 7.41 (s, 1H), 7.36-7.31 (m, 1H), 7.09-7.05 (m, 2H), 6.93 (d, J=7.2 Hz, 1H), 4.63-4.58 (m, 1H), 3.88 (s, 3H), 3.77 (s, 3H), 3.75-3.63 (m, 2H), 0.73 (s, 9H). MS observed (ESI$^+$) [(M+H)$^+$]: 434.

Example 37

6-(tert-butyl)-10-methoxy-9-(6-methylpyridin-3-yl)-2-oxo-6,7-dihydro-2H-pyrido[2,1-a]isoquinoline-3-carboxylic Acid

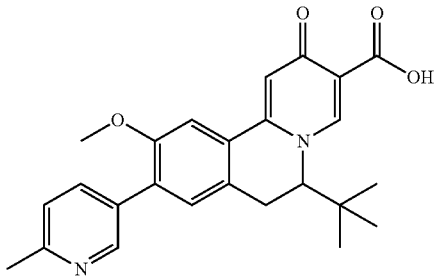 [SMILES: COc1cc2c(cc1-c1ccc(C)nc1)CC(C(C)(C)C)n1cc(C(=O)O)c(=O)cc1-2]

Step 37: Preparation of 6-(tert-butyl)-10-methoxy-9-(6-methylpyridin-3-yl)-2-oxo-6,7-dihydro-2H-pyrido[2,1-a]isoquinoline-3-carboxylic Acid

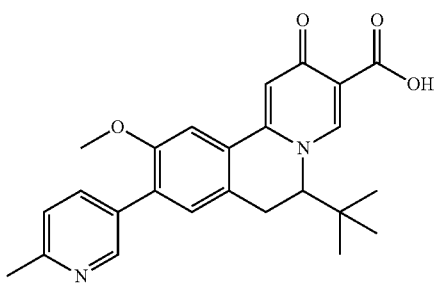

To a solution of ethyl 9-bromo-6-(tert-butyl)-10-methoxy-2-oxo-6,7-dihydro-2H-pyrido[2,1-a]isoquinoline-3-carboxylate (50 mg, 0.115 mmol) in DME (3 mL) and water (1 mL) was added (6-methylpyridin-3-yl)boronic acid (20.49 mg, 0.149 mmol), K$_2$CO$_3$ (23.9 mg, 0.172 mmol) and Pd(PPh$_3$)$_4$ (13.3 mg, 0.011 mmol), and the reaction mixture was exchanged with nitrogen three times, then, allowed to heat at 85° C. for 20 h. The reaction mixture was diluted with EtOAc (20 mL), and the organic phase was washed with water (30 mL) and brine (20 mL), dried over anhydrous sodium sulfate, filtered and concentrated, then purified by preparative TLC to provide 6-(tert-butyl)-10-methoxy-9-(6-methylpyridin-3-yl)-2-oxo-6,7-dihydro-2H-pyrido[2,1-a]isoquinoline-3-carboxylic acid (30 mg) as off-white solid. $^1$H NMR (400 MHz, DMSO-d$_6$): δ 16.52 (s, 1H), 8.78 (s, 1H), 8.61 (s, 1H), 7.87-7.84 (m, 1H), 7.66 (s, 1H), 7.65 (s, 1H), 7.47 (s, 1H), 7.33 (d, J=8.0 Hz, 1H), 4.64-4.63 (m, 1H), 3.91 (s, 3H), 3.45-3.37 (m, 2H), 2.23 (s, 3H), 0.75 (s, 9H). MS observed (ESI$^+$) [(M+H)$^+$]: 419.

Example 38

6-(tert-butyl)-10-methoxy-9-(2-methylpyridin-4-yl)-2-oxo-6,7-dihydro-2H-pyrido[2,1-a]isoquinoline-3-carboxylic Acid

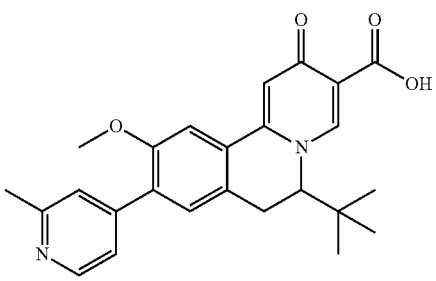 [SMILES: COc1cc2c(cc1-c1ccnc(C)c1)CC(C(C)(C)C)n1cc(C(=O)O)c(=O)cc1-2]

Step 38: Preparation of 6-(tert-butyl)-10-methoxy-9-(2-methylpyridin-4-yl)-2-oxo-6,7-dihydro-2H-pyrido[2,1-a]isoquinoline-3-carboxylic Acid

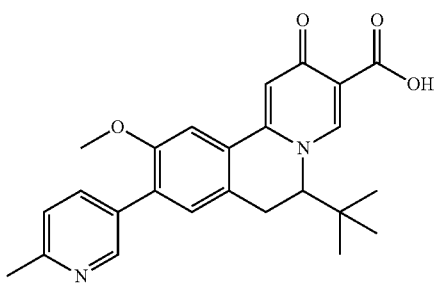

6-(tert-butyl)-10-methoxy-9-(2-methylpyridin-4-yl)-2-oxo-6,7-dihydro-2H-pyrido[2,1-a]isoquinoline-3-carboxylic acid (40 mg) as light yellow solid was prepared by using ethyl 9-bromo-6-(tert-butyl)-10-methoxy-2-oxo-6,7-dihydro-2H-pyrido[2,1-a]-isoquinoline-3-carboxylate (50 mg, 0.115 mmol) and (2-methyl pyridin-4-yl)boronic acid (17.3 mg, 0.127 mmol) according to method in example 37, step 37. $^1$H NMR (400 MHz, DMSO-d$_6$): δ 16.49 (s, 1H), 8.79 (s, 1H), 8.48 (d, J=8.0 Hz, 1H), 7.69 (s, 1H), 7.68 (s, 1H), 7.49 (s, 1H), 7.42 (s, 1H), 7.37-7.36 (m, 1H), 4.65-4.64 (m, 1H), 3.92 (s, 3H), 3.45-3.34 (m, 2H), 2.52 (s, 3H), 0.75 (s, 9H). MS observed (ESI$^+$) [(M+H)$^+$]: 419.

Example 39

6-(tert-butyl)-10-methoxy-9-(2-methylpyridin-3-yl)-2-oxo-6,7-dihydro-2H-pyrido[2,1-a]isoquinoline-3-carboxylic Acid

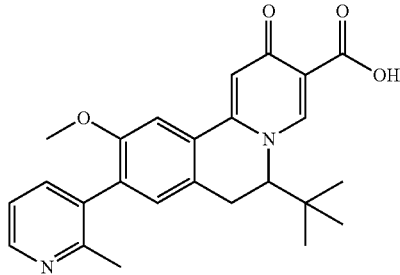 [SMILES: COc1cc2c(cc1-c1cccnc1C)CC(C(C)(C)C)n1cc(C(=O)O)c(=O)cc1-2]

Example 40

6-(tert-butyl)-10-methoxy-9-(6-morpholinylpyridin-3-yl)-2-oxo-6,7-dihydro-2H-pyrido[2,1-a]isoquinoline-3-carboxylic Acid

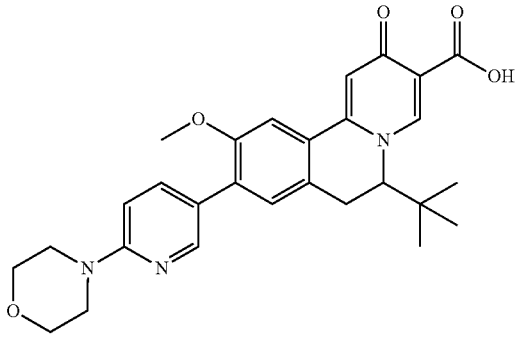

Step 39: Preparation of 6-(tert-butyl)-10-methoxy-9-(2-methylpyridin-3-yl)-2-oxo-6,7-dihydro-2H-pyrido[2,1-a]isoquinoline-3-carboxylic Acid

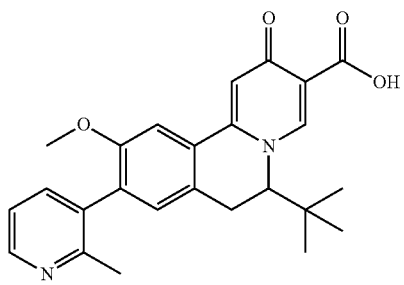 [SMILES: COc1cc2c(cc1-c1cccnc1C)CC(C(C)(C)C)n1cc(C(=O)O)c(=O)cc1-2]

Step 40: Preparation of 6-(tert-butyl)-10-methoxy-9-(6-morpholinylpyridin-3-yl)-2-oxo-6,7-dihydro-2H-pyrido[2,1-a]isoquinoline-3-carboxylic Acid

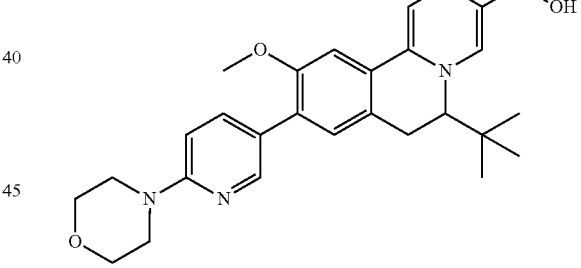

6-(tert-butyl)-10-methoxy-9-(2-methylpyridin-3-yl)-2-oxo-6,7-dihydro-2H-pyrido[2,1-a]isoquinoline-3-carboxylic acid (7.2 mg) as yellow solid was prepared by using ethyl 9-bromo-6-(tert-butyl)-10-methoxy-2-oxo-6,7-dihydro-2H-pyrido[2,1-a]-isoquinoline-3-carboxylate (50 mg, 0.115 mmol) and (2-methylpyridin-3-yl)boronic acid (20 mg, 0.115 mmol) according to method in example 37, step 37. $^1$H NMR (400 MHz, DMSO-$d_6$): δ 8.78 (s, 1H), 8.47 (d, J=8.0 Hz, 1H), 7.67 (s, 1H), 7.65 (s, 1H), 7.55 (d, J=8.0 Hz, 1H), 7.30-7.28 (m, 2H), 4.64-4.63 (m, 1H), 3.86 (s, 3H), 3.44-3.42 (m, 2H), 2.26 (s, 3H), 0.75 (s, 9H). MS observed (ESI$^+$) [(M+H)$^+$]: 419.

6-(tert-butyl)-10-methoxy-9-(6-morpholinylpyridin-3-yl)-2-oxo-6,7-dihydro-2H-pyrido[2,1-a]isoquinoline-3-carboxylic acid (27 mg) as yellow solid was prepared by using ethyl 9-bromo-6-(tert-butyl)-10-methoxy-2-oxo-6,7-dihydro-2H-pyrido[2,1-a]-isoquinoline-3-carboxylate (100 mg, 0.23 mmol) and 4-(5-(4,4,5,5-tetramethyl-1,3,2-dioxaborolan-2-yl)pyridin-2-yl)morpholine (87 mg, 0.3 mmol) according to method in example 37, step 37. $^1$H NMR (400 MHz, DMSO-$d_6$): δ 16.55 (s, 1H), 8.77 (s, 1H), 8.37 (s, 1H), 7.81-7.79 (m, 1H), 7.62 (s, 1H), 7.60 (s, 1H), 7.43 (s, 1H), 6.90 (d, J=8.0 Hz, 1H), 4.62-4.61 (m, 1H), 3.91 (s, 3H), 3.71 (t, J=4.0 Hz, 4H), 3.50 (t, J=4.0 Hz, 4H), 3.39-3.35 (m, 2H), 0.75 (s, 9H). MS observed (ESI$^+$) [(M+H)$^+$]: 490.

Example 41

6-(tert-butyl)-10-methoxy-2-oxo-9-(6-trifluoromethylpyridin-3-yl)-6,7-dihydro-2H-pyrido[2,1-a]isoquinoline-3-carboxylic Acid

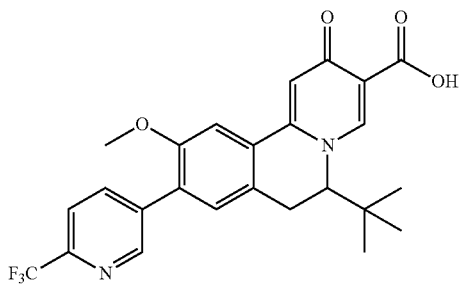 [SMILES: COc1cc2c(cc1-c1ccc(C(F)(F)F)nc1)CC(C(C)(C)C)n1cc(C(=O)O)c(=O)cc1-2]

Step 41: Preparation of 6-(tert-butyl)-10-methoxy-2-oxo-9-(6-trifluoromethylpyridin-3-yl)-6,7-dihydro-2H-pyrido[2,1-a]isoquinoline-3-carboxylic Acid

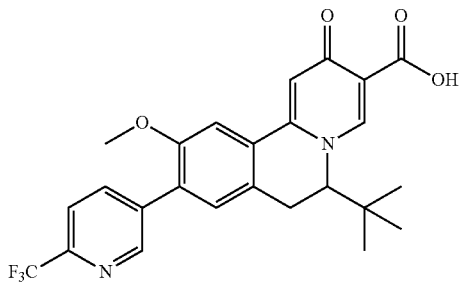 [SMILES: COc1cc2c(cc1-c1ccc(C(F)(F)F)nc1)CC(C(C)(C)C)n1cc(C(=O)O)c(=O)cc1-2]

6-(tert-butyl)-10-methoxy-2-oxo-9-(6-trifluoromethylpyridin-3-yl)-6,7-dihydro-2H-pyrido[2,1-a]isoquinoline-3-carboxylic acid (44 mg) as yellow solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (6-trifluoromethylpyridin-3-yl)boronic acid (58 mg, 0.3 mmol) according to method in example 37, step 37. $^1$H NMR (400 MHz, DMSO-d$_6$): δ 16.46 (s, 1H), 8.96 (s, 1H), 8.80 (s, 1H), 8.28 (d, J=8.0 Hz, 1H), 7.99 (d, J=8.0 Hz, 1H), 7.72 (s, 1H), 7.71 (s, 1H), 7.59 (s, 1H), 4.66-4.65 (m, 1H), 3.95 (s, 3H), 3.47-3.34 (m, 2H), 0.76 (s, 9H). MS observed (ESI$^+$) [(M+H)$^+$]: 473.

Example 42

6-(tert-butyl)-10-methoxy-9-(6-(2-methoxyethoxy) pyridin-3-yl)-2-oxo-6,7-dihydro-2H-pyrido[2,1-a]isoquinoline-3-carboxylic Acid

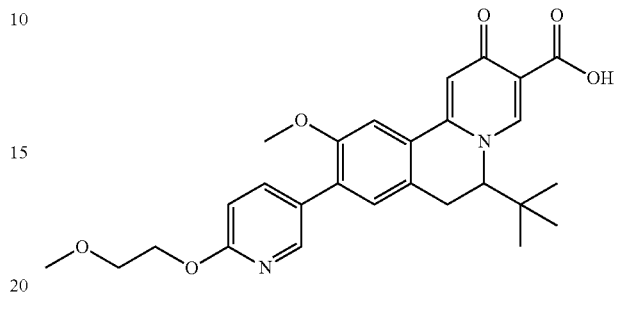

Step 42: Preparation of 6-(tert-butyl)-10-methoxy-9-(6-(2-methoxyethoxy) pyridin-3-yl)-2-oxo-6,7-dihydro-2H-pyrido[2,1-a]isoquinoline-3-carboxylic Acid

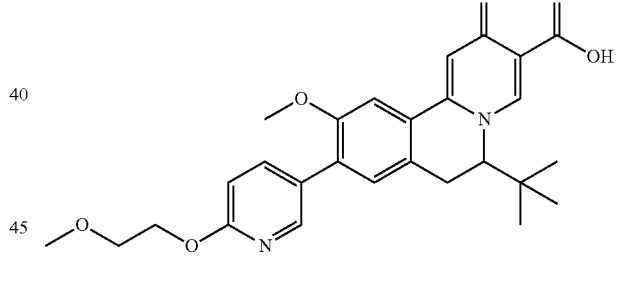

6-(tert-butyl)-10-methoxy-9-(6-(2-methoxyethoxy)pyridin-3-yl)-2-oxo-6,7-dihydro-2H-pyrido[2,1-a]isoquinoline-3-carboxylic acid (30 mg) as white solid was prepared by using ethyl 9-bromo-6-(tert-butyl)-10-methoxy-2-oxo-6,7-dihydro-2H-pyrido-[2,1-a]isoquinoline-3-carboxylate (50 mg, 0.115 mmol) and (6-(2-methoxy-ethoxy)pyridin-3-yl) boronic acid (30 mg, 0.15 mmol) according to method in example 37, step 37. $^1$H NMR (400 MHz, DMSO-d$_6$): δ 16.53 (s, 1H), 8.77 (s, 1H), 8.35 (s, 1H), 7.93-7.90 (m, 1H), 7.65 (s, 1H), 7.64 (s, 1H), 7.46 (s, 1H), 6.91 (d, J=8.4 Hz, 1H), 4.62 (s, 1H), 4.42 (t, J=4.4 Hz, 2H), 3.91 (s, 3H), 3.68 (t, J=4.0 Hz, 2H), 3.38-3.36 (m, 2H), 3.31 (s, 3H), 0.75 (s, 9H). MS observed (ESI$^+$) [(M+H)$^+$]: 479.

Example 43

6-(tert-butyl)-9-(6-(dimethylamino)pyridin-3-yl)-10-methoxy-2-oxo-6,7-dihydro-2H-pyrido[2,1-a]isoquinoline-3-carboxylic Acid

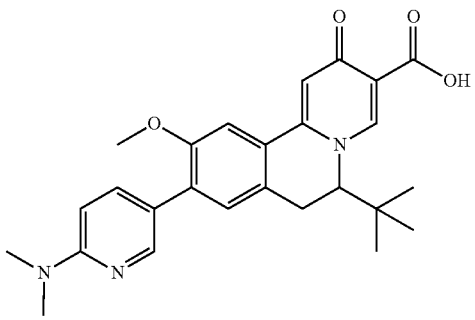 [SMILES: COc1cc2c(cc1-c1ccc(N(C)C)nc1)CC(C(C)(C)C)n1cc(C(=O)O)c(=O)cc1-2]

Step 43: Preparation of 6-(tert-butyl)-9-(6-(dimethylamino) pyridin-3-yl)-10-methoxy-2-oxo-6,7-dihydro-2H-pyrido[2,1-a]isoquinoline-3-carboxylic Acid

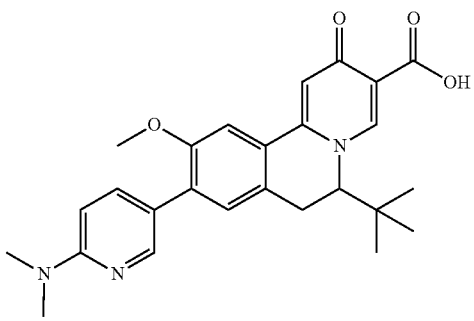 [SMILES: COc1cc2c(cc1-c1ccc(N(C)C)nc1)CC(C(C)(C)C)n1cc(C(=O)O)c(=O)cc1-2]

6-(tert-butyl)-9-(6-(dimethylamino)pyridin-3-yl)-10-methoxy-2-oxo-6,7-dihydro-2H-pyrido[2,1-a]isoquinoline-3-carboxylic acid (63.1 mg) as yellow solid was prepared by using ethyl 9-bromo-6-(tert-butyl)-10-methoxy-2-oxo-6,7-dihydro-2H-pyrido[2,1-a]isoquinoline-3-carboxylate (100 mg, 0.225 mmol) and (6-(dimethylamino)-pyridin-3-yl)boronic acid (50 mg, 0.3 mmol) according to method in example 37, step 37. $^1$H NMR (400 MHz, DMSO-$d_6$): δ 16.58 (s, 1H), 8.76 (s, 1H), 8.33 (d, J=1.6 Hz, 1H), 7.75 (dd, J=8.8, 2.0 Hz, 1H), 7.61 (s, 1H), 7.59 (s, 1H), 7.41 (s, 1H), 6.70 (d, J=8.4 Hz, 1H), 4.61 (d, J=5.2 Hz, 1H), 3.90 (s, 3H), 3.44-3.35 (m, 2H), 3.07 (s, 6H), 0.75 (s, 9H). MS observed (ESI$^+$) [(M+H)$^+$]: 448.

Example 44

6-(tert-butyl)-10-methoxy-2-oxo-9-(6-(pyrrolidin-1-yl)pyridin-3-yl)-6,7-dihydro-2H-pyrido[2,1-a]isoquinoline-3-carboxylic Acid

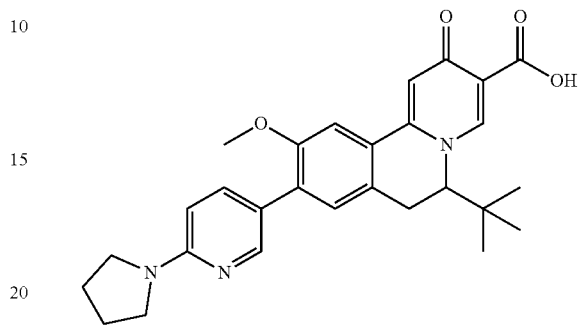

Step 44: Preparation of 6-(tert-butyl)-10-methoxy-2-oxo-9-(6-(pyrrolidin-1-yl)pyridin-3-yl)-6,7-dihydro-2H-pyrido[2,1-a]isoquinoline-3-carboxylic Acid

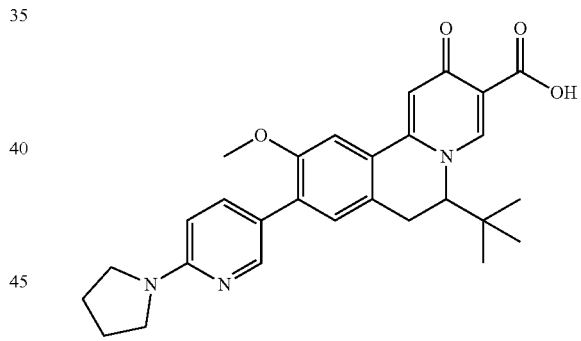

6-(tert-butyl)-10-methoxy-2-oxo-9-(6-(pyrrolidin-1-yl)pyridin-3-yl)-6,7-dihydro-2H-pyrido[2,1-a]isoquinoline-3-carboxylic acid (25 mg) as yellow solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (6-(pyrrolidin-1-yl)pyridin-3-yl)boronic acid (58 mg, 0.3 mmol) according to method in example 37, step 37. $^1$H NMR (400 MHz, DMSO-$d_6$): δ 8.75 (s, 1H), 8.29 (s, 1H), 7.76 (d, J=8.0 Hz, 1H), 7.60 (s, 1H), 7.58 (s, 1H), 7.41 (s, 1H), 6.55 (d, J=8.0 Hz, 1H), 4.61-4.60 (m, 1H), 3.90 (s, 3H), 3.53-3.43 (m, 6H), 2.02-1.96 (m, 4H), 0.74 (s, 9H). MS observed (ESI$^+$) [(M+H)$^+$]: 474.

Example 45

6-(tert-butyl)-10-methoxy-2-oxo-9-(6-(piperazin-1-yl)pyridin-3-yl)-6,7-dihydro-2H-pyrido[2,1-a]isoquinoline-3-carboxylic Acid

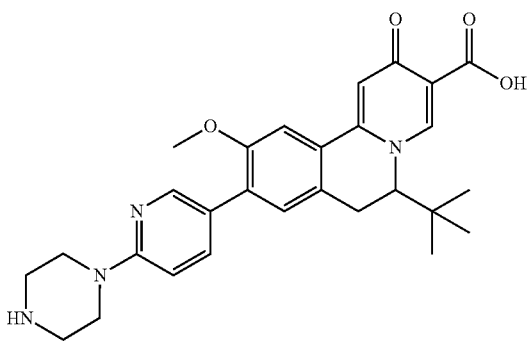 [SMILES: COc1cc2c(cc1-c1ccc(N3CCNCC3)nc1)CC(C(C)(C)C)n1cc(C(=O)O)c(=O)cc1-2]

Step 45a: Preparation of ethyl 9-(6-(4-(tert-butoxycarbonyl)piperazin-1-yl)pyridin-3-yl)-6-(tert-butyl)-10-methoxy-2-oxo-6,7-dihydro-2H-pyrido[2,1-a]isoquinoline-3-carboxylate

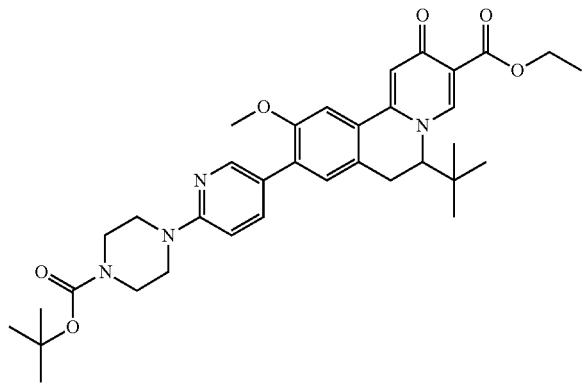 [SMILES: CCOC(=O)c1cn2c(cc1=O)-c1cc(OC)c(-c3ccc(N4CCN(C(=O)OC(C)(C)C)CC4)nc3)cc1CC2C(C)(C)C]

Ethyl 9-(6-(4-(tert-butoxycarbonyl)piperazin-1-yl)pyridin-3-yl)-6-(tert-butyl)-10-methoxy-2-oxo-6,7-dihydro-2H-pyrido[2,1-a]isoquinoline-3-carboxylate (96 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and 6-(4-(tert-butoxycarbonyl)piperazin-1-yl)pyridin-3-yl)boronic acid (108 mg, 0.35 mmol) according to method in example 1, step 1h.

Step 45b: Preparation of ethyl 6-(tert-butyl)-10-methoxy-2-oxo-9-(6-(piperazin-1-yl)pyridin-3-yl)-6,7-dihydro-2H-pyrido[2,1-a]isoquinoline-3-carboxylate

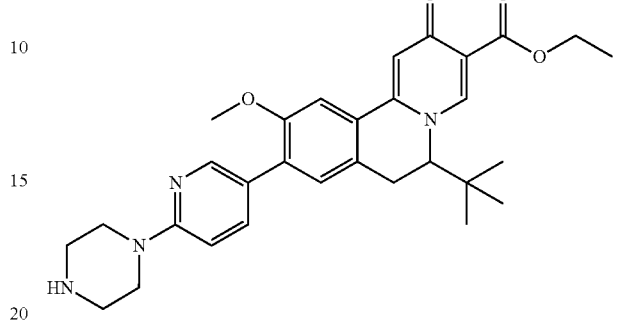

To a solution of ethyl 9-(6-(4-(tert-butoxycarbonyl)piperazin-1-yl)pyridin-3-yl)-6-(tert-butyl)-10-methoxy-2-oxo-6,7-dihydro-2H-pyrido[2,1-a]isoquinoline-3-carboxylate (96 mg, 0.156 mmol) in DCM (2 mL) was added trifluoroacetic acid (0.5 mL), and the reaction mixture was allowed to stir at RT for 2 h. LC-MS detected that the reaction was finished. Then, the mixture was concentrated and dissolved into saturated sodium carbonate solution (20 mL), extracted with EtOAc (20 mL×3), and the combined organic phase was washed with water (20 mL×5), dried over anhydrous sodium sulfate, filtered and concentrated, then purified by column chromatography to provide ethyl 6-(tert-butyl)-10-methoxy-2-oxo-9-(6-(piperazin-1-yl)pyridin-3-yl)-6,7-dihydro-2H-pyrido[2,1-a]isoquinoline-3-carboxylate (61 mg) as yellow solid.

Step 45c: Preparation of 6-(tert-butyl)-10-methoxy-2-oxo-9-(6-(piperazin-1-yl)pyridin-3-yl)-6,7-dihydro-2H-pyrido[2,1-a]isoquinoline-3-carboxylic Acid

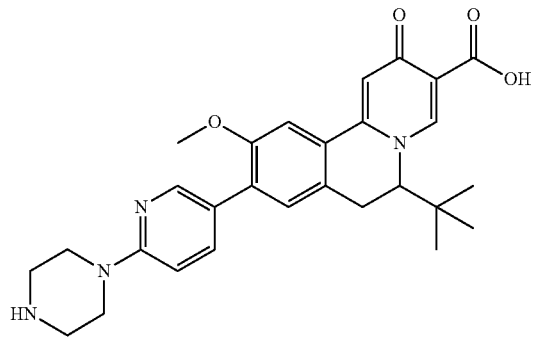

6-(tert-butyl)-10-methoxy-2-oxo-9-(6-(piperazin-1-yl)pyridin-3-yl)-6,7-dihydro-2H-pyrido[2,1-a]isoquinoline-3-carboxylic acid (25 mg) as yellow solid was prepared by using ethyl 6-(tert-butyl)-10-methoxy-2-oxo-9-(6-(piperazin-1-yl)-pyridin-3-yl)-6,7-dihydro-2H-pyrido[2,1-a]isoquinoline-3-carboxylate (61 mg, 0.118 mmol) according to method in example 1, step 1i. $^1$H NMR (400 MHz, DMSO-$d_6$): δ 8.77 (s, 1H), 8.38 (s, 1H), 7.82 (d, J=8.0 Hz, 1H), 7.62 (s, 1H), 7.61 (s, 1H), 7.43 (s, 1H), 6.95 (d, J=8.0 Hz, 1H), 4.63-4.61 (m, 1H), 3.91 (s, 3H), 3.68-3.61 (m, 6H), 3.08-3.03 (m, 4H), 0.75 (s, 9H). MS observed (ESI$^+$) [(M+H)$^+$]: 489.

Example 46

9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylic Acid

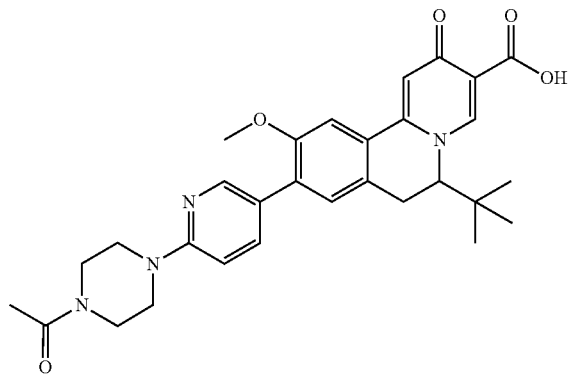 [SMILES: COc1cc2c(cc1-c1ccc(N3CCN(C(C)=O)CC3)nc1)CC(C(C)(C)C)n1cc(C(=O)O)c(=O)cc1-2]

Step 46a: Preparation of ethyl 9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylate

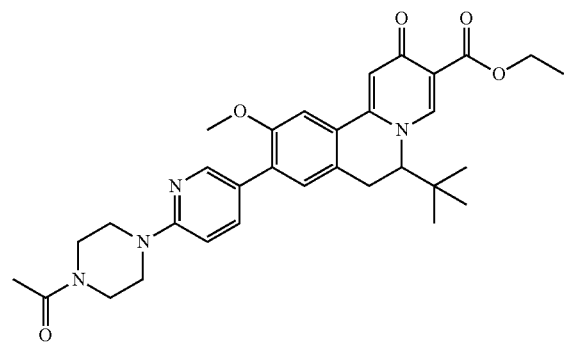 [SMILES: CCOC(=O)c1cn2c(cc1=O)-c1cc(OC)c(-c3ccc(N4CCN(C(C)=O)CC4)nc3)cc1CC2C(C)(C)C]

To a solution of ethyl 6-(tert-butyl)-10-methoxy-2-oxo-9-(6-(piperazin-1-yl)pyridin-3-yl)-6,7-dihydro-2H-pyrido[2,1-a]isoquinoline-3-carboxylate (50 mg, 0.096 mmol) in DCE (2 mL) was added acetic anhydride (14.7 mg, 0.144 mmol) ane trimethylamine (29 mg, 0.288 mmol), and the reaction mixture was allowed to stir at RT for 16 h. TLC showed that the reaction was finished. Then, the mixture was concentrated and purified by preparative TLC to provide ethyl 9-(6-(4-acetylpiperazin-1-yl)pyridin-3-yl)-6-(tert-butyl)-10-methoxy-2-oxo-6,7-dihydro-2H-pyrido[2,1-a]iso-quino-line-3-carboxylate (40 mg) as yellow solid.

Step 46b: Preparation of 9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylic Acid 9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylic acid (12.2 mg) as yellow solid was prepared by using ethyl 9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylate (40 mg, 0.071 mmol) according to method in example 1, step 1i. $^1$H NMR (400 MHz, DMSO-d$_6$): δ 8.76 (s, 1H), 8.37 (d, J=2.3 Hz, 1H), 7.80 (dd, J=8.8, 2.1 Hz, 1H), 7.62 (s, 1H), 7.60 (s, 1H), 7.43 (s, 1H), 6.92 (d, J=9.0 Hz, 1H), 4.63-4.60 (m, 1H), 3.90 (s, 3H), 3.66-3.49 (m, 10H), 2.06 (s, 3H), 0.75 (s, 9H). MS observed (ESI$^+$) [(M+H)$^+$]: 531.

Example 47

6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylic Acid

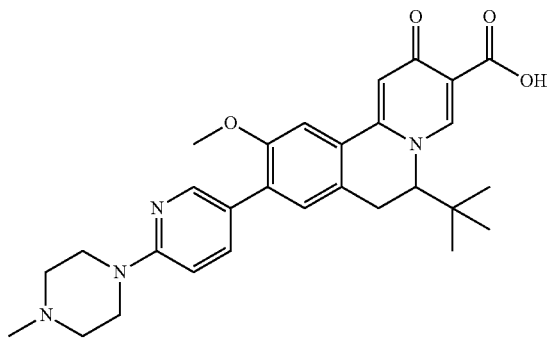 [SMILES: COc1cc2c(cc1-c1ccc(N3CCN(C)CC3)nc1)CC(C(C)(C)C)n1cc(C(=O)O)c(=O)cc1-2]

Step 47a: Preparation of ethyl 6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylate

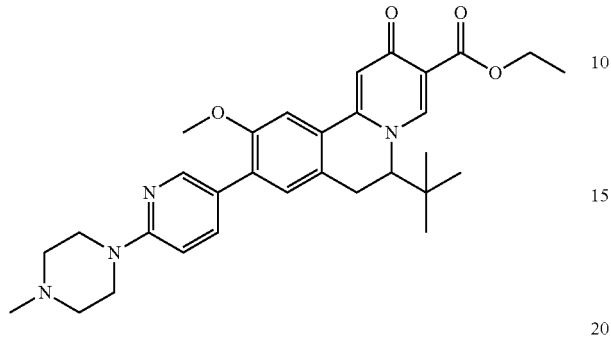

To a solution of ethyl 6-(tert-butyl)-10-methoxy-2-oxo-9-(6-(piperazin-1-yl) pyridin-3-yl)-6,7-dihydro-2H-pyrido[2,1-a]isoquinoline-3-carboxylate (50 mg, 0.096 mmol) in MeOH (2 mL) was added paraformaldehyde (20 mg) and NaBH$_3$CN (18 mg, 0.288 mmol), and the reaction mixture was allowed to heat at 50° C. for 2 h. LC-MS detected that the reaction was finished, and the mixture was concentrated to afford a crude product (60 mg), which was used for next stage without further purification.

Step 47b: Preparation of 6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylic Acid

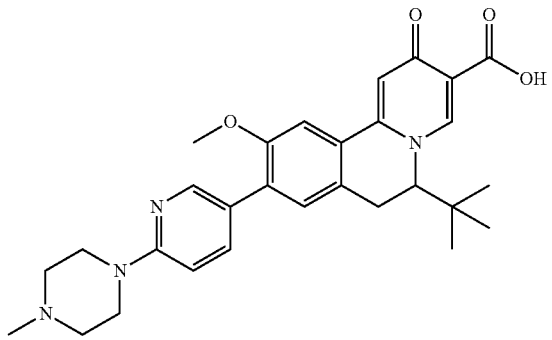 [SMILES: COc1cc2c(cc1-c1ccc(N3CCN(C)CC3)nc1)CC(C(C)(C)C)n1cc(C(=O)O)c(=O)cc1-2]

6-(tert-butyl)-10-methoxy-9-(6-(4-methylpiperazin-1-yl) pyridin-3-yl)-2-oxo-6,7-dihydro-2H-pyrido[2,1-a]isoquinoline-3-carboxylic acid (12.2 mg) as yellow solid was prepared by using ethyl 6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylate (60 mg, 0.113 mmol) according to method in example 1, step 1i. $^1$H NMR (400 MHz, DMSO-d$_6$): δ 16.56 (s, 1H), 8.77 (s, 1H), 8.37 (d, J=2.1 Hz, 1H), 7.81 (dd, J=8.8, 2.1 Hz, 1H), 7.63 (s, 1H), 7.61 (s, 1H), 7.43 (s, 1H), 6.96 (d, J=9.0 Hz, 1H), 4.63-4.61 (m, 1H), 3.91 (s, 3H), 3.69-3.62 (m, 6H), 2.86-2.82 (m, 4H), 2.50 (s, 3H), 0.75 (s, 9H). MS observed (ESI$^+$) [(M+H)$^+$]: 503.

Example 48

6-(tert-butyl)-9-(6-fluoro-4-methylpyridin-3-yl)-10-methoxy-2-oxo-6,7-dihydro-2H-pyrido[2,1-a]isoquinoline-3-carboxylic Acid

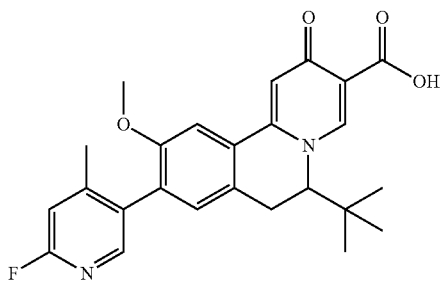

Step 48a: Preparation of ethyl 6-(tert-butyl)-9-(6-fluoro-4-methylpyridin-3-yl)-10-methoxy-2-oxo-6,7-dihydro-2H-pyrido[2,1-a]isoquinoline-3-carboxylate

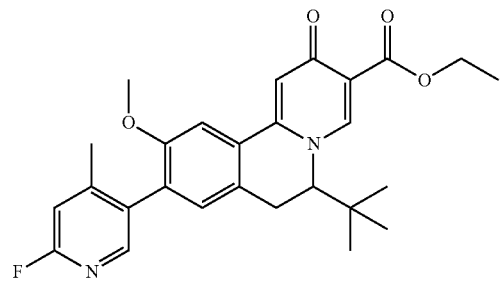 [SMILES: CCOC(=O)c1cn2c(cc1=O)-c1cc(OC)c(-c3cnc(F)cc3C)cc1CC2C(C)(C)C]

Ethyl 6-(tert-butyl)-9-(6-fluoro-4-methylpyridin-3-yl)-10-methoxy-2-oxo-6, 7-dihydro-2H-pyrido[2,1-a]isoquinoline-3-carboxylate as off-white solid was prepared by using ethyl 9-bromo-6-(tert-butyl)-10-methoxy-2-oxo-6,7-dihydro-2H-pyrido[2,1-a]-isoquinoline-3-carboxylate (100 mg, 0.23 mmol) and (6-fluoro-4-methylpyridin-3-yl)boronic acid (46.4 mg, 0.3 mmol) according to method in example 16, step 16a.

Step 48b: Preparation of 6-(tert-butyl)-9-(6-fluoro-4-methylpyridin-3-yl)-10-methoxy-2-oxo-6,7-dihydro-2H-pyrido[2,1-a]isoquinoline-3-carboxylic Acid

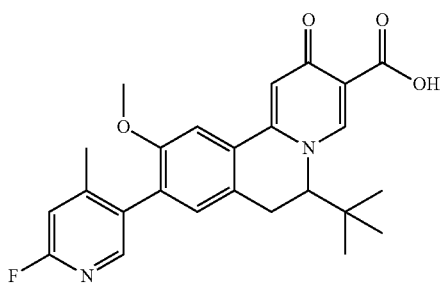

6-(tert-butyl)-9-(6-fluoro-4-methylpyridin-3-yl)-10-methoxy-2-oxo-6,7-dihydro-2H-pyrido[2,1-a]isoquinoline-3-carboxylic acid (22.3 mg) as white solid was prepared by using ethyl 6-(tert-butyl)-9-(6-fluoro-4-methylpyridin-3-yl)-10-methoxy-2-oxo-6,7-dihydro-2H-pyrido[2,1-a]isoquinoline-3-carboxylate according to method in example 16, step 16b. $^1$H NMR (400 MHz, DMSO-$d_6$): δ 16.51 (s, 1H), 8.79 (s, 0.5H), 8.63 (s, 0.5H), 7.98 (s, 1H), 7.67 (d, J=11.2 Hz, 1H), 7.32-7.26 (m, 2H), 7.17 (s, 1H), 4.65 (s, 1H), 4.47 (s, 1H), 3.84 (s, 3H), 3.65-3.50 (m, 1H), 2.14 (s, 3H), 0.75 (s, 9H). MS observed (ESI$^+$) [(M+H)$^+$]: 479.

Example 49

6-(tert-butyl)-9-(6-fluoropyridin-3-yl)-10-methoxy-2-oxo-6,7-dihydro-2H-pyrido[2,1-a]isoquinoline-3-carboxylic Acid

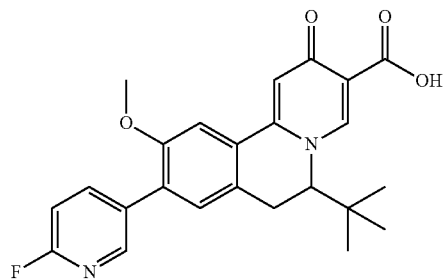 [SMILES: COc1cc2c(cc1-c1ccc(F)nc1)CC(C(C)(C)C)n1cc(C(=O)O)c(=O)cc1-2]

Step 49a: Preparation of ethyl 6-(tert-butyl)-9-(6-fluoropyridin-3-yl)-10-methoxy-2-oxo-6,7-dihydro-2H-pyrido[2,1-a]isoquinoline-3-carboxylate

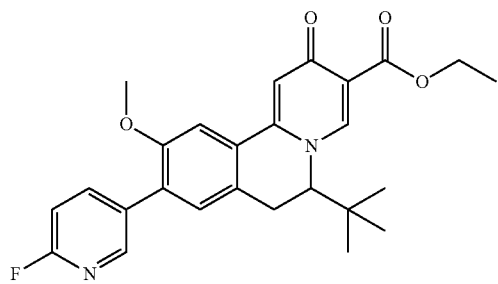 [SMILES: CCOC(=O)c1cn2c(cc1=O)-c1cc(OC)c(-c3ccc(F)nc3)cc1CC2C(C)(C)C]

Ethyl 6-(tert-butyl)-9-(6-fluoropyridin-3-yl)-10-methoxy-2-oxo-6,7-dihydro-2H-pyrido[2,1-a]isoquinoline-3-carboxylate as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (6-fluoropyridin-3-yl) boronic acid (42 mg, 0.3 mmol) according to method in example 16, step 16a.

Step 49b: Preparation of 6-(tert-butyl)-9-(6-fluoropyridin-3-yl)-10-methoxy-2-oxo-6,7-dihydro-2H-pyrido[2,1-a]isoquinoline-3-carboxylic Acid

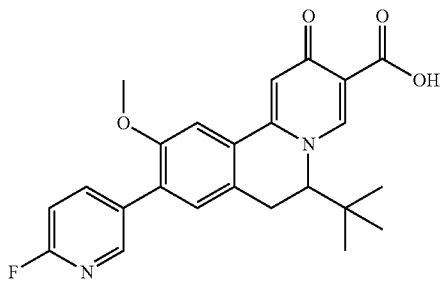

6-(tert-butyl)-9-(6-fluoropyridin-3-yl)-10-methoxy-2-oxo-6,7-dihydro-2H-pyrido[2,1-a]isoquinoline-3-carboxylic acid (72 mg) as light yellow solid was prepared by using ethyl 6-(tert-butyl)-9-(6-fluoropyridin-3-yl)-10-methoxy-2-oxo-6,7-dihydro-2H-pyrido[2,1-a]isoquinoline-3-carboxylate according to method in example 16, step 16b. $^1$H NMR (400 MHz, DMSO-$d_6$): δ 16.48 (s, 1H), 8.76 (s, 1H), 8.39 (d, J=2.8 Hz, 1H), 8.18-8.15 (m, 1H), 7.66 (s, 1H), 7.65 (s, 1H), 7.49 (s, 1H), 7.26-7.23 (m, 1H), 4.61 (d, J=5.6 Hz, 1H), 3.90 (s, 3H), 3.39-3.32 (m, 2H), 0.72 (s, 9H). MS observed (ESI$^+$) [(M+H)$^+$]: 423.

Example 50

9-(6-(azetidin-1-yl)pyridin-3-yl)-6-(tert-butyl)-10-methoxy-2-oxo-6,7-dihydro-2H-pyrido[2,1-a]isoquinoline-3-carboxylic Acid

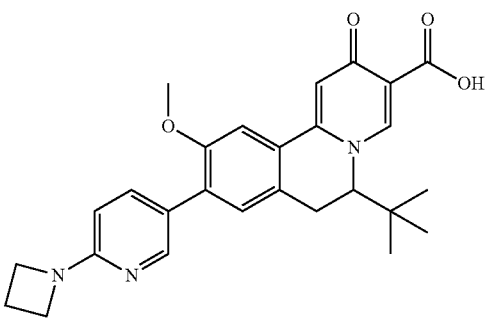 [SMILES: COc1cc2c(cc1-c1ccc(N3CCC3)nc1)CC(C(C)(C)C)n1cc(C(=O)O)c(=O)cc1-2]

Step 50: Preparation of 9-(6-(azetidin-1-yl)pyridin-3-yl)-6-(tert-butyl)-10-methoxy-2-oxo-6,7-dihydro-2H-pyrido[2,1-a]isoquinoline-3-carboxylic Acid Step 51: Preparation of 6-(tert-butyl)-9-(6-(4-hydroxypiperidin-1-yl) pyridin-3-yl)-10-methoxy-2-oxo-6,7-dihydro-2H-pyrido[2,1-a]isoquinoline-3-carboxylic Acid

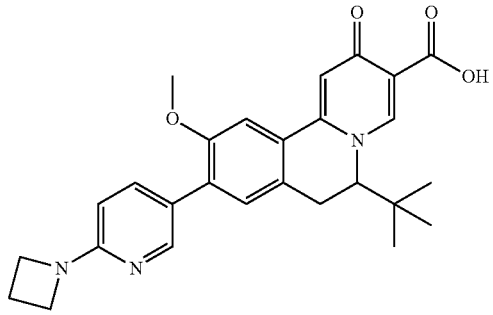 [SMILES: COc1cc2c(cc1-c1ccc(N3CCC3)nc1)CC(C(C)(C)C)n1cc(C(=O)O)c(=O)cc1-2]

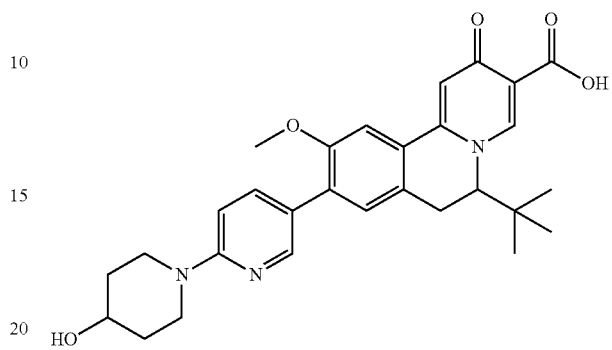

To a solution of 6-(tert-butyl)-9-(6-fluoropyridin-3-yl)-10-methoxy-2-oxo-6,7-dihydro-2H-pyrido[2,1-a]isoquinoline-3-carboxylic acid (42.2 mg, 0.1 mmol) in NMP (3 mL) in sealed tube was added azetidine hydrochloride (74.4 mg, 0.8 mmol and $K_2CO_3$ (165.6 mg, 1.2 mmol), and the reaction mixture was allowed to heat at 130° C. for 16 h, then cooled to RT. Water (10 mL) was added to the reaction mixture, and was extracted with EtOAc for three times, and the combined organic phase was dried over anhydrous sodium sulfate, filtered, concentrated, and purified by preparative TLC to provide 9-(6-(azetidin-1-yl)pyridin-3-yl)-6-(tert-butyl)-10-methoxy-2-oxo-6,7-dihydro-2H-pyrido[2,1-a]-isoquinoline-3-carboxylic acid (13 mg) as yellow solid. $^1$H NMR (400 MHz, DMSO-$d_6$): δ 16.58 (s, 1H), 8.76 (s, 1H), 8.28 (d, J=2.4 Hz, 1H), 7.74-7.71 (m, 1H), 7.61 (s, 1H), 7.59 (s, 1H), 7.40 (s, 1H), 6.41 (d, J=8.8 Hz, 1H), 4.62 (d, J=5.6 Hz, 1H), 3.98 (t, J=7.2 Hz, 4H), 3.89 (s, 3H), 3.39-3.36 (m, 2H), 2.36-2.32 (m, 2H), 0.74 (s, 9H). MS observed (ESI$^+$) [(M+H)$^+$]: 460.

6-(tert-butyl)-9-(6-(4-hydroxypiperidin-1-yl)pyridin-3-yl)-10-methoxy-2-oxo-6,7-dihydro-2H-pyrido[2,1-a]isoquinoline-3-carboxylic acid (26.4 mg) as yellow solid was prepared by using ethyl 9-bromo-6-(tert-butyl)-10-methoxy-2-oxo-6,7-dihydro-2H-pyrido-[2,1-a]isoquinoline-3-carboxylate (50 mg, 0.115 mmol) and (6-(4-hydroxypiperidin-1-yl)pyridin-3-yl)boronic acid (33.5 mg, 0.15 mmol) according to method in example 37, step 37. $^1$H NMR (400 MHz, DMSO-$d_6$): δ 16.50 (s, 1H), 8.68 (s, 1H), 8.26 (d, J=2.0 Hz, 1H), 7.67 (d, J=10.0 Hz, 1H), 7.51 (s, 2H), 7.36 (s, 1H), 6.82 (d, J=8.8 Hz, 1H), 4.71 (d, J=4.0 Hz, 1H), 4.02-3.95 (m, 2H), 3.83 (s, 3H), 3.70-3.58 (m, 2H), 3.10-3.01 (m, 3H), 1.98-1.88 (m, 2H), 1.75-1.68 (m, 2H), 0.67 (s, 9H). MS observed (ESI$^+$) [(M+H)$^+$]: 504.

Example 51

6-(tert-butyl)-9-(6-(4-hydroxypiperidin-1-yl)pyridin-3-yl)-10-methoxy-2-oxo-6,7-dihydro-2H-pyrido[2,1-a]isoquinoline-3-carboxylic Acid Example 52

6-(tert-butyl)-9-(6-(cyclopropylmethylamino)pyridin-3-yl)-10-methoxy-2-oxo-6,7-dihydro-2H-pyrido[2,1-a]isoquinoline-3-carboxylic Acid

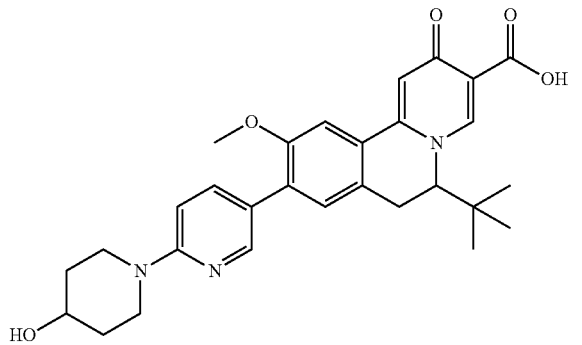 [SMILES: COc1cc2c(cc1-c1ccc(N3CCC(O)CC3)nc1)CC(C(C)(C)C)n1cc(C(=O)O)c(=O)cc1-2]

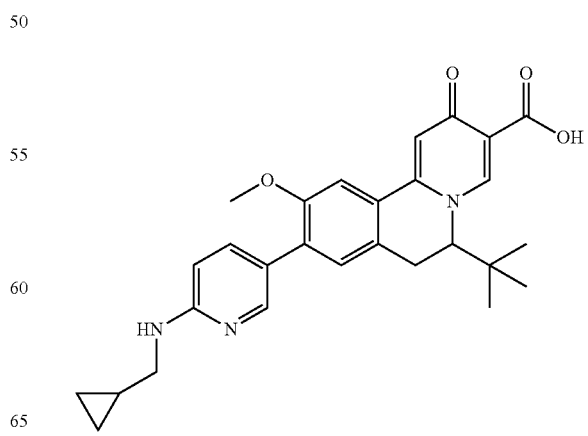

103

Step 52: Preparation of 6-(tert-butyl)-9-(6-(cyclopropylmethylamino) pyridin-3-yl)-10-methoxy-2-oxo-6,7-dihydro-2H-pyrido[2,1-a]isoquinoline-3-carboxylic Acid

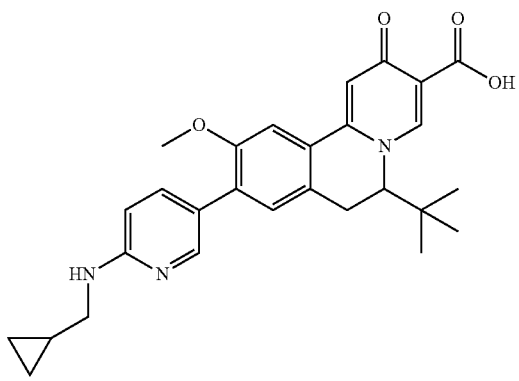 [SMILES: COc1cc2c(cc1-c1ccc(NCC3CC3)nc1)CC(C(C)(C)C)n1cc(C(=O)O)c(=O)cc1-2]

6-(tert-butyl)-9-(6-(cyclopropylmethylamino)pyridin-3-yl)-10-methoxy-2-oxo-6,7-dihydro-2H-pyrido[2,1-a]isoquinoline-3-carboxylic acid (18.7 mg) was prepared by using 6-(tert-butyl)-9-(6-fluoropyridin-3-yl)-10-methoxy-2-oxo-6,7-dihydro-2H-pyrido-[2,1-a]isoquinoline-3-carboxylic acid (42.2 mg, 0.1 mmol) and cyclopropylmethylamine (56.8 mg, 0.8 mmol) in DMSO (3 mL) according to method in example 50, step 50. $^1$H NMR (400 MHz, DMSO-$d_6$): δ 16.52 (s, 1H), 8.68 (s, 1H), 8.12 (s, 1H), 7.57-7.47 (m, 4H), 7.31 (s, 1H), 6.48 (d, J=9.2 Hz, 1H), 5.24 (s, 2H), 4.53 (d, J=4.8 Hz, 1H), 4.07-4.03 (m, 1H), 3.82 (s, 3H), 3.10-3.07 (m, 2H), 0.66 (s, 9H), 0.40-0.32 (m, 3H), 0.16-0.12 (m, 2H). MS observed (ESI$^+$) [(M+H)$^+$]: 474.

Example 53

9-(6-(azetidin-1-yl)-4-methylpyridin-3-yl)-6-(tert-butyl)-10-methoxy-2-oxo-6,7-dihydro-2H-pyrido 2,1-a isoquinoline-3-carboxylic Acid

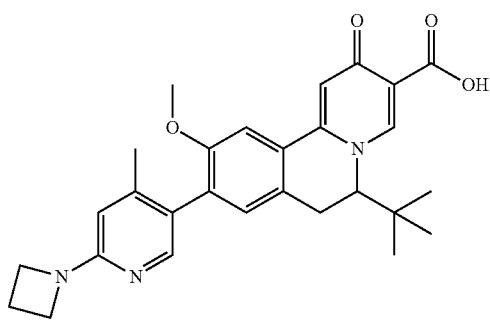 [SMILES: COc1cc2c(cc1-c1cnc(N3CCC3)cc1C)CC(C(C)(C)C)n1cc(C(=O)O)c(=O)cc1-2]

104

Step 53: Preparation of 9-(6-(azetidin-1-yl)-4-methylpyridin-3-yl)-6-(tert-butyl)-10-methoxy-2-oxo-6,7-dihydro-2H-pyrido[2,1-a]isoquinoline-3-carboxylic Acid

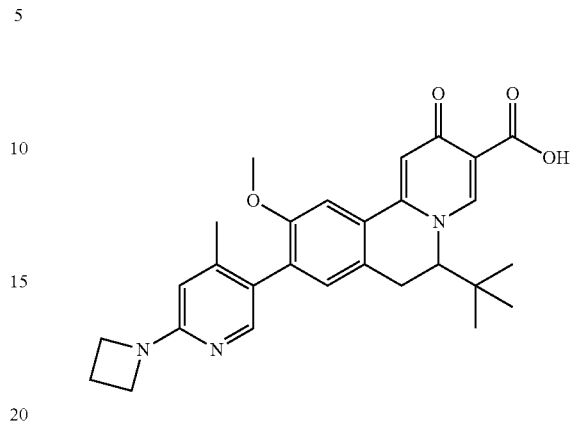

9-(6-(azetidin-1-yl)-4-methylpyridin-3-yl)-6-(tert-butyl)-10-methoxy-2-oxo-6,7-dihydro-2H-pyrido[2,1-a]isoquinoline-3-carboxylic acid (21.5 mg) was prepared by using 6-(tert-butyl)-9-(6-fluoro-4-methylpyridin-3-yl)-10-methoxy-2-oxo-6,7-dihydro-2H-pyrido-[2,1-a]isoquinoline-3-carboxylic acid (43.6 mg, 0.1 mmol) and azetidine hydrochloride (74.4 mg, 0.8 mmol) according to method in example 50, step 50. $^1$H NMR (400 MHz, DMSO-$d_6$): δ 16.48 (s, 1H), 8.70 (s, 1H), 7.69 (s, 1H), 7.56 (s, 1H), 7.50 (s, 1H), 7.13 (s, 1H), 6.22 (s, 1H), 5.24 (t, J=5.2 Hz, 2H), 4.56 (d, J=5.2 Hz, 1H), 3.88 (t, J=8.0 Hz, 4H), 3.76 (s, 3H), 3.26-3.24 (m, 2H), 1.92 (s, 3H), 0.66 (s, 9H). MS observed (ESI$^+$) [(M+H)$^+$]: 474.

Example 54

9-(6-aminopyridin-3-yl)-6-(tert-butyl)-10-methoxy-2-oxo-6,7-dihydro-2H-pyrido[2,1-a]isoquinoline-3-carboxylic Acid

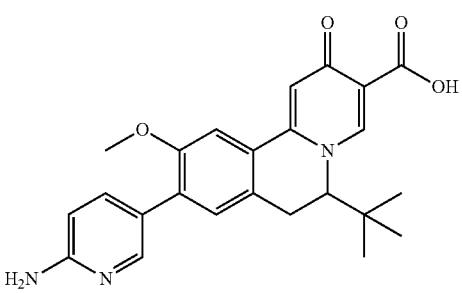 [SMILES: COc1cc2c(cc1-c1ccc(N)nc1)CC(C(C)(C)C)n1cc(C(=O)O)c(=O)cc1-2]

Step 54: Preparation of 9-(6-aminopyridin-3-yl)-6-(tert-butyl)-10-methoxy-2-oxo-6,7-dihydro-2H-pyrido[2,1-a]isoquinoline-3-carboxylic Acid

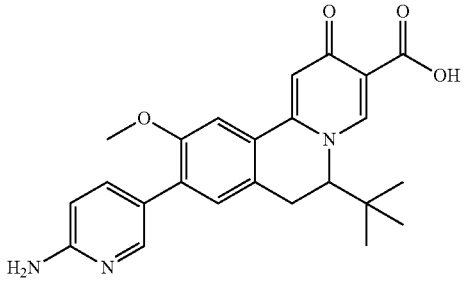

9-(6-aminopyridin-3-yl)-6-(tert-butyl)-10-methoxy-2-oxo-6,7-dihydro-2H-pyrido[2,1-a]isoquinoline-3-carboxylic acid (21.3 mg) as yellow solid was prepared by using ethyl 9-bromo-6-(tert-butyl)-10-methoxy-2-oxo-6,7-dihydro-2H-pyrido-[2,1-a]-isoquinoline-3-carboxylate (50 mg, 0.115 mmol) and (6-aminopyridin-3-yl)boronic acid (20.7 mg, 0.15 mmol) according to method in example 37, step 37. $^1$H NMR (400 MHz, DMSO-d$_6$): δ 16.60 (s, 1H), 8.76 (s, 1H), 8.15 (d, J=1.6 Hz, 1H), 7.68-7.66 (m, 1H), 7.61 (s, 1H), 7.58 (s, 1H), 7.40 (s, 1H), 6.56 (d, J=8.8 Hz, 1H), 6.34 (s, 2H), 4.61 (d, J=5.6 Hz, 1H), 3.89 (s, 3H), 3.32-3.28 (m, 2H), 0.74 (s, 9H). MS observed (ESI$^+$) [(M+H)$^+$]: 420.

Step 55: Preparation of ethyl 6-(tert-butyl)-10-methoxy-9-(6-methylpyridin-3-yl)-2-oxo-6,7-dihydro-2H-pyrido[2,1-a]isoquinoline-3-carboxylate

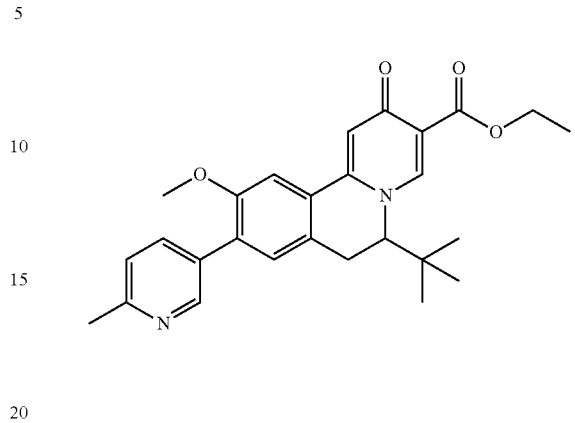

Ethyl 6-(tert-butyl)-10-methoxy-9-(6-methylpyridin-3-yl)-2-oxo-6,7-dihydro-2H-pyrido[2,1-a]isoquinoline-3-carboxylate (16.5 mg) as grey brown solid was prepared by using ethyl 9-bromo-6-(tert-butyl)-10-methoxy-2-oxo-6,7-dihydro-2H-pyrido[2,1-a]-isoquinoline-3-carboxylate (50 mg, 0.115 mmol) and (6-methylpyridin-3-yl)boronic acid (17.5 mg, 0.127 mmol) according to method in example 16, step 16a. $^1$H NMR (400 MHz, DMSO-d$_6$): δ 8.60 (s, 1H), 8.38 (s, 1H), 7.85-7.83 (m, 1H), 7.52 (s, 1H), 7.42 (s, 1H), 7.33-7.32 (m, 1H), 7.12 (s, 1H), 4.37-4.36 (m, 1H), 4.22 (q, J=8.0 Hz, 2H), 3.89 (s, 3H), 3.31-3.27 (m, 2H), 2.51 (s, 3H), 1.27 (t, J=8.0 Hz, 3H), 0.74 (s, 9H). MS observed (ESI$^+$) [(M+H)$^+$]: 447.

Example 55

Ethyl 6-(tert-butyl)-10-methoxy-9-(6-methylpyridin-3-yl)-2-oxo-6,7-dihydro-2H-pyrido[2,1-a]isoquinoline-3-carboxylate

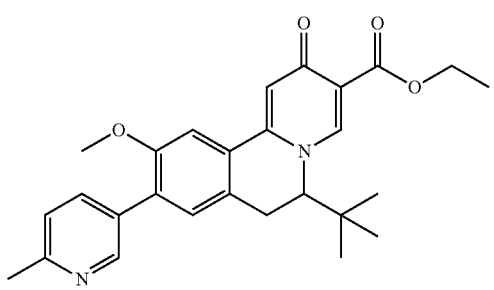 [SMILES: CCOC(=O)c1cn2c(cc1=O)-c1cc(OC)c(-c3ccc(C)nc3)cc1CC2C(C)(C)C]

Example 56

6-(tert-butyl)-9-(6-(cyclobutylamino)pyridin-3-yl)-10-methoxy-2-oxo-6,7-dihydro-2H-pyrido[2,1-a]isoquinoline-3-carboxylic Acid

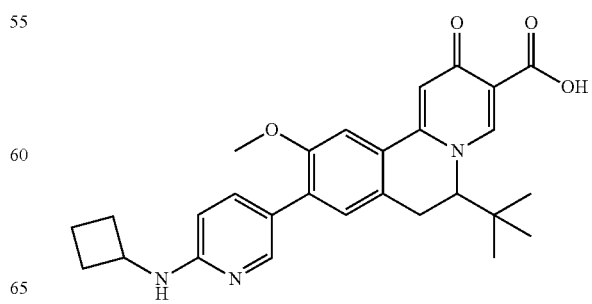

Step 56: Preparation of 6-(tert-butyl)-9-(6-(cyclobutylamino)pyridin-3-yl)-10-methoxy-2-oxo-6,7-dihydro-2H-pyrido[2,1-a]isoquinoline-3-carboxylic Acid

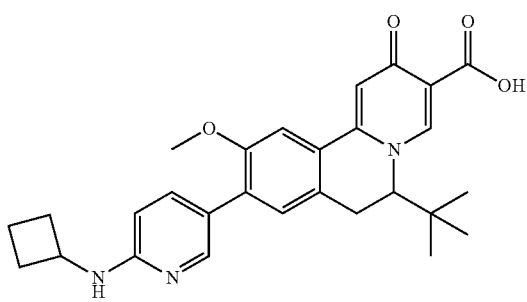 [SMILES: COc1cc2c(cc1-c1ccc(NC3CCC3)nc1)CC(C(C)(C)C)n1cc(C(=O)O)c(=O)cc1-2]

6-(tert-butyl)-9-(6-(cyclobutylamino)pyridin-3-yl)-10-methoxy-2-oxo-6,7-dihydro-2H-pyrido[2,1-a]isoquinoline-3-carboxylic acid (12.5 mg) was prepared by using 6-(tert-butyl)-9-(6-fluoropyridin-3-yl)-10-methoxy-2-oxo-6,7-dihydro-2H-pyrido[2,1-a]isoquinoline-3-carboxylic acid (42.2 mg, 0.1 mmol) and cyclobutylamine (56.8 mg, 0.8 mmol) in DMSO (3 mL) according to method in example 50, step 50. $^1$H NMR (400 MHz, DMSO-$d_6$): δ 16.54 (s, 1H), 8.72 (s, 1H), 8.15 (d, J=2.0 Hz, 1H), 7.61-7.60 (m, 1H), 7.56 (s, 1H), 7.53 (s, 1H), 7.35 (s, 1H), 7.06 (s, 1H), 6.46 (d, J=9.2 Hz, 1H), 4.58 (d, J=6.4 Hz, 1H), 4.29-4.23 (m, 1H), 3.85 (s, 3H), 3.35-3.31 (m, 2H), 2.28-2.22 (m, 2H), 1.88-1.81 (m, 2H), 1.67-1.60 (m, 2H), 0.70 (s, 9H). MS observed (ESI$^+$) [(M+H)$^+$]: 474.

Example 57

9-(6-acetamidopyridin-3-yl)-6-(tert-butyl)-10-methoxy-2-oxo-6,7-dihydro-2H-pyrido[2,1-a]isoquinoline-3-carboxylic Acid

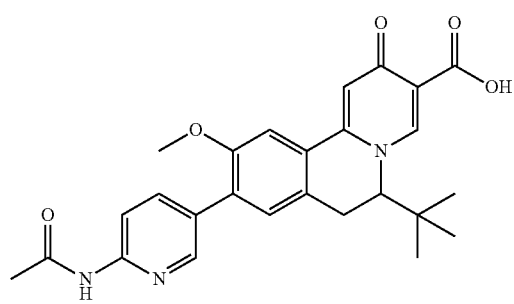 [SMILES: COc1cc2c(cc1-c1ccc(NC(C)=O)nc1)CC(C(C)(C)C)n1cc(C(=O)O)c(=O)cc1-2]

Step 57a: Preparation of ethyl 9-(6-aminopyridin-3-yl)-6-(tert-butyl)-10-methoxy-2-oxo-6,7-dihydro-2H-pyrido[2,1-a]isoquinoline-3-carboxylate

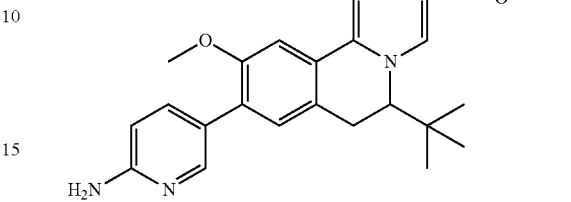

Ethyl 9-(6-aminopyridin-3-yl)-6-(tert-butyl)-10-methoxy-2-oxo-6,7-dihydro-2H-pyrido[2,1-a]isoquinoline-3-carboxylate (112 mg) as yellow solid was prepared by using ethyl 9-bromo-6-(tert-butyl)-10-methoxy-2-oxo-6,7-dihydro-2H-pyrido[2,1-a]-isoquino-line-3-carboxylate (200 mg, 0.46 mmol) and (6-aminopyridin-3-yl)boronic acid (82.8 mg, 0.6 mmol) according to method in example 16, step 16a.

Step 57b: Preparation of ethyl 9-(6-acetamidopyridin-3-yl)-6-(tert-butyl)-10-methoxy-2-oxo-6,7-dihydro-2H-pyrido[2,1-a]isoquinoline-3-carboxylate

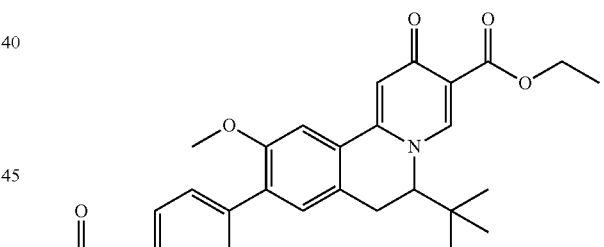

To a solution of ethyl 9-(6-aminopyridin-3-yl)-6-(tert-butyl)-10-methoxy-2-oxo-6,7-dihydro-2H-pyrido[2,1-a]isoquinoline-3-carboxylate (44.7 mg, 0.1 mmol) and acetic anhydride (96.8 mg, 0.8 mmol) in EtOH was added trimethylamine (80.9 mg, 0.8 mmol), and the reaction mixture was heated at 60° C. and stirred for 16 h. Then, saturated NaHCO$_3$ solution (1 mL) was added to quench the reaction, and the mixture was concentrated to afford ethyl 9-(6-acetamidopyridin-3-yl)-6-(tert-butyl)-10-methoxy-2-oxo-6,7-dihydro-2H-pyrido[2,1-a]isoquinoline-3-carboxylate as crude product.

Step 57c: Preparation of 9-(6-acetamidopyridin-3-yl)-6-(tert-butyl)-10-methoxy-2-oxo-6,7-dihydro-2H-pyrido[2,1-a]isoquinoline-3-carboxylic Acid

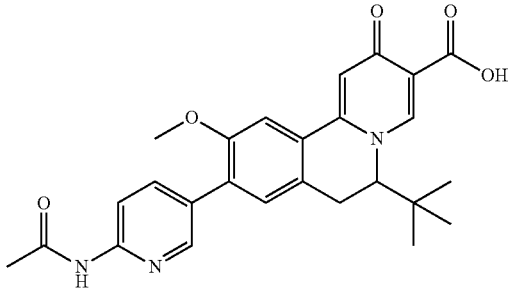 [SMILES: COc1cc2c(cc1-c1ccc(NC(C)=O)nc1)CC(C(C)(C)C)n1cc(C(=O)O)c(=O)cc1-2]

9-(6-acetamidopyridin-3-yl)-6-(tert-butyl)-10-methoxy-2-oxo-6,7-dihydro-2H-pyrido[2,1-a]isoquinoline-3-carboxylic acid (9.2 mg) as white solid was prepared by using crude product of ethyl 9-(6-acetamidopyridin-3-yl)-6-(tert-butyl)-10-methoxy-2-oxo-6,7-dihydro-2H-pyrido[2,1-a]isoquinoline-3-carboxylate according to method in example 1, step 1i. $^1$H NMR (400 MHz, DMSO-d$_6$): δ 16.50 (s, 1H), 10.57 (s, 1H), 8.74 (s, 1H), 8.45 (d, J=2.8 Hz, 1H), 8.09 (d, J=8.8 Hz, 1H), 7.95-7.92 (m, 1H), 7.62 (s, 1H), 7.60 (s, 1H), 7.45 (s, 1H), 4.59 (d, J=4.8 Hz, 1H), 3.87 (s, 3H), 3.37-3.32 (m, 2H), 2.07 (s, 3H), 0.70 (s, 9H). MS observed (ESI$^+$) [(M+H)$^+$]: 462.

Step 58: Preparation of 6-(tert-butyl)-10-methoxy-9-(2-methylpyrimidin-5-yl)-2-oxo-6,7-dihydro-2H-pyrido[2,1-a]isoquinoline-3-carboxylic Acid

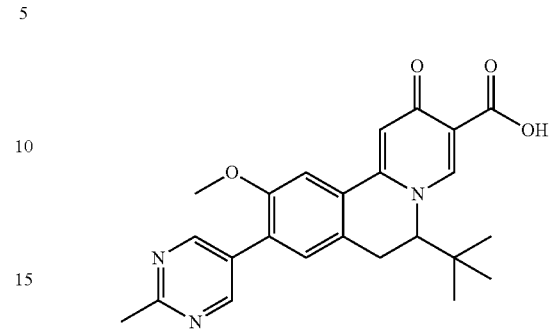

6-(tert-butyl)-10-methoxy-9-(2-methylpyrimidin-5-yl)-2-oxo-6,7-dihydro-2H-pyrido[2,1-a]isoquinoline-3-carboxylic acid (19 mg) as light yellow solid was prepared by using ethyl 9-bromo-6-(tert-butyl)-10-methoxy-2-oxo-6,7-dihydro-2H-pyrido[2,1-a]-isoquinoline-3-carboxylate (100 mg, 0.23 mmol) and (2-methylpyrimidin-5-yl)boronic acid (32 mg, 0.23 mmol) according to method in example 37, step 37. $^1$H NMR (400 MHz, DMSO-d$_6$): δ 16.49 (s, 1H), 8.89 (s, 2H), 8.79 (s, 1H), 7.69 (s, 2H), 7.56 (s, 1H), 4.65 (d, J=4.0 Hz, 1H), 3.93 (s, 3H), 3.46-3.40 (m, 2H), 2.67 (s, 3H), 0.75 (s, 9H). MS observed (ESI$^+$)[(M+H)$^+$]: 420.

Example 58

6-(tert-butyl)-10-methoxy-9-(2-methylpyrimidin-5-yl)-2-oxo-6,7-dihydro-2H-pyrido[2,1-a]isoquinoline-3-carboxylic Acid

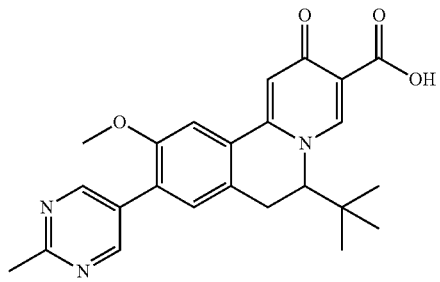

Example 59

6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylic Acid

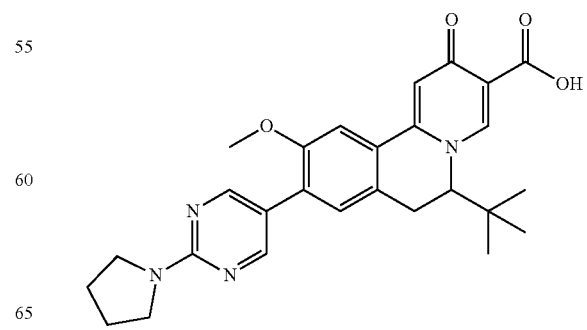

Step 59a: Preparation of ethyl 6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylate

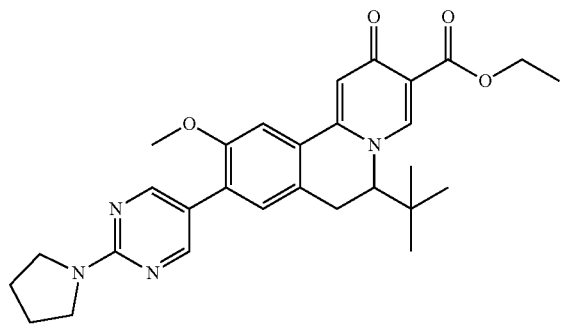 [SMILES: CCOC(=O)c1cn2c(cc1=O)-c1cc(OC)c(-c3cnc(N4CCCC4)nc3)cc1CC2C(C)(C)C]

Ethyl 6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylate (98 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (2-(pyrrolidin-2-yl)pyrimidin-5-yl)boronic acid (68 mg, 0.35 mmol) according to method in example 1, step 1h.

Step 59b: Preparation of 6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylic Acid

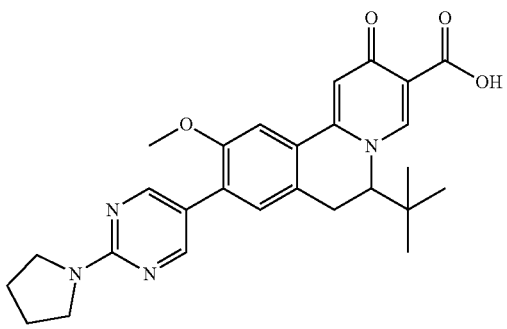 [SMILES: COc1cc2c(cc1-c1cnc(N3CCCC3)nc1)CC(C(C)(C)C)n1cc(C(=O)O)c(=O)cc1-2]

6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylic acid (53.3 mg) as yellow solid was prepared by using ethyl 6-(tert-butyl)-10-methoxy-2-oxo-9-(2-(pyrrolidin-1-yl) pyrimidin-5-yl)-6,7-dihydro-2H-pyrido[2,1-a]isoquinoline-3-carboxylate (98 mg, 0.195 mmol) according to method in example 1, step 1i. $^1$H NMR (400 MHz, DMSO-$d_6$): δ 16.54 (s, 1H), 8.77 (s, 1H), 8.58 (s, 2H), 7.63 (s, 1H), 7.62 (s, 1H), 7.46 (s, 1H), 4.63-4.61 (m, 1H), 3.92 (s, 3H), 3.55-3.48 (m., 4H), 3.39 (d, J=6.2 Hz, 2H), 1.98-1.92 (m., 4H), 0.75 (s, 9H). MS observed (ESI$^+$) [(M+H)$^+$]: 475.

Example 60

6-(tert-butyl)-10-methoxy-9-(2-(methylamino)pyrimidin-5-yl)-2-oxo-6,7-dihydro-2H-pyrido[2,1-a]isoquinoline-3-carboxylic Acid

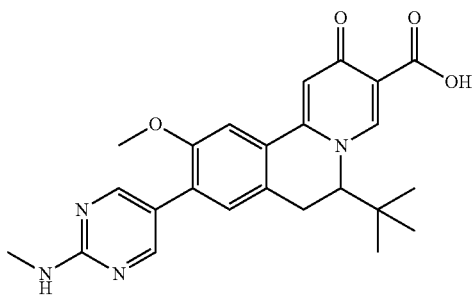 [SMILES: CNc1ncc(-c2cc3c(cc2OC)-c2cc(=O)c(C(=O)O)cn2C(C(C)(C)C)C3)cn1]

Step 60a: Preparation of methyl 6-(tert-butyl)-10-methoxy-9-(2-(methylamino)pyrimidin-5-yl)-2-oxo-6,7-dihydro-2H-pyrido[2,1-a]isoquinoline-3-carboxylate

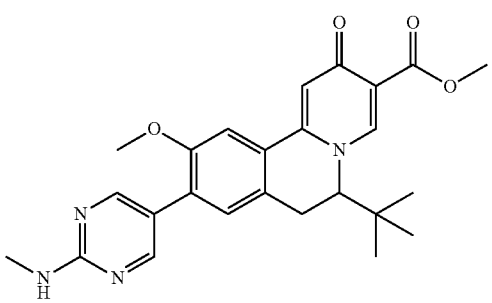

Methyl 6-(tert-butyl)-10-methoxy-9-(2-(methylamino) pyrimidin-5-yl)-2-oxo-6,7-dihydro-2H-pyrido[2,1-a]isoquinoline-3-carboxylate (20 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (2-(methylamino)pyrimidin-5-yl)boronic acid (39 mg, 0.25 mmol) according to method in example 1, step 1h.

Step 60b: Preparation of 6-(tert-butyl)-10-methoxy-9-(2-(methylamino) pyrimidin-5-yl)-2-oxo-6,7-dihydro-2H-pyrido[2,1-a]isoquinoline-3-carboxylic Acid

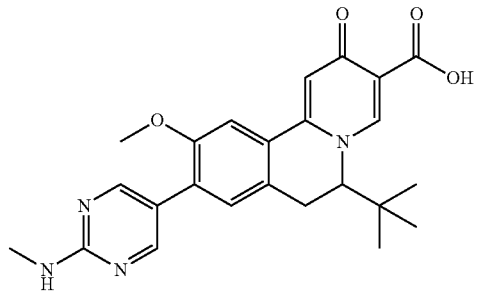 [SMILES: CNc1ncc(-c2cc3c(cc2OC)-c2cc(=O)c(C(=O)O)cn2C(C(C)(C)C)C3)cn1]

6-(tert-butyl)-10-methoxy-9-(2-(methylamino)pyrimidin-5-yl)-2-oxo-6,7-dihydro-2H-pyrido-[2,1-a]isoquinoline-3-carboxylic acid (11.2 mg) as yellow solid was prepared by using methyl 6-(tert-butyl)-10-methoxy-9-(2-(methylamino) pyrimidin-5-yl)-2-oxo-6,7-dihydro-2H-pyrido[2,1-a]isoquinoline-3-carboxylate (20 mg, 0.04 mmol) according to method in example 1, step 1i. $^1$H NMR (400 MHz, DMSO-$d_6$): δ 16.54 (s, 1H), 8.77 (s, 1H), 8.53 (s, 2H), 7.63 (s, 1H), 7.61 (s, 1H), 7.46 (s, 1H), 7.29 (s, 1H) 4.62 (d, J=5.6 Hz, 1H), 3.92 (s, 3H), 3.38 (d, J=6.0 Hz, 2H), 2.85 (d, J=4.4 Hz, 3H), 0.75 (s, 9H). MS observed (ESI$^+$) [(M+H)$^+$]: 435.

Example 61

6-(tert-butyl)-9-(2-(dimethylamino)pyrimidin-5-yl)-10-methoxy-2-oxo-6,7-dihydro-2H-pyrido[2,1-a]isoquinoline-3-carboxylic Acid

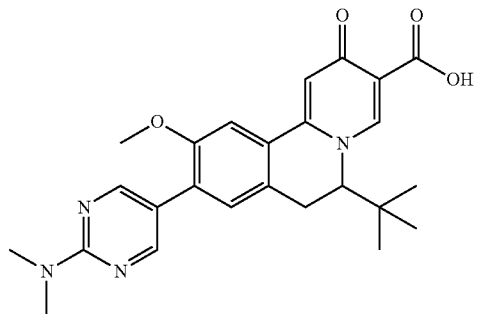 [SMILES: COc1cc2c(cc1-c1cnc(N(C)C)nc1)CC(C(C)(C)C)n1cc(C(=O)O)c(=O)cc1-2]

Step 61a: Preparation of methyl 6-(tert-butyl)-9-(2-(dimethylamino) pyrimidin-5-yl)-10-methoxy-2-oxo-6,7-dihydro-2H-pyrido[2,1-a]isoquinoline-3-carboxylate

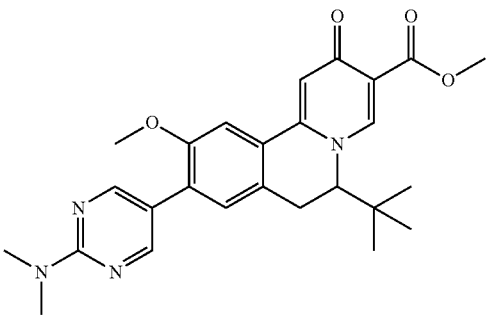

Methyl 6-(tert-butyl)-9-(2-(dimethylamino)pyrimidin-5-yl)-10-methoxy-2-oxo-6,7-dihydro-2H-pyrido[2,1-a]isoquinoline-3-carboxylate (18 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (2-(dimethylamino)-pyrimidin-5-yl) boronic acid (43 mg, 0.25 mmol) according to method in example 1, step 1h.

Step 61b: Preparation of 6-(tert-butyl)-9-(2-(dimethylamino)pyrimidin-5-yl)-10-methoxy-2-oxo-6,7-dihydro-2H-pyrido[2,1-a]isoquinoline-3-carboxylic Acid

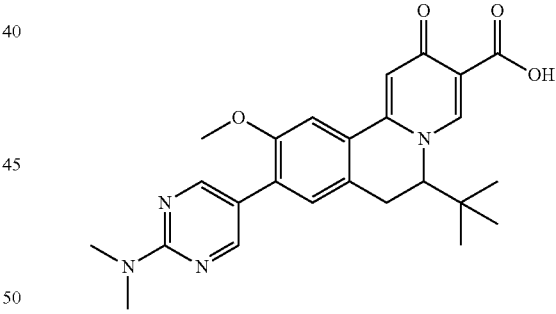

6-(tert-butyl)-9-(2-(dimethylamino)pyrimidin-5-yl)-10-methoxy-2-oxo-6,7-dihydro-2H-pyrido[2,1-a]isoquinoline-3-carboxylic acid (10.1 mg) as yellow solid was prepared by using methyl 6-(tert-butyl)-9-(2-(dimethylamino)pyrimidin-5-yl)-10-methoxy-2-oxo-6,7-dihydro-2H-pyrido[2,1-a]isoquinoline-3-carboxylate (18 mg, 0.04 mmol) according to method in example 1, step 1i. $^1$H NMR (400 MHz, DMSO-$d_6$): δ 8.77 (s, 1H), 8.59 (s, 2H), 7.63 (s, 1H), 7.62 (s, 1H), 7.60-7.44 (m, 1H), 4.62 (s, 1H), 3.92 (s, 3H), 3.39-3.35 (m, 2H), 3.17 (s, 6H), 0.75 (s, 9H). MS observed (ESI$^+$) [(M+H)$^+$]: 449.

Example 62

6-(tert-butyl)-10-methoxy-9-(2-morpholinylpyrimidin-5-yl)-2-oxo-6,7-dihydro-2H-pyrido[2,1-a]isoquinoline-3-carboxylic Acid

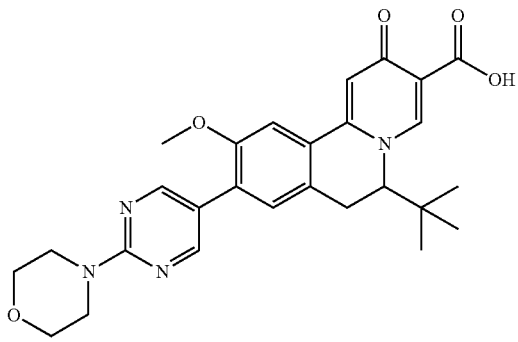 [SMILES: COc1cc2c(cc1-c1cnc(N3CCOCC3)nc1)CC(C(C)(C)C)n1cc(C(=O)O)c(=O)cc1-2]

Step 62a: Preparation of methyl 6-(tert-butyl)-10-methoxy-9-(2-morpholinylpyrimidin-5-yl)-2-oxo-6,7-dihydro-2H-pyrido[2,1-a]isoquinoline-3-carboxylate

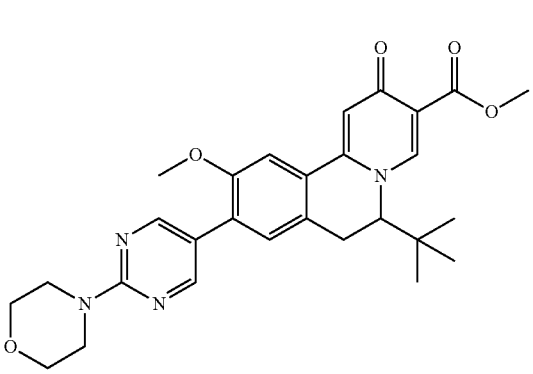 [SMILES: COC(=O)c1cn2c(cc1=O)-c1cc(OC)c(-c3cnc(N4CCOCC4)nc3)cc1CC2C(C)(C)C]

Methyl 6-(tert-butyl)-10-methoxy-9-(2-morpholinylpyrimidin-5-yl)-2-oxo-6,7-dihydro-2H-pyrido[2,1-a]isoquinoline-3-carboxylate (20 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (2-morpholinyl-pyrimidin-5-yl)boronic acid (53 mg, 0.25 mmol) according to method in example 1, step 1h.

Step 62b: Preparation of 6-(tert-butyl)-10-methoxy-9-(2-morpholinyl-pyrimidin-5-yl)-2-oxo-6,7-dihydro-2H-pyrido[2,1-a]isoquinoline-3-carboxylic Acid

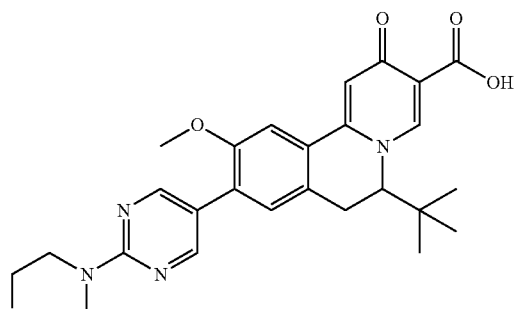

6-(tert-butyl)-10-methoxy-9-(2-morpholinylpyrimidin-5-yl)-2-oxo-6,7-dihydro-2H-pyrido[2,1-a]isoquinoline-3-carboxylic acid (13.5 mg) as yellow solid was prepared by using methyl 6-(tert-butyl)-10-methoxy-9-(2-morpholinylpyrimidin-5-yl)-2-oxo-6,7-dihydro-2H-pyrido[2,1-a]isoquinoline-3-carboxylate (20 mg, 0.04 mmol) according to method in example 1, step 1i. $^1$H NMR (400 MHz, DMSO-$d_6$): δ 8.77 (s, 1H), 8.63 (s, 2H), 7.64 (s, 1H), 7.63 (s, 1H), 7.48 (s, 1H), 4.62 (d, J=6.0 Hz, 1H), 3.92 (s, 3H), 3.78-3.74 (m, 4H), 3.70-3.66 (m, 4H), 3.39 (d, J=6.4 Hz, 2H), 0.75 (s, 9H). MS observed (ESI$^+$) [(M+H)$^+$]: 491.

Example 63

6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylic Acid

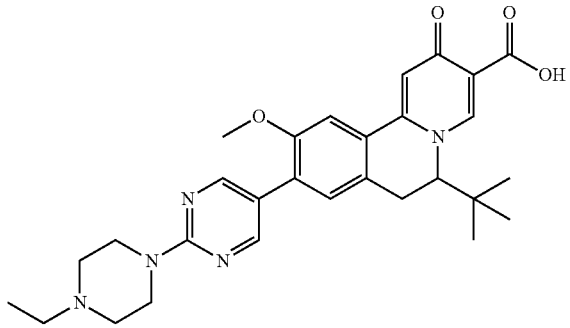 [SMILES: CCN1CCN(c2ncc(-c3cc4c(cc3OC)-c3cc(=O)c(C(=O)O)cn3C(C(C)(C)C)C4)cn2)CC1]

Step 63: Preparation of ethyl 6-(tert-butyl)-9-(2-(4-ethylpiperazin-1-yl) pyrimidin-5-yl)-10-methoxy-2-oxo-6,7-dihydro-2H-pyrido[2,1-a]isoquinoline-3-carboxylate

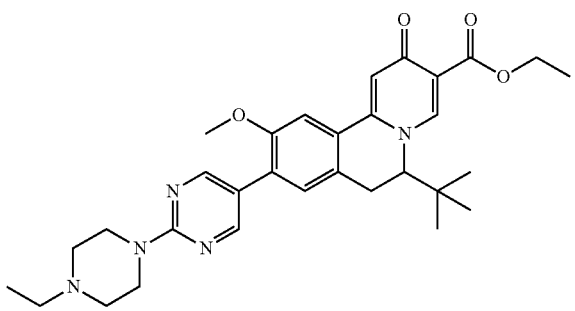 [SMILES: CCOC(=O)c1cn2c(cc1=O)-c1cc(OC)c(-c3cnc(N4CCN(CC)CC4)nc3)cc1CC2C(C)(C)C]

To a solution of ethyl 9-bromo-6-(tert-butyl)-10-methoxy-2-oxo-6,7-dihydro-2H-pyrido[2,1-a]isoquinoline-3-carboxylate (50 mg, 0.115 mmol) in dioxane (5 mL) and MeOH (3 mL) was added (2-(4-ethylpiperazin-1-yl)pyrimidin-5-yl)boronic acid (26.8 mg, 0.15 mmol), PdCl$_2$(dppf) (16.8 mg, 0.023 mmol) and K$_3$PO$_4$ (37 mg, 0.175 mmol), and the mixture was exchanged with nitrogen three times, followed by heating at 90° C. and stirred for 18 h. The reaction mixture was diluted with EtOAc (20 mL), washed with water (30 mL) and brine (20 mL), and the organic phase was dried over anhydrous sodium sulfate, filtered and concentrated under reduced pressure, the resulted residue was purified by preparative TLC to provide ethyl 6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylate as off-yellow solid.

Step 64: Preparation of 6-(tert-butyl)-9-(2-(4-ethylpiperazin-1-yl) pyrimidin-5-yl)-10-methoxy-2-oxo-6,7-dihydro-2H-pyrido[2,1-a]isoquinoline-3-carboxylic Acid

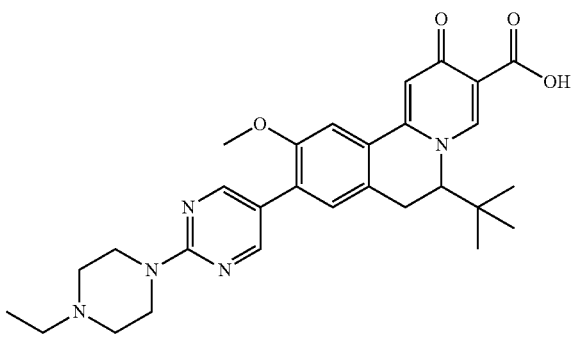 [SMILES: CCN1CCN(c2ncc(-c3cc4c(cc3OC)-c3cc(=O)c(C(=O)O)cn3C(C(C)(C)C)C4)cn2)CC1]

6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylic acid (51.6 mg) as yellow solid was prepared by using ethyl 6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylate according to method in example 1, step 1i. $^1$H NMR (400 MHz, DMSO-d$_6$): δ 16.55 (s, 1H), 8.77 (s, 1H), 8.63 (s, 2H), 7.64 (s, 1H), 7.63 (s, 1H), 7.49 (s, 1H), 5.33-5.30 (m, 1H), 4.63 (d, J=6.0 Hz, 2H), 3.92 (s, 3H), 2.55 (d, J=7.2 Hz, 2H), 2.36-2.30 (m, 2H), 2.21-2.14 (m, 2H), 2.00-1.97 (m, 4H), 0.85 (t, J=6.4 Hz, 3H), 0.74 (s, 9H). MS observed (ESI$^+$) [(M+H)$^+$]: 518.

Example 64

6-(tert-butyl)-9-(2-(cyclopropylamino)pyrimidin-5-yl)-10-methoxy-2-oxo-6,7-dihydro-2H-pyrido[2,1-a]isoquinoline-3-carboxylic Acid

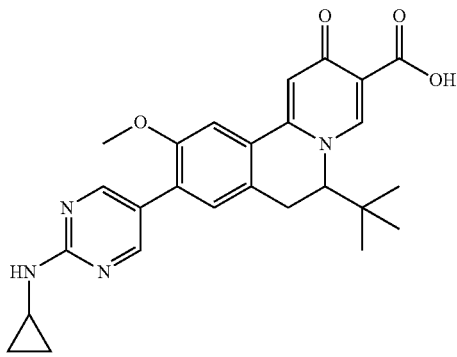 [SMILES: COc1cc2c(cc1-c1cnc(NC3CC3)nc1)CC(C(C)(C)C)n1cc(C(=O)O)c(=O)cc1-2]

Example 65

9-(2-aminopyrimidin-5-yl)-6-(tert-butyl)-10-methoxy-2-oxo-6,7-dihydro-2H-pyrido[2,1-a]isoquinoline-3-carboxylic Acid

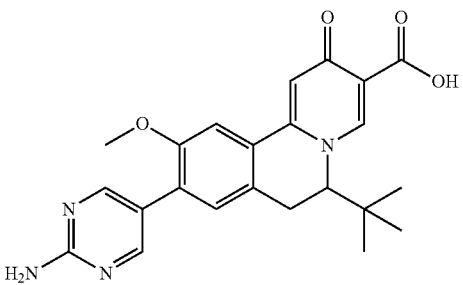

Step 65: Preparation of 6-(tert-butyl)-9-(2-(cyclopropylamino)pyrimidin-5-yl)-10-methoxy-2-oxo-6,7-dihydro-2H-pyrido[2,1-a]isoquinoline-3-carboxylic acid and 9-(2-aminopyrimidin-5-yl)-6-(tert-butyl)-1-methoxy-2-oxo-6,7-dihydro-2H-pyrido-[2,1-a]isoquinoline-3-carboxylic Acid

Example 66

6-(tert-butyl)-10-methoxy-9-(2-methoxypyrimidin-5-yl)-2-oxo-6,7-dihydro-2H-pyrido[2,1-a]isoquinoline-3-carboxylic Acid

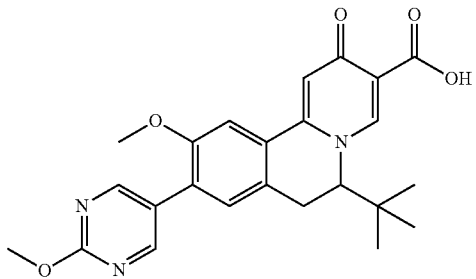

Step 66a: Preparation of ethyl 6-(tert-butyl)-9-(2-chloropyrimidin-5-yl)-10-methoxy-2-oxo-6,7-dihydro-2H-pyrido[2,1-a]isoquinoline-3-carboxylate

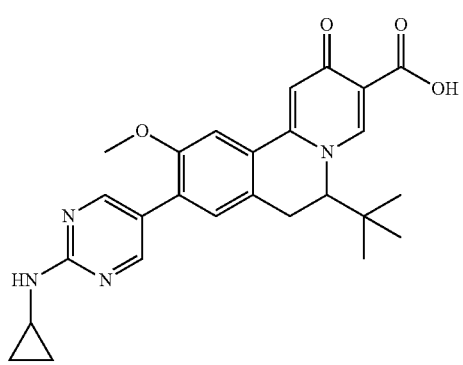

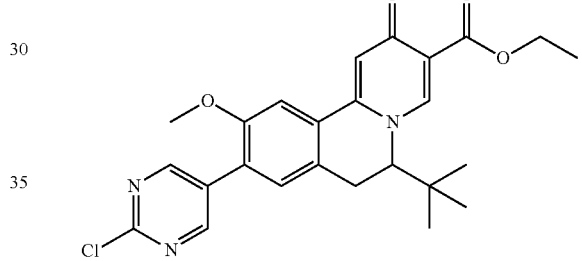

Ethyl 6-(tert-butyl)-9-(2-chloropyrimidin-5-yl)-10-methoxy-2-oxo-6,7-dihydro-2H-pyrido[2,1-a]isoquinoline-3-carboxylate as brown solid was prepared by using ethyl 9-bromo-6-(tert-butyl)-10-methoxy-2-oxo-6,7-dihydro-2H-pyrido [2,1-a]isoquinoline-3-carboxylate (50 mg, 0.115 mmol) and (2-chloropyrimidin-5-yl) boronic acid (23.7 mg, 0.15 mmol) according to method in example 37, step 37.

Step 66b: Preparation of 6-(tert-butyl)-10-methoxy-9-(2-methoxypyrimidin-5-yl)-2-oxo-6,7-dihydro-2H-pyrido[2,1-a]isoquinoline-3-carboxylic Acid

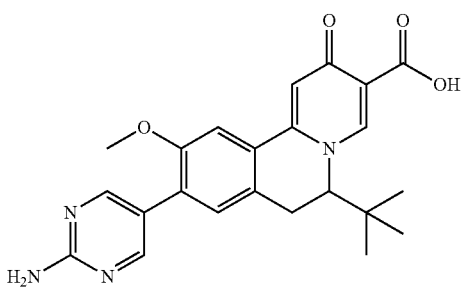

6-(tert-butyl)-9-(2-(cyclopropylamino)pyrimidin-5-yl)-10-methoxy-2-oxo-6,7-dihydro-2H-pyrido[2,1-a]isoquinoline-3-carboxylic acid (2.4 mg) as light yellow solid was prepared by using ethyl 9-bromo-6-(tert-butyl)-10-methoxy-2-oxo-6,7-dihydro-2H-pyrido[2,1-a]isoquinoline-3-carboxylate (50 mg, 0.115 mmol) and (2-cyclopropylaminopyrimidin-5-yl)boronic acid (26.9 mg, 0.15 mmol) according to method in example 37, step 37. $^{1}$H NMR (400 MHz, DMSO-$d_6$): δ 16.50 (s, 1H), 8.71 (s, 1H), 8.49 (s, 2H), 7.57 (s, 1H), 7.55 (s, 1H), 7.54 (s, 1H), 7.42 (s, 1H), 4.57 (d, J=5.6 Hz, 1H), 3.87 (s, 3H), 3.38-3.32 (m, 2H), 2.70-2.66 (m, 1H), 0.69 (s, 9H), 0.65-0.60 (m, 2H), 0.46-0.42 (m, 2H). MS observed (ESI$^+$) [(M+H)$^+$]: 461.

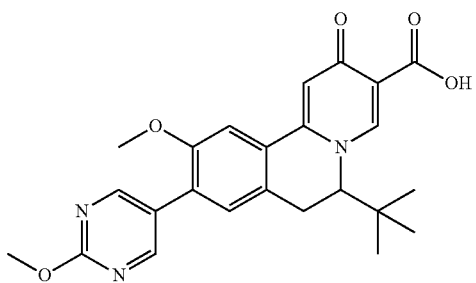 [SMILES: COc1ncc(-c2cc3c(cc2OC)-c2cc(=O)c(C(=O)O)cn2C(C(C)(C)C)C3)cn1]

And 9-(2-aminopyrimidin-5-yl)-6-(tert-butyl)-10-methoxy-2-oxo-6,7-dihydro-2H-pyrido[2,1-a]isoquinoline-3-carboxylic acid (16.1 mg) was obtained as light yellow solid. $^{1}$H NMR (400 MHz, DMSO-$d_6$): δ 16.50 (s, 1H), 8.69 (s, 1H), 8.41 (s, 2H), 7.55 (s, 1H), 7.53 (s, 1H), 7.40 (s, 1H), 6.77 (s, 2H), 4.56 (d, J=6.8 Hz, 1H), 3.85 (s, 3H), 3.45-3.42 (m, 2H), 0.67 (s, 9H). MS observed (ESI$^+$) [(M+H)$^+$]: 421.

To a solution of ethyl 6-(tert-butyl)-9-(2-chloropyrimidin-5-yl)-10-methoxy-2-oxo-6,7-dihydro-2H-pyrido[2,1-a]isoquinoline-3-carboxylate in MeOH (3 mL) and water (1 mL) was added lithium hydroxide monohydrate (19.3 mg, 0.46 mmol), and the mixture was stir at RT for 1 h. Then, the mixture was concentrated, and the residue was dissolved in water (20 mL), extracted with EtOAc (20 mL×5), the water phase was acidified with 1M HCl till pH=2, and extracted with EtOAc (10 mL×5), and the combined organic phase was washed with water (20 mL×5), and then concentrated to provide 6-(tert-butyl)-10-methoxy-9-(2-methoxypyrimidin-5-yl)-2-oxo-6,7-dihydro-2H-pyrido[2,1-a]isoquinoline-3-carboxylic acid (28.7 mg) as yellow solid. $^1$H NMR (400 MHz, DMSO-d$_6$): δ 16.44 (s, 1H), 8.76 (s, 2H), 8.72 (s, 1H), 7.61 (s, 1H), 7.60 (s, 1H), 7.48 (s, 1H), 4.57 (d, J=4.4 Hz, 1H), 3.90 (s, 3H), 3.86 (s, 3H), 3.32-3.28 (m, 2H), 0.68 (s, 9H). MS observed (ESI$^+$) [(M+H)$^+$]: 436.

Example 67

6-(tert-butyl)-9-(2-(cylcopropylmethylamino)pyrimidin-5-yl)-10-methoxy-2-oxo-6,7-dihydro-2H-pyrido[2,1-a]isoquinoline-3-carboxylic Acid

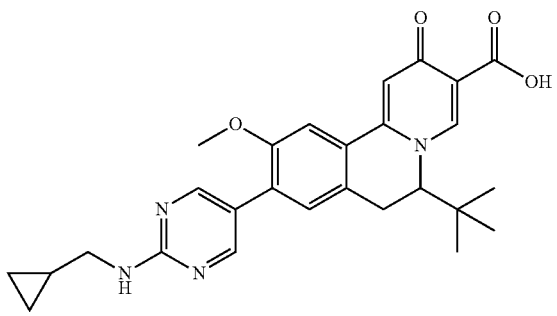 [SMILES: COc1cc2c(cc1-c1cnc(NCC3CC3)nc1)CC(C(C)(C)C)n1cc(C(=O)O)c(=O)cc1-2]

Step 67a: Preparation of (2-((cyclopropylmethyl)amino)pyrimidin-5-yl) boronic Acid

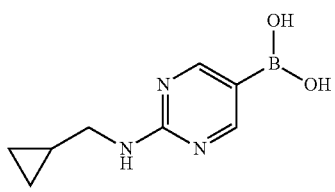 [SMILES: OB(O)c1cnc(NCC2CC2)nc1]

To a solution of (2-chloropyrimidin-5-yl)boronic acid (100 mg, 0.63 mmol) in CH$_3$CN (4 mL) was added cyclopropylmethylamine (179.2 mg, 2.52 mmol) under nitrogen, and the mixture was allowed to heat at 80° C. and stirred for 16 h. LC-MS showed the reaction was completed. Then, the mixture was concentrated to dryness to provide (2-((cyclopropylmethyl)amino)pyrimidin-5-yl)boronic acid (200 mg) as crude product, which was directly used for next stage without further purification.

Step 67b: Preparation of ethyl 6-(tert-butyl)-9-(2-(cylcopropylmethylamino)pyrimidin-5-yl)-10-methoxy-2-oxo-6,7-dihydro-2H-pyrido[2,1-a]isoquinoline-3-carboxylate

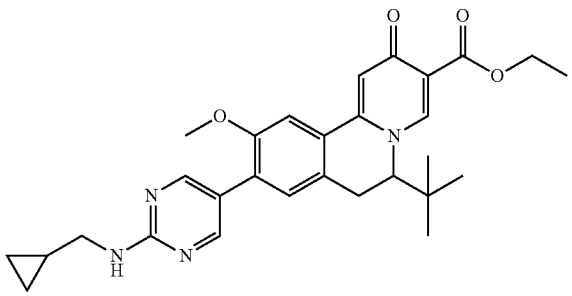 [SMILES: CCOC(=O)c1cn2c(cc1=O)-c1cc(OC)c(-c3cnc(NCC4CC4)nc3)cc1CC2C(C)(C)C]

Ethyl 6-(tert-butyl)-9-(2-(cylcopropylmethylamino)pyrimidin-5-yl)-10-methoxy-2-oxo-6,7-dihydro-2H-pyrido[2,1-a]isoquinoline-3-carboxylate (53 mg) as brown solid was prepared by using ethyl 9-bromo-6-(tert-butyl)-10-methoxy-2-oxo-6,7-dihydro-2H-pyrido[2,1-a]isoquinoline-3-carboxylate (200 mg, 0.46 mmol) and (2-((cyclopropylmethyl)amino)pyrimidin-5-yl)boronic acid (177.6 mg, 0.92 mmol) according to method in example 1, step 1h.

Step 67c: Preparation of 6-(tert-butyl)-9-(2-(cylcopropylmethylamino) pyrimidin-5-yl)-10-methoxy-2-oxo-6,7-dihydro-2H-pyrido[2,1-a]isoquinoline-3-carboxylic Acid

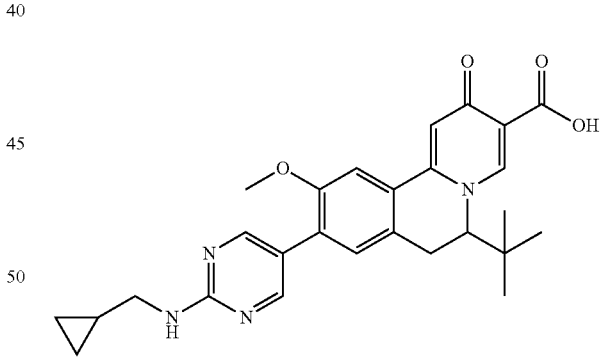

6-(tert-butyl)-9-(2-(cylcopropylmethylamino)pyrimidin-5-yl)-10-methoxy-2-oxo-6,7-dihydro-2H-pyrido[2,1-a]isoquinoline-3-carboxylic acid (2.7 mg) as yellow solid was prepared by using ethyl 6-(tert-butyl)-9-(2-(cylcopropylmethylamino)pyrimidin-5-yl)-10-methoxy-2-oxo-6,7-dihydro-2H-pyrido[2,1-a]isoquinoline-3-carboxylate (53 mg, 0.105 mmol) according to method in example 1, step 1i. $^1$H NMR (400 MHz, DMSO-d$_6$): δ 8.77 (s, 1H), 8.52 (s, 2H), 7.64 (s, 1H), 7.61 (s, 1H), 7.45-7.52 (m, 2H), 4.63-4.61 (m, 1H), 3.92 (s, 3H), 3.40-3.38 (m, 2H), 3.20 (t, J=6.3 Hz, 2H), 1.09-1.06 (m, 1H), 0.74 (s, 9H), 0.45-0.39 (m, 2H), 0.26-0.20 (m, 2H). MS observed (ESI$^+$) [(M+H)$^+$]: 475.

Example 68

6-(tert-butyl)-9-(2-chloropyrimidin-5-yl)-10-methoxy-2-oxo-6,7-dihydro-2H-pyrido[2,1-a]isoquinoline-3-carboxylic Acid

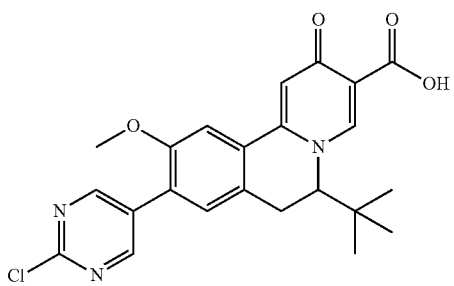 [SMILES: COc1cc2c(cc1-c1cnc(Cl)nc1)CC(C(C)(C)C)n1cc(C(=O)O)c(=O)cc1-2]

Step 68a: Preparation of ethyl 6-(tert-butyl)-9-(2-chloropyrimidin-5-yl)-10-methoxy-2-oxo-6,7-dihydro-2H-pyrido[2,1-a]isoquinoline-3-carboxylate

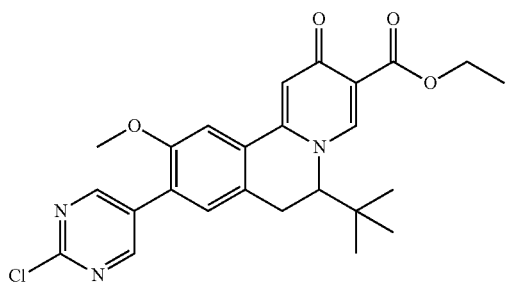 [SMILES: CCOC(=O)c1cn2c(cc1=O)-c1cc(OC)c(-c3cnc(Cl)nc3)cc1CC2C(C)(C)C]

Ethyl 6-(tert-butyl)-9-(2-chloropyrimidin-5-yl)-10-methoxy-2-oxo-6,7-dihydro-2H-pyrido[2,1-a]isoquinoline-3-carboxylate as brown solid was prepared by using ethyl 9-bromo-6-(tert-butyl)-10-methoxy-2-oxo-6,7-dihydro-2H-pyrido[2,1-a]isoquinoline-3-carboxylate (50 mg, 0.115 mmol) and (2-chloropyrimidin-5-yl)boronic acid (23.7 mg, 0.15 mmol) according to method in example 1, step 1h.

Step 68b: Preparation of 6-(tert-butyl)-9-(2-chloropyrimidin-5-yl)-10-methoxy-2-oxo-6,7-dihydro-2H-pyrido[2,1-a]isoquinoline-3-carboxylic Acid

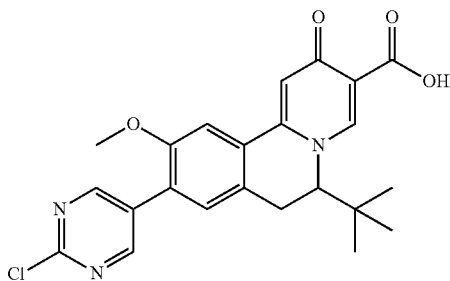 [SMILES: COc1cc2c(cc1-c1cnc(Cl)nc1)CC(C(C)(C)C)n1cc(C(=O)O)c(=O)cc1-2]

To a solution of ethyl 6-(tert-butyl)-9-(2-chloropyrimidin-5-yl)-1-methoxy-2-oxo-6,7-dihydro-2H-pyrido[2,1-a]isoquinoline-3-carboxylate in CH$_3$—CN (3 m) and water (1 mL) was added lithium hydroxide hydrate (19.3 mg, 0.46 mmol), and the mixture was stirred at RT for 1 h. The mixture was concentrated, and the resulted residue was dissolved in water (20 mL), extracted with EtOAc (20 mL×5), and the water phase was acidified with 1M HCl till pH=2, extracted with EtOAc (10 mL×5), and the combined organic phase was washed with water (20 mL×5), and then concentrated to provide 6-(tert-butyl)-9-(2-chloropyrimidin-5-yl)-10-methoxy-2-oxo-6,7-dihydro-2H-pyrido[2,1-a]isoquinoline-3-carboxylic acid (20.4 mmol) as yellow solid. $^1$H NMR (400 MHz, DMSO-d$_6$): δ 16.43 (s, 1H), 8.97 (s, 2H), 8.76 (s, 1H), 7.67 (s, 2H), 7.58 (s, 1H), 4.61 (s, 1H), 3.91 (s, 3H), 3.33-3.30 (m, 2H), 0.70 (s, 9H). MS observed (ESI$^+$) [(M+H)$^+$]: 440.

Example 69

9-(2-(azetidin-1-yl)pyrimidin-5-yl)-6-(tert-butyl)-10-methoxy-2-oxo-6,7-dihydro-2H-pyrido[2,1-a]isoquinoline-3-carboxylic Acid

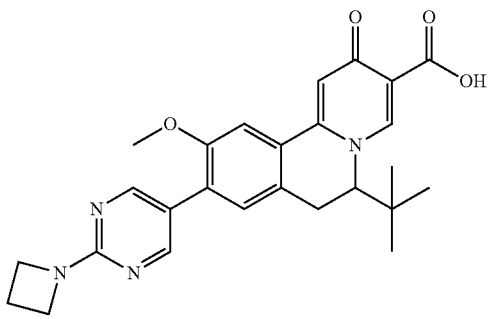 [SMILES: COc1cc2c(cc1-c1cnc(N3CCC3)nc1)CC(C(C)(C)C)n1cc(C(=O)O)c(=O)cc1-2]

Step 69a: Preparation of (2-(azetidin-1-yl)pyrimidin-5-yl)boronic Acid

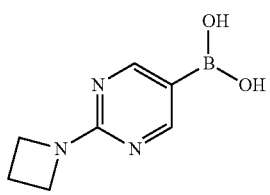 [SMILES: OB(O)c1cnc(N2CCC2)nc1]

To a solution of (2-chloropyrimidin-5-yl)boronic acid (100 mg, 0.63 mmol) in DMF (3 mL) was added azetidine hydrochloride (235.7 mg, 2.52 mmol), and the reaction mixture was heated at 80° C. and stirred for 16 h. LC-MS showed that the reaction was completed, and the crude (2-(azetidin-1-yl) pyrimidin-5-yl)boronic acid was directly used for next stage without further purification.

Step 69b: Preparation of ethyl 9-(2-(azetidin-1-yl)pyrimidin-5-yl)-6-(tert-butyl)-10-methoxy-2-oxo-6,7-dihydro-2H-pyrido[2,1-a]isoquinoline-3-carboxylate

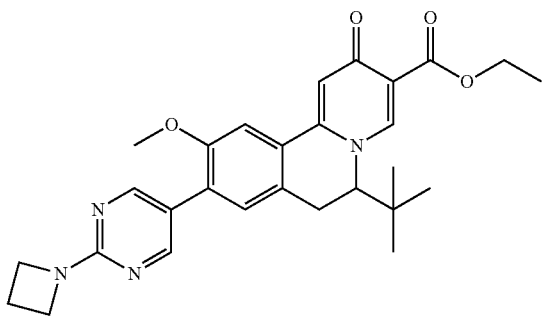 [SMILES: CCOC(=O)c1cn2c(cc1=O)-c1cc(OC)c(-c3cnc(N4CCC4)nc3)cc1CC2C(C)(C)C]

Ethyl 9-(2-(azetidin-1-yl)pyrimidin-5-yl)-6-(tert-butyl)-10-methoxy-2-oxo-6,7-dihydro-2H-pyrido[2,1-a]isoquinoline-3-carboxylate (92 mg) as brown solid was prepared by using ethyl 9-bromo-6-(tert-butyl)-10-methoxy-2-oxo-6,7-dihydro-2H-pyrido[2,1-a]isoquinoline-3-carboxylate (200 mg, 0.46 mmol) and (2-(azetidin-1-yl)pyrimidin-5-yl)boronic acid in DMF (3 mL, 0.21 M) from step 69a according to method in example 1, step 1h.

Step 69c: Preparation of 9-(2-(azetidin-1-yl)pyrimidin-5-yl)-6-(tert-butyl)-10-methoxy-2-oxo-6,7-dihydro-2H-pyrido[2,1-a]isoquinoline-3-carboxylic Acid

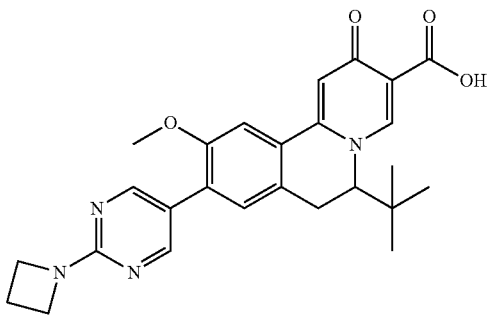

9-(2-(azetidin-1-yl)pyrimidin-5-yl)-6-(tert-butyl)-10-methoxy-2-oxo-6,7-dihydro-2H-pyrido[2,1-a]isoquinoline-3-carboxylic acid (15.3 mg) as yellow solid was prepared by using ethyl 9-(2-(azetidin-1-yl)pyrimidin-5-yl)-6-(tert-butyl)-10-methoxy-2-oxo-6,7-dihydro-2H-pyrido[2,1-a]isoquinoline-3-carboxylate (92 mg, 0.188 mmol) according to method in example 1, step 1i. $^1$H NMR (400 MHz, DMSO-$d_6$): δ 16.57 (s, 1H), 8.78 (s, 1H), 8.56 (s, 2H), 7.65 (s, 1H), 7.62 (s, 1H), 7.46 (s, 1H), 4.64-4.61 (m, 1H), 4.09 (t, J=7.5 Hz, 4H), 3.91 (s, 3H), 3.45-3.35 (m, 2H), 2.37-2.30 (m, 2H), 0.74 (s, 9H). MS observed (ESI$^+$) [(M+H)$^+$]: 475.

Example 70

Ethyl 6-(tert-butyl)-9-(1-(1-ethoxy-2-methyl-1-oxoprop-2-yl)-6-oxo-1,6-dihydropyridin-3-yl)-10-methoxy-2-oxo-6,7-dihydro-2H-pyrido[2,1-a]isoquinoline-3-carboxylate

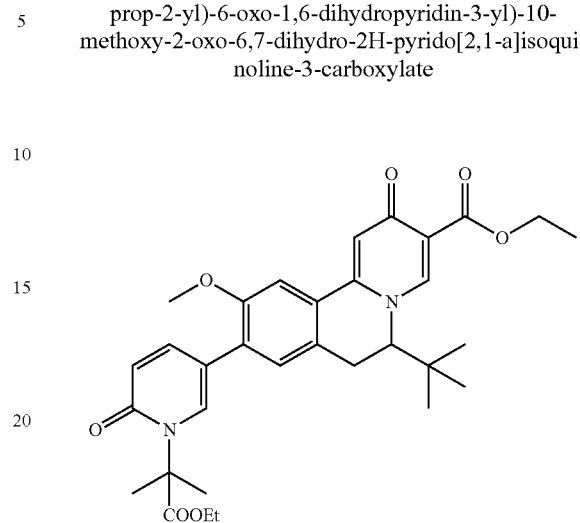

Step 70: Preparation of ethyl 6-(tert-butyl)-9-(1-(1-ethoxy-2-methyl-1-oxoprop-2-yl)-6-oxo-1,6-dihydropyridin-3-yl)-10-methoxy-2-oxo-6,7-dihydro-2H-pyrido[2,1-a]isoquinoline-3-carboxylate

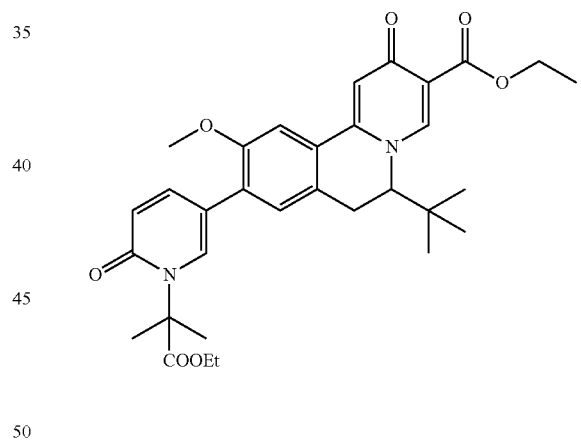

Ethyl 6-(tert-butyl)-9-(1-(1-ethoxy-2-methyl-1-oxoprop-2-yl)-6-oxo-1,6-dihydropyridin-3-yl)-10-methoxy-2-oxo-6,7-dihydro-2H-pyrido[2,1-a]isoquinoline-3-carboxylate (7 mg) as white solid was prepared by using ethyl 9-bromo-6-(tert-butyl)-10-methoxy-2-oxo-6,7-dihydro-2H-pyrido[2,1-a]isoquinoline-3-carboxylate (50 mg, 0.115 mmol) and ethyl 2-methyl-2-(2-oxo-5-(4,4,5,5-tetramethyl-1,3,2-dioxaborolan-2-yl)pyridin-1(2H)-yl)propanoate (46 mg, 0.138 mmol) according to method in example 16, step 16a. $^1$H NMR (400 MHz, DMSO-$d_6$): δ 8.37 (s, 1H), 7.90 (s, 1H), 7.70 (d, J=8.0 Hz, 1H), 7.47 (s, 1H), 7.33 (s, 1H), 7.09 (s, 1H), 6.45 (d, J=8.0 Hz, 1H), 4.36-4.34 (m, 1H), 4.25-4.20 (m, 2H), 4.13-3.99 (m, 4H), 3.90 (s, 3H), 1.23 (s, 6H), 1.12-1.07 (m, 6H), 0.74 (s, 9H). MS observed (ESI$^+$) [(M+H)$^+$]: 563.

Example 71

Ethyl 6-(tert-butyl)-9-(1-(2-ethoxy-2-oxoethyl)-6-oxo-1,6-dihydropyridin-3-yl)-10-methoxy-2-oxo-6,7-dihydro-2H-pyrido[2,1-a]isoquinoline-3-carboxylate

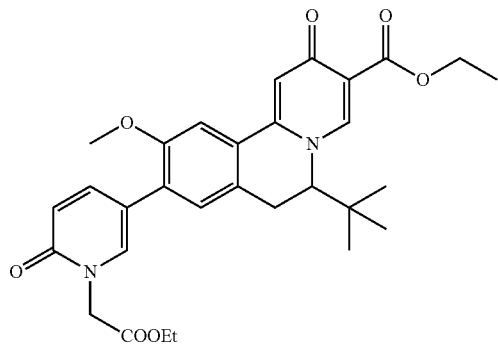 [SMILES: CCOC(=O)Cn1cc(-c2cc3c(cc2OC)-c2cc(=O)c(C(=O)OCC)cn2C(C(C)(C)C)C3)ccc1=O]

Step 71: Preparation of ethyl 6-(tert-butyl)-9-(1-(2-ethoxy-2-oxoethyl)-6-oxo-1,6-dihydropyridin-3-yl)-10-methoxy-2-oxo-6,7-dihydro-2H-pyrido[2,1-a]isoquinoline-3-carboxylate

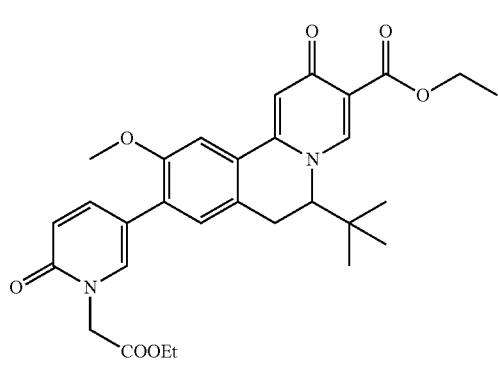 [SMILES: CCOC(=O)Cn1cc(-c2cc3c(cc2OC)-c2cc(=O)c(C(=O)OCC)cn2C(C(C)(C)C)C3)ccc1=O]

Ethyl 6-(tert-butyl)-9-(1-(2-ethoxy-2-oxoethyl)-6-oxo-1,6-dihydropyridin-3-yl)-10-methoxy-2-oxo-6,7-dihydro-2H-pyrido[2,1-a]isoquinoline-3-carboxylate (12 mg) as light yellow solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and ethyl 2-(2-oxo-5-(4,4,5,5-tetramethyl-1,3,2-dioxaborolan-2-yl)pyridin-1(2H)-yl)acetate (85 mg, 0.28 mmol) according to method in example 16, step 16a. $^1$H NMR (400 MHz, DMSO-$d_6$): δ 8.41-8.37 (m, 1H), 7.99 (s, 1H), 7.75 (d, J=8.0 Hz, 1H), 7.48 (s, 1H), 7.34 (s, 1H), 7.12-7.10 (m, 1H), 6.47 (d, J=8.0 Hz, 1H), 4.76 (s, 2H), 4.36-4.13 (m, 4H), 3.90 (s, 3H), 3.75-3.70 (m, 1H), 3.26-3.22 (m, 2H), 1.29-1.22 (m, 6H), 0.74 (s, 9H). MS observed (ESI$^+$) [(M+H)$^+$]: 535.

Example 72

Ethyl 6-(tert-butyl)-9-(1-(3-ethoxy-3-oxopropyl)-6-oxo-1,6-dihydropyridin-3-yl)-10-methoxy-2-oxo-6,7-dihydro-2H-pyrido[2,1-a]isoquinoline-3-carboxylate

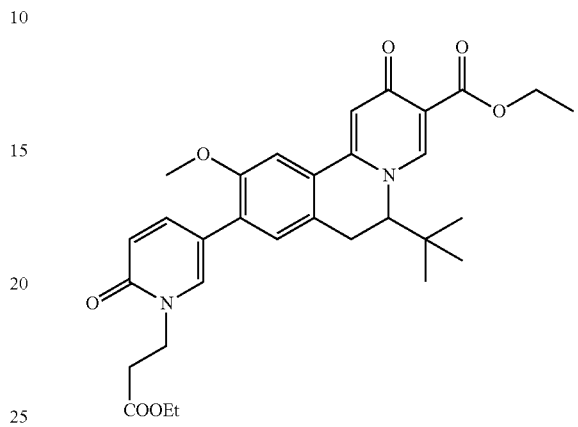

Step 72: Preparation of ethyl 6-(tert-butyl)-9-(1-(3-ethoxy-3-oxopropyl)-6-oxo-1,6-dihydropyridin-3-yl)-10-methoxy-2-oxo-6,7-dihydro-2H-pyrido[2,1-a]isoquinoline-3-carboxylate Ethyl 6-(tert-butyl)-9-(1-(3-ethoxy-3-oxopropyl)-6-oxo-1,6-dihydropyridin-3-yl)-10-methoxy-2-oxo-6,7-dihydro-2H-pyrido[2,1-a]isoquinoline-3-carboxylate (4.4 mg) as light yellow solid was prepared by using ethyl 9-bromo-6-(tert-butyl)-10-methoxy-2-oxo-6,7-dihydro-2H-pyrido[2,1-a]isoquinoline-3-carboxylate (80 mg, 0.18 mmol) and ethyl 3-(2-oxo-5-(4,4,5,5-tetramethyl-1,3,2-dioxaborolan-2-yl)pyridin-1(2H)-yl)-propanoate (80 mg, 0.22 mmol) according to method in example 16, step 16a. $^1$H NMR (400 MHz, DMSO-$d_6$): δ 8.40-8.37 (m, 1H), 7.97 (s, 1H), 7.70 (d, J=8.0 Hz, 1H), 7.47 (s, 1H), 7.35 (s, 1H), 7.11-7.09 (m, 1H), 6.44 (d, J=8.0 Hz, 1H), 4.36-4.15 (m, 4H), 4.09-4.04 (m, 2H), 3.90 (s, 3H), 3.75-3.70 (m, 1H), 3.24-3.20 (m, 2H), 2.78 (t, J=8.0 Hz, 2H), 1.29-1.25 (m, 3H), 1.16-1.13 (m, 3H), 0.74 (s, 9H). MS observed (ESI$^+$) [(M+H)$^+$]: 549.

Example 73

6-(tert-butyl)-9-(2-(4-carboxypiperidin-1-yl)pyrimidin-5-yl)-1-methoxy-2-oxo-6,7-dihydro-2H-pyrido[2,1-a]isoquinoline-3-carboxylic Acid

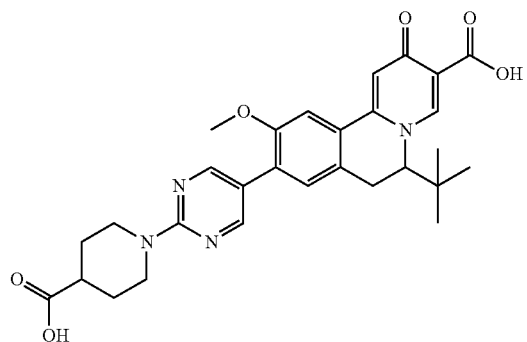 [SMILES: COc1cc2c(cc1-c1cnc(N3CCC(C(=O)O)CC3)nc1)CC(C(C)(C)C)n1cc(C(=O)O)c(=O)cc1-2]

Step 73a: Preparation of (2-(4-(methoxycarbonyl)piperidin-1-yl) pyrimidin-5-yl)boronic Acid

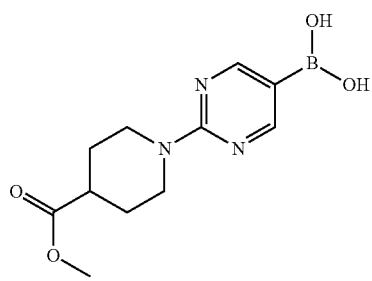 [SMILES: COC(=O)C1CCN(c2ncc(B(O)O)cn2)CC1]

(2-(4-(methoxycarbonyl)piperidin-1-yl)pyrimidin-5-yl) boronic acid (150 mg) was prepared by using (2-chloropyrimidin-5-yl)boronic acid (200 mg, 1.26 mmol) and methyl piperidine-4-carboxylate hydrochloride (452 mg, 2.52 mmol) according to method in example 67, step 67a.

Step 73b: Preparation of 6-(tert-butyl)-10-methoxy-9-(2-(4-(methoxycarbonyl)piperidin-1-yl)pyrimidin-5-yl)-2-oxo-6,7-dihydro-2H-pyrido[2,1-a]isoquinoline-3-carboxylic Acid

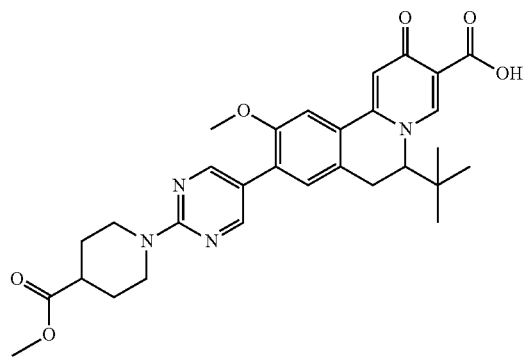 [SMILES: COC(=O)C1CCN(c2ncc(-c3cc4c(cc3OC)-c3cc(=O)c(C(=O)O)cn3C(C(C)(C)C)C4)cn2)CC1]

6-(tert-butyl)-10-methoxy-9-(2-(4-(methoxycarbonyl)piperidin-1-yl) pyrimidin-5-yl)-2-oxo-6,7-dihydro-2H-pyrido[2,1-a]isoquinoline-3-carboxylic acid (20 mg) as colorless oil was prepared by using 9-bromo-6-(tert-butyl)-10-methoxy-2-oxo-6,7-dihydro-2H-pyrido[2,1-a]isoquinoline-3-carboxylic acid (150 mg, 0.37 mmol) and (2-(4-(methoxycarbonyl) piperidin-1-yl)pyrimidin-5-yl)boronic acid (148 mg, 0.56 mmol) according to method in example 1, step 1h.

Step 73c: Preparation of 6-(tert-butyl)-9-(2-(4-carboxypiperidin-1-yl) pyrimidin-5-yl)-10-methoxy-2-oxo-6,7-dihydro-2H-pyrido[2,1-a]isoquinoline-3-carboxylic Acid

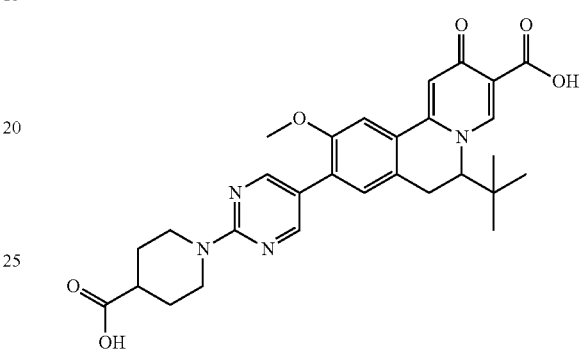

6-(tert-butyl)-9-(2-(4-carboxypiperidin-1-yl)pyrimidin-5-yl)-10-methoxy-2-oxo-6,7-dihydro-2H-pyrido[2,1-a]isoquinoline-3-carboxylic acid (3.0 mg) as yellow solid was prepared by using 6-(tert-butyl)-10-methoxy-9-(2-(4-(methoxycarbonyl)piperidin-1-yl)pyrimidin-5-yl)-2-oxo-6,7-dihydro-2H-pyrido[2,1-a]isoquinoline-3-carboxylic acid (20 mg, 0.037 mmol) according to method in example 1, step 1i. $^1$H NMR (DMSO-$d_6$, 400 MHz): δ 16.55 (s, 1H), 12.23 (s, 1H), 8.77 (s, 1H), 8.60 (s, 2H), 7.64 (s, 1H), 7.62 (s, 1H), 7.48 (s, 1H), 4.66-4.51 (m, 4H), 3.92 (s, 3H), 3.45-3.37 (m, 2H), 3.12-3.09 (m, 2H), 1.92-1.89 (m, 2H), 1.55-1.48 (m, 2H), 0.74 (s, 9H). MS observed (ESI$^+$) [(M+H)$^+$]: 533.

Example 74

Ethyl 6-(tert-butyl)-9-(1-(1-ethoxy-1-oxoprop-2-yl)-6-oxo-1,6-dihydro-pyridin-3-yl)-10-methoxy-2-oxo-6,7-dihydro-2H-pyrido[2,1-a]isoquinoline-3-carboxylate

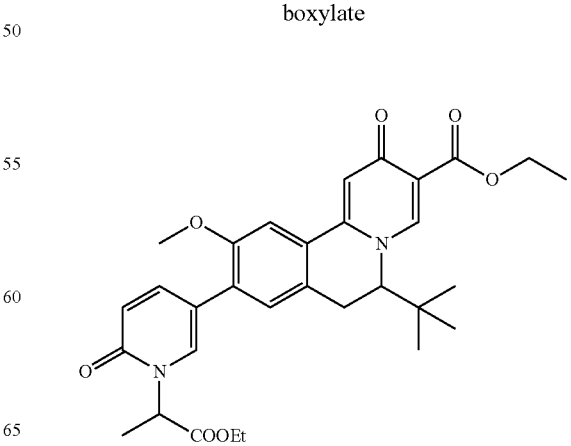

Step 74: Preparation of ethyl 6-(tert-butyl)-9-(1-(1-ethoxy-1-oxoprop-2-yl)-6-oxo-1,6-dihydropyridin-3-yl)-10-methoxy-2-oxo-6,7-dihydro-2H-pyrido[2,1-a]isoquinoline-3-carboxylate

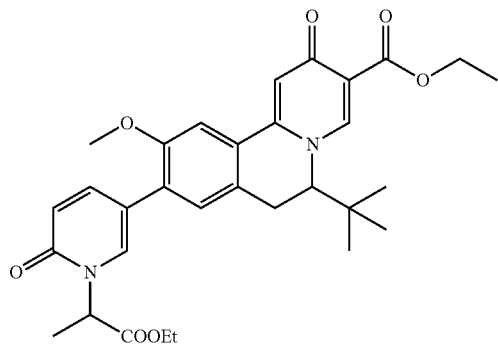 [SMILES: CCOC(=O)c1cn2c(cc1=O)-c1cc(OC)c(-c3ccc(=O)n(C(C)C(=O)OCC)c3)cc1CC2C(C)(C)C]

Ethyl 6-(tert-butyl)-9-(1-(1-ethoxy-1-oxoprop-2-yl)-6-oxo-1,6-dihydropyridin-3-yl)-10-methoxy-2-oxo-6,7-dihydro-2H-pyrido[2,1-a]isoquinoline-3-carboxylate (18.4 mg) as light yellow solid was prepared by using ethyl 9-bromo-6-(tert-butyl)-10-methoxy-2-oxo-6,7-dihydro-2H-pyrido[2,1-a]isoquinoline-3-carboxylate (80 mg, 0.18 mmol) and ethyl 2-(2-oxo-5-(4,4,5,5-tetramethyl-1,3,2-dioxaborolan-2-yl)pyridin-1(2H)-yl)propanoate (89 mg, 0.28 mmol) according to method in example 16, step 16a. $^1$H NMR (400 MHz, DMSO-$d_6$): δ 8.41-8.37 (m, 1H), 7.97 (s, 1H), 7.72 (d, J=8.0 Hz, 1H), 7.48 (s, 1H), 7.39-7.38 (m, 1H), 7.12-7.10 (m, 1H), 6.46 (d, J=8.0 Hz, 1H), 5.20-5.17 (m, 1H), 4.36-4.20 (m, 2H), 4.15-4.10 (m, 2H), 3.91 (s, 3H), 3.75-3.64 (m, 1H), 3.31-3.23 (m, 2H), 1.59 (d, J=8.0 Hz, 3H), 1.29-1.23 (m, 3H), 1.19-1.15 (m, 3H), 0.74 (s, 9H). MS observed (ESI$^+$) [(M+H)$^+$]: 549.

Example 75

Ethyl 6-(tert-butyl)-9-(1-(4-ethoxy-4-oxobutyl)-6-oxo-1,6-dihydropyridin-3-yl)-10-methoxy-2-oxo-6,7-dihydro-2H-pyrido[2,1-a]isoquinoline-3-carboxylate

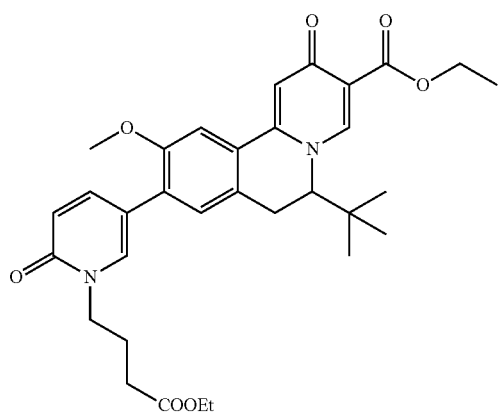 [SMILES: CCOC(=O)CCCn1cc(-c2cc3c(cc2OC)-c2cc(=O)c(C(=O)OCC)cn2C(C(C)(C)C)C3)ccc1=O]

Step 75: Preparation of ethyl 6-(tert-butyl)-9-(1-(4-ethoxy-4-oxobutyl)-6-oxo-1,6-dihydropyridin-3-yl)-10-methoxy-2-oxo-6,7-dihydro-2H-pyrido[2,1-a]isoquinoline-3-carboxylate

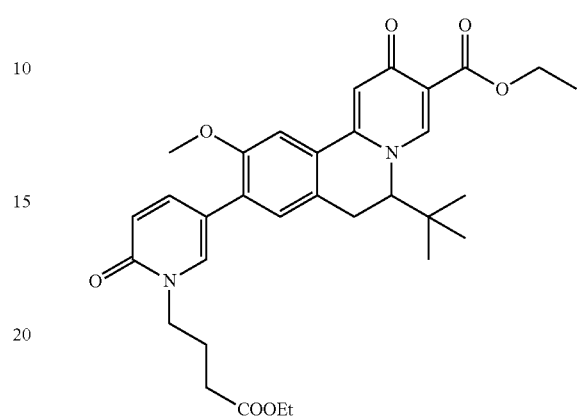

Ethyl 6-(tert-butyl)-9-(1-(4-ethoxy-4-oxobutyl)-6-oxo-1,6-dihydropyridin-3-yl)-10-methoxy-2-oxo-6,7-dihydro-2H-pyrido[2,1-a]isoquinoline-3-carboxylate (33 mg) as light yellow solid was prepared by using ethyl 9-bromo-6-(tert-butyl)-10-methoxy-2-oxo-6,7-dihydro-2H-pyrido[2,1-a]isoquinoline-3-carboxylate (80 mg, 0.18 mmol) and ethyl 4-(2-oxo-5-(4,4,5,5-tetramethyl-1,3,2-dioxaborolan-2-yl)pyridin-1(2H)-yl)butanoate (93 mg, 0.28 mmol) according to method in example 16, step 16a. $^1$H NMR (400 MHz, DMSO-$d_6$): δ 8.41-8.37 (m, 1H), 7.92-7.91 (m, 1H), 7.69-7.66 (m, 1H), 7.47 (s, 1H), 7.37 (m, 1H), 7.11-7.09 (m, 1H), 6.43 (d, J=8.0 Hz, 1H), 4.36-4.20 (m, 2H), 4.06-4.01 (m, 2H), 3.99-3.95 (m, 2H), 3.90 (s, 3H), 3.75 (s, 1H), 3.29-3.22 (m, 2H), 2.35 (t, J=8.0 Hz, 2H), 1.98-1.91 (m, 2H), 1.29-1.23 (m, 3H), 1.18-1.14 (m, 3H), 0.74 (s, 9H). MS observed (ESI$^+$) [(M+H)$^+$]: 563.

Example 76

6-(tert-butyl)-9-(2-(cyclobutylamino)pyrimidin-5-yl)-10-methoxy-2-oxo-6,7-dihydro-2H-pyrido[2,1-a]isoquinoline-3-carboxylic Acid

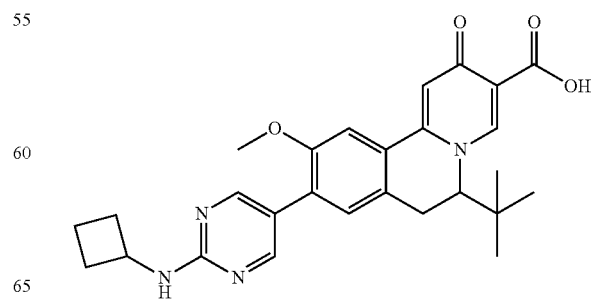

133

Step 76a: Preparation of (2-(cyclobutylamino)pyrimidin-5-yl)boronic Acid

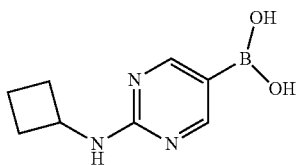 [SMILES: OB(O)c1cnc(NC2CCC2)nc1]

(2-(cyclobutylamino)pyrimidin-5-yl)boronic acid (54 mg) as yellow oil was prepared by using (2-chloropyrimidin-5-yl)boronic acid (100 mg, 0.63 mmol) and cyclobutylamine (179 mg, 2.52 mmol) according to method in example 67, step 67a.

Step 76b: Preparation of ethyl 6-(tert-butyl)-9-(2-(cyclobutylamino) pyrimidin-5-yl)-10-methoxy-2-oxo-6,7-dihydro-2H-pyrido[2,1-a]isoquinoline-3-carboxylate

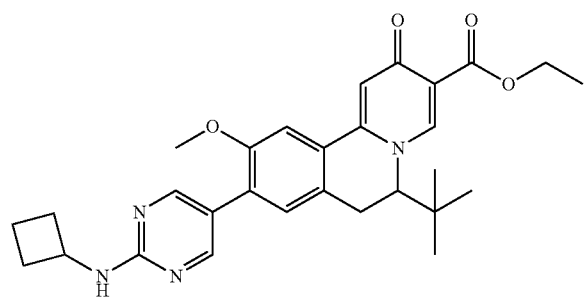 [SMILES: CCOC(=O)c1cn2c(cc1=O)-c1cc(OC)c(-c3cnc(NC4CCC4)nc3)cc1CC2C(C)(C)C]

Ethyl 6-(tert-butyl)-9-(2-(cyclobutylamino)pyrimidin-5-yl)-10-methoxy-2-oxo-6,7-dihydro-2H-pyrido[2,1-a]isoquinoline-3-carboxylate (74 mg) as brown solid was prepared by using ethyl 9-bromo-6-(tert-butyl)-10-methoxy-2-oxo-6,7-dihydro-2H-pyrido-[2,1-a]isoquinoline-3-carboxylate (100 mg, 0.23 mmol) and (2-cyclo-butylamino)pyrimidin-5-yl)boronic acid (54 mg, 0.28 mmol) according to method in example 1, step 1h.

Step 76c: Preparation of 6-(tert-butyl)-9-(2-(cyclobutylamino)pyrimidin-5-yl)-10-methoxy-2-oxo-6,7-dihydro-2H-pyrido[2,1-a]isoquinoline-3-carboxylic Acid

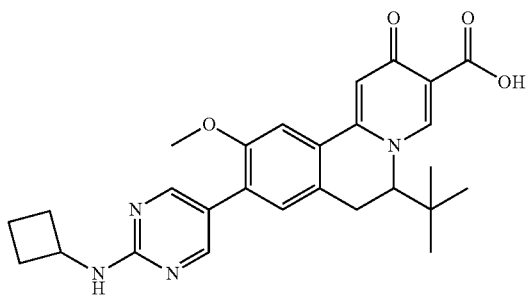 [SMILES: COc1cc2c(cc1-c1cnc(NC3CCC3)nc1)CC(C(C)(C)C)n1cc(C(=O)O)c(=O)cc1-2]

134

6-(tert-butyl)-9-(2-(cyclobutylamino)pyrimidin-5-yl)-10-methoxy-2-oxo-6,7-dihydro-2H-pyrido[2,1-a]isoquinoline-3-carboxylic acid (35.5 mg) as yellow solid was prepared by using ethyl 6-(tert-butyl)-9-(2-(cyclobutylamino)pyrimidin-5-yl)-10-methoxy-2-oxo-6,7-dihydro-2H-pyrido[2,1-a]isoquinoline-3-carboxylate (74 mg, 0.147 mmol) according to method in example 1, step 1i. $^1$H NMR (DMSO-$d_6$, 400 MHz): δ 16.56 (s, 1H), 8.77 (s, 1H), 8.51 (s, 1H), 7.70 (d, J=7.5 Hz, 1H), 7.64 (s, 1H), 7.61 (s, 1H), 7.46 (s, 1H), 4.63-4.60 (m, 1H), 4.46-4.33 (m, 1H), 3.92 (s, 3H), 3.44-3.35 (m, 2H), 2.31-2.18 (m, 2H), 2.05-1.91 (m, 2H), 1.71-1.59 (m, 2H), 0.74 (s, 9H). MS observed (ESI$^+$) [(M+H)$^+$]: 475.

Example 77

6-(tert-butyl)-9-(2-(3-carboxypyrrolidin-1-yl)pyrimidin-5-yl)-10-m ethoxy-2-oxo-6,7-dihydro-2H-pyrido[2,1-a]isoquinoline-3-carboxylic Acid

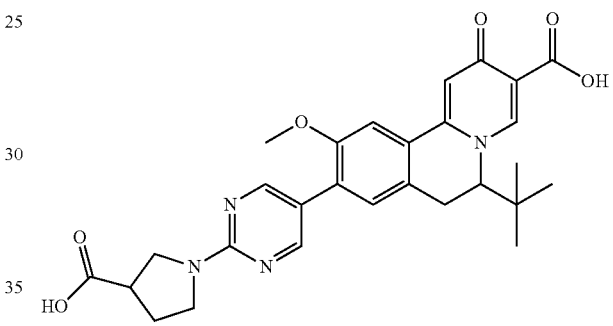

Step 77a: Preparation of (2-(3-(ethoxycarbonyl) pyrrolidin-1-yl) pyrimidin-5-yl)boronic Acid

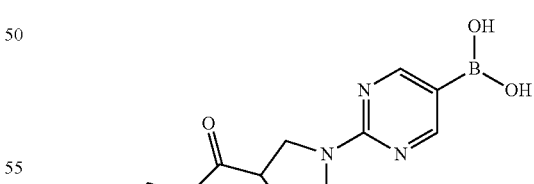

2-(3-(ethoxycarbonyl)pyrrolidin-1-yl)pyrimidin-5-yl)boronic acid (104 mg) as yellow oil was prepared by using (2-chloropyrimidin-5-yl)boronic acid (200 mg, 1.26 mmol) and ethyl pyrrolidine-3-carboxylate hydrochloride (452 mg, 2.52 mmol) according to method in example 67, step 67a.

Step 77b: Preparation of ethyl 6-(tert-butyl)-9-(2-(3-(ethoxycarbonyl) pyrrolidin-1-yl)pyrimidin-5-yl)-10-methoxy-2-oxo-6,7-dihydro-2H-pyrido[2,1-a]isoquinoline-3-carboxylate

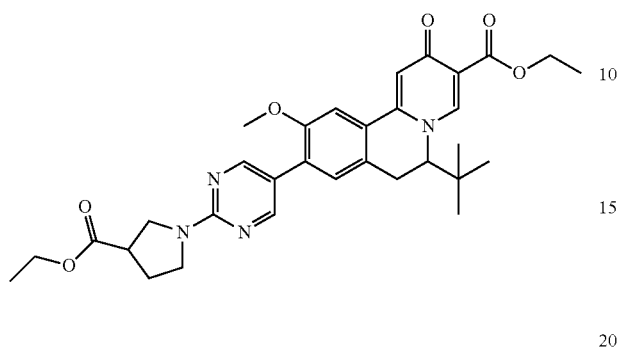

Ethyl 6-(tert-butyl)-9-(2-(3-(ethoxycarbonyl)pyrrolidin-1-yl)pyrimidin-5-yl)-10-methoxy-2-oxo-6,7-dihydro-2H-pyrido[2,1-a]isoquinoline-3-carboxylate (55 mg) as brown solid was prepared by using ethyl 9-bromo-6-(tert-butyl)-10-methoxy-2-oxo-6,7-dihydro-2H-pyrido[2,1-a]isoquinoline-3-carboxylate (100 mg, 0.23 mmol) and (2-(3-(ethoxycarbonyl) piperidin-1-yl)pyrimidin-5-yl)boronic acid (74 mg, 0.28 mmol) according to method in example 1, step 1h.

Step 77c: Preparation of 6-(tert-butyl)-9-(2-(3-carboxypyrrolidin-1-yl) pyrimidin-5-yl)-10-methoxy-2-oxo-6,7-dihydro-2H-pyrido[2,1-a]isoquinoline-3-carboxylic Acid

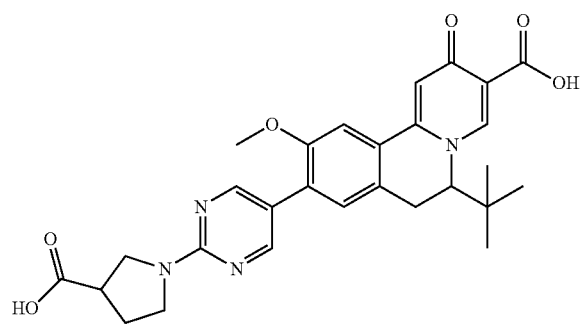 [SMILES: COc1cc2c(cc1-c1cnc(N3CCC(C(=O)O)C3)nc1)CC(C(C)(C)C)n1cc(C(=O)O)c(=O)cc1-2]

6-(tert-butyl)-9-(2-(3-carboxypyrrolidin-1-yl)pyrimidin-5-yl)-10-methoxy-2-oxo-6,7-dihydro-2H-pyrido[2,1-a]isoquinoline-3-carboxylic acid (10.6 mg) as yellow solid was prepared by using ethyl 6-(tert-butyl)-9-(2-(3-ethoxycarbonylpyrrolidin-1-yl)pyrimidin-5-yl)-10-methoxy-2-oxo-6,7-dihydro-2H-pyrido[2,1-a]isoquinoline-3-carboxylate (55 mg, 0.096 mmol) according to method in example 1, step 1i. $^1$H NMR (DMSO-d$_6$, 400 MHz): δ 8.77 (s, 1H), 8.59 (s, 2H), 7.63 (s, 1H), 7.62 (s, 1H), 7.47 (s, 1H), 4.63-4.60 (m, 1H), 3.92 (s, 3H), 3.72 (d, J=7.0 Hz, 2H), 3.63-3.51 (m, 3H), 3.44-3.40 (m, 2H), 2.22-2.13 (m, 2H), 0.75 (s, 9H). MS observed (ESI$^+$) [(M+H)$^+$]: 519.

Example 78

6-(tert-butyl)-9-(2-((carboxymethyl)amino)pyrimidin-5-yl)-10-methoxy-2-oxo-6,7-dihydro-2H-pyrido[2,1-a]isoquinoline-3-carboxylic Acid

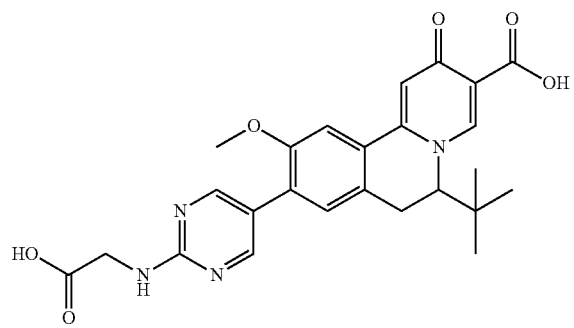 [SMILES: COc1cc2c(cc1-c1cnc(NCC(=O)O)nc1)CC(C(C)(C)C)n1cc(C(=O)O)c(=O)cc1-2]

Step 78a: Preparation of (2-(methoxycarbonylmethylamino)pyrimidin-5-yl)boronic Acid

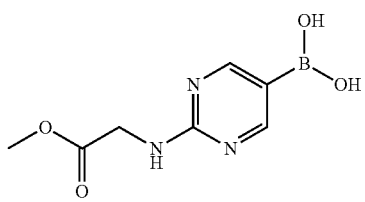

(2-(methoxycarbonylmethyl)aminopyrimidin-5-yl)boronic acid (35.9 mg) as yellow oil was prepared by using (2-chloropyrimidin-5-yl)boronic acid (100 mg, 0.63 mmol) and methyl glycinate hydrochloride (316 mg, 2.52 mmol) according to method in example 67, step 67a.

Step 78b: Preparation of ethyl 6-(tert-butyl)-10-methoxy-9-(2-((2-methoxy-2-oxoethyl)amino)pyrimidin-5-yl)-2-oxo-6,7-dihydro-2H-pyrido[2,1-a]isoquinoline-carboxylate

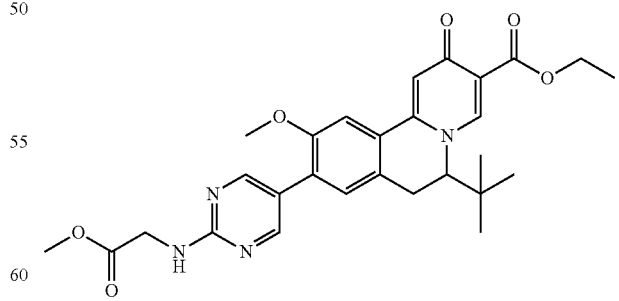

Ethyl 6-(tert-butyl)-10-methoxy-9-(2-((2-methoxy-2-oxoethyl)amino) pyrimidin-5-yl)-2-oxo-6,7-dihydro-2H-pyrido[2,1-a]isoquinoline-3-carboxylate (25 mg) as brown solid was prepared by using ethyl 9-bromo-6-(tert-butyl)-10-methoxy-2-oxo-6,7-dihydro-2H-pyrido[2,1-a]isoquinoline-3-carboxylate (60 mg, 0.14 mmol) and (2-(methoxycarbonylmethyl) aminopyrimidin-5-yl)boronic acid (35.9 mg, 0.17 mmol) according to method in example 1, step 1h.

Step 78c: Preparation of 6-(tert-butyl)-9-(2-((carboxymethyl)amino) pyrimidin-5-yl)-10-methoxy-2-oxo-6,7-dihydro-2H-pyrido[2,1-a]isoquinoline-3-carboxylic Acid

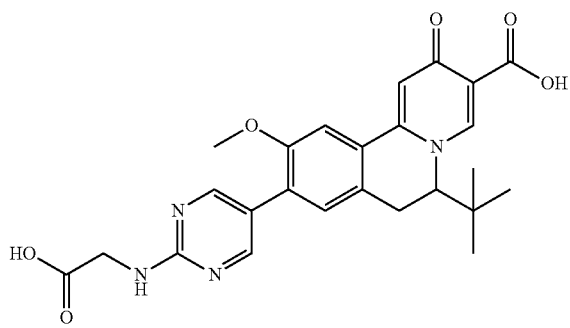 [SMILES: COc1cc2c(cc1-c1cnc(NCC(=O)O)nc1)CC(C(C)(C)C)n1cc(C(=O)O)c(=O)cc1-2]

6-(tert-butyl)-9-(2-((carboxymethyl)amino)pyrimidin-5-yl)-10-methoxy-2-oxo-6,7-dihydro-2H-pyrido[2,1-a]isoquinoline-3-carboxylic acid (1.2 mg) as yellow solid was prepared by using ethyl 6-(tert-butyl)-10-methoxy-9-(2-((2-methoxy-2-oxoethyl)amino)pyrimidin-5-yl)-2-oxo-6,7-dihydro-2H-pyrido[2,1-a]isoquinoline-3-carboxylate (25 mg, 0.48 mmol) according to method in example 1, step 1i. $^1$H NMR (DMSO-$d_6$, 400 MHz): δ 8.77 (s, 1H), 8.53 (s, 2H), 7.64 (s, 1H), 7.61 (s, 1H), 7.47 (s, 1H), 4.64-4.60 (m, 1H), 3.92 (s, 3H), 3.85 (d, J=5.4 Hz, 2H), 3.62-3.57 (m, 2H), 0.74 (s, 9H). MS observed (ESI$^+$) [(M+H)$^+$]: 479.

The biological implementation data are described in detail below to further elaborate the technical scheme of the invention.

Materials and Methods

HBV Cell Line:

HepG2.2.15 cells (Sells et al, Proc Natl Acad Sci USA. 1987 February; 84(4):1005-9.), a constitutively HBV-expressing cell line, were cultured in DMEM medium supplemented with 10% FBS and 400 g/mL G418, and maintained in 5% $CO_2$ at 37° C.

HBsAg Assay:

HepG2.2.15 cells were seeded into 96-well plates at $3 \times 10^4$ cells/well. The next day, the cells were treated with a five-fold serial dilution series of the compound in DMSO. The final DMSO concentration in all wells was 0.5% and 0.5% DMSO was used as no drug control. After four days of incubation with compounds, the supernatants were harvested and measured for HBsAg concentration The HBsAg chemiluminescence immunoassay (CLIA) kit was used to measure the levels of secreted HBsAg. Specifically, 50 μL of culture supernatant was transferred to the CLIA assay plate and 50 μL of enzyme conjugate reagent was added into each well. The plates were sealed and incubated for 1 hour at room temperature. The supernatant-enzyme-mixture was discarded and wells were washed for 6 times. The residual liquid was removed by plating on tissue paper. 25 μL of substrate A and B were added into each well. Luminance was measured using a spectrometer (Tecan Infinite® F200) after 10 minutes incubation. $IC_{50}$ value was extrapolated based the dose-response curves generated from the data.

Results

The compounds of example 1 to example 78 were tested for their capacity to inhibit HBsAg as described herein and the results are given in Table 3.

TABLE 3

| Activity Data in HBsAg assay | | | |
|---|---|---|---|
| Example No. | $IC_{50}$ (uM) | Examples No. | $IC_{50}$ (uM) |
| 1 | 0.014 | 2 | 0.008 |
| 3 | 0.018 | 4 | 0.024 |
| 5 | 0.014 | 6 | 0.006 |
| 7 | 0.036 | 8 | 0.009 |
| 9 | 0.290 | 10 | 0.006 |
| 11 | 0.003 | 12 | 0.002 |
| 13 | 0.018 | 14 | 0.002 |
| 15 | 0.004 | 16 | 0.002 |
| 17 | 0.025 | 18 | 0.077 |
| 19 | 0.068 | 20 | 0.007 |
| 21 | 0.016 | 22 | 0.007 |
| 23 | 0.040 | 24 | 0.008 |
| 25 | 0.007 | 26 | 0.008 |
| 27 | 0.004 | 28 | 0.0002 |
| 29 | 0.012 | 30 | 0.013 |
| 31 | 0.826 | 32 | 0.097 |
| 33 | 0.020 | 34 | 0.036 |
| 35 | 0.290 | 36 | 0.010 |
| 37 | 0.009 | 38 | 0.005 |
| 39 | 0.025 | 40 | 0.006 |
| 41 | 0.002 | 42 | 0.002 |
| 43 | 0.001 | 44 | 0.010 |
| 45 | 0.014 | 46 | 0.003 |
| 47 | 0.002 | 48 | 0.068 |
| 49 | 0.014 | 50 | 0.0005 |
| 51 | 0.0008 | 52 | 0.012 |
| 53 | 1.396 | 54 | 0.001 |
| 55 | 0.0008 | 56 | 0.001 |
| 57 | 0.001 | 58 | 0.004 |
| 59 | 0.010 | 60 | 0.0001 |
| 61 | 0.004 | 62 | 0.005 |
| 63 | 0.027 | 64 | 0.007 |
| 65 | 0.080 | 66 | 0.0008 |
| 67 | 0.0003 | 68 | 0.0006 |
| 69 | 0.005 | 70 | 0.044 |
| 71 | 0.192 | 72 | 0.565 |
| 73 | 0.067 | 74 | 0.129 |
| 75 | 0.466 | 76 | 0.0004 |
| 77 | 0.150 | 78 | 0.045 |

The cytotoxicity $CC_{50}$ of part of the examples was measured according to methods below:

HepG2.2.15 cells were seeded into 96-well white plate at 5000 cells/well and treated with serially diluted compounds. The plates were incubated in incubator with 5% $CO_2$ at 37° C. for four days. The plate was taken out of incubator and adapted to room temperature for 30 minutes, followed by adding 25 μl CellTiter-Glo (Promega) reagent into each well and vortexed at room temperature before being measured for luminance using spectrometer (Tecan Infinite® F200). The $CC_{50}$ of each compound was defined as the compound concentration at which the treated well's cell viability is 50% compared to that of the DMSO treated well. The assay results were given in table 4.

TABLE 4

| $CC_{50}$ of part of the examples | | | |
|---|---|---|---|
| Example No. | $CC_{50}$ | Example No. | $CC_{50}$ |
| 18 | B | 19 | B |
| 20 | A | 21 | B |
| 22 | B | 24 | B |
| 25 | B | 28 | A |

TABLE 4-continued

CC$_{50}$ of part of the examples

| Example No. | CC$_{50}$ | Example No. | CC$_{50}$ |
|---|---|---|---|
| 31 | B | 32 | B |
| 37 | B | 50 | B |
| 51 | A | 60 | B |
| 63 | B | 69 | B |
| 70 | B | 71 | A |
| 72 | B | 73 | A |
| 74 | B | 75 | B |

(A: CC$_{50}$ > 100 μM; B: 100 μM > CC$_{50}$ > 50 μM)

The assay results indicated that none of the examples showed apparent cytotoxicity (CC$_{50}$>50 μM). Currently all the anti-HBV drugs on market are nucleotide/nucleoside analogs and work as HBV polymerase inhibitors. However, these inhibitors can also interfere with human DNA and RNA polymerases and lead to undesired toxicities, while the compounds of this invention are non-nucleoside analogs and do not elicit aforementioned side-effects.

A single intravenous injection (IV, dose 2 mg/kg) and a single oral administration (PO, dose 10 mg/kg) in ICR mice were used to assess the pharmacokinetic properties of several examples in this invention, respectively. The mean values of drug concentrations in plasma and liver are shown in Table 5 below.

TABLE 5

Mean value and ratio of drug concentrations in plasma and liver in ICR mice
Mean drug concentrations

| | IV (ng/mL) | | | PO (ng/mL) | | |
|---|---|---|---|---|---|---|
| Time (h) | Plasma | Liver | L/P ratio | Plasma | Liver | L/P ratio |
| 1 | 247.3 | 11173.3 | 45.2 | 668.0 | 9093.3 | 13.6 |
| 8 | 2.4 | 30.2 | 12.8 | 18.7 | 292.5 | 15.7 |
| 24 | 1.2 | 4.1 | 3.5 | 1.7 | 6.4 | 3.7 |

As is shown in Table 5, the average drug concentration of several examples in this invention was significantly higher in liver than that in plasma after intravenous administration and oral administration, indicating that the compound of this invention can be more enriched in the liver, which can be used to liver disease therapy.

Further, it will be understood by those skilled in this field that all of the compounds involved in the above-described compounds of Formula I, the different realizations of compounds of Formula I, and the embodiments of the compounds of Formula I can be prepared to corresponding isomers, solvates, hydrates, prodrugs, stable isotope derivatives, and pharmaceutically acceptable salts. Preferably, the compound is made into a pharmaceutically acceptable derivative, which is any one of a prodrug, a salt, an ester, an amide, a salt of an ester, a salt of an amide, and a metabolite.

Further, the pharmaceutically acceptable salt refers to a conventional non-toxic salt obtained formed by using a inorganic acid (for example, hydrochloric acid, hydrobromic acid, hydroiodic acid, perchloric acid, sulfuric acid or phosphoric acid and the like) or an organic acid (for example, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid, malic acid and the like) The reviews of suitable pharmaceutically acceptable salts can refer to: Berge S M et al, J. Pharm. Sci. 1977, 66, 1-19; Gould P L Int. J. Pharm 1986, 33, 201-277 and Bighley et al., Encyclopedia of Pharmaceutical Technology, Marcel Dekker Inc, New York, 1996, Vol. 13, pp. 453-497.

Further, an isotope can be introduced into any of the compounds of this invention by a stable isotope derivative, and the introduced isotope is any one of $^{2}$H, $^{3}$H, $^{13}$C, $^{14}$C, $^{15}$N, $^{17}$O, $^{18}$O, $^{31}$P, $^{32}$P, $^{35}$S, $^{18}$F, $^{36}$Cl. Specific isotope derivatives can be prepared by conventional techniques.

Further, as an actual product, the compound described herein can be formulated to any one of a tablet, a capsule, an injection, a granule, a pulvis, a suppository, a pill, a cream, a paste, a gel, a powder, an oral solution, an inhalation, a suspension, a dry suspension, a patch, and a lotion.

Further, just as mentioned above, a mixture can also be formed with any one of a pharmaceutically acceptable carrier, adjuvant and excipient.

Further, just as mentioned above, a composition comprising: the compounds described herein and any one of the following substances: an HBV polymerase inhibitor, interferon α-2a, interferon α-2b, a pegylated interferon α-2a, ribavirin, an HBV preventive vaccine, an HBV therapeutic vaccine, an HBV capsid inhibitor, an RNA replication inhibitor of HBV, an siRNA, an inhibitor of HBsAg generation or secretion, an HBV antibody, and a TLR7 agonist.

All of the compounds and mixtures, compositions and the like described herein can be administered to a living body by any administration route. The administration route can be oral administration, intravenous injection, intramuscular injection, subcutaneous injection, rectal administration, vaginal administration, sublingual administration, nasal inhalation, oral inhalation, eye drop, or local or systemic transdermal administration.

All the compounds and mixtures, compositions and the like described herein can be formulated into a single dose containing the active compound of this invention together with a carrier, an excipient and the like. And the dosage form can be a tablet or a capsule, injections, granules, powders, suppositories, pills, creams, pastes, gels, powders, oral solutions, inhalants, suspensions, dry suspensions, patches, lotions and the like These dosage forms may contain ingredients commonly used in pharmaceutical formulations, such as diluents, absorbents, wetting agents, binders, disintegrating agents, coloring agents, pH adjusting agents, antioxidants, bacteriostatic agents, isotonicity adjusting agents, anti-adhesive agent.

Suitable formulations of dosage forms described herein are available from public sources, for example, Remington: The Science and Practice of Pharmacy, 21st edition, published by Lippincott Williams & Wilkins in 2006 and Rowe, Raymond C. Handbook of Pharmaceutical Excipients, Chicago, Pharmaceutical Press Published in 2005. It can therefore be easily prepared by those skilled in this field.

The dosage of the compounds of this invention can be 0.01 to 500 mg/kg per day depending on the individual nature, intensity, age, sex, body weight, route of administration, etc. Preferably, the daily dose is 1-100 mg/kg, which can be administered in a single or multiple doses.

It is understood by those skilled in this field that all of the compounds involved in this invention and mixtures, compositions and the like comprising the compounds of the present invention are typically used for medical use, in particular for the prevention or treatment of hepatitis B virus infection. The specific indications are as follows: The novel compound described herein can inhibit the production or secretion of hepatitis B surface antigen (HBsAg), thus it can be used to treat and prevent HBV infection.

The novel compound described herein can be used to inhibit the production or secretion of hepatitis B surface antigen (HBsAg) The novel compound described herein can be used to treat and prevent HBV infection Further, the compounds of the formula I in this invention can be used in combination with other drugs, including HBV polymerase inhibitors, such as lamivudine, telbivudine, tenofovir disoproxil fumarate, Adelphi Divonide, entecavir or tenofovir alafenamide fumaric acid; interferon alpha-2a; interferon alpha-2b; peginterferon alfa-2a; ribavirin; HBV prophylactic vaccine; HBV treatment vaccine; HBV capsid inhibitor; HBV RNA replication inhibitor, siRNA; HBsAg production or secretion inhibitor; HBV antibody; TLR 7 agonist.

The specific embodiments of this invention have been described above. It should be understood that the present invention is not limited to the specific embodiments described above, and various modifications and changes can be made by those skilled in this field, this does not affect the substance of the present invention.

The invention claimed is:

1. A compound of general formula I:

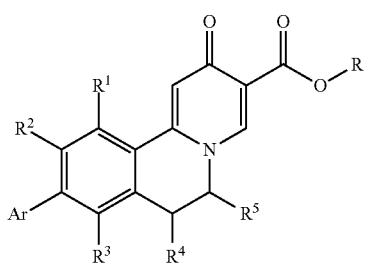

I wherein:
R is any one of hydrogen and $C_{1-6}$ alkyl;
$R^1$ is any one of hydrogen, deuterium, halogen, $C_{1-6}$ alkyl, $C_{1-6}$ alkylamino, and $C_{1-6}$ alkoxy;
$R^2$ is any one of hydrogen, deuterium, halogen, $C_{1-6}$ alkyl, $C_{1-6}$ alkyl substituted with at least one fluorine, $C_{3-7}$ cycloalkyl, $C_{1-6}$ alkylamino, $C_{1-6}$ alkoxy, and heterocycloalkyl;
Ar is any one of phenyl, thienyl, pyridinyl, pyrimidinyl, pyrazinyl, pyridazinyl, pyridin-2(1H)-keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, oxadiazolyl, naphthyl, benzothiophenyl, indolyl, benzimidazolyl, benzothiazolyl, benzofuryl, quinolyl, isoquinolyl, and quinazolinyl;
$R^3$ is any one of hydrogen, deuterium, halogen, cyano, $C_{1-6}$ alkyl, $C_{3-7}$ cycloalkyl, $C_{1-6}$ alkylamino, $C_{1-6}$ alkoxy, and heterocycloalkyl;
$R^4$ is any one of hydrogen, deuterium, and $C_{1-6}$ alkyl;
$R^5$ is any one of hydrogen, deuterium, $C_{1-6}$ alkyl, $C_{1-6}$ alkyl substituted with at least one fluorine, and $C_{3-7}$ cycloalkyl,
an enantiomer, a diastereomer, a solvate, a hydrate, a prodrug, a stable isotope derivative or a pharmaceutically acceptable salt thereof.

2. The compound according to claim 1, wherein Ar is substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, —N($R^7$)—C(=O)—$R^8$, —$C_{1-6}$ alkylamino-C(=O)—$C_{1-6}$ alkyl, and —$C_{1-6}$ alkylamino-C(=O)-amino $C_{1-6}$ alkyl, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein,
$R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;
$R^7$ is any one of hydrogen, deuterium, $C_{1-6}$ alkyl, and $C_{3-7}$ cycloalkyl;
$R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl.

3. The compound according to claim 1, wherein R is any one of hydrogen, methyl, ethyl, propyl, isopropyl, and tert-butyl;
$R^1$ is any one of hydrogen, deuterium, fluorine, chlorine, bromine, methyl, ethyl, isopropyl, tert-butyl, methylamino, ethylamino, methoxy, ethoxy, and isopropoxy;
$R^2$ is any one of hydrogen, deuterium, fluorine, chlorine, bromine, methyl, ethyl, isopropyl, tert-butyl, trifluoromethyl, trifluoromethylmethyl, cyclopropyl, cyclopentyl, methylamino, ethylamino, methoxy, ethoxy, isopropoxy, pyrrolidinyl, and morpholinyl;
Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, methyl, ethyl, and cyano;

$R^4$ is any one of hydrogen, deuterium, methyl, and ethyl;

$R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

4. The compound according to claim 1, wherein R is any one of hydrogen and $C_{1-6}$ alkyl;

$R^1$ is any one of hydrogen, deuterium, halogen, and $C_{1-6}$ alkyl;

$R^2$ is any one of hydrogen, deuterium, halogen, $C_{1-6}$ alkyl, $C_{1-6}$ alkyl substituted with at least one fluorine, $C_{3-7}$ cycloalkyl, and $C_{1-6}$ alkoxy;

Ar is any one of phenyl, thienyl, pyridinyl, pyrimidinyl, pyrazinyl, pyridazinyl, pyridin-2(1H)keto, pyridin-4(1H)-keto, pyrrolyl, pyrazolyl, thiazolyl, 1, 2, 3-triazolyl, 1, 2, 4-triazolyl, imidazolyl, tetrazolyl, isothiazolyl, oxazolyl, isoxazolyl, thiadiazolyl, and oxadiazolyl;

$R^3$ is any one of hydrogen, deuterium, halogen, cyano, $C_{1-6}$ alkyl, and $C_{3-7}$ cycloalkyl;

$R^4$ is any one of hydrogen, deuterium, and $C_{1-6}$ alkyl;

$R^5$ is any one of hydrogen, deuterium, $C_{1-6}$ alkyl, $C_{1-6}$ alkyl substituted with at least one fluorine, and $C_{3-7}$ cycloalkyl.

5. The compound according to claim 4, wherein Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, di-$C_{1-6}$ alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, and —N($R^7$)—C(=O)—$R^8$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;

$R^7$ is any one of hydrogen, deuterium, and $C_{1-6}$ alkyl;

$R^8$ is any one of hydrogen, deuterium, $C_{1-6}$ alkyl, $C_{3-7}$ cycloalkyl, and $C_{3-7}$ heterocycloalkyl.

6. The compound according to claim 4, wherein R is any one of hydrogen, methyl, ethyl, and isopropyl;

$R^1$ is any one of hydrogen, deuterium, fluorine, chlorine, bromine, methyl, ethyl, isopropyl, and tert-butyl;

$R^2$ is any one of hydrogen, deuterium, fluorine, chlorine, bromine, methyl, ethyl, isopropyl, tert-butyl, trifluoromethyl, trifluoromethylmethyl, cyclopropyl, cyclopentyl, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, bromine, cyano, methyl, ethyl, and cyclopropyl;

$R^4$ is any one of hydrogen, deuterium, methyl, and ethyl;

$R^5$ is any one of hydrogen, deuterium, methyl, ethyl, isopropyl, butyl, sec-butyl, isobutyl, tert-butyl, and cyclopropyl.

7. The compound according to claim 1, wherein Ar is substituted with any one or more of deuterium, halogen, hydroxy, cyano, amino, $C_{1-6}$ alkyl, a substituted $C_{1-6}$ alkyl, $C_{3-7}$ heterocycloalkyl, $C_{1-6}$ alkoxy, $C_{1-6}$ alkoxy $C_{1-6}$ alkoxy, $C_{1-6}$ alkylamino, alkylamino, $C_{3-7}$ cycloalkylamino, $C_{3-7}$ heterocycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —C(=O)—$R^6$, —$C_{1-6}$ alkyl-C(=O)—$R^6$, —S(=O)$_2$—$R^6$, —$C_{1-6}$ alkyl-S(=O)$_2$—$R^6$, and —N($R^7$)—C(=O)—$R^8$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl;

$R^7$ is any one of hydrogen, deuterium, and $C_{1-6}$ alkyl;

$R^8$ is any one of hydrogen, deuterium, $C_{1-6}$ alkyl, $C_{3-7}$ cycloalkyl, and $C_{3-7}$ heterocycloalkyl.

8. The compound according to claim 7, wherein R is any one of hydrogen, methyl, ethyl, and isopropyl;

$R^1$ is any one of hydrogen, deuterium, fluorine, chlorine, bromine, methoxy, ethoxy, and isopropoxy;

$R^2$ is any one of hydrogen, deuterium, fluorine, chlorine, bromine, methylamino, ethylamino, methoxy, ethoxy, and isopropoxy;

Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino; or pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl; or pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino; or 1, 2, 4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl; or thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl; or pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino; or pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, piperidyl, piperazinyl, ethoxycarbonylmethyl, ethoxycarbonylethyl, and ethoxycarbonylpropyl;

$R^3$ is any one of hydrogen, deuterium, fluorine, chlorine, and bromine;

$R^4$ is hydrogen or deuterium;

$R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

9. The compound according to claim 1, wherein Ar is phenyl substituted with any one or more of deuterium, halogen, hydroxy, cyano, $C_{1-6}$ alkyl, a substituted $C_{1-6}$ alkyl, $C_{1-6}$ alkoxy, and $C_{1-6}$ alkylamino, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl.

10. The compound according to claim 1, wherein Ar is phenyl substituted with any one or more of deuterium, fluorine, chlorine, bromine, hydroxy, cyano, methyl, ethyl, trifluoromethyl, trifluoromethylmethyl, hydroxymethyl, cyanomethyl, benzyl, pyrazolylmethyl, aminomethyl, methoxymethyl, methoxyethyl, methoxypropyl, methylaminoethyl, cyclopropylmethyl, carboxymethyl, morpholinylethyl, methoxy, and methylamino.

11. The compound according to claim 1, wherein Ar is pyrazolyl substituted with any one or more of deuterium, halogen, hydroxy, cyano, $C_{1-6}$ alkyl, a substituted $C_{1-6}$ alkyl, $C_{1-6}$ alkoxy, $C_{1-6}$ alkylamino, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, aryl, heteroaryl, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

12. The compound according to claim 1, wherein Ar is pyrazolyl substituted with any one or more of deuterium, fluorine, chlorine, bromine, hydroxy, cyano, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, benzyl, pyrazolylmethyl, aminomethyl, methoxymethyl, methoxyethyl, methoxypropyl, methylaminoethyl, cyclopropylmethyl, carboxymethyl, carboxyethyl, carboxypropyl, morpholinylethyl, methoxy, methylamino, oxetanyl, piperidyl, and ethoxycarbonylethyl.

13. The compound according to claim 1, wherein Ar is pyridinyl substituted with any one or more of deuterium, halogen, hydroxy, amino, cyano, $C_{1-6}$ alkyl, a substituted $C_{1-6}$ alkyl, and $C_{3-7}$ heterocycloalkyl, $C_{1-6}$ alkoxy, $C_{1-6}$ alkoxy $C_{1-6}$ alkoxy, $C_{1-6}$ alkylamino, alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, —$C_{1-6}$ alkyl-C(=O)—$R^6$, and —N($R^7$)—C(=O)—$R^8$, wherein the substituted $C_{1-6}$ alkyl is substituted with any one or more of fluorine, $C_{1-6}$ alkoxy, $C_{1-6}$ alkylamino, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl, $R^7$ is any one of hydrogen, deuterium, $C_{1-6}$ alkyl, and $C_{3-7}$ cycloalkyl;

$R^8$ is any one of hydrogen, deuterium, $C_{1-6}$ alkyl, aryl, heteroaryl, $C_{3-7}$ cycloalkyl, aryl $C_{1-6}$ alkyl, heteroaryl $C_{1-6}$ alkyl, and $C_{3-7}$ heterocycloalkyl.

14. The compound according to claim 1, wherein Ar is pyridinyl substituted with any one or more of deuterium, fluorine, chlorine, bromine, hydroxy, amino, cyano, methyl, ethyl, propyl, isopropyl, butyl, sec-butyl, isobutyl, tert-butyl, trifluoromethyl, trifluoromethylmethyl, methoxymethyl, methoxyethyl, methoxypropyl, methylaminoethyl, morpholinylethyl, morpholinyl, piperidyl, piperazinyl, pyrrolidinyl, azetidinyl, methoxy, methoxyethoxy, methylamino, dimethylamino, cyclopropylamino, cyclobutylamino, cyclopropylmethylamino, 4-hydroxypiperidyl, 4-methylpiperazinyl, 4-ethylpiperazinyl, 4-acetylpiperazinyl, ethoxycarbonylethyl, acetylamino, and carboxymethylamino.

15. The compound according to claim 1, wherein Ar is 1,2,4-triazolyl substituted with any one or more of deuterium, halogen, hydroxy, amino, $C_{1-6}$ alkyl, and $C_{1-6}$ alkyl substituted with any one or more of fluorine, hydroxy, amino, $C_{1-6}$ alkoxy, $C_{1-6}$ alkylamino, $C_{3-7}$ cycloalkyl, carboxyl, and $C_{3-7}$ heterocycloalkyl.

16. The compound according to claim 1, wherein Ar is 1,2,4-triazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, aminomethyl, methoxymethyl, methoxyethyl, methoxypropyl, methylaminoethyl, cyclopropylmethyl, carboxymethyl, carboxyethyl, and morpholinylethyl.

17. The compound according to claim 1, wherein Ar is thiazolyl substituted with any one or more of deuterium, halogen, hydroxy, amino, $C_{1-6}$ alkyl, a substituted $C_{1-6}$ alkyl, $C_{3-7}$ heterocycloalkyl, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

18. The compound according to claim 1, wherein Ar is thiazolyl substituted with any one or more of deuterium, fluorine, chlorine, bromine, hydroxy, amino, methyl, ethyl, propyl, isopropyl, butyl, sec-butyl, isobutyl, tert-butyl, difluoromethyl, trifluoromethyl, trifluoromethylmethyl, hydroxymethyl, hydroxyethyl, hydroxypropyl, cyanomethyl, aminomethyl, methoxymethyl, methoxyethyl, methoxypropyl, methylaminoethyl, cyclopropylmethyl, carboxymethyl, carboxyethyl, carboxypropyl, morpholinylethyl, oxetanyl, piperidyl, morpholinyl, piperazinyl, 4-hydroxypiperidyl, 4-methylpiperazinyl, and ethoxycarbonylethyl.

19. The compound according to claim 1, wherein Ar is pyrimidyl substituted with any one or more of deuterium, halogen, hydroxy, amino, cyano, $C_{1-6}$ alkyl, a substituted $C_{1-6}$ alkyl, $C_{3-7}$ heterocycloalkyl, $C_{1-6}$ alkoxy, $C_{1-6}$ alkylamino, di-$C_{1-6}$ alkylamino, $C_{3-7}$ cycloalkylamino, $C_{3-7}$ cycloalkyl $C_{1-6}$ alkylamino, carboxyl $C_{1-6}$ alkylamino, —$C_{3-7}$ heterocycloalkyl-$R^6$, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

20. The compound according to claim 1, wherein Ar is pyrimidyl substituted with any one or more of deuterium, fluorine, chlorine, bromine, hydroxy, amino, cyano, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinylethyl, morpholinyl, pyrrolidinyl, azetidinyl, piperidyl, piperazinyl, methoxy, methylamino, dimethylamino, cyclopropylamino, cyclopropylmethylamino, 4-ethylpiperazinyl, ethoxycarbonylethyl, 4-carboxypiperidyl, cyclobutylamino, 3-carboxypyrrolidinyl, and carboxymethylamino.

21. The compound according to claim 1, wherein Ar is pyridin-2(1H)-keto substituted with any one or more of deuterium, $C_{1-6}$ alkyl, a substituted $C_{1-6}$ alkyl, $C_{3-7}$ heterocycloalkyl, and —$C_{1-6}$ alkyl-C(=O)—$R^6$, wherein the substituted $C_{1-6}$ alkyl is substituted with any one or more of fluorine, hydroxy, cyano, amino, $C_{1-6}$ alkoxy, $C_{1-6}$ alkylamino, $C_{3-7}$ cycloalkyl, carboxyl, and $C_{3-7}$ heterocycloalkyl; wherein $R^6$ is any one of hydroxy, amino, carboxyl, $C_{1-6}$ alkyl, $C_{3-7}$ cycloalkyl, $C_{3-7}$ heterocycloalkyl, $C_{1-6}$ alkoxy, $C_{1-6}$ alkylamino, $C_{3-7}$ cycloalkylamino, $C_{3-7}$ heterocycloalkylamino, and —C(=O)—$C_{1-6}$ alkyl.

22. The compound according to claim 1, wherein Ar is pyridin-2(1H)-keto substituted with any one or more of deuterium, methyl, ethyl, propyl, isopropyl, butyl, sec-butyl, isobutyl, tert-butyl, difluoromethyl, trifluoromethyl, trifluoromethylmethyl, hydroxyethyl, cyanomethyl, aminoethyl, methoxymethyl, methoxyethyl, methoxypropyl, methylaminoethyl, cyclopropylmethyl, carboxymethyl, carboxyethyl, carboxypropyl, morpholinyl ethyl, morpholinyl, pyrrolidinyl, piperidyl, piperazinyl, ethoxycarbonylmethyl, ethoxycarbonylethyl, and ethoxycarbonylpropyl.

23. The compound according to claim 1, wherein $R^3$ is hydrogen or deuterium.

24. The compound according to claim 1, wherein $R^4$ is hydrogen or deuterium.

25. The compound according to claim 1, wherein $R^5$ is any one of hydrogen, deuterium, methyl, ethyl, isopropyl, butyl, sec-butyl, isobutyl, tert-butyl, trifluoromethyl, trifluoromethylmethyl, and cyclopropyl.

26. The compound according to claim 1, selected from the group consisting of:
  6-isopropyl-10-methoxy-2-oxo-9-(1H-pyrazol-4-yl)-6,7-dihydro-2H-pyrido[2,1-a]isoquinoline-3-carboxylic acid;
  6-isopropyl-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid;
  6-isopropyl-10-methoxy-9-(1-(2-methoxyethyl)-1H-pyrazol-4-yl)-2-oxo-6,7-dihydro-2H-pyrido[2,1-a]isoquinoline-3-carboxylic acid;
  9-(1-(3-hydroxypropyl)-1H-pyrazol-4-yl)-6-isopropyl-10-methoxy-2-oxo-6,7-dihydro-2H-pyrido[2,1-a]isoquinoline-3-carboxylic acid;
  9-(1-isobutyl-1H-pyrazol-4-yl)-6-isopropyl-10-methoxy-2-oxo-6,7-dihydro-2H-pyrido[2,1-a]isoquinoline-3-carboxylic acid;
  6-isopropyl-10-methoxy-2-oxo-9-(1-propyl-1H-pyrazol-4-yl)-6,7-dihydro-2H-pyrido[2,1-a]isoquinoline-3-carboxylic acid;
  6-isopropyl-10-methoxy-9-(6-methylpyridin-3-yl)-2-oxo-6,7-dihydro-2H-pyrido[2,1-a]isoquinoline-3-carboxylic acid;
  6-(tert-butyl)-10-methoxy-2-oxo-9-(1H-pyrazol-4-yl)-6,7-dihydro-2H-pyrido[2,1-a]isoquinoline-3-carboxylic acid;
  6-(tert-butyl)-9-(1-(3-hydroxypropyl)-1H-pyrazol-4-yl)-10-methoxy-2-oxo-6,7-dihydro-2H-pyrido[2,1-a]isoquinoline-3-carboxylic acid;
  6-(tert-butyl)-10-methoxy-2-oxo-9-(1-(2,2,2-trifluoroethyl)-1H-pyrazol-4-yl)-6,7-dihydro-2H-pyrido[2,1-a]isoquinoline-3-carboxylic acid;
  6-(tert-butyl)-10-methoxy-9-(1-(oxetan-3-yl)-1H-pyrazol-4-yl)-2-oxo-6,7-dihydro-2H-pyrido[2,1-a]isoquinoline-3-carboxylic acid;
  6-(tert-butyl)-9-(1-(2-hydroxypropyl)-1H-pyrazol-4-yl)-10-methoxy-2-oxo-6,7-dihydro-2H-pyrido[2,1-a]isoquinoline-3-carboxylic acid;
  6-(tert-butyl)-10-methoxy-9-(1-methyl-1H-pyrazol-5-yl)-2-oxo-6,7-dihydro-2H-pyrido[2,1-a]isoquinoline-3-carboxylic acid;
  6-(tert-butyl)-9-(1-(difluoromethyl)-1H-pyrazol-4-yl)-10-methoxy-2-oxo-6,7-dihydro-2H-pyrido[2,1-a]isoquinoline-3-carboxylic acid;
  6-(tert-butyl)-9-(1,3-dimethyl-1H-pyrazol-5-yl)-10-methoxy-2-oxo-6,7-dihydro-2H-pyrido[2,1-a]isoquinoline-3-carboxylic acid;
  6-(tert-butyl)-10-methoxy-9-(1-(2-morpholinoethyl)-1H-pyrazol-4-yl)-2-oxo-6,7-dihydro-2H-pyrido[2,1-a]isoquinoline-3-carboxylic acid;
  6-(tert-butyl)-10-methoxy-2-oxo-9-(1-(piperidin-4-yl)-1H-pyrazol-4-yl)-6,7-dihydro-2H-pyrido[2,1-a]isoquinoline-3-carboxylic acid hydrochloride;
  6-(tert-butyl)-9-(1-isopropyl-1H-pyrazol-5-yl)-10-methoxy-2-oxo-6,7-dihydro-2H-pyrido[2,1-a]isoquinoline-3-carboxylic acid;
  6-(tert-butyl)-9-(1,4-dimethyl-1H-pyrazol-5-yl)-10-methoxy-2-oxo-6,7-dihydro-2H-pyrido[2,1-a]isoquinoline-3-carboxylic acid;
  6-(tert-butyl)-9-(1-(carboxymethyl)-1H-pyrazol-4-yl)-10-methoxy-2-oxo-6,7-dihydro-2H-pyrido[2,1-a]isoquinoline-3-carboxylic acid;
  ethyl 6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylate;
  6-(tert-butyl)-9-(1-(2-carboxyethyl)-1H-pyrazol-4-yl)-10-methoxy-2-oxo-6,7-dihydro-2H-pyrido[2,1-a]isoquinoline-3-carboxylic acid;
  6-(tert-butyl)-9-(1-(3-ethoxy-3-oxopropyl)-1H-pyrazol-4-yl)-10-methoxy-2-oxo-6,7-dihydro-2H-pyrido[2,1-a]isoquinoline-3-carboxylic acid;
  6-(tert-butyl)-9-(1-(3-carboxypropyl)-1H-pyrazol-4-yl)-10-methoxy-2-oxo-6,7-dihydro-2H-pyrido[2,1-a]isoquinoline-3-carboxylic acid;
  6-(tert-butyl)-10-methoxy-9-(3-methyl-1H-pyrazol-4-yl)-2-oxo-6,7-dihydro-2H-pyrido[2,1-a]isoquinoline-3-carboxylic acid;
  6-(tert-butyl)-9-(1-(1-carboxyethyl)-1H-pyrazol-4-yl)-10-methoxy-2-oxo-6,7-dihydro-2H-pyrido[2,1-a]isoquinoline-3-carboxylic acid;
  6-(tert-butyl)-9-(1-(2-carboxypropan-2-yl)-1H-pyrazol-4-yl)-10-methoxy-2-oxo-6,7-dihydro-2H-pyrido[2,1-a]isoquinoline-3-carboxylic acid;
  6-(tert-butyl)-10-methoxy-9-(2-methylthiazol-5-yl)-2-oxo-6,7-dihydro-2H-pyrido[2,1-a]isoquinoline-3-carboxylic acid;
  6-(tert-butyl)-10-methoxy-2-oxo-9-(1H-1,2,4-triazol-3-yl)-6,7-dihydro-2H-pyrido[2,1-a]isoquinoline-3-carboxylic acid;
  6-(tert-butyl)-9-(1-(carboxymethyl)-1H-1,2,4-triazol-3-yl)-10-methoxy-2-oxo-6,7-dihydro-2H-pyrido[2,1-a]isoquinoline-3-carboxylic acid;
  6-(tert-butyl)-9-(4-(3-hydroxypropyl)-4H-1,2,4-triazol-3-yl)-10-methoxy-2-oxo-6,7-dihydro-2H-pyrido[2,1-a]isoquinoline-3-carboxylic acid;

6-(tert-butyl)-9-(1-(3-hydroxypropyl)-1H-1,2,4-triazol-3-yl)-10-methoxy-2-oxo-6,7-dihydro-2H-pyrido[2,1-a]isoquinoline-3-carboxylic acid;

6-(tert-butyl)-10-methoxy-2-oxo-9-phenyl-6,7-dihydro-2H-pyrido[2,1-a]isoquinoline-3-carboxylic acid;

6-(tert-butyl)-9-(4-ethylphenyl)-10-methoxy-2-oxo-6,7-dihydro-2H-pyrido[2,1-a]isoquinoline-3-carboxylic acid;

6-(tert-butyl)-10-methoxy-9-(4-methoxyphenyl)-2-oxo-6,7-dihydro-2H-pyrido[2,1-a]isoquinoline-3-carboxylic acid;

6-(tert-butyl)-10-methoxy-9-(3-methoxyphenyl)-2-oxo-6,7-dihydro-2H-pyrido[2,1-a]isoquinoline-3-carboxylic acid;

6-(tert-butyl)-10-methoxy-9-(6-methylpyridin-3-yl)-2-oxo-6,7-dihydro-2H-pyrido[2,1-a]isoquinoline-3-carboxylic acid;

6-(tert-butyl)-10-methoxy-9-(2-methylpyridin-4-yl)-2-oxo-6,7-dihydro-2H-pyrido[2,1-a]isoquinoline-3-carboxylic acid;

6-(tert-butyl)-10-methoxy-9-(2-methylpyridin-3-yl)-2-oxo-6,7-dihydro-2H-pyrido[2,1-a]isoquinoline-3-carboxylic acid;

6-(tert-butyl)-10-methoxy-9-(6-morpholinopyridin-3-yl)-2-oxo-6,7-dihydro-2H-pyrido[2,1-a]isoquinoline-3-carboxylic acid;

6-(tert-butyl)-10-methoxy-2-oxo-9-(6-(trifluoromethyl)pyridin-3-yl)-6,7-dihydro-2H-pyrido[2,1-a]isoquinoline-3-carboxylic acid;

6-(tert-butyl)-10-methoxy-9-(6-(2-methoxyethoxy)pyridin-3-yl)-2-oxo-6,7-dihydro-2H-pyrido[2,1-a]isoquinoline-3-carboxylic acid;

6-(tert-butyl)-9-(6-(dimethylamino)pyridin-3-yl)-10-methoxy-2-oxo-6,7-dihydro-2H-pyrido[2,1-a]isoquinoline-3-carboxylic acid;

6-(tert-butyl)-10-methoxy-2-oxo-9-(6-(pyrrolidin-1-yl)pyridin-3-yl)-6,7-dihydro-2H-pyrido[2,1-a]isoquinoline-3-carboxylic acid;

6-(tert-butyl)-10-methoxy-2-oxo-9-(6-(piperazin-1-yl)pyridin-3-yl)-6,7-dihydro-2H-pyrido[2,1-a]isoquinoline-3-carboxylic acid;

9-(6-(4-acetylpiperazin-1-yl)pyridin-3-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(6-(4-methylpiperazin-1-yl)pyridin-3-yl)-2-oxo-6,7-dihydro-2H-pyrido[2,1-a]isoquinoline-3-carboxylic acid;

6-(tert-butyl)-9-(6-fluoro-4-methylpyridin-3-yl)-10-methoxy-2-oxo-6,7-dihydro-2H-pyrido[2,1-a]isoquinoline-3-carboxylic acid;

6-(tert-butyl)-9-(6-fluoropyridin-3-yl)-10-methoxy-2-oxo-6,7-dihydro-2H-pyrido[2,1-a]isoquinoline-3-carboxylic acid;

9-(6-(azetidin-1-yl)pyridin-3-yl)-6-(tert-butyl)-10-methoxy-2-oxo-6,7-dihydro-2H-pyrido[2,1-a]isoquinoline-3-carboxylic acid;

6-(tert-butyl)-9-(6-(4-hydroxypiperidin-1-yl)pyridin-3-yl)-10-methoxy-2-oxo-6,7-dihydro-2H-pyrido[2,1-a]isoquinoline-3-carboxylic acid;

6-(tert-butyl)-9-(6-((cyclopropylmethyl)amino)pyridin-3-yl)-10-methoxy-2-oxo-6,7-dihydro-2H-pyrido[2,1-a]isoquinoline-3-carboxylic acid;

9-(6-(azetidin-1-yl)-4-methylpyridin-3-yl)-6-(tert-butyl)-10-methoxy-2-oxo-6,7-dihydro-2H-pyrido[2,1-a]isoquinoline-3-carboxylic acid;

9-(6-aminopyridin-3-yl)-6-(tert-butyl)-10-methoxy-2-oxo-6,7-dihydro-2H-pyrido[2,1-a]isoquinoline-3-carboxylic acid;

ethyl 6-(tert-butyl)-10-methoxy-9-(6-methylpyridin-3-yl)-2-oxo-6,7-dihydro-2H-pyrido[2,1-a]isoquinoline-3-carboxylate;

6-(tert-butyl)-9-(6-(cyclobutylamino)pyridin-3-yl)-10-methoxy-2-oxo-6,7-dihydro-2H-pyrido[2,1-a]isoquinoline-3-carboxylic acid;

9-(6-acetamidopyridin-3-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(2-methylpyrimidin-5-yl)-2-oxo-6,7-dihydro-2H-pyrido[2,1-a]isoquinoline-3-carboxylic acid;

6-(tert-butyl)-10-methoxy-2-oxo-9-(2-(pyrrolidin-1-yl)pyrimidin-5-yl)-6,7-dihydro-2H-pyrido[2,1-a]isoquinoline-3-carboxylic acid;

6-(tert-butyl)-10-methoxy-9-(2-(methylamino)pyrimidin-5-yl)-2-oxo-6,7-dihydro-2H-pyrido[2,1-a]isoquinoline-3-carboxylic acid;

6-(tert-butyl)-9-(2-(dimethylamino)pyrimidin-5-yl)-10-methoxy-2-oxo-6,7-dihydro-2H-pyrido[2,1-a]isoquinoline-3-carboxylic acid;

6-(tert-butyl)-10-methoxy-9-(2-morpholinopyrimidin-5-yl)-2-oxo-6,7-dihydro-2H-pyrido[2,1-a]isoquinoline-3-carboxylic acid;

6-(tert-butyl)-9-(2-(4-ethylpiperazin-1-yl)pyrimidin-5-yl)-10-methoxy-2-oxo-6,7-dihydro-2H-pyrido[2,1-a]isoquinoline-3-carboxylic acid;

6-(tert-butyl)-9-(2-(cyclopropylamino)pyrimidin-5-yl)-10-methoxy-2-oxo-6,7-dihydro-2H-pyrido[2,1-a]isoquinoline-3-carboxylic acid;

9-(2-aminopyrimidin-5-yl)-6-(tert-butyl)-10-methoxy-2-oxo-6,7-dihydro-2H-pyrido[2,1-a]isoquinoline-3-carboxylic acid;

6-(tert-butyl)-10-methoxy-9-(2-methoxypyrimidin-5-yl)-2-oxo-6,7-dihydro-2H-pyrido[2,1-a]isoquinoline-3-carboxylic acid;

6-(tert-butyl)-9-(2-((cyclopropylmethyl)amino)pyrimidin-5-yl)-10-methoxy-2-oxo-6,7-dihydro-2H-pyrido[2,1-a]isoquinoline-3-carboxylic acid;

6-(tert-butyl)-9-(2-chloropyrimidin-5-yl)-10-methoxy-2-oxo-6,7-dihydro-2H-pyrido[2,1-a]isoquinoline-3-carboxylic acid;

9-(2-(azetidin-1-yl)pyrimidin-5-yl)-6-(tert-butyl)-10-methoxy-2-oxo-6,7-dihydro-2H-pyrido[2,1-a]isoquinoline-3-carboxylic acid;

ethyl 6-(tert-butyl)-9-(1-(1-ethoxy-2-methyl-1-oxopropan-2-yl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(2-ethoxy-2-oxoethyl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(3-ethoxy-3-oxopropyl)-6-oxo-1,6-dihydropyridin-3-yl)-10-methoxy-2-oxo-6,7-dihydro-2H-pyrido[2,1-a]isoquinoline-3-carboxylate;

6-(tert-butyl)-9-(2-(4-carboxypiperidin-1-yl)pyrimidin-5-yl)-10-methoxy-2-oxo-6,7-dihydro-2H-pyrido[2,1-a]isoquinoline-3-carboxylic acid;

ethyl 6-(tert-butyl)-9-(1-(1-ethoxy-1-oxopropan-2-yl)-6-oxo-1,6-dihydropyridin-3-yl)-10-methoxy-2-oxo-6,7-dihydro-2H-pyrido[2,1-a]isoquinoline-3-carboxylate;

ethyl 6-(tert-butyl)-9-(1-(4-ethoxy-4-oxobutyl)-6-oxo-1,6-dihydropyridin-3-yl)-10-methoxy-2-oxo-6,7-dihydro-2H-pyrido[2,1-a]isoquinoline-3-carboxylate;

6-(tert-butyl)-9-(2-(cyclobutylamino)pyrimidin-5-yl)-10-methoxy-2-oxo-6,7-dihydro-2H-pyrido[2,1-a]isoquinoline-3-carboxylic acid;

6-(tert-butyl)-9-(2-(3-carboxypyrrolidin-1-yl)pyrimidin-5-yl)-10-methoxy-2-oxo-6,7-dihydro-2H-pyrido[2,1-a]isoquinoline-3-carboxylic acid; and 6-(tert-butyl)-9-(2-((carboxymethyl)amino)pyrimidin-5-yl)-10-methoxy-2-oxo-6,7-dihydro-2H-pyrido[2,1-a]isoquinoline-3-carboxylic acid.

* * * * *